US010954523B2

(12) United States Patent
Kelliher et al.

(10) Patent No.: US 10,954,523 B2
(45) **Date of Patent: *Mar. 23, 2021**

(54) HAPLOID INDUCTION COMPOSITIONS AND METHODS FOR USE THEREFOR

(71) Applicant: Syngenta Participations AG, Basel (CH)

(72) Inventors: Timothy Kelliher, Research Triangle Park, NC (US); Satya Chintamanani, Slater, IA (US); Brent Delzer, Janesville, WI (US); Michael L Nuccio, Durham, NC (US); Robert Arthur Dietrich, Research Triangle Park, NC (US); Suresh Babu Kadaru, Hydrabad (IN); Todd Lee Warner, Stanton, MN (US); William Paul Bullock, Slater, IA (US)

(73) Assignee: Syngenta Participations AG, Basel (CH)

( * ) Notice: Subject to any disclaimer, the term of this patent is extended or adjusted under 35 U.S.C. 154(b) by 19 days.

This patent is subject to a terminal disclaimer.

(21) Appl. No.: 16/218,529

(22) Filed: Dec. 13, 2018

(65) Prior Publication Data

US 2019/0100763 A1 Apr. 4, 2019

Related U.S. Application Data

(62) Division of application No. 15/586,649, filed on May 4, 2017, now Pat. No. 10,190,125, which is a division of application No. 14/212,504, filed on Mar. 14, 2014, now Pat. No. 9,677,082.

(60) Provisional application No. 61/852,428, filed on Mar. 15, 2013.

(51) Int. Cl.

| | |
|---|---|
| ***C12N 15/82*** | (2006.01) |
| ***C12Q 1/6895*** | (2018.01) |
| ***C12N 9/18*** | (2006.01) |
| ***A01H 1/04*** | (2006.01) |
| ***A01H 1/08*** | (2006.01) |
| *C12Q 1/686* | (2018.01) |

(52) U.S. Cl.

CPC ........... *C12N 15/8216* (2013.01); *A01H 1/04* (2013.01); *A01H 1/08* (2013.01); *C12N 9/18* (2013.01); *C12N 15/8218* (2013.01); *C12N 15/8261* (2013.01); *C12N 15/8287* (2013.01); *C12Q 1/6895* (2013.01); *C12Q 1/686* (2013.01); *Y02A 40/146* (2018.01)

(58) Field of Classification Search

CPC ................................................. C12N 15/8216
USPC ......................................................... 800/285
See application file for complete search history.

(56) References Cited

U.S. PATENT DOCUMENTS

| | | | | |
|---|---|---|---|---|
| 7,411,117 | B2 | 8/2008 | Bohning | |
| 9,677,082 | B2 * | 6/2017 | Chintamanani .... | C12N 15/8218 |
| 10,190,125 | B2 * | 1/2019 | Chintamanani .... | C12N 15/8218 |
| 2015/0184194 | A1 | 7/2015 | Bidney et al. | |

FOREIGN PATENT DOCUMENTS

| | | | |
|---|---|---|---|
| WO | 201230893 | A1 | 3/2012 |
| WO | 2016177887 | A1 | 11/2016 |

OTHER PUBLICATIONS

Colliver et al, 1997, "Differential Modification of Flavonoid and Isoflavonoid Biosynthesis with an Antisense Chalcone Synthase Construct in Transgenic Lotus Corniculatus", Plant Molecular Bioogy 35, pp. 509-522.
EMBO "Hybrid Plant Breeding: Secrets Behind Haploid Inducers, A Powerful Tool in Maize Breeding", pp. 1-3, Feb. 22, 2017.
Thomas et al, The Plant Journal Issue 25, vol. 4, pp. 417-425.
Yibrah et al., Hereditas, "Antisense RNA Inhibition of uidA Gene Expression in Transgenic Plants: Evidence for Interaction Between First and Second Trnasformation Events", vol. 118, pp. 273-280, 1993.
Dong et al., "Fine mapping of qhir1 influencing in vivo haploid induction in maize.", Theor. Appl. Genet. vol. 126: 2013, pp. 1713-1720.
Kelliher et al., "Unresolved issues in pre-meiotic anther development", Frontiers in Plant Science, Plant Evolution and Development, published Jul. 21, 2014, vol. 5, Article 341, pp. 1-9.
Qiu et al., "Morphological, cellular and molecular evidences of chromosomerandom elimination in vivo upon haploid induction in maize", Current Plant Biology 1 (2014) pp. 83-90.
Schnable et al., "The B73 Maize Genome: Complexity, Diversity, and Dynamics", Downloaded from www.sciencemag.org on Nov. 16, 2015, Science Magizine, vol. 326, Nov. 20, 20019.
Hu et al., "The Genetic Basis of Haploid Induction in Maize Identified with a Novel Genome-Wide Association Method", Genetics, vol. 202, pp. 1267-1276, Apr. 2016.

* cited by examiner

*Primary Examiner* — Li Zheng
(74) *Attorney, Agent, or Firm* — Christopher Leming

(57) ABSTRACT

Provided are isolated cDNAs comprising a nucleotide sequence having at least 90% identity to SEQ ID NO: 33, SEQ ID NO: 37, SEQ ID NO: 52 or SEQ ID NO: 53. Also provided are expression cassettes; vectors; transgenic plant cells; plants, plant parts, and seeds; isolated polypeptides; amplicons and informative fragments of the presently disclosed nucleic acids; compositions that include amplification primer pairs; methods for producing plants that exhibit HI; methods for identifying the presence or absence of an allele associated with HI in a plant; methods for introgressing Haploid—inducing nucleotide sequences into plants; and methods for selecting parental plants predicted to produce progeny generations with plants that exhibit Haploid Induction trait.

2 Claims, No Drawings

Specification includes a Sequence Listing.

SEQUENCE LISTING

```
<160> NUMBER OF SEQ ID NOS: 67

<210> SEQ ID NO 1
<211> LENGTH: 1302
<212> TYPE: DNA
<213> ORGANISM: Zea mays

<400> SEQUENCE: 1

cccgctacct gttcaccgcg cgccagcgaa acctccgcac gcccactgcc catctgttcc      60

ccgtgcgcca gcgaaacatc cgcacgcccg cggcccgcct gttccccgcg catcccgctg     120

cacgacttct gctaccgcaa cggccaccca cgcacgcccg cctgttcacc gcgcatcccg     180

ctgacctccc cttcacgctc gcacacgctc cgttccccca ccccaccgca atccccgacg     240

aactcattac cagtagaatc agttactaac tgcttttctt tttcttggat tagaatggct     300

ggggctatct ctcaccatgc gctagcattt tcacaatccc actggtgcag tgcgaagaac     360
```

```
tctagattcg gaaagaggac gggcaatgct cgcctggttt atctaaaagg aagatgtggt    420

tcaggcagca gaaaactggg tttgatgtgg gcctcgagct cgcagtcttc tgtcatggag    480

ccgacgcacc taccatctga tggcaacagc agccacaccc caaaaaaatc aagtgaaagc    540

gctcttatat tgatttggca tggtgaatcc ctgtggaacg agaaaaatct atttcctggc    600

tgcatcgatg taccccctgac accgaagggt gttgaggagg ccattgaggc aggtaaaagg    660

atatgcaata tcccaatcga tgtgatatat acttcatcac tgatttgtgc tcagatgacc    720

gcaatgcttg ccatgatgca gcatcgacgc aagaagatcc tagttatcac gcataatgag    780

agtgaacaag ctcacaggtg gagtcagata tacagtgagg agacaatgaa acagtccatt    840

cctgtcatca cagcttggca attgaatgaa cggatgtatg gtgagctaca aggccttaac    900

aagcaagaaa ctgtagatcg atttggcaaa gaacaagttc atgagtggcg ccgcagttat    960

gatattcctc cgccaaatgg agaaagtcta gagaagtgtg ctgagagagc tgttgcttat   1020

ttcaaagatc agattattcc acaacttgtg gctggaaaac atgtgatggt tgctgcacat   1080

gggaattcac ttcgttcaat tataatgcat ctggacaaat taacttctca gaaggtaata   1140

agccttgagc tgtctactgg cattcccatg ctttacatat tcaaagaggg aaagtttatt   1200

cgacgtggga ctccagtagg accttcggag gccagtgttt atgcttatac caggaccaaa   1260

cgatttgctg agcacattac atttcagaac aaattggcct ag                      1302
```

<210> SEQ ID NO 2
<211> LENGTH: 335
<212> TYPE: PRT
<213> ORGANISM: Zea mays

<400> SEQUENCE: 2

```
Met Ala Gly Ala Ile Ser His His Ala Leu Ala Phe Ser Gln Ser His
1               5                   10                  15

Trp Cys Ser Ala Lys Asn Ser Arg Phe Gly Lys Arg Thr Gly Asn Ala
            20                  25                  30

Arg Leu Val Tyr Leu Lys Gly Arg Cys Gly Ser Gly Ser Arg Lys Leu
        35                  40                  45

Gly Leu Met Trp Ala Ser Ser Ser Gln Ser Ser Val Met Glu Pro Thr
    50                  55                  60

His Leu Pro Ser Asp Gly Asn Ser Ser His Thr Pro Lys Lys Ser Ser
65                  70                  75                  80

Glu Ser Ala Leu Ile Leu Ile Trp His Gly Glu Ser Leu Trp Asn Glu
                85                  90                  95

Lys Asn Leu Phe Pro Gly Cys Ile Asp Val Pro Leu Thr Pro Lys Gly
            100                 105                 110

Val Glu Glu Ala Ile Glu Ala Gly Lys Arg Ile Cys Asn Ile Pro Ile
        115                 120                 125

Asp Val Ile Tyr Thr Ser Ser Leu Ile Cys Ala Gln Met Thr Ala Met
    130                 135                 140

Leu Ala Met Met Gln His Arg Arg Lys Lys Ile Leu Val Ile Thr His
145                 150                 155                 160

Asn Glu Ser Glu Gln Ala His Arg Trp Ser Gln Ile Tyr Ser Glu Glu
                165                 170                 175

Thr Met Lys Gln Ser Ile Pro Val Ile Thr Ala Trp Gln Leu Asn Glu
            180                 185                 190

Arg Met Tyr Gly Glu Leu Gln Gly Leu Asn Lys Gln Glu Thr Val Asp
        195                 200                 205
```

```
Arg Phe Gly Lys Glu Gln Val His Glu Trp Arg Arg Ser Tyr Asp Ile
    210                 215                 220

Pro Pro Pro Asn Gly Glu Ser Leu Glu Lys Cys Ala Glu Arg Ala Val
225                 230                 235                 240

Ala Tyr Phe Lys Asp Gln Ile Ile Pro Gln Leu Val Ala Gly Lys His
                245                 250                 255

Val Met Val Ala Ala His Gly Asn Ser Leu Arg Ser Ile Ile Met His
            260                 265                 270

Leu Asp Lys Leu Thr Ser Gln Lys Val Ile Ser Leu Glu Leu Ser Thr
        275                 280                 285

Gly Ile Pro Met Leu Tyr Ile Phe Lys Glu Gly Lys Phe Ile Arg Arg
    290                 295                 300

Gly Thr Pro Val Gly Pro Ser Glu Ala Ser Val Tyr Ala Tyr Thr Arg
305                 310                 315                 320

Thr Lys Arg Phe Ala Glu His Ile Thr Phe Gln Asn Lys Leu Ala
                325                 330                 335
```

<210> SEQ ID NO 3
<211> LENGTH: 2992
<212> TYPE: DNA
<213> ORGANISM: Zea mays

<400> SEQUENCE: 3

```
ttcaaccacc aaaatcaatt aggaaaaggt gtaagcctat ttccctttca ggaggcgtac      60

gtgagaggga gaggtgaaaa ggaacaacgc gtataccaga taaggtccca cagcctaagt     120

aggtagcctt ctgatatctc tactaactat taaggagaga gtgtagactg cccccgctcc     180

ctacccaacg cccccccgcta cctgttcacc gcgcgccagc gaaacctccg cacgcccact    240

gcccatctgt tccccgtgcg ccagcgaaac atccgcacgc ccgcggcccg cctgttcccc     300

gcgcatcccg ctgcacgact tctgctaccg caacggccac ccccgcacgc ccgcctgttc     360

accgcgcatc ccgctgacct ccccttcacg ctcgcacacg ctccgttccc ccaccccacc     420

gcaatccccg acgctataag agcggtaacc aactccatct ccctggtgcc acgcattgtt     480

gagttcttaa ggtgcgtttc gttgaggact tgttcatttt tgttggtcat gtattccatt     540

ttactgctct accattttgt ggaataaagg gaggaatgtt ttcactagaa gagttcatca     600

atcttatgtt ggtttcttgg atcagttttg ctctatggct aaatggtcga attgagccta     660

tttcattata aagttagcga gcgaataatt gttcagcctc ttcctagaac tcattaccag     720

tagaatcagt tactaactgc ttttcttttt cttggattag aatggctggg gctatctctc     780

accatgcgct agcattttca caatcccact ggtgcagtgc gaagaactct agattcggaa     840

agaggacggg caatgctcgc ctggtttatc taaaaggaag atgtggttca ggcagcagaa     900

aactgggttt gatgtgggcc tcgagctcgc agtcttctgt catggagccg acgcacctac     960

catctgatgg caacagcagc cacaccccaa aaaaatcaag taattttaac gacctcctat    1020

ggtggttatt tgtttttaat ttgagaaaac tatccatttg acacatttaa ctttgggctt    1080

ctcagaattt ggggcatata ataagatctg ctaatctgtt atctctatgt cgttgtaggt    1140

gaaagcgctc ttatattgat ttggcatggt gaatccctgt ggaacgagaa aaatctattt    1200

actggctgca tcgatgtacc cctgacaccg aagggtgttg aggaggccat tgaggcaggt    1260

aaaaggatat gcaatatccc aatcgatgtg atatatactt catcactgat ttgtgctcag    1320

atgaccgcaa tgcttgccat gatgcagcat cgacgcaaga aggtttgtgt ctttcctttg    1380

aaattccagt aatttcttct agcatttgta tgaacttgcc ggagaaatca tgctttgctg    1440
```

```
gtgatatatg tatttataga tcccagttat cacgcataat gagagtgaac aagctcacag   1500
gtggagtcag atatacagtg aggagacaat gaaacagtcc attcctgtca tcacagcttg   1560
gcaattgaat gaacggatgt aatactttct ccatactctt tgatttgcta attactccct   1620
ctgtctcaaa atagtattaa ttttagctct tgatttttat gtctatattc aaatagatga   1680
tgataaatct agattctaga cacaaatata aaacatatac atcaagtatt atatgaatct   1740
attaatttac taagaccaat tttaatttgg gacagaggga gtatacgatt ataatagttg   1800
tttgactgtg cttctcttta aatatccctt gacatttcta ggtatggtga gctacaaggc   1860
cttaacaagc aagaaactgt agatcgattt ggcaaagaac aagttcatga gtggcaccgc   1920
agttatgata ttcctccgcc aaatggagaa agtctagaga agtgtgctga gagagctgtt   1980
gcttatttca aagatcaggc acatctagca aggccacttt acactaattg aaagatacac   2040
tttttacttg ggttattggt cttgctgcag tattggtatg catgctaaag gttattcttg   2100
aatcgatgaa ttcctctact atgggatgca gaaatgcatg tgcttagttt tctttctatt   2160
gtgctagctc atatcaaatt tataacctga atttttattt tatgttcgac tctaaaaaac   2220
agtttttct agctcgattt gacctatagt aatttttccg taatagatta ttccacaact    2280
tgtggctgga aaacatgtga tggttgctgc acatgggaat tcacttcgtt caattataat   2340
gcatctggac aaattaactt ctcagaaggt aattcactgt cgtttttgtc tttccatcaa   2400
aaaggactcg gctaaacaga acatgtagca ttatgttaag tttgggagtg agcctttcgt   2460
cccttcaggt aataagcctt gagctgtcta ctggcattcc catgctttac atattcaaag   2520
agggaaagtt tattcgacgt gggactccag taggaccttc ggaggccagt gtttatgctt   2580
ataccagggt aagattcttt cccccacatg ttctaccata ggacgatact ccagtttaca   2640
aaccttatct gtacagacca aacgatttgc tgagcacatt acatttcaga acaaattggc   2700
ctagaagata aggggtgttt ggtttgagaa atcactctat tcaaaatgag atggtgtatc   2760
atgggtccat ttctcaaatt tggtgggatg accctattcc tcatattagt actaactagg   2820
tgagtgtccg tgcgttgcaa cgggaacata taataacatg ataacttata tacaaaatgt   2880
gtcttatatt gttataagaa aatgtttcat aatctatttg tgatcctggc catacataaa   2940
ttttgttatt ttaatttaac tgtttcacta ctacattgaa atcatcagta tc           2992
```

<210> SEQ ID NO 4
<211> LENGTH: 6916
<212> TYPE: DNA
<213> ORGANISM: Artificial Sequence
<220> FEATURE:
<223> OTHER INFORMATION: Synthetic

<400> SEQUENCE: 4

```
cctcgggacc cttgtcgcgt tgttcgttcc attgccgcat cacctccttt ctcatcgtgc     60
attacgaggt cttcaaaggg cttttggtca tcagccggga gcgcctccat cgccggcttg    120
atgatgttgg tagtggagat cttggtgtga tccttaaaac cggccattta tgggccgatt    180
tttagcagat ctagacacct attccccagc ggagtcgcca aaagtatgtt gacgcttttt    240
cggagcgcca atcactcaag aagaaccggc ggcggtgccc tctgcacagg ggcggacgct    300
ccgcgcgcag gggccggacg ctccgcggcc tggtgcgagg cggcggcgct ctctggttag    360
acgcggacgg tgcgcggcac agggccggac ggtgcgcgac ctagtgcagg agcacgggtt    420
ccctgcctga cggccggacg ctccgcgctc tagggccgga cggtgcgcgc gtgcgcaggg    480
```

```
gcggcggaag atcgccggcg gcgcctggat ctcgctcccg ggagggagcc cgtcggggag    540
gagagatcct aggagttgtc taggctcggg ccggccgacc tagactcctc taatcgacgt    600
agagtcgagg agaggcagag aatttgggga ttggaatact aaactagggc taaactagaa    660
ctagactaga actactccta attgtgctga aaataaatgc gagatagaag ttgtattggt    720
tcgattgttg gggtcaatc ggccgtagcc cttcatctat ataaagggga ggtctggatc    780
cgtttccaac tgatttccga gttaatcccg cggttttagg taacaaatcc cgcgagaaac    840
taggaaccct aactgactct gcgcacgcgc cgaccgtccg cgccaccacc gcggacggtc    900
ccgaccgcgg agcgtccggc ctccgggccg gagcgtccgc acggtcattt tgggttcgaa    960
cagagtccca acgaggttag taaatgtagt gatgaaatta agttttgtac gaagtttgta   1020
aatttaagga cctgttttac ataactattg gagaagagtt ttctctgaaa aattcttaaa   1080
tttatattta gggagttgtt tatataacta ttggcatttg agatgctcta aggaagcgaa   1140
ggaaataact tggcggcgat cctagtcgac aaccgttgaa ttcgtgagaa tcaatcattc   1200
tgtaggagta aaaaaataaa ataaaatatg catttcctcg ttcctatacg cttaaattag   1260
acgaccctgg actggaacca ggaactagga aggggcaccg atgtcatttg cgaagcaaca   1320
acaacatgcg tgaggacgac caagtcaaac gttgcgtcgc gttgcctcgc cggcgggccg   1380
gtcccaccaa gacgtggcgc catgcaagtg cgtcgtcgac cctcttctct ctctctcttg   1440
tagtcttgtt cctgttatct ctctcggctg tccgctgccc cgtgatctga gcgcgtttct   1500
ctcccgtcct ctcttctccc tctcccgcaa caaacacctg ctatccggtc tccctctccc   1560
ctgccatctc tctctagcgc attgctagcg cgagcgcaga aggcacacac gtagagcctt   1620
ggtgatacct cctcctcctc ctcctcctcc tcctgatctc ctctcctcct ccggcctccg   1680
tatacctata actaaaagat gatcatcgtg cgatgcaggc gaactcgtcg tccgaaaacc   1740
atggatccaa ctcattacca gtagaatcag ttactaactg cttttctttt tcttggatta   1800
gaatggctgg ggctatctct caccatgcgc tagcattttc acaatcccac tggtgcagtg   1860
cgaagaactc tagattcgga aagaggacgg gcaatgctcg cctggtttat ctaaaaggaa   1920
gatgtggttc aggcagcaga aaactgggtt tgatgtgggc ctcgtgctcg cagtcttctg   1980
tcatggagcc gacgcaccta ccatctgatg gcaacagcag ccacacccca aaaaaatcaa   2040
gtgaaagcgc tcttatattg atttggcatg gtgaatccct gtggaacgag aaaaatctat   2100
ttcctggctg catcgatgta cccctgacac cgaagggtgt tgaggaggcc attgaggcag   2160
gtaaaaggat atgcaatatc ccaatcgatg tgatatatac ttcatcactg atttgtgctc   2220
agatgaccgc aatgcttgcc atgatgcact cgagaaatct gaagaagaga catcagtagg   2280
aaaaccatga aacaactcac caagtgataa aactttgata aattcattca aaagtatcat   2340
gttctacgtg attcgcttgt atgccaaatt atctaaatat tagtaagaat taactactcg   2400
gacgatcatc agcaaatgaa aatgaaacag cacaccaatt gagactgatc agatcagaaa   2460
ccagaaaaac atctcaacat ggataaattc atcagcaata ctgtagcatt gatatatttg   2520
tgtttcttga aagaaagaca tcaaagaaac tttgcaatta tgtagtattg tttatttttc   2580
tgttacaaac ttaatcaact gacatgtaat gtgtctctat tgtcagttca agtattagac   2640
tatccattgt cacctttttaa atgtaccttt actgtcagcg tacgagataa agttggccga   2700
ttgaattcta agctactata aaagcaactt tattatatag acatggcaaa caatcgttaa   2760
caaactgttt ttctttttga ttgattagga cttggaaaca cactgaacat gatcaaagtc   2820
acaaaagtca cttggttgcc tagtctgaca gcaagcgcag gtgtaaattc agaatgatag   2880
```

```
tgaaccaaaa ctcatctgct tccagtacca aattcgtcag aaggcagaac ggaggcataa   2940
gcacaaaggg catgctcacc cgagtcgagt gcatcatggc aagcattgcg gtcatctgag   3000
cacaaatcag tgatgaagta tatatcacat cgattgggat attgcatatc cttttacctg   3060
cctcaatggc ctcctcaaca cccttcggtg tcaggggtac atcgatgcag ccaggaaata   3120
gatttttctc gttccacagg gattcaccat gccaaatcaa tataagagcg ctttcacttg   3180
atttttttgg ggtgtggctg ctgttgccat cagatggtag gtgcgtcggc tccatgacag   3240
aagactgcga gcacgaggcc cacatcaaac ccagttttct gctgcctgaa ccacatcttc   3300
cttttagata aaccaggcga gcattgcccg tcctctttcc gaatctagag ttcttcgcac   3360
tgcaccagtg ggattgtgaa aatgctagcg catggtgaga gatagcccca gccattctaa   3420
tccaagaaaa agaaaagcag ttagtaactg attctactgg taatgagttg gatctccatg   3480
ggagctctcg tcatcgtcct actatcaagc aacacgatcg accaccacct cgattatata   3540
tgcatcatta tagtatcgtt tattaatttc agacccaccc actgctaacc acatcgtcca   3600
cgagagatta tattcatccg tggactacgc tctcgatctt acaatttgaa acctttctat   3660
tttcctaatt actatgtatt ccaggttcat tttgattgtg accattcttc agttctttct   3720
gtaaggatcg gagcatatta tatactctat gtggctatgc caattatatt gttgggtata   3780
agaatgcatt ttgtttctgt aatacggaaa aatatatttt ctttaagcaa caacaaggta   3840
aaaacttgcc tcgttgcata ttttctttat gtcaatctcc ttttgttcgt tgtatgatcc   3900
tctgtttgga aactgaatac tgatcgaaca actgatcagg agttaaaaca tattgtaaat   3960
atatataaaa acttgctgtg tacaactctt ctttattgta taagtttctt gaggtaaccg   4020
aaatagatag taaatcccaa tacaaataga ttcctccgtt actaactaat ctgaacataa   4080
atgctaataa aaaaagtata aatttctatc tgcgtatgta ccttgacctt acctttattc   4140
tattaactcc tgattttcta ttcagatttt gaacggtctg ttacttcctt tctattctgt   4200
tctggtttcg tcgtcgtttg tttccgaacg gtctgctact tctgattttc tatttgttct   4260
tacgtttggt tttgccgttc tagtttcttg cgtttttcca tataaatata gaaacacaaa   4320
ataaatgtaa tgttgtagat acttgaacta tcgatctttt cctttaaaaa atgatattgc   4380
taccactaat gtagttttaa ttaggaacaa aacttacaac caatgatcaa ctaatgaacc   4440
ggtctagaac agtctatatg gacatggtga gcaagcgtac gtaattccgg accgcgcggg   4500
cggccgcact agtcccgggc ccatcgatga tatcagatct ggttctatag tgtcacctaa   4560
atcgtatgtg tatgatacat aaggttatgt attaattgta gccgcgttct aacgacaata   4620
tgtccatatg gtgcactctc agtacaatct gctctgatgc cgcatagtta agccagcccc   4680
gacacccgcc aacacccgct gacgcgccct gacgggcttg tctgctcccg gcatccgctt   4740
acagacaagc tgtgaccgtc tccgggagct gcatgtgtca gaggttttca ccgtcatcac   4800
cgaaacgcgc gagacgaaag ggcctcgtga tacgcctatt tttataggtt aatgtcatga   4860
taataatggt ttcttagacg tcaggtggca cttttcgggg aaatgtgcgc ggaaccccta   4920
tttgtttatt tttctaaata cattcaaata tgtatccgct catgagacaa taaccctgat   4980
aaatgcttca ataatattga aaaaggaaga gtatgagtat tcaacatttc cgtgtcgccc   5040
ttattccctt ttttgcggca ttttgccttc ctgtttttgc tcacccagaa acgctggtga   5100
aagtaaaaga tgctgaagat cagttgggtg cacgagtggg ttacatcgaa ctggatctca   5160
acagcggtaa gatccttgag agttttcgcc ccgaagaacg ttttccaatg atgagcactt   5220
```

```
ttaaagttct gctatgtggc gcggtattat cccgtattga cgccgggcaa gagcaactcg   5280
gtcgccgcat acactattct cagaatgact tggttgagta ctcaccagtc acagaaaagc   5340
atcttacgga tggcatgaca gtaagagaat tatgcagtgc tgccataacc atgagtgata   5400
acactgcggc caacttactt ctgacaacga tcggaggacc gaaggagcta accgcttttt   5460
tgcacaacat gggggatcat gtaactcgcc ttgatcgttg ggaaccggag ctgaatgaag   5520
ccataccaaa cgacgagcgt gacaccacga tgcctgtagc aatggcaaca acgttgcgca   5580
aactattaac tggcgaacta cttactctag cttcccggca acaattaata gactggatgg   5640
aggcggataa agttgcagga ccacttctgc gctcggccct tccggctggc tggtttattg   5700
ctgataaatc tggagccggt gagcgtgggt ctcgcggtat cattgcagca ctggggccag   5760
atggtaagcc ctcccgtatc gtagttatct acacgacggg gagtcaggca actatggatg   5820
aacgaaatag acagatcgct gagataggtg cctcactgat taagcattgg taactgtcag   5880
accaagttta ctcatatata ctttagattg atttaaaact tcatttttaa tttaaaagga   5940
tctaggtgaa gatccttttt gataatctca tgaccaaaat cccttaacgt gagttttcgt   6000
tccactgagc gtcagacccc gtagaaaaga tcaaaggatc ttcttgagat cctttttttc   6060
tgcgcgtaat ctgctgcttg caaacaaaaa aaccaccgct accagcggtg gtttgtttgc   6120
cggatcaaga gctaccaact ctttttccga aggtaactgg cttcagcaga gcgcagatac   6180
caaatactgt tcttctagtg tagccgtagt taggccacca cttcaagaac tctgtagcac   6240
cgcctacata cctcgctctg ctaatcctgt taccagtggc tgctgccagt ggcgataagt   6300
cgtgtcttac cgggttggac tcaagacgat agttaccgga taaggcgcag cggtcgggct   6360
gaacgggggg ttcgtgcaca cagcccagct tggagcgaac gacctacacc gaactgagat   6420
acctacagcg tgagctatga gaaagcgcca cgcttcccga agggagaaag gcggacaggt   6480
atccggtaag cggcagggtc ggaacaggag agcgcacgag ggagcttcca gggggaaacg   6540
cctggtatct ttatagtcct gtcgggtttc gccacctctg acttgagcgt cgatttttgt   6600
gatgctcgtc aggggggcgg agcctatgga aaaacgccag caacgcggcc tttttacggt   6660
tcctggcctt ttgctggcct tttgctcaca tgttctttcc tgcgttatcc cctgattctg   6720
tggataaccg tattaccgcc tttgagtgag ctgataccgc tcgccgcagc cgaacgaccg   6780
agcgcagcga gtcagtgagc gaggaagcgg aagagcgccc aatacgcaaa ccgcctctcc   6840
ccgcgcgttg gccgattcat taatgcaggt taacctggct tatcgaaatt aatacgactc   6900
actataggga gaccgg                                                   6916

<210> SEQ ID NO 5
<211> LENGTH: 335
<212> TYPE: PRT
<213> ORGANISM: Zea mays

<400> SEQUENCE: 5

Met Ala Gly Ala Ile Ser His His Ala Leu Ala Phe Ser Gln Ser His
1               5                   10                  15

Trp Cys Ser Ala Lys Asn Ser Arg Phe Gly Lys Arg Thr Gly Asn Ala
            20                  25                  30

Arg Leu Val Tyr Leu Lys Gly Arg Cys Gly Ser Gly Ser Arg Lys Leu
        35                  40                  45

Gly Leu Met Trp Ala Ser Ser Ser Gln Ser Ser Val Met Glu Pro Thr
    50                  55                  60

His Leu Pro Ser Asp Gly Asn Ser Ser His Thr Pro Lys Lys Ser Ser
```

```
65                  70                  75                  80

Glu Ser Ala Leu Ile Leu Ile Trp His Gly Glu Ser Leu Trp Asn Glu
                85                  90                  95

Lys Asn Leu Phe Thr Gly Cys Ile Asp Val Pro Leu Thr Pro Lys Gly
            100                 105                 110

Val Glu Glu Ala Ile Glu Ala Gly Lys Arg Ile Cys Asn Ile Pro Ile
        115                 120                 125

Asp Val Ile Tyr Thr Ser Ser Leu Ile Cys Ala Gln Met Thr Ala Met
    130                 135                 140

Leu Ala Met Met Gln His Arg Arg Lys Lys Ile Pro Val Ile Thr His
145                 150                 155                 160

Asn Glu Ser Glu Gln Ala His Arg Trp Ser Gln Ile Tyr Ser Glu Glu
                165                 170                 175

Thr Met Lys Gln Ser Ile Pro Val Ile Thr Ala Trp Gln Leu Asn Glu
            180                 185                 190

Arg Met Tyr Gly Glu Leu Gln Gly Leu Asn Lys Gln Glu Thr Val Asp
        195                 200                 205

Arg Phe Gly Lys Glu Gln Val His Glu Trp His Arg Ser Tyr Asp Ile
    210                 215                 220

Pro Pro Pro Asn Gly Glu Ser Leu Glu Lys Cys Ala Glu Arg Ala Val
225                 230                 235                 240

Ala Tyr Phe Lys Asp Gln Ile Ile Pro Gln Leu Val Ala Gly Lys His
                245                 250                 255

Val Met Val Ala Ala His Gly Asn Ser Leu Arg Ser Ile Ile Met His
            260                 265                 270

Leu Asp Lys Leu Thr Ser Gln Lys Val Ile Ser Leu Glu Leu Ser Thr
        275                 280                 285

Gly Ile Pro Met Leu Tyr Ile Phe Lys Glu Gly Lys Phe Ile Arg Arg
    290                 295                 300

Gly Thr Pro Val Gly Pro Ser Glu Ala Ser Val Tyr Ala Tyr Thr Arg
305                 310                 315                 320

Thr Lys Arg Phe Ala Glu His Ile Thr Phe Gln Asn Lys Leu Ala
                325                 330                 335


<210> SEQ ID NO 6
<211> LENGTH: 335
<212> TYPE: PRT
<213> ORGANISM: Zea mays

<400> SEQUENCE: 6

Met Ala Gly Ala Ile Ser His His Ala Leu Ala Phe Ser Gln Ser His
1               5                   10                  15

Trp Cys Ser Ala Lys Asn Ser Arg Phe Gly Lys Arg Thr Gly Asn Ala
            20                  25                  30

Arg Leu Val Tyr Leu Lys Gly Arg Cys Gly Ser Gly Ser Arg Lys Leu
        35                  40                  45

Gly Leu Met Trp Ala Ser Ser Ser Gln Ser Ser Val Met Glu Pro Thr
    50                  55                  60

His Leu Pro Ser Asp Gly Asn Ser Ser His Thr Pro Lys Lys Ser Ser
65                  70                  75                  80

Glu Ser Ala Leu Ile Leu Ile Trp His Gly Glu Ser Leu Trp Asn Glu
                85                  90                  95

Lys Asn Leu Phe Pro Gly Cys Ile Asp Val Pro Leu Thr Pro Lys Gly
            100                 105                 110
```

```
Val Glu Glu Ala Ile Glu Ala Gly Lys Arg Ile Cys Asn Ile Pro Ile
        115                 120                 125

Asp Val Ile Tyr Thr Ser Ser Leu Ile Cys Ala Gln Met Thr Ala Met
    130                 135                 140

Leu Ala Met Met Gln His Arg Arg Lys Lys Ile Pro Val Ile Thr His
145                 150                 155                 160

Asn Glu Ser Glu Gln Ala His Arg Trp Ser Gln Ile Tyr Ser Glu Glu
                165                 170                 175

Thr Met Lys Gln Ser Ile Pro Val Ile Thr Ala Trp Gln Leu Asn Glu
            180                 185                 190

Arg Met Tyr Gly Glu Leu Gln Gly Leu Asn Lys Gln Glu Thr Val Asp
        195                 200                 205

Arg Phe Gly Lys Glu Gln Val His Glu Trp His Arg Ser Tyr Asp Ile
    210                 215                 220

Pro Pro Pro Asn Gly Glu Ser Leu Glu Lys Cys Ala Glu Arg Ala Val
225                 230                 235                 240

Ala Tyr Phe Lys Asp Gln Ile Ile Pro Gln Leu Val Ala Gly Lys His
                245                 250                 255

Val Met Val Ala Ala His Gly Asn Ser Leu Arg Ser Ile Ile Met His
            260                 265                 270

Leu Asp Lys Leu Thr Ser Gln Lys Val Ile Ser Leu Glu Leu Ser Thr
        275                 280                 285

Gly Ile Pro Met Leu Tyr Ile Phe Lys Glu Gly Lys Phe Ile Arg Arg
    290                 295                 300

Gly Thr Pro Val Gly Pro Ser Glu Ala Ser Val Tyr Ala Tyr Thr Arg
305                 310                 315                 320

Thr Lys Arg Phe Ala Glu His Ile Thr Phe Gln Asn Lys Leu Ala
                325                 330                 335


<210> SEQ ID NO 7
<211> LENGTH: 335
<212> TYPE: PRT
<213> ORGANISM: Zea mays

<400> SEQUENCE: 7

Met Ala Gly Ala Ile Ser His His Ala Leu Ala Phe Ser Gln Ser His
1               5                   10                  15

Trp Cys Ser Ala Lys Asn Ser Arg Phe Gly Lys Arg Thr Gly Asn Ala
            20                  25                  30

Arg Leu Val Tyr Leu Lys Gly Arg Cys Gly Ser Gly Ser Arg Lys Leu
        35                  40                  45

Gly Leu Met Trp Ala Ser Ser Ser Gln Ser Ser Val Met Glu Pro Thr
    50                  55                  60

His Leu Pro Ser Asp Gly Asn Ser Ser His Thr Pro Lys Lys Ser Ser
65                  70                  75                  80

Glu Ser Ala Leu Ile Leu Ile Trp His Gly Glu Ser Leu Trp Asn Glu
                85                  90                  95

Lys Asn Leu Phe Thr Gly Cys Ile Asp Val Pro Leu Thr Pro Lys Gly
            100                 105                 110

Val Glu Glu Ala Ile Glu Ala Gly Lys Arg Ile Cys Asn Ile Pro Ile
        115                 120                 125

Asp Val Ile Tyr Thr Ser Ser Leu Ile Cys Ala Gln Met Thr Ser Met
    130                 135                 140

Leu Ala Met Met Gln His Arg Arg Lys Lys Ile Pro Val Ile Thr His
145                 150                 155                 160
```

```
Asn Glu Ser Glu Gln Ala His Arg Trp Ser Gln Ile Tyr Ser Glu Glu
                165                 170                 175

Thr Met Lys Gln Ser Ile Pro Val Ile Thr Ala Trp Gln Leu Asn Glu
            180                 185                 190

Arg Met Tyr Gly Glu Leu Gln Gly Leu Asn Lys Gln Glu Thr Val Asp
        195                 200                 205

Arg Phe Gly Lys Glu Gln Val His Glu Trp His Arg Ser Tyr Asp Ile
    210                 215                 220

Pro Pro Pro Asn Gly Glu Ser Leu Glu Lys Cys Ala Glu Arg Ala Val
225                 230                 235                 240

Ala Tyr Phe Lys Asp Gln Ile Ile Pro Gln Leu Val Ala Gly Lys His
                245                 250                 255

Val Met Val Ala Ala His Gly Asn Ser Leu Arg Ser Ile Ile Met His
            260                 265                 270

Leu Asp Lys Leu Thr Ser Gln Lys Val Ile Ser Leu Glu Leu Ser Thr
        275                 280                 285

Gly Ile Pro Met Leu Tyr Ile Phe Lys Glu Gly Lys Phe Ile Arg Arg
    290                 295                 300

Gly Thr Pro Val Gly Pro Ser Glu Ala Ser Val Tyr Ala Tyr Thr Arg
305                 310                 315                 320

Thr Lys Arg Phe Ala Glu His Ile Thr Phe Gln Asn Lys Leu Ala
                325                 330                 335


<210> SEQ ID NO 8
<211> LENGTH: 335
<212> TYPE: PRT
<213> ORGANISM: Zea mays

<400> SEQUENCE: 8

Met Ala Gly Ala Ile Ser His His Ala Leu Ala Phe Ser Gln Ser His
1               5                   10                  15

Trp Cys Ser Ala Lys Asn Ser Arg Phe Gly Lys Arg Thr Gly Asn Ala
            20                  25                  30

Arg Leu Val Tyr Leu Lys Gly Arg Cys Gly Ser Gly Ser Arg Lys Leu
        35                  40                  45

Gly Leu Met Trp Ala Ser Ser Ser Gln Ser Ser Val Met Glu Pro Thr
    50                  55                  60

His Leu Pro Ser Asp Gly Asn Ser Ser His Thr Pro Lys Lys Ser Ser
65                  70                  75                  80

Glu Ser Ala Leu Ile Leu Ile Trp His Gly Glu Ser Leu Trp Asn Glu
                85                  90                  95

Lys Asn Leu Phe Thr Gly Cys Ile Asp Val Pro Leu Thr Pro Lys Gly
            100                 105                 110

Val Glu Glu Ala Ile Glu Ala Gly Lys Arg Ile Cys Asn Ile Pro Ile
        115                 120                 125

Asp Val Ile Tyr Thr Ser Ser Leu Ile Cys Ala Gln Met Thr Ser Met
    130                 135                 140

Leu Ala Met Met Gln His Arg Arg Lys Lys Ile Pro Val Ile Thr His
145                 150                 155                 160

Asn Glu Ser Glu Gln Ala His Arg Trp Ser Gln Ile Tyr Ser Glu Glu
                165                 170                 175

Thr Met Lys Gln Ser Ile Pro Val Ile Thr Ala Trp Gln Leu Asn Glu
            180                 185                 190

Arg Met Tyr Gly Glu Leu Gln Gly Leu Asn Lys Gln Glu Thr Val Asp
```

```
        195                 200                 205

Arg Phe Gly Lys Glu Gln Val His Glu Trp Arg Arg Ser Tyr Asp Ile
    210                 215                 220

Pro Pro Pro Asn Gly Glu Ser Leu Glu Lys Cys Ala Glu Arg Ala Val
225                 230                 235                 240

Ala Tyr Phe Lys Asp Gln Ile Ile Pro Gln Leu Val Ala Gly Lys His
                245                 250                 255

Val Met Val Ala Ala His Gly Asn Ser Leu Arg Ser Ile Ile Met His
            260                 265                 270

Leu Asp Lys Leu Thr Ser Gln Lys Val Ile Ser Leu Glu Leu Ser Thr
        275                 280                 285

Gly Ile Pro Met Leu Tyr Ile Phe Lys Glu Gly Lys Phe Ile Arg Arg
    290                 295                 300

Gly Thr Pro Val Gly Pro Ser Glu Ala Ser Val Tyr Ala Tyr Thr Arg
305                 310                 315                 320

Thr Lys Arg Phe Ala Glu His Ile Thr Phe Gln Asn Lys Leu Ala
                325                 330                 335


<210> SEQ ID NO 9
<211> LENGTH: 4921
<212> TYPE: DNA
<213> ORGANISM: Zea mays

<400> SEQUENCE: 9

attgctataa gtataataat atctaagaga tggaagaaga ctggccggcc gggtagtgac      60

aataatgaat gaccaacggc agaaaagttg gtgcgaagat gttttaggtg aatgcaagtc     120

acaaaaggaa aaggctggca tctcgaatag aactcctata ccacggatca agaaacaatt     180

aaaaccatac ataattgtcg gagtaatatg ctaatcctag taattttagt cacatcattg     240

gaggtccttc gttccattca atttttttc tttcttcatg aacatttgtt caagatttat     300

ctcccacatg tttcaaagca tgcattattt attattattg gcaaatttca tgatctttca     360

aaagatatct cttgggcctg gcatggatat gctctatctc tagtaagtaa ttggctctgc     420

aataatgagt tggatattgc cacgaagaac cacgccttgc ttggaagaaa cttgatgaat     480

gccaaatctt gctctttttc aacatgttga tttaggaaat tatttggcaa ccaaacataa     540

tgtgactaga attagcacac ttctaatgac aaaaatataa tcacatttct gcgcgcacaa     600

aatatttgct tgccaaaatg caatcatgtt ttgatgtaca gttcgataga cattgaaaaa     660

gaatgcattt aggaaccttt tagtaccact ttgatcaatt tctgccatct acacgtcaaa     720

ctagataaaa agaataatgg cagccacatc ctacagaaaa aaaaagacat atcaagaatt     780

caacttaatt tcagaatata caagatttca tagtgacctt taacattgat ttttcgactc     840

acatcttata agcgggtgaa gcagtatata aaagaattcc acaaaaaaat ctacaacagc     900

cataagcatt aattacacat aaacgctcac caccctataa aacacccaga ccttcacatt     960

tcttcttcag acctccaaca agcagcagat agatagagaa atgaagagat agattagagt    1020

taccatcata tccccaacaa tggcatagcc aacaagttgg atccttcgga ccctgtagct    1080

cctggtccat gaattgccaa gagaacacct tttagtttct ttgagcaacc tcgatctcgc    1140

catggggttc cgctgtggcc gtgcctcctc ttcgctgctg tgtgaagagg acgtggccgg    1200

catgtttgga tgcaatgggc acgacgacga agaggtgggg cttctggtgt tggggatgga    1260

cacgactttt gctgcgctgc catcacagag cgacgaggtc gtagcatccc tgatggagaa    1320

ggagaaggag cagctgcata gcgttgcgac gggggattac ctccagaggc tgagcagtgg    1380
```

```
aggactggag tcatcttgta ggattgccgc cattgattgg ataaaaaagg tttctgcttc   1440
tccatccata ctatatagta tgtatatgat ttctcgcgca tcgatcctag ttagaatctc   1500
atgtttctgt gttttgcagc aaaatgcaat ttatttgact ccaagtttga cttaaacttc   1560
agtttgttca aaaaaaaaaa gtttgccctt gcttgaccaa aacctcgttt tgcatatata   1620
gataaatata tagttactga aatgtgtact acttgtctct tacatgtgta ttaattgcag   1680
gcccaggctt atcacgactt tggaccgttg tctgcttatc ttgctgttaa ctaccttgat   1740
agggtcctct ccacaaatca agtcccagtg agttctacaa atgtacccaa cttgtttatt   1800
ctttttteta catgtccaat cagcatgtgg ttgtcagagg tctttgcctc tccctctcta   1860
gaaaacctta tggcatgttt ggttcagcgg cggaccagga actaaagaca gcctatgcga   1920
gattataagt gtcaataact atagctaatt tcatataaaa aaatacatgc atatttggat   1980
ttgagatgca ctttcgtccg atcagtagat aaggtcattt ggtttaggat catgagttga   2040
gttaggactt agcactattg gaatcgagct ctttgtcaat tgtctgaagc actcggcaaa   2100
gctgggaaaa cactcgacga cgtctttgcc gagtgtagca ctcggcaaag agagctcggc   2160
gaacagtata tcgacacggc ttctttgccg agtatttttt atcgggcact cgacaaagac   2220
tttgccgagt gtcactcggt actcggcaaa gaaaagtcgc cgtcaaggcg accggaaacg   2280
gagacagcgc ctttgccgag tgttctaggt gacactcggc aaagagatta cctttgtcga   2340
gtgtccgcca gtctacactc gccaaagggg ctaccagcgg accccttttgt cagtttcttt   2400
gccgagtgcg ctagaaggca ctcggcaaag cttgcttctt tgtcgagtgc caaggccaca   2460
gcactcggca aataagcttt accggtgccc aggaatggca ctcggcaaaa tgttctttat   2520
cgagtgtcag gcgataggac actcggcaaa gtagcttctt tgccgaatgc caaagcctag   2580
cgttcggcat agataacagc cgtcagctat agacggctgc tgacggttct ttgcctagca   2640
ccgaattgtg tcgagtgttt ggcactcgac aaagtagtct ttgccactac tttgccgagt   2700
gtctttctgt gccgagagtc ctattatcgg caaacgcgat cgttatcgag agtgaaactt   2760
tgtcgagtgt ggcactcggc aaagaagtgt cgagtgcccg ataaaaaaca cttggcaaag   2820
agccaaattc cgatagcgta gcattcgtgc agccgtacgt tagaattgga cagacgaggg   2880
atgtgactgt gctcggctgt tccagctata tcctgcaacc aaacacaacc ttacattttg   2940
atggggcaca aatcttatgt gagtttcttg gtgtaggctg atgctgacca ccagccctgg   3000
atgccacagc tgctgtccgt tgcttgccta accattgcag ccaagatgga ggagaccgtg   3060
gttcctcgcc gtctggacat ccatcagaat caggtggaca aaattggata tatagtacag   3120
tttcacgttt gagttcacca aatctttatc tttattatat atatatatat gtcacaggtt   3180
ctcagcgaga agtacagatt cgatttagat gctattcaga ggatggagat ttacattcta   3240
gactctctga attggaggat gcaagctgtg acgccattct cttacatcaa ctatttcgtg   3300
gacaagttca ctgatgggaa gccgctaagt tgcggattca tttctcggtg caccgagatc   3360
atacttggca gtcttgaagg tacatcagat tacttcatgc atgagcgagc gaatcggact   3420
tacccgcctt ttccattcga taagcaattg ttactatgtg attggaacat gcatctaaat   3480
agatgtctgt gtgcatttga tttgcagcaa cgaagctcct acagttcagg ccttctgaga   3540
tggcagcagc agtggttctg tcagcagctg ctgagtctca agtcattgcc ttcagcggcg   3600
ctcttttagc ttctaatatc cttgtcaata aggtgtagat cctctctctc tatgaaggtt   3660
tagtattttt tttaatgtac gtatttacat ttctaggaaa atgtaaggag atgccatgaa   3720
```

```
gcattgcaag aagtgggatt agtgaagaag aaaacagact acagtgcgag tccatctcgc   3780
gtgctagatg cctcatgctt cagcttcaag actgacgata accagacagc cggttcatcc   3840
caatcccaag caaacaacaa tggcaactac aaccaggctt actctccagc tagcaagagg   3900
acaaggctag acatctagac tcaatcagga aaaattgcat gagatcatag acgtacacat   3960
atacacacaa agttttctta gataaaggat acataaagtt aaatttgatt ctggctacat   4020
ttctgagtac gtgcttctca actcagaaga gttcataggg aacattatac atgcatgcat   4080
gctaacaggc aaaagaaggc tgaattatta agagcaatcc tatttatttc ctcctttgtt   4140
cctttgttaa ctttttcttt cttcttgtct actttaaatc atggcattag caaagacatt   4200
tgcgtgtatg ggacaggtga tgcaatgata caacataaaa gaaggctagg cattgttttc   4260
aacataagca gaggtaatct cgtttcagga aaaaaatgag cgccaggaac tttgatatct   4320
gatcaaggga gaagcaaagt tagttgttgt gggaatctgt ggctgagttc ttggttctcg   4380
atttcttgtt tgtttgtttg tctgtgatga atatttttca gatttattca atgaactgac   4440
catgttatgc tatagagcaa gtacaacaat aggttctaag caggataaat gatgaggtac   4500
aggagagaga agatgagaga gaggataagc gagctataaa cttacaacca tctaagactt   4560
agatataaga ataaaaaaac tttgagagag acaaatgagt tatgtattag tagtgaacgg   4620
ttaactatta tgtagatgga ctaagagata ggacgcaaat agccaatagt cagctatatt   4680
attagcctcg ctcttattca gcacccgggc aattttatcg tccaaatttg ttagcatgca   4740
tgctacttct tatagaatga atattagata tgcattaggc ttcacatcct attcaaaata   4800
aggtgctaga ggccttaaaa tttaagtgtt ttagatgagt tccatggatg aatcttagtt   4860
gcgccataca tataattaat ttaaaacaca caaaaaaaac actagccata tacttactat   4920
g                                                                   4921
```

<210> SEQ ID NO 10
<211> LENGTH: 1071
<212> TYPE: DNA
<213> ORGANISM: Zea mays

<400> SEQUENCE: 10

```
atgaagagat agattagagt taccatcata tccccaacaa tggcatagcc aacaagttgg     60
atccttcgga ccctgtagct cctggtccat gaattgccaa gagaacacct tttagtttct    120
ttgagcaacc tcgatctcgc catggggttc cgctgtggcc gtgcctcctc ttcgctgctg    180
tgtgaagagg acgtggccgg catgtttgga tgcaatgggc acgacgacga agaggtgggg    240
cttctggtgt tggggatgga cacgactttt gctgcgctgc catcacagag cgacgaggtc    300
gtagcatccc tgatggagaa ggagaaggag cagctgcata gcgttgcgac gggggattac    360
ctccagaggc tgagcagtgg aggactggag tcatcttgta ggattgccgc cattgattgg    420
ataaaaaagg cccaggctta tcacgacttt ggaccgttgt ctgcttatct tgctgttaac    480
taccttgata gggtcctctc cacaaatcaa gtcccagtga gttctacaaa taagtacaga    540
ttcgatttag atgctattca gaggatggag atttacattc tagactctct gaattggagg    600
atgcaagctg tgacgccatt ctcttacatc aactatttcg tggacaagtt cactgatggg    660
aagccgctaa gttgcggatt catttctcgg tgcaccgaga tcatacttgg cagtcttgaa    720
gcaacgaagc tcctacagtt caggccttct gagatggcag cagcagtggt tctgtcagca    780
gctgctgagt ctcaagtcat tgccttcagc ggcgctcttt tagcttctaa tatccttgtc    840
aataaggaaa atgtaaggag atgccatgaa gcattgcaag aagtgggatt agtgaagaag    900
```

```
aaaacagact acagtgcgag tccatctcgc gtgctagatg cctcatgctt cagcttcaag     960

actgacgata accagacagc cggttcatcc caatcccaag caaacaacaa tggcaactac    1020

aaccaggctt actctccagc tagcaagagg acaaggctag acatctagac t             1071
```

<210> SEQ ID NO 11
<211> LENGTH: 5918
<212> TYPE: DNA
<213> ORGANISM: Zea mays

<400> SEQUENCE: 11

```
ttggtagtgg aattagctag ctaacaaata actatctaac tattaactaa tttaccaaaa      60

atagctaata gttgaactat taactaaagt gtttggatgt ctcaactaat tttagctact     120

aactattagc tctagtgcat tcaaacaccc cttaagtgaa tgtcatggta tgggctgaca     180

tttcgagagg tggagagtgt catggtatgg gctgccatgt gggccgagag tccgagaccg     240

ggctaaatga gctgggctga ataggactga ctgcaggtag aaaggcaagc gcaacatttg     300

gcaccgttag ctctccacta aacttgtcag atgcaataat ttatgttttt attaatggca     360

aagccctcct gccagccagt gccttccttc cgggtcaacc actggtacag tcacatcacg     420

aattcccact ggcagtacga taacctcact gagcggtagg gcctcccgtc ccagaatcct     480

gcaggaccca tcgatcatgg ccccacgggt cctgctcctg cgtgggttcc aattccaagt     540

cgcccaccgt gacgcccatc gagtcaaccg aacccaagcc gtgtggcgac tggcgaggcg     600

agtgccccag ttcctaactc cggtgggcgc gctcccaccg ccgcgcggct caaaacccgc     660

cctcagcctc ccgcgctcca gtccacacgg gagcgggtgg tgtcgtctga agcggcgcga     720

tcaaggagtc ttcgggcgct ccggtgagct atctagatct caacatcctc tcccctctgt     780

agtctgtagt tgtactctcc cgcccgatgg ttcagttaag ttatatcctc tccccttatt     840

tttactcggt cgataccatt tcgttgtgga ttgggcgccc ccgcaggttg aaatgctgcc     900

catcatgctg cggccctgta ctatgaggat ggttctagtt ttgcgtctgg caatttgggg     960

cgtacatgct tttggctgcg tactgttact gatcggagaa aatgtttgta acgtatgatt    1020

cgtttttcag gacgtaacgt gctggcggtt gcttatctcc ggatgtatat ataagcggaa    1080

atgttctcct tgttctatgg cctgtggaag tatgtgttcg ccaaggacga gttccgtgtt    1140

ctgattcttg gtgttgacag agctggcaag acggtagctg ctagctccca gccttcatat    1200

atatatttcc ctttctgaac tagaaattga tgatacttac ctgtacacga tgtttctgga    1260

accgttgcca tagactttgc tggagaagtt gaaatcgata tatctcaagg gggaaggact    1320

tccgcctgac cgtgtcgttc caacagttgg gctcaacatt ggccgcatcg aagacgcaaa    1380

ggcaaaactt gttttctggg atctaggtgg tcaggtaaga acgtttacgt acgtagtaaa    1440

gtgagccttc tgttgccgtg gcaccaccct acgatcgttg atatttgagt cttgtcagtt    1500

tggtgctata tcagggtttc taatgcctgg gaaatacatg tcataaattc aaattactag    1560

gatgtggttg ctttagttat taacctagca tctttttgcg ttccagcaga atatatataa    1620

tctagttata tggaatgctc aatagaattt tcagaaagca aagatatgct ctgttggcta    1680

acattcacag tactcaatag aattgtttac tagtagaaca gcatcagctt ctctgctatg    1740

ttataagaat tagtgtaaaa ctaacttcag tatcactgct tgctagtatg ataattaagc    1800

ttccatgcca agttcagtat ttcttacaca cttgcctgct tggcaggtta gcctacgaac    1860

aatctgggag aaatactatg aagaggccca tgccataatg tacgttattg acgctgccac    1920
```

```
agcatcgtca tttgaagatt ccaaatctgc tctgggtaag gttcttattt gtgttaatta   1980
taaactactc cctccattcc aaattataag acattttggc ctttttctta gataaataaa   2040
ttttgctatg gacttaaata ttatttatat atatatatat atatatataa aatgtcctgg   2100
tacatagtta aaacattata tcttaaaaag ctaaaacatt gtcttataac ttggaacaag   2160
ggagtactgg tttgtttcta ttgctagatc ttccgagaag atgcattgcc tctctggtaa   2220
atgggatgag aactcattct agctagagaa cctaacctaa atttcttact tcagagaagg   2280
ttattcgcca tgaacatctg agaggagcac cactcttgat agttgcaaac aaacaggtga   2340
agggtttact tccactttct atattttgta ccacagtaca taattatgat tgaaagattc   2400
agtgcttaca ataaagttgc catcgtagta aaataaagat tttgtttttg tcatgtgccc   2460
atgctgtgag gcatacaaat ctaaattcct acgttgcaaa gcgcctatgc gccattgcga   2520
ggttgaatac cagatgtagt ttggccaatt gtgatgtaca gatgtgccac attgacaatt   2580
gacacgcagt ttaaaggaga gtcagactac tagtttttc attgcccaac atatacccttt   2640
ggccacttat tgaaaatgtg agagatcatt tgagtttgaa cagtaagttt tgtgagatat   2700
cattttattt agtaatcatg cacacatgtc tagaattgtg aaatgcacaa taaagacgca   2760
aactcccacg agcatgcagg tacacccgat tgaggattct cagcgaatgt tccagtttcg   2820
agaatcaaac aacatataac aatgatgaat tttttaaatc aattaaaact tcctgaaaag   2880
atcacatgga aaccaatgac tacatgcact gtctgtttct gttaagctgg gtacacatta   2940
ttctatcaaa ttgtttatta tttacctctt gttctcatgt ttggagggtg cttctggatt   3000
tcttttggca ggatttacct ggagccattg atgaggaaga attggctaaa tttctgcata   3060
aagaactgga tgagaggcca tatacatttc aggctgtatc tgcatatgat gggtgagcgc   3120
agaaactcaa ctggttcctg aggaaatttg actcgccatg aaaaaaaatg acaattttac   3180
tcaaagatac aaaaaaattca cacattcgtc tgttatattg tttcctgggt gcatgaaact   3240
caactggttc gtgaggaaat ttgactcgcc atgaaaaaaa tgacaatttt actcaaagat   3300
acaaaaaatt cacacattcg tctgttatat tgtttcctgg gtgcatgata ttctaaagat   3360
ctgttatatt gtttaaatgt gacaccggct cttgcagcag ggggatcaaa tctggcatag   3420
actggctggt ggaacaaatg gaaaaaagca aacgtaccga gacactgcag gctcgtgctg   3480
gcgtagctgg acaaatttag aatggggtga atttgttaaa gaacaaagca ttggatagga   3540
cggcttcctt cgtatcgcgt aagcagccat ttgctgcatt ccgggattat cgttccaggt   3600
cgcccagagt gctgcaagaa atgtttggct ggttgctcct gtggtggtgg tgattggtga   3660
ggcgattcgt ttggtattat tgaggttgca ttcatatgta cctaaaggtc gcaagcatac   3720
atgtctatat gatgcttttc aattttcgta gcaaactagt agcttcaata cagaggatca   3780
aagagagccg tgttctttaa cttgtttgtg ataaaaaaaa aggaagaaag gaaagcgaag   3840
aaggaattat tggtgcatct gaaagtcttt attgcatatg tctaaaccat tttaaccgat   3900
gctggatgag cttttcttcg caccgatgtt acatctagtc tatcatatgt atcctcgttt   3960
catactcgca ccgatgttac atctagtcta tcatatgtat cctcgtttca tactcgatcc   4020
tttttatgg ccaaactcca acacaacata tacatttctg tagcgcatac gtattgaaca   4080
tgtcttttttt agactaacat tctgcaccga acaatatagc agatcgaatt gtcatcctat   4140
aaagattatt tttaactttt gtggtatcct attgtcatat ttattgaggt tgcattcata   4200
tgtacctaaa ggtcgcaagc atacatgtct atatgatgct tttcaatttt cgtagcaaac   4260
tagtagcttc aatacagagg atcaaagaga gccgtgttct ttaacttgtt tgtgataaaa   4320
```

aaaaaggaag aaaggaaagc gaagaaggaa ttattggtgc atctgaaagt ctttattgca 4380
tatgtctaaa ccattttaac cgatgctgga tgagcttttc ttcgcaccga tgttacatct 4440
agtctatcat atgtatcctc gtttcatact cgcaccgatg ttacatctag tctatcatat 4500
gtatcctcgt ttcatactcg atcctttttt atggccaaac tccaacacaa catatacatt 4560
tctgtagcgc atacgtattg aacatgtctt ttttagacta acattctgca ccgaacaata 4620
tagcagatcg aattgtcatc ctataaagat tctttttaac ttttgtggta tcctattgtc 4680
atatagaaca tcaaatgttt ggcgccacct catcctttga ctaatacctt tatcactatc 4740
tctacgtagc ctttcgtagc atagatccta aatatctatg catagatcct aaatatctat 4800
gcatagatcc taaatatcta aagatgtcct ttcagaacac tacttgattt ttcaaactaa 4860
catgtctttc ctcatatgta gtagcataga ttctaaatat ctaaagatgt ccttccggac 4920
actacttgat tttcaaact aacatgtctt tcctcatatg tagtagtgtt gaaatcacat 4980
cttttatatt caatttgagt tctactgatc gagtccaaaa tcgtccaaaa cctttaaact 5040
ctagaatctc ccacgacaac tctagttttc catttactcg tgcttagctt tcatcaacta 5100
acactacatc cataaaaaca tatgttaaga gatccctttg tgatcttatc catagactca 5160
aagctaattt ttttatgtag tcatattcta atcggaaagt cacatgtgtc tccatcattt 5220
attcaaacat attcataaca ttgttgttgg aactttgctt cctcaaaaaa tagggataaa 5280
aaaaacagta aaaggaattg gcccttcagg ctagggctgc tgatatcccc actaagctgg 5340
gccaatcggc caagaaactt tgcttcattc agggcatggt atggacaacc cactgcgggt 5400
tgccaaacaa aggagttagt aagaaaccac aaaatgctta gtctgagctt tgaagagttc 5460
tacttggtga gtaaaacagt taatcttaac tactgcttgg ctaagataag atgttagtca 5520
aaagaattct gtagatgtgc aatctcaaac caatctgcct ttgcatcatt tagaaaactg 5580
ctttaaaatt cgaaatattt tgcttaccat agctcatagc acagaagaat attatagaac 5640
aaaccaaggc aagtgacttt ctgaaacaca gttttcaaga acaggttcag attaaactag 5700
ataacaggat gccagcgttg gtaataagtg tactccccaa gagaagtcgc tgttttgttc 5760
tatctcaatg aaaaataacg acacgaaaat gaactatggc cgtctgcatt aatatggata 5820
ctcagcaaaa atggacatga gtaactcaaa atcgtcaatt gcttgctatg ttaggcaccc 5880
aagtcaatga tttctattcc atgctatcac aaagatta 5918

<210> SEQ ID NO 12
<211> LENGTH: 1288
<212> TYPE: DNA
<213> ORGANISM: Zea mays

<400> SEQUENCE: 12
ttccaagtcg cccaccgtga cgcccatcga gtcaaccgaa cccaagccgt gtggcgactg 60
gcgaggcgag tgccccagtt cctaactccg gtgggcgcgc tcccaccgcc gcgcggctca 120
aaacccgccc tcagcctccc gcgctccagt ccacacggga gcgggtggtg tcgtctgaag 180
cggcgcgatc aaggagtctt cgggcgctcc ggacgtaacg tgctggcggt tgcttatctc 240
cggatgtata tataagcgga aatgttctcc ttgttctatg gcctgtggaa gtatgtgttc 300
gccaaggacg agttccgtgt tctgattctt ggtgttgaca gagctggcaa gacgactttg 360
ctggagaagt tgaaatcgat atatctcaag ggggaaggac ttccgcctga ccgtgtcgtt 420
ccaacagttg ggctcaacat tggccgcatc gaagacgcaa aggcaaaact tgttttctgg 480

-continued

```
gatctaggtg gtcaggttag cctacgaaca atctgggaga aatactatga agaggcccat    540
gccataatgt acgttattga cgctgccaca gcatcgtcat ttgaagattc caaatctgct    600
ctggagaagg ttattcgcca tgaacatctg agaggagcac cactcttgat agttgcaaac    660
aaacaggatt tacctggagc cattgatgag gaagaattgg ctaaatttct gcataaagaa    720
ctggatgaga ggccatatac atttcaggct gtatctgcat atgatggcag gggatcaaa     780
tctggcatag actggctggt ggaacaaatg gaaaaaagca aacgtaccga gacactgcag    840
gctcgtgctg gcgtagctgg acaaatttag aatggggtga atttgttaaa gaacaaagca    900
ttggatagga cggcttcctt cgtatcgcgt aagcagccat ttgctgcatt ccgggattat    960
cgttccaggt cgcccagagt gctgcaagaa atgtttggct ggttgctcct gtggtggtgg   1020
tgattggtga ggcgattcgt ttggtattat tgaggttgca ttcatatgta cctaaaggtc   1080
gcaagcatac atgtctatat gatgcttttc aattttcgta gcaaactagt agcttcaata   1140
cagaggatca aagagagccg tgttctttaa cttgtttgtg ataaaaaaaa aggaagaaag   1200
gaaagcgaag aaggaattat tggtgcatct gaaagtcttt attgcatatg tctaaaccat   1260
tttaaccgat gctggatgag cttttctt                                      1288
```

<210> SEQ ID NO 13
<211> LENGTH: 979
<212> TYPE: DNA
<213> ORGANISM: Zea mays

<400> SEQUENCE: 13

```
aatcgagtca accgaaccca agccgtgtgg cgactggcga ggcgagtgcc ccagttccta     60
actccggtgg gcgcgctccc accgccgcgc ggctcaaaac ccgccctcag cctcccgcgc    120
tccagtccac acgggagcgg gtggtgtcgt ctgaagcggc gcgatcaagg agtcttcggg    180
cgctccggac gtaacgtgct ggcggttgct tatcaccgga tatatatata taagcggaaa    240
tgttctcctt gttctatggc ctgtggaagt atgtgttcgc caaggacgag ttccgtgttc    300
tgattcttgg tgttgacaga gctggcaaga cgactttgct ggagaagttg aaatcgatat    360
atctcaaggg ggaaggactt ccgcctgacc gtgtcgttcc aacagttggg ctcaacattg    420
gccgcatcga agacgcaaag gcaaaacttg ttttctggga tctaggtggt caggttagcc    480
tacgaacaat ctgggagaaa tactatgaag aggcccatgc cataatgtac gttattgacg    540
ctgccacagc atcgtcattt gaagattcca aatctgctct ggagaaggtt attcgccatg    600
aacatctgag aggagcacca ctcttgatag ttgcaaacaa acaggattta cctggagcca    660
ttgatgagga agaattggct aaatttctgc ataaagaact ggatgagagg ccatatacat    720
ttcaggctgt atctgcatat gatgggtgag cgcagaaact caactggttc ctgaggaaat    780
ttgactcgcc atgaaaaaaa atgacaattt tactcaaaga tacaaaaaat tcacacattc    840
gtctgttata ttgtttcctg ggtgcatgaa actcaactgg ttcgtgagga aatttgactc    900
gccatgaaaa aaatgacaat tttactcaaa gatacaaaaa attcacacat tcgtcaaaaa    960
aaaaaaaaaa aaaaaaaaa                                                 979
```

<210> SEQ ID NO 14
<211> LENGTH: 1305
<212> TYPE: DNA
<213> ORGANISM: Zea mays

<400> SEQUENCE: 14

```
aaccgaaccc aagccgtgtg gcgactggcg aggcgagtgc cccagttcct aactccggtg     60
```

```
ggcgcgctcc caccgtcgcg cggctcaaaa cccgccctca gcctcccgcg ctccagtcca    120

cacgggagcg ggtggtgtcg tctgaagcgg cgcgatcaag gagtcttcgg gcgctccgga    180

cgtaacgtgc tggcggttgc ttatcaccgg atatatatat ataagcggaa atgttctcct    240

tgttctatgg cctgtggaag tatgtgttcg ccaaggacga gttccgtgtt ctgattcttg    300

gtgttgacag agctggcaag acgactttgc tggagaagtt gaaatcgata tatctcaagg    360

gggaaggact tccgcctgac cgtgtcgttc caacagttgg gctcaacatt ggccgcatcg    420

aagacgcaaa ggcaaaactt gttttctggg atctaggtgg tcaggttagc ctacgaacaa    480

tctgggagaa atactatgaa gaggcccatg ccataatgta cgttattgac gctgccacag    540

catcgtcatt tgaagattcc aaatctgctc tggagaaggt tattcgccat gaacatctga    600

gaggagcacc actcttgata gttgcaaaca aacaggattt acctggagcc attgatgagg    660

aagaattggc taaatttctg cataaagaac tggatgagag gccatataca tttcaggctg    720

tatctgcata tgatgggagg gggatcaaat ctggcataga ctggctggtg gaacaaatgg    780

aaaaaagcaa acgtaccgag acactgcagg ctcgtgctgg cgtagctgga caaatttaga    840

atggtaagct tgcagctgcg accggatgaa tttgttaaaa gaacaaagca ttggatagga    900

cggcttcctt cgtatcgcgt aagcagccat ttgctggatt acagggatta tcgttccagg    960

ccgcccagag tgctgcaaga aatgtttggc tggttgctcc tgtggtggtg gtgattggtg   1020

aggcgattcg tttggtatta gaggttgcat tcatatgtac ctaaaggtca cgagcataca   1080

tgtctatatg atgcttttca attttcgtag caaactagta gcttcaacac agaggatcaa   1140

agagagccgt gttctttaac ttgtttgtga taaaaaaaag gaagaaagga aagcgaagaa   1200

ggaatcactg gtgcatctga aagtctttat tggatatgtc taaaccattt caactgatgc   1260

tggataagtt tttcttaaaa aaaaaaaata aaaaaaaaaa aaaaa                   1305
```

<210> SEQ ID NO 15
<211> LENGTH: 3993
<212> TYPE: DNA
<213> ORGANISM: Zea mays
<220> FEATURE:
<221> NAME/KEY: misc_feature
<222> LOCATION: (2094)..(2094)
<223> OTHER INFORMATION: n is a, c, g, or t

<400> SEQUENCE: 15

```
tgaaaatata tattgaataa cttttaacgg cttttagtgg tttccatcaa acggttttta     60

gctttttaac atctcacagc ccacagtaac tttttccaca gctcacaacc tatagcagct    120

tttttcacag ccacatccca actaaaaaga ccctaagtga atgtcatggt atgggctgac    180

atttcgagag gtggacaaat ggagaatggc atgatatggg ctgccatgtg ggccgagggt    240

ctgagaccgg gctaaatgag ctgggctgaa gaggactgac tgtaggtaga aaggcaagcg    300

caacatttgg caccgttagc tctccactaa acttgtcaga tgcaataatt tatgtttttt    360

aaatggcaaa gccctcctgc cagccagtgc cttccttccg ggtcaaccac tggtaccgtc    420

acatcacgaa ttcccactgg cagtacgata acctcactga gcggtagggc ctcccgtccc    480

agaatcctgc aggacccatc gatcatggcc ccacgggtcc tgctcctgcg tgggttccaa    540

ttccaagtcg cccaccgtga cgcccatcga gtcaaccgaa cccaagccgt gtggcgactg    600

gcgaggcgag tgccccagtt cctaactccg gtgggcgcgc tcccaccgcc gcgcggctca    660

aaacccgccc tcagcctccc gcgctccagt ccacacggga gcgggtggtg tcgtctgaag    720
```

```
cggcgcgatc aaggagtctt cgggcgctcc ggtgagctat ctagatctca acatcctctc    780
ccctctgtag tctgtagttg tactctcccg cccgatggtt cagttaagtt atatcctctc    840
cccttatttt tactcggtcg ataccatttc gttgtggatt gggcgccccc gcaggttgaa    900
atgctgccca tcatgctgcg gccctgtact atgaggatgg ttctagtttt gcgtctggca    960
atttggggcg tacatgcttt tggctgcgta ctgttactga tcggagaaaa tgtttgtaac   1020
gtatgattcg tttttcagga cgtaacgtgc tggcggttgc ttatctccgg atgtatatat   1080
aagcggaaat gttctccttg ttctatggcc tgtggaagta tgtgttcgcc aaggacgagt   1140
tccgtgttct gattcttggt gttgacagag ctggcaagac ggtagctgct agctcccagc   1200
cttcatatat atatttccct ttctgaacta gaaattgatg atacttacct gtacacgatg   1260
tttctggaac cgttgccata gactttgctg gagaagttga aatcgatata tctcaagggg   1320
gaaggacttc cgcctgaccg tgtcgttcca acagttgggc tcaacattgg ccgcatcgaa   1380
gacgcaaagg caaaacttgt tttctgggat ctaggtggtc aggtaagaac gtttacgtac   1440
gtagtaaagt gagccttctg ttgccgtggc accaccctac gatcgttgat atttgagtct   1500
tgtcagtttg gtgctatatc agggtttcta atgcctggga aatacatgtc ataaattcaa   1560
attactagga tgtggttgct ttagttatta acctagcatc tttttgcgtt ccagcagaat   1620
atatataatc tagttatatg gaatgctcaa tagaattttc agaaagcaaa gatatgctct   1680
gttggctaac attcacagta ctcaatagaa ttgtttacta gtagaacagc atcagcttct   1740
ctgctatgtt ataagaatta gtgtaaaact aacttcagta tcactgcttg ctagtatgat   1800
aattaagctt ccatgccaag ttcagtattt cttacacact tgcctgcttg gcaggttagc   1860
ctacgaacaa tctgggagaa atactatgaa gaggcccatg ccataatgta cgttattgac   1920
gctgccacag catcgtcatt tgaagattcc aaatctgctc tgggtaaggt tcttatttgt   1980
gttaattata aactactccc tccattccaa attataagac attttggcct tttttctaga   2040
taaataaatt ttgctatgga cttaaatatt atttatatat atatatatat atantatata   2100
tatatatata tataaaatgt cctggtacat agttaaaaca ttatatctta aaaagctaaa   2160
acattgtctt ataacttgga acaagggagt actggtttgt ttctattgct agatcttccg   2220
agaagatgca ttgcctctct ggtaaatggg atgagaactc attctagcta gagaacctaa   2280
cctaaatttc ttacttcaga gaaggttatt cgccatgaac atctgagagg agcaccactc   2340
ttgatagttg caaacaaaca ggtgaagggt ttacttccac tttctatatt ttgtaccaca   2400
gtacataatt atgattgaaa gattcagtgc ttacaataaa gttgccatcg tagtaaaata   2460
aagattttgt ttttgtcatg tgcccatgct gtgaggcata caaatctaaa ttcctacgtt   2520
gcaaagcgcc tatgcgccat tgcgaggttg aataccagat gtagtttggc caattgtgat   2580
gtacagatgt gccacattga caattgacac gcagtttaaa ggagagtcag actactagtt   2640
ttttcattgc ccaacatata cctttggcca cttattgaaa atgtgagaga tcatttgagt   2700
ttgaacagta agttttgtga gatatcattt tatttagtaa tcatgcacac atgtctagaa   2760
ttgtgaaatg cacaataaag acgcaaactc ccacgagcat gcaggtacac ccgattgagg   2820
attctcagcg aatgttccag tttcgagaat caaacaacat ataacaatga tgaatttttt   2880
aaatcaatta aaacttcctg aaaagatcac atggaaacca atgactacat gcactgtctg   2940
tttctgttaa gctgggtaca cattattcta tcaaattgtt tattatttac ctcttgttct   3000
catgtttgga gggtgcttct ggatttcttt tggcaggatt tacctggagc cattgatgag   3060
gaagaattgg ctaaatttct gcataaagaa ctggatgaga ggccatatac atttcaggct   3120
```

```
gtatctgcat atgatgggtg agcgcagaaa ctcaactggt tcctgaggaa atttgactcg   3180
ccatgaaaaa aaatgacaat tttactcaaa gatacaaaaa attcacacat tcgtctgtta   3240
tattgtttcc tgggtgcatg aaactcaact ggttcgtgag gaaatttgac tcgccatgaa   3300
aaaaatgaca attttactca aagatacaaa aaattcacac attcgtctgt tatattgttt   3360
cctgggtgca tgatattcta aagatctgtt atattgttta aatgtgacac cggctcttgc   3420
agcaggggga tcaaatctgg catagactgg ctggtggaac aaatggaaaa aagcaaacgt   3480
accgagacac tgcaggctcg tgctggcgta gctggacaaa tttagaatgg ggtgaatttg   3540
ttaaagaaca aagcattgga taggacggct tccttcgtat cgcgtaagca gccatttgct   3600
gcattccggg attatcgttc caggtcgccc agagtgctgc aagaaatgtt tggctggttg   3660
ctcctgtggt ggtggtgatt ggtgaggcga ttcgtttggt attattgagg ttgcattcat   3720
atgtacctaa aggtcgcaag catacatgtc tatatgatgc ttttcaattt tcgtagcaaa   3780
ctagtagctt caatacagag gatcaaagag agccgtgttc tttaacttgt ttgtgataaa   3840
aaaaaaggaa gaaaggaaag cgaagaagga attattggtg catctgaaag tctttattgc   3900
atatgtctaa accattttaa ccgatgctgg atgagctttt cttcgcaccg atgttacatc   3960
tagtctatca tatgtatcct cgtttcatac tcg                                3993
```

<210> SEQ ID NO 16
<211> LENGTH: 6492
<212> TYPE: DNA
<213> ORGANISM: Zea mays

<400> SEQUENCE: 16

```
cgaagaacaa ggaaagcact tgtccatcaa ttgcacttga gtagcaaagg tttcaggttg     60
tcggtgctga catctcttct actctgttaa gaccaggcta aggggggtgtt tgaatgcact   120
agaactaata gttagttggc taaaaattgg tagtggaatt agctagctaa caaataacta   180
tctaactatt aactaattta ccaaaaatag ctaatagttg aactattaac taaagtgttt   240
ggatgtctca actaatttta gctactaact attagctcta gtgcattcaa acacccctta   300
agtgaatgtc atggtatggg ctgacatttc gagaggtgga gagtgtcatg gtatgggctg   360
ccatgtgggc cgagagtccg agaccgggct aaatgagctg ggctgaatag gactgactgc   420
aggtagaaag gcaagcgcaa catttggcac cgttagctct ccactaaact tgtcagatgc   480
aataatttat gtttttatta atggcaaagc cctcctgcca gccagtgcct tccttccggg   540
tcaaccactg gtacagtcac atcacgaatt cccactggca gtacgataac ctcactgagc   600
ggtagggcct cccgtcccag aatcctgcag gacccaccga tcatagcccc acgggtcctg   660
ctcctgcgtg ggttccagtt ccaagtcgcc caccgtgacg cccatcgagt caaccgaacc   720
caagccgtgt ggcgactggc gaggcgagtg ccccagttcc taactccggt gggcgcgctc   780
ccaccgccgc gcggctcaaa acccgccctc agcctcccgc gctccagtcc acacgggagc   840
gggtggtgtc gtctgaagcg gcgcgatcaa ggagccttcg agcgctccgg tgagctatct   900
agatctcaac atcctctccc ctctgtagtc tgtagttgta ctctcccgcc cgatggttca   960
gttaagttat atcctctccc cttattttta ctcggtcgat accatttcgt tgtggattga  1020
aatgctgcgg ccctgtacta tgaggatggt tcctagtttt gcgtctggca atttggggcg  1080
tacatgcttt tggctgcgta ctgttactga tcggagaaaa tgtttgtaac gtatgattcg  1140
tttttcagga cgtaacgtgc tggcggttgc ttatcgccgg atatatatat ataagcggaa  1200
```

-continued

```
atgttctcct tgttctatgg cctgtggaag tatgtgttcg ccaaggacga gttccgtgtt   1260
ctgattcttg gtgttgacag agctggcaag acggtagctg ctagctccca gccttcatat   1320
atatatattt ccctttctga actagaaatt gatgaaactt acctgtacac aatgtttctg   1380
gaaccgttgc catagacttt gctggagaag ttgaaatcga tatatctcaa gggggaagga   1440
cttccgcctg accgtgtcgt tccaacagtt gggctcaaca ttggccgcat cgaagacgca   1500
aaggcaaaac ttgttttctg ggatctaggt ggtcaggtaa gaacgtttac gtacgtagta   1560
aagtgagcct tctgttgccg tggcaccacc ctacgatcgt tgatatttga gtcttgtcag   1620
tttggtgcta tatcagggtt tctaatgcct gggaaataca tgtcataaaa tcaaattact   1680
aggatgtggt tgctttagtt attaacctag catctttttg cgttccagca gaatatatat   1740
aatctagtta tatggaatgc tcaatagaat tttcagaaag caaagatatg ctctgttggc   1800
taacattcac agtactcaat agaattgggt ggctagtaga acagcatcag cttctctgct   1860
atgttataag aattagtgta aaactaactt cagtatcact gcttgctagt atgataatta   1920
agcttccatg ccaagttcag tatttcttac acacttgcct gcttggcagg ttagcctacg   1980
aacaatctgg gagaaatact atgaagaggc ccatgccata atgtacgtta ttgacgctgc   2040
cacagcatcg tcatttgaag attccaaatc tgctttgggt aaggttctta tttgtgtcaa   2100
ttataaacta cgccatccat tccaaattat aagacatttt ggcctttttc tagataaata   2160
aattttgcta tggacttaaa tattaaaaat atatataatg tcctggtaca tagttaaaac   2220
aatatatcta gaaaagctaa aacatcgtct tataacttgg aacagaggga gtactggttt   2280
gtttctattg ctagatcttt ccagaagatg caatgcctct ctggtaaatg ggatgagaac   2340
tcattctaga gaacctaacc taaatttctt acttcagaga aggttattcg ccatgaacat   2400
ctgagaggag caccactctt gatagttgca aacaaacagg tgaagggttt acttccactt   2460
tctatatttt gtaccacagt acataattat gattgaaaga tttagtgctt acaataaagt   2520
tgccatcgta gttaaaataa agattttgtt tttgtcatgt gcacatgctg tgaggcatac   2580
aaatataaat tcctacgttg caaagcgcct atgcgccatt gcgaggttga ataccagatg   2640
tagtttttaa atcaattaaa acttcctgaa aagatcacat ggaaaccaat gactacatgc   2700
actgtctgtt tctgttaagc tgggtacaca ttattctatc aaattgttta ttatttacct   2760
ctagcttgtt ctcatgtttg gagggtgctt ctggatttct tttggcagga tttacctgga   2820
gccattgatg aggaagaatt ggctaaattt ctgcataaag aactggatga gaggacatat   2880
acatttcagg ctgtatctgc atatgatggg tgagcgcaga aactcaactg gttcctgagg   2940
aaatttgact cgccatgaaa aaaatgacaa ttttactcaa agatacaaaa aaattcacac   3000
attcgtctgt tatattgttt cctgggtgca tgatattcta aagatctgtt atattgttta   3060
aatgtgacac cggctcttgc aggaggggga tcaaatctgg catagactgg ctggtggaac   3120
aaatggaaaa aagcaaacgt accgagacac tgcaggctcg tgctggcgta gctggacaaa   3180
tttagaatgg ggtgaatttg ttaaagaaca aagcattgga taggaccgct tccttcgtat   3240
cgcgtaagca gccatttgct gcattccggg attatcgttc caggtcgccc agagtgctgc   3300
aagaaatgtt tggctggttg ctcctgtggt ggtggtgatt ggtgaggcga ttcgtttggt   3360
attattgagg ttgcattctt atgtacctaa aggtcgcaag catacatgtt tatatgatgc   3420
ttttcaattt tcgtagcaaa ctagtagctt caatacagag gatcaaagag agccgtgttc   3480
tttaacttgt ttgtgataaa aaaaaggaag aaaggaaagc gaagaaggaa ttattggtgc   3540
atctgaaagt ctttattgat atgtctaaac catttcaacc gatgttggat gaggttttct   3600
```

```
tcgcaccggt gttacatcta gtctatcata tgtatcgtcg tttcatactc gatccttttt   3660
tatggccaaa ctccaacaca acatatgcat ttctgtagcg catatgtatt gaacatgtct   3720
tttttagact aacattttgc accgaacaac atagcagatc gaattgtcat cctataaaac   3780
ttctttttaa cttttgtggt atcctattgt catatagaat atcaaatgtt tggcgctacc   3840
tcatccattg actaatacct ttatcaatat ctctacgtag catagatcct aaatatctaa   3900
agatgtcctt catggacact acttgatttt tcaaactaac atgtctttcc taatatgtag   3960
tagcatagat cctaaatatc taaagatgtc cttcctggac actacttgat tttcaaact    4020
aacatgtctt tcctcatatg tagtagtgtt gaaatcacat cttttatatt caatttgagt   4080
tctactgatc gagtccaaaa tcgtccaaaa cctttaaact ctagaatctc ccaccacaac   4140
tctagtttc tatttactcg tgcttagctt tcatcaacta acactacatc cataaaaaac    4200
atatgttaag agatatccct ttgtgatctt atccatagac tcagctaatt ttttatgtag   4260
tcatattcta atcgaaaagt cacatgtgtc tccatcattt attcaaacat attcataaca   4320
ttgttgttgg aactttgctt cctcaaaaaa cagggataaa aaacagtaaa aggaattggc   4380
ccttcaggct agagctgctg atatccccac taagctgggc caatcggcca agaaactttg   4440
cttcattcag ggcatgatat ggacaaccca ctgcggattg ccaaacaaag aagttagtaa   4500
gaaaccacaa aatgcttagt ctgagctttg aagagttcta cttggtgagt aaaacagtta   4560
atcttaacta ctgcttggct aagataagat gttagctaaa agaattctgt agatgtgcaa   4620
tctcaaacca atctgccttt gcatcattta gaaaactgct ttaaaattcg aaatattttg   4680
cttacaatag ctcatagcac agaagaatat tatagaacaa accaaggcaa gtgactttct   4740
gaaacacagt tttcaagaac aggttcagat taaactagat aacaggatgc cagcgttggt   4800
aataagtcta ctccccaaga gaagtcactg ttttgttctt tctcaatgaa aaataacgac   4860
acaaaaatga actatggccg tctgcattaa tatggatacg cagcaaaaat ggacatgagt   4920
aactcaaaat cgtcaagtgc ttgctatgtt aagcacccaa gtcaatgatt tatattccat   4980
gatatcgcaa agattatcta taacaagttc tgagtgtgtt tcaaacatta aatgatccat   5040
gaaaggtaag cacttgtatt tagcggacag tactagtctg ctgtgggatt aacccatttt   5100
ttatggttct cgatggcctt ttgcttcaag ataatatctg atccaattaa tagacaaaat   5160
cacaagtaat ctttgttaca tgtcatcatc gaatcctatc ttctgtagga gcaaacttaa   5220
acggtgacat atcaagcaac actatgagaa ttcatgtgta tctgataaag gatcattcac   5280
ttcacatgta gacatatatg actacaaaag tggtatgaat attgttaaca gaatcaatgg   5340
aaaatggaat atatctcatt aggtaacata tggaattgta agcaggctat aaaaaatcag   5400
aggtattaag tatcaattca gacagcagaa tgatgcaatg atcacaacca agtcaacaag   5460
ttatcataac taagattagt ccttttgtag ccaaagaagt ttaccgaact cagaaagcag   5520
aacataattc acttacttga tctcaacaac attttgtgtc accatgccag gaagaaacca   5580
gaagtggcat ggtaagcatt gccagtccaa ccagacctct gtgaagcatt atcccatcac   5640
tggaaacctc cacaaagcgt gtttgctaag gcaaatggca tgtatctcca tctaatgaac   5700
atacaaattt tgccctgcct gatgttaagt aactacaggt accaggtaga ctacaagtct   5760
acaactacaa cattacataa cagggatgga acaattacac tcaaatgaac acttgaacag   5820
caagagccag tctctgagac atctgcttcg gcctggctaa tcatagcccc agtaaaccat   5880
aacaacagtt aaatcatccg tccaagattg tccaccctca agaagtgcat gttgtgcaaa   5940
```

```
ttccccaata tatcctcaga tgcatcaaca tcgatatgaa agttgctgat atcttcaact   6000

ccgccagcac cgctaacatt aaccctacca gtgccatctg tagcatgtgc tgcctcattt   6060

atgttaattc tcctcacctc ctcggccctt ccatctccag cgttctcatc cccagcccag   6120

ccttcctgcc cgagcatcga agaatcaatg ccactctcca caccaagaga acgtctcctg   6180

agccctaccc cgaccttctt gcgggccgtc gtcttcttga tcctacctct agaagagcca   6240

ccacgagcac tgtcattctg tggctgccta ccaccatggt ttccgtgact cctaccacca   6300

ccaccttggc cactgggagc cgtgttccaa ggaaacatct tgtagaatgg cttccagttg   6360

gcacccaggt cggccgcgtt gggaaatccg agggggaaga acccccaggc gcagtggtac   6420

atttcagtgc ccggcacaac ggtgggtggg gtcgggagct cagaagccac gaatccgcgg   6480

cggcagcccg cg                                                       6492
```

```
<210> SEQ ID NO 17
<211> LENGTH: 10054
<212> TYPE: DNA
<213> ORGANISM: Zea mays

<400> SEQUENCE: 17

tttggatgtc tcaactaatt ttagctacta actattagct ctagtgcatt caaacacccc     60

ttaagtgaat gtcatggtat gggctgacat ttcgagaggt ggagagtgtc atggtatggg    120

ctgccatgtg ggccgagagt ccgagaccgg gctaaatgag ctgggctgaa taggactgac    180

tgcaggtaga aaggcaagcg caacatttgg caccgttagc tctccactaa acttgtcaga    240

tgcaataatt tatgttttta ttaatggcaa agccctcctg ccagccagtg ccttccttcc    300

gggtcaacca ctggtacagt cacatcacga attcccactg gcagtacgat aacctcactg    360

agcggtaggg cctcccgtcc cagaatcctg caggacccac cgatcatagc cccacgggtc    420

ctgctcctgc gtgggttcca gttccaagtc gcccaccgtg acgcccatcg agtcaaccga    480

acccaagccg tgtggcgact ggcgaggcga gtgccccagt tcctaactcc ggtgggcgcg    540

ctcccaccgc cgcgcggctc aaaacccgcc ctcagcctcc cgcgctccag tccacacggg    600

agcgggtggt gtcgtctgaa gcggcgcgat caaggagcct tcgagcgctc cggtgagcta    660

tctagatctc aacatcctct cccctctgta gtctgtagtt gtactctccc gcccgatggt    720

tcagttaagt tatatcctct ccccttattt ttactcggtc gataccattt cgttgtggat    780

tgaaatgctg cggccctgta ctatgaggat ggttcctagt tttgcgtctg gcaatttggg    840

gcgtacatgc ttttggctgc gtactgttac tgatcggaga aaatgtttgt aacgtatgat    900

tcgtttttca ggacgtaacg tgctggcggt tgcttatcgc cggatatata tatataagcg    960

gaaatgttct ccttgttcta tggcctgtgg aagtatgtgt tcgccaagga cgagttccgt   1020

gttctgattc ttggtgttga cagagctggc aagacggtag ctgctagctc ccagccttca   1080

tatatatata tttccctttc tgaactagaa attgatgaaa cttacctgta cacaatgttt   1140

ctggaaccgt tgccatagac tttgctggag aagttgaaat cgatatatct caagggggaa   1200

ggacttccgc ctgaccgtgt cgttccaaca gttgggctca acattggccg catcgaagac   1260

gcaaaggcaa aacttgtttt ctgggatcta ggtggtcagg taagaacgtt tacgtacgta   1320

gtaaagtgag ccttctgttg ccgtggcacc accctacgat cgttgatatt tgagtcttgt   1380

cagtttggtg ctatatcagg gtttctaatg cctgggaaat acatgtcata aaatcaaatt   1440

actaggatgt ggttgcttta gttattaacc tagcatcttt ttgcgttcca gcagaatata   1500

tataatctag ttatatggaa tgctcaatag aattttcaga aagcaaagat atgctctgtt   1560
```

```
ggctaacatt cacagtactc aatagaattg ggtggctagt agaacagcat cagcttctct   1620
gctatgttat aagaattagt gtaaaactaa cttcagtatc actgcttgct agtatgataa   1680
ttaagcttcc atgccaagtt cagtatttct tacacacttg cctgcttggc aggttagcct   1740
acgaacaatc tgggagaaat actatgaaga ggcccatgcc ataatgtacg ttattgacgc   1800
tgccacagca tcgtcatttg aagattccaa atctgctttg ggtaaggttc ttatttgtgt   1860
caattataaa ctacgccatc cattccaaat tataagacat tttggccttt ttctagataa   1920
ataaattttg ctatggactt aaatattaaa aatatatata atgtcctggt acatagttaa   1980
aacaatatat ctagaaaagc taaaacatcg tcttataact tggaacagag ggagtactgg   2040
tttgtttcta ttgctagatc tttccagaag atgcaatgcc tctctggtaa atgggatgag   2100
aactcattct agagaaccta acctaaattt cttacttcag agaaggttat tcgccatgaa   2160
catctgagag gagcaccact cttgatagtt gcaaacaaac aggtgaaggg tttacttcca   2220
ctttctatat tttgtaccac agtacataat tatgattgaa agatttagtg cttacaataa   2280
agttgccatc gtagttaaaa taaagatttt gtttttgtca tgtgcacatg ctgtgaggca   2340
tacaaatata aattcctacg ttgcaaagcg cctatgcgcc attgcgaggt tgaataccag   2400
atgtagtttt taaatcaatt aaaacttcct gaaaagatca catggaaacc aatgactaca   2460
tgcactgtct gtttctgtta agctgggtac acattattct atcaaattgt ttattattta   2520
cctctagctt gttctcatgt ttggagggtg cttctggatt tcttttggca ggatttacct   2580
ggagccattg atgaggaaga attggctaaa tttctgcata aagaactgga tgagaggaca   2640
tatacatttc aggctgtatc tgcatatgat gggtgagcgc agaaactcaa ctggttcctg   2700
aggaaatttg actcgccatg aaaaaaatga caattttact caaagataca aaaaaattca   2760
cacattcgtc tgttatattg tttcctgggt gcatgatatt ctaaagatct gttatattgt   2820
ttaaatgtga caccggctct tgcaggaggg ggatcaaatc tggcatagac tggctggtgg   2880
aacaaatgga aaaaagcaaa cgtaccgaga cactgcaggc tcgtgctggc gtagctggac   2940
aaatttagaa tggggtgaat ttgttaaaga acaaagcatt ggataggacc gcttccttcg   3000
tatcgcgtaa gcagccattt gctgcattcc gggattatcg ttccaggtcg cccagagtgc   3060
tgcaagaaat gtttggctgg ttgctcctgt ggtggtggtg attggtgagg cgattcgttt   3120
ggtattattg aggttgcatt cttatgtacc taaaggtcgc aagcatacat gtttatatga   3180
tgcttttcaa ttttcgtagc aaactagtag cttcaataca gaggatcaaa gagagccgtg   3240
ttctttaact tgtttgtgat aaaaaaaagg aagaaaggaa agcgaagaag gaattattgg   3300
tgcatctgaa agtctttatt gatatgtcta aaccatttca accgatgttg gatgaggttt   3360
tcttcgcacc ggtgttacat ctagtctatc atatgtatcg tcgtttcata ctcgatcctt   3420
ttttatggcc aaactccaac acaacatatg catttctgta gcgcatatgt attgaacatg   3480
tcttttttag actaacattt tgcaccgaac aacatagcag atcgaattgt catcctataa   3540
aacttctttt taacttttgt ggtatcctat tgtcatatag aatatcaaat gtttggcgct   3600
acctcatcca ttgactaata cctttatcaa tatctctacg tagcatagat cctaaatatc   3660
taaagatgtc cttcatggac actacttgat ttttcaaact aacatgtctt tcctaatatg   3720
tagtagcata gatcctaaat atctaaagat gtccttcctg gacactactt gatttttcaa   3780
actaacatgt ctttcctcat atgtagtagt gttgaaatca catcttttat attcaatttg   3840
agttctactg atcgagtcca aaatcgtcca aaacctttaa actctagaat ctcccaccac   3900
```

```
aactctagtt ttctatttac tcgtgcttag ctttcatcaa ctaacactac atccataaaa   3960
aacatatgtt aagagatatc cctttgtgat cttatccata gactcagcta attttttatg   4020
tagtcatatt ctaatcgaaa agtcacatgt gtctccatca tttattcaaa catattcata   4080
acattgttgt tggaactttg cttcctcaaa aaacagggat aaaaaacagt aaaaggaatt   4140
ggcccttcag gctagagctg ctgatatccc cactaagctg ggccaatcgg ccaagaaact   4200
ttgcttcatt cagggcatga tatggacaac ccactgcgga ttgccaaaca aagaagttag   4260
taagaaacca caaaatgctt agtctgagct ttgaagagtt ctacttggtg agtaaaacag   4320
ttaatcttaa ctactgcttg gctaagataa gatgttagct aaaagaattc tgtagatgtg   4380
caatctcaaa ccaatctgcc tttgcatcat ttagaaaact gctttaaaat tcgaaatatt   4440
ttgcttacaa tagctcatag cacagaagaa tattatagaa caaaccaagg caagtgactt   4500
tctgaaacac agttttcaag aacaggttca gattaaacta gataacagga tgccagcgtt   4560
ggtaataagt ctactcccca agagaagtca ctgttttgtt ctttctcaat gaaaaataac   4620
gacacaaaaa tgaactatgg ccgtctgcat taatatggat acgcagcaaa aatggacatg   4680
agtaactcaa aatcgtcaag tgcttgctat gttaagcacc caagtcaatg atttatattc   4740
catgatatcg caaagattat ctataacaag ttctgagtgt gtttcaaaca ttaaatgatc   4800
catgaaaggt aagcacttgt atttagcgga cagtactagt ctgctgtggg attaacccat   4860
tttttatggt tctcgatggc cttttgcttc aagataatat ctgatccaat taatagacaa   4920
aatcacaagt aatctttgtt acatgtcatc atcgaatcct atcttctgta ggagcaaact   4980
taaacggtga catatcaagc aacactatga gaattcatgt gtatctgata aaggatcatt   5040
cacttcacat gtagacatat atgactacaa aagtggtatg aatattgtta acagaatcaa   5100
tggaaaatgg aatatatctc attaggtaac atatggaatt gtaagcaggc tataaaaaat   5160
cagaggtatt aagtatcaat tcagacagca gaatgatgca atgatcacaa ccaagtcaac   5220
aagttatcat aactaagatt agtccttttg tagccaaaga agtttaccga actcagaaag   5280
cagaacataa ttcacttact tgatctcaac aacattttgt gtcaccatgc caggaagaaa   5340
ccagaagtgg catggtaagc attgccagtc caaccagacc tctgtgaagc attatcccat   5400
cactggaaac ctccacaaag cgtgtttgct aaggcaaatg gcatgtatct ccatctaatg   5460
aacatacaaa ttttgccctg cctgatgtta agtaactaca ggtaccaggt agactacaag   5520
tctacaacta caacattaca taacagggat ggaacaatta cactcaaatg aacacttgaa   5580
cagcaagagc cagtctctga gacatctgct tcggcctggc taatcatagc cccagtaaac   5640
cataacaaca gttaaatcat ccgtccaaga ttgtccaccc tcaagaagtg catgttgtgc   5700
aaattcccca atatatcctc agatgcatca acatcgatat gaaagttgct gatatcttca   5760
actccgccag caccgctaac attaacccta ccagtgccat ctgtagcatg tgctgcctca   5820
tttatgttaa ttctcctcac ctcctcggcc cttccatctc cagcgttctc atccccagcc   5880
cagccttcct gcccgagcat cgaagaatca atgccactct ccacaccaag agaacgtctc   5940
ctgagcccta ccccgacctt cttgcgggcc gtcgtcttct tgatcctacc tctagaagag   6000
ccaccacgag cactgtcatt ctgtggctgc ctaccaccat ggtttccgtg actcctacca   6060
ccaccacctt ggccactggg agccgtgttc caaggaaaca tcttgtagaa tggcttccag   6120
ttggcaccca ggtcggccgc gttgggaaat ccgaggggga agaaccccca ggcgcagtgg   6180
tacatttcag tgcccggcac aacggtgggt ggggtcggga gctcagaagc cacgaatccg   6240
cggcggcagc ccgcgttggg gcacttgagg gcgcgcccga tcaggctgcg cgggtactgg   6300
```

```
tgcacgtagc agcagaaggg gcacgccgtc cagaactccg ggtgtccga ggcgggagcg   6360
gccgcggcgg gatactggga ggagtaaggg gtaccagtgg cgggatcggc gggcggcggg   6420
gggcggcgag agggatccga gaggaaggcg taggcgtcgt tgacgaggcg gagcgccatc   6480
tcggctcccg ggtgcgggtt gctggggccg aggaggagcg cgaggcggcg gaaggcgcgg   6540
gacacggcgg cctggtcggg gctgactccg ggcggcagct ggaggatggc gagcgggtcc   6600
ggctggcccg aggggcccat gaactgggaa gcgaggagga cgtcggcgac ggcgaggagc   6660
tcgtcaacgc cagcgaggag cgggttcgcc tccatcgacc gctccgcgaa gcgcttgcag   6720
ccgacgaggt cgcgcgccgc gaggagcttc tcggcgatct ccagccagcg ctccgcctgc   6780
gcggggccgt cgctggcgcc tccgccgccc ccgctcacgc tcccgccggt ggagaagtcc   6840
atggtttggg ggaggaaaag gtggatgctg tcggaggcag ctggtttggt tttggggagg   6900
gggaagatcc tgctgcccga ggggctcttg actggcgact gtctgtcagt ccgagagtat   6960
tttgttgggc agcacattta ttttaaggac aactgtgatt atacgttttc aacttcgtga   7020
attattgatt acgaaaatta aaaatgaggg gtaaaatcat aattgtaagg gaagagaagg   7080
atatactcaa aattaatctg aaaataatat taaacttttt atggttaatt gtgattatag   7140
ccttctctca ctttacaatt gtgattttac cccttatttt tatttttaat cactaattct   7200
gatttttatt aacgttgata aggcggtgca aacaacggct ttgttttcaa aacagagggg   7260
taacaaagtt aaaaaagaag ggataaaatc acaattaaaa tattagaaaa gggtataatc   7320
acaattatcc cttgatttta ttaggctctc tccaatcatt ctccatctca aatcccacat   7380
ttggactttc tattcatatt taaatatcct catcttcact attatttccc tattttacct   7440
cctctccaag catccctcta ttcagctctc cctttaccct ttaactaagc tatttgactt   7500
ttctacatca gtttttagag tttttaatat ttataatatc ataatacaca ttgtcactta   7560
accaaactta tagcagatta attttatagt taaaaacact aattagtgaa gagtagggtt   7620
ctatctttct cgttttacaa ggtgttttcc ttctctcacc ctacaagagg gaggagaggg   7680
acctgttgaa gctctctcga tgtacgaaat caccgaatac gtcgtgaagg ggaggggaaa   7740
ggatccgttg gagagcgtct tatagcctgt tagcttcgaa ttaaagtcag ttgtttagat   7800
tattgtagct gcaattcaca gagaccaaaa cactacagaa atagtaaaag ccgtttcgaa   7860
ttaaaaccaa gggaacgggc tattagtttt cccatatgca aacataccag accattgtag   7920
cgccccaccg cagagcaagt tttgcataca atcaatgtat aattggacta ccaaaaacca   7980
taaaaaattc taaaaatata taaatataat ttattgttta ctttattaga ttataaaatt   8040
ttaagtttaa atttatacaa tagtaaaaga aaaaatatat tcaattagat aaaaaaaatt   8100
ccctcaattc cgtaaaataa ggcctgcatt ttaaaaaaaa aagactcaat gttttaaaac   8160
ttttgactag taattcagcc aaaagcatat attttagtat atacatgtta tatacttgat   8220
ttgtattcaa aaattacttt aatttaatgc tcgttatgtt tttattgata gcatattttg   8280
aaataaacaa atagtcaaag tttcgctcca aagactgtac caaaaatata taccttgtta   8340
tataagatga atgaattata tattaacata gcataaatca atctaggatc ttaaatatga   8400
tatattgata aagtaaataa tatatatgta taatttttta aatatttttg tgacttttga   8460
tagttggatt gtatagaatg tttggttgca caatagtatt ttcctcaagt gaaagatctt   8520
catcaatgtt gtaatacagt gacatgtcat catcaagcct ggttagatct atcctcaaaa   8580
tctactccat aaatttaagg gccaattccc tgtatgccac tagaaaatat actcattcct   8640
```

```
tgtatgccac tgaccccaca tgtcatagac accaaaaaat atacctatat gccactcagt    8700

ggcacacaag gaatgagtat aaaatttgat ggcataccag gaattttctc taaatttaat    8760

ttagagtttc tagagtactt ctcttttaac ttcacctttt ttagctacac ttgtttggtt    8820

gaaatataga gccgcacagt cccaaacaaa ctctaaggat gagttgatgt atccccaagt    8880

atatcttaca aaaaatgata taatgactct atttatctta tagggtattt gtgattatac    8940

cctctctggt cttgaaattg tgattttacc catcgttttt caactttgtg atattttatc    9000

ccttcatttt gaaaacgaag agttgccata cccttgtgcc gttagatgca gttaacaatg    9060

ttaaatttga tgcaaaagat aaaaataccc aagcaattta ttttgatttt accctcgtta    9120

tattatgtaa tagtgatttc acccctatta gggttgtgcc cataaagaat agaaaaaggt    9180

agtttgaacc tttcacccat ttattttctc attttttttat ttttaatcac taattctgat    9240

tttcactaac gatgttgaga gtgaagggca aatggtagct tcgtatttaa aacggaggtg    9300

taaaattaga aagttgaaaa tgcagagtaa aatcacaatt gcaaggccaa cgaagggtat    9360

aatcacaatt atctcttatc ttactagtag taattattag attgtgagga ataaagtaat    9420

ggcagattat ttcattctat tttataaacc aaacaaaact tggaaaagta aaaatatgat    9480

ggagtgtatg tgggggtggt tagggaggaa aggcccaaaa caaagggttt tcgaatctta    9540

cctaaataaa aatcatggca agctaaattg ctaaaacaag aatctaacgt gtttgtttgg    9600

cacttgcata aagatggtat cttttctatt aattatatgt ataaattctt agttactaat    9660

ggaattaatg ttttatgaat aatttggtgt ctaaagatac ctttaaagat aaaaatcttc    9720

atgtagttct ttcaaaaaaa gagggtcatt ctcacaatct cacaaaaggt aattttatca    9780

aaaagaaatt gaaatagtga cacaacttgc tcttttgagc cacaaaccat ctgatacata    9840

ttttctttga gtgcacttat gctaggttac tatagagaga agtttatatt tttttttctc    9900

gaacacgcag gaaaactgcg catcattata ttgaaagaga gaaaggtccg aaatggacca    9960

aagtacaaag ccaagcaggc aaaaaataaa aaggaaaaat agtacagcct catgcactag   10020

gaatagccct gatcctagca aaagcagcca gaag                               10054
```

<210> SEQ ID NO 18
<211> LENGTH: 5714
<212> TYPE: DNA
<213> ORGANISM: Zea mays

<400> SEQUENCE: 18

```
atcacgcctc gcccgagcct agcctcgggc aagggcagcc gaccccgaag gggtttccgt      60

ctcgcccgag gcccccc ttc aacggcggac acatctccgg cttgcccgag gccttgcctt     120

cgctgagaag caaccctgac tgaatcgccg caccgaccgg ccaagtcgca ggagcattta     180

acgcaaagga aaccaggccc tgccaaaggc accataggaa actccgctcc gcccaaccca     240

gggctcggac tcgggcaaag ccccggaaga cggcgaactc cgctccgccc gacccagggc     300

tcggactcgg gctaagcccc ggaagacggc gaactccgct ccgcccgacc cagggctcgg     360

actcgggcta agccccggaa gacggcgaac tccgctccgc ccgaccaagg gctcggactc     420

gggctaagcc ccggaagacg gcgaactccg ctccgcccga ccaagggctc ggactcgggc     480

taagccccgg aagacggcga actccgctcc gcccgaccaa gggctcggac tcgggctaag     540

ccccggaaga cgacgaactc cgcctcgccc gacctagggg ctcggactcg gcctctgctg     600

acgaactctg cctcgcccga cccaggggct cggactcggc ctctgctgac gaactccgcc     660

tcgcccgacc caggggctcg gactcggcct ctgctgacga actccgcctc gcccgacccg     720
```

```
ggggctcgga ctcggcctct gctgacgacc tccgcctcgc ccgacccagg ggctcggact    780
cggcttctgc tgacgacctc cgcctcgccc gacccagggg ctcggactcg gcctcggcca    840
tggaagacag actcgacccc ggcttcggag gagcctccac gtcgcccaac ctagggccca    900
ggccagccac gtcgacagga agcgccatca tcaccctacc ccgagccgac tcgggtcgca    960
gagaacaaga cctgtgtccc atctggctgg ctccgccaga taggcaatga tggcgccccg   1020
ctagccccgt gacgacggcg gctctcagct ctcttacgga agcagggcga cgtcagcaag   1080
gacacaaccg ttccaacagc tgtccctccg ccaggctccg ttgctcctcc gacagccacg   1140
acatcacgcc agcagggtgc caagatctct ccggctgcca tattggcatg tacttagggc   1200
actagctctc cccccgctag acacgtagca ctccgctaca ccccattgta cgcctggatc   1260
ctctccttac gcctataaaa ggaaggacca gggccttctt agagaaggtt ggccgcgcgg   1320
ggacgaggac ggggacaggc actctcttgc ggccgctcgc ttccctcacc cgtgtggacg   1380
cttgtaaccc cctattgcaa gcgcacccga cctgggcgcg ggacgaacac gaaggccgcg   1440
ggattcccac ctctctctcg ccggactccg gcctcctcgc tcctttcccc cttcgcgctc   1500
gcccacgcgc tcgacccatc tgggctgggg cacgcagcac actcactcgt cggcttaggg   1560
accccccggt ctcgaaacgc cgacactact cttgaggaga ttattagatt atcataatct   1620
aggctttaga ttatataatc tgaacacata atctagttgt ttgtttatct aatggattat   1680
ttacgctaga ttatataatc tggagagatt ataatctgaa acaaacatgg ccttagtgat   1740
taaaaataaa aataaggggt aaaatcacaa ttgtaaagtg agagaaggct ataatcacaa   1800
ttaaccataa aaagtttaat attattttca ggttaatttt gagtatatcc ttctcttccc   1860
ttacagttat gattttaccc cttattttta atttttgtaa tcaataattc acaaagttga   1920
aaacgtataa tcacagttgt ccttaaaatt aaatgtgctg cccaacaaaa tactctcgga   1980
ctgacagaca gtcgccagtc aagagcccct cgggcagcag gatcttcccc ctccccaaaa   2040
ccaaaccagc tgcctccgac agcatccacc ttttcctccc ccaaaccatg gacttctcca   2100
ccggcgggag cgtgagcggg ggcggcggag gcgccagcga cggccccgcg caggcggagc   2160
gctggctgga gatcgccgag aagctcctcg cggcgcgcga cctcgtcggc tgcaagcgct   2220
tcgcggagcg gtcggtggag gcgaacccgc tcctcgccgg cgttgacgaa ctcctcgccg   2280
tcgccgacgt cctcctcgct tcccagttca tgggcacctc gggccagccg gacccgctcg   2340
ccatcctcca gctgccgccc ggagtcagcc ccgaccaggc cgccgtgtcc cgcgccttcc   2400
gccgcctcgc gctcctcctc ggtcccagca acccgcaccc gggagccgag atggcgctcc   2460
gcctcgtcaa cgacgcctac gccttcctct cggatccctc tcgccgcccc ccgccgcccg   2520
ccgatcccgc cactggtacc ccttactcct cccagtatcc cgccgcggcc gctcccgcct   2580
ccgacacccc ggagttctgg acggcgtgcc ccttctgctg ctacgtgcac cagtacccgc   2640
gcagcctgat cgggcgcgcc ctcaagtgcc ccaacgcggg ctgccgccgc ggattcgtgg   2700
cttctgagct cccgacccca cccacggttg tgccgggcac tgaaatgtac cactgcgcct   2760
gggggttctt ccccctcgga tttcccaacg cggccgacct gggtgccaac tggaagccat   2820
tctacaagat gttcccttgg aacacggctc ccagtggcca aggtggtggt ggtaggagtc   2880
acggaaacca tggtggtagg cagccacaga atgacagtgc tcgtggtggc tcttctagag   2940
gtaggatcaa gaagacgacg gcccgcaaga aggtcggggt agggctcagg agacgttctc   3000
ttggtgtgga gagtggcatt gattcttcga tgctcgggca ggaaggctgg gctggggatg   3060
```

-continued

```
agaacgctgg agatggaagg gccgaggagg tgaggagaat taacataaat gaggcagcac   3120
atgctacaga tggcactggt agggttaatg ttagcggtgc tggcggagtt gaagatatcg   3180
gcaactttca tatcgatgtt gatgcatccg aggatatatt ggggaatttg cacaacatgc   3240
acttcttgag ggtggacaat cttggacgga tgatttaact gttgttatgg tttactgggg   3300
ctatgattag ccaggccgac tcttgctgtt caagtgttca tttgagtgta attgttccat   3360
ccctgttatg taatgttgta gttgtagact tgtagtctac ctggtacctg tagttactta   3420
acatcaggca gggaaaaatt tgtatgttca ttagatggag atacatgcca tttgccttag   3480
caaacacact ttgtggaggt ttccagtgat gggataatgc ttcgcagagg tgtggttgga   3540
ctggcaatgc ttaccatgcc acttctggtt tcttcctggc atggtgacac aaaatgttgt   3600
tgagatcaag taagtgaatt atgttctgct ttctgagttc ggtaaacttc tttggctaca   3660
aaaggactaa gcttagttat gctaacttgt tgatttggtt gtgatcattg catcattctg   3720
ctgtgtgaat tgatacttaa tacctctgat tttttatagc ctgcttacaa ttacatatgt   3780
tacctaatga gatatattcc attttccatt gattctgtta acaatattca taccactttg   3840
gtcgtgataa attcatttga ctattgtata gaagtcatat atgtctacat gtgaagtgaa   3900
tgatccatta tcagatacac atgaattctc atagtgttgc ttgatatgtc accgtttaag   3960
tttgctccta cagaagatag gattcgatga ttacatgtaa caaagattag ttgtgatttt   4020
gtctattaat tggatgagat attatcttga agcaaaaggt catcgagaac cataaaaaat   4080
gggttaatcc cacagcagac tagtactgtc cgctaaatac aagtgcttac ctttcctgga   4140
ccatttaatc tttgaaacac acgcagaact tgttatagat aatctttgtg atagcatgga   4200
atagaaatca ttgacttggg tgcctaacat agcaagcaat tgacgatttt gagttactca   4260
tgtccatttt tgctgagtat ccatattaat gcagacggcc atagttcatt ttcgtgtcgt   4320
tatttttcat tgagatagaa caaaacagcg acttctcttg ggagtacacc ttattaccaa   4380
cgctggcatc ctgttatcta gtttaatctg aacctgttct tgaaaactgt gtttcagaaa   4440
gtcacttgcc ttggtttgtt ctataatatt cttctgtgct atgagctatg gtaagcaaaa   4500
tatttcgaat tttaaagcag ttttctaaat gatgcaaagg cagattggtt tgagattgca   4560
catctacaga attcttttga ctaacatctt atcttagcca agcagtagtt aagattaact   4620
gttttactca ccaagtagaa ctcttcaaag ctcagactaa gcattttgtg gtttcttact   4680
aactcctttg tttggcaacc cgcagtgggt tgtccatacc atgccctgaa tgaagcaaag   4740
tttcttggcc gattggccca gcttagtggg gatatcagca gccctagcct gaagggccaa   4800
ttcctttttac tgttttttttt atccctattt tttgaggaag caaagttcca acaacaatgt   4860
tatgaatatg tttgaataaa tgatggagac acatgtgact ttccgattag aatatgacta   4920
cataaaaaaa ttagctttga gtctatggat aagatcacaa agggatctct taacatatgt   4980
ttttatggat gtagtgttag ttgatgaaag ctaagcacga gtaaatggaa aactagagtt   5040
gtcgtgggag attctagagt ttaaaggttt tggacgattt tggactcgat cagtagaact   5100
caaattgaat ataaaagatg tgatttcaac actactacat atgaggaaag acatgttagt   5160
ttgaaaaatc aagtagtgtc cggaaggaca tctttagata tttagaatct atgctactac   5220
atatgaggaa agacatgtta gtttgaaaaa tcaagtagtg ttctgaaagg acatctttag   5280
atatttagga tctatgcata gatatttagg atctatgcat agatatttag gatctatgct   5340
acgaaaggct acgtagagat agtgataaag gtattagtca aaggatgagg tggcgccaaa   5400
catttgatgt tctatatgac aataggatac cacaaaagtt aaaaagaatc tttataggat   5460
```

```
gacaattcga tctgctatat tgttcggtgc agaatgttag tctaaaaaag acatgttcaa   5520

tacgtatgcg ctacagaaat gtatatgttg tgttggagtt tggccataaa aaaggatcga   5580

gtatgaaacg aggatacata tgatagacta gatgtaacat cggtgcgagt atgaaacgag   5640

gatacatatg atagactaga tgtaacatcg gtgcgaagaa aagctcatcc agcatcggtt   5700

aaaatggttt agac                                                      5714
```

```
<210> SEQ ID NO 19
<211> LENGTH: 577
<212> TYPE: DNA
<213> ORGANISM: Zea mays

<400> SEQUENCE: 19

actcgatcct tcctcttcct caaccgtgcg ggcgatcgat cgcaccgccc cctcgcccga     60

ccccatgcct tccacgtcgc ggtcggggta gggctcagga gacgttctct tggtgtggag    120

agtggcattg attcttcgat gctcgggcag gaaggctggg ctggggatga gaacgctgga    180

gatggaaggg ccgaggaggt gaggagaatt aacataaatg aggcagcaca tgctacagat    240

ggcactggta gggttaatgt tagcggtgct ggcggagttg aagatatcgg caactttcat    300

atcgatgttg atgcatccga ggatatattg gggaatttgc acaacatgca cttcttgagg    360

gtggacaatc ttggacggat gatttaactg ttgttatggt ttactggggc tatgattagc    420

caggccgact cttgctgttc aagtgttcat ttgagtgtaa ttgttccatc cctgttatgt    480

aatgttgtag ttgtagactt gtagtctacc tggtacctgt agttacttaa catcaggcag    540

ggaaaaattt gtatgttcat taaaaaaaaa aaaaaaa                             577
```

```
<210> SEQ ID NO 20
<211> LENGTH: 4090
<212> TYPE: DNA
<213> ORGANISM: Zea mays

<400> SEQUENCE: 20

cacactcact cgtcggctta gggacccccc ggtctcgaaa cgccgacact actcttgagg     60

agattattag attatcataa tctaggcttt agattatata atctgaacac ataatctagt    120

tgtttgttta tctaatggat tatttacgct agattatata atctggagag attataatct    180

gaaacaaaca tggccttagt gattaaaaat aaaaataagg ggtaaaatca caattgtaaa    240

gtgagagaag gctataatca caattaacca taaaaagtta atattatttt caggttaatt    300

ttgagtatat ccttctcttc ccttacagtt atgattttac cccttatttt taatttttgt    360

aatcaataat tcacaaagtt gaaaacgtat aatcacagtt gtccttaaaa ttaaatgtgc    420

tgcccaacaa aatactctcg gactgacaga cagtcgccag tcaagagccc ctcgggcagc    480

aggatcttcc ccctccccaa aaccaaacca gctgcctccg acagcatcca ccttttcctc    540

ccccaaacca tggacttctc caccggcggg agcgtgagcg ggggcggcgg aggcgccagc    600

gacggccccg cgcaggcgga gcgctggctg gagatcgccg agaagctcct cgcggcgcgc    660

gacctcgtcg gctgcaagcg cttcgcggag cggtcggtgg aggcgaaccc gctcctcgcc    720

ggcgttgacg aactcctcgc cgtcgccgac gtcctcctcg cttcccagtt catgggcacc    780

tcgggccagc cggacccgct cgccatcctc cagctgccgc ccggagtcag ccccgaccag    840

gccgccgtgt cccgcgcctt ccgccgcctc gcgctcctcc tcggtcccag caacccgcac    900

ccgggagccg agatggcgct ccgcctcgtc aacgacgcct acgccttcct ctcggatccc    960
```

```
tctcgccgcc ccccgccgcc cgccgatccc gccactggta cccccttactc ctcccagtat   1020

cccgccgcgg ccgctcccgc ctccgacacc ccggagttct ggacggcgtg cccccttctgc   1080

tgctacgtgc accagtaccc gcgcagcctg atcgggcgcg ccctcaagtg ccccaacgcg   1140

ggctgccgcc gcggattcgt ggcttctgag ctcccgaccc cacccacggt tgtgccgggc   1200

actgaaatgt accactgcgc ctgggggttc ttccccctcg gatttcccaa cgcggccgac   1260

ctgggtgcca actggaagcc attctacaag atgttccctt ggaacacggc tcccagtggc   1320

caaggtggtg gtggtaggag tcacggaaac catggtggta ggcagccaca gaatgacagt   1380

gctcgtggtg gctcttctag aggtaggatc aagaagacga cggcccgcaa gaaggtcggg   1440

gtagggctca ggagacgttc tcttggtgtg gagagtggca ttgattcttc gatgctcggg   1500

caggaaggct gggctgggga tgagaacgct ggagatggaa gggccgagga ggtgaggaga   1560

attaacataa atgaggcagc acatgctaca gatggcactg gtagggttaa tgttagcggt   1620

gctggcggag ttgaagatat cggcaacttt catatcgatg ttgatgcatc cgaggatata   1680

ttggggaatt tgcacaacat gcacttcttg agggtggaca atcttggacg gatgatttaa   1740

ctgttgttat ggtttactgg ggctatgatt agccaggccg actcttgctg ttcaagtgtt   1800

catttgagtg taattgttcc atccctgtta tgtaatgttg tagttgtaga cttgtagtct   1860

acctggtacc tgtagttact taacatcagg cagggaaaaa tttgtatgtt cattagatgg   1920

agatacatgc catttgcctt agcaaacaca ctttgtggag gtttccagtg atgggataat   1980

gcttcgcaga ggtgtggttg gactggcaat gcttaccatg ccacttctgg tttcttcctg   2040

gcatggtgac acaaaatgtt gttgagatca agtaagtgaa ttatgttctg ctttctgagt   2100

tcggtaaact tctttggcta caaaaggact aagcttagtt atgctaactt gttgatttgg   2160

ttgtgatcat tgcatcattc tgctgtgtga attgatactt aatacctctg atttttttata   2220

gcctgcttac aattacatat gttacctaat gagatatatt ccattttcca ttgattctgt   2280

taacaatatt cataccactt tggtcgtgat aaattcattt gactattgta tagaagtcat   2340

atatgtctac atgtgaagtg aatgatccat tatcagatac acatgaattc tcatagtgtt   2400

gcttgatatg tcaccgttta agtttgctcc tacagaagat aggattcgat gattacatgt   2460

aacaaagatt agttgtgatt ttgtctatta attggatgag atattatctt gaagcaaaag   2520

gtcatcgaga accataaaaa atgggttaat cccacagcag actagtactg tccgctaaat   2580

acaagtgctt acctttcctg gaccatttaa tctttgaaac acacgcagaa cttgttatag   2640

ataatctttg tgatagcatg gaatagaaat cattgacttg ggtgcctaac atagcaagca   2700

attgacgatt ttgagttact catgtccatt tttgctgagt atccatatta atgcagacgg   2760

ccatagttca ttttcgtgtc gttatttttc attgagatag aacaaaacag cgacttctct   2820

tggggagtac acttattacc aacgctggca tcctgttatc tagtttaatc tgaacctgtt   2880

cttgaaaact gtgtttcaga aagtcacttg ccttggtttg ttctataata ttcttctgtg   2940

ctatgagcta tggtaagcaa aatatttcga attttaaagc agttttctaa atgatgcaaa   3000

ggcagattgg tttgagattg cacatctaca gaattctttt gactaacatc ttatcttagc   3060

caagcagtag ttaagattaa ctgttttact caccaagtag aactcttcaa agctcagact   3120

aagcattttg tggtttctta ctaactcctt tgtttggcaa cccgcagtgg gttgtccata   3180

ccatgccctg aatgaagcaa agtttcttgg ccgattggcc cagcttagtg gggatatcag   3240

cagccctagc ctgaagggcc aattcctttt actgtttttt ttatccctat tttttgagga   3300

agcaaagttc caacaacaat gttatgaata tgtttgaata aatgatggag acacatgtga   3360
```

```
ctttccgatt agaatatgac tacataaaaa aattagcttt gagtctatgg ataagatcac   3420
aaagggatct cttaacatat gtttttatgg atgtagtgtt agttgatgaa agctaagcac   3480
gagtaaatgg aaaactagag ttgtcgtggg agattctaga gtttaaaggt tttggacgat   3540
tttggactcg atcagtagaa ctcaaattga atataaaaga tgtgatttca acactactac   3600
atatgaggaa agacatgtta gtttgaaaaa tcaagtagtg tccggaagga catctttaga   3660
tatttagaat ctatgctact acatatgagg aaagacatgt tagtttgaaa aatcaagtag   3720
tgttctgaaa ggacatcttt agatatttag gatctatgca tagatattta ggatctatgc   3780
atagatattt aggatctatg ctacgaaagg ctacgtagag atagtgataa aggtattagt   3840
caaaggatga ggtggcgcca aacatttgat gttctatatg acaataggat accacaaaag   3900
ttaaaaagaa tctttatagg atgacaattc gatctgctat attgttcggt gcagaatgtt   3960
agtctaaaaa agacatgttc aatacgtatg cgctacagaa atgtatatgt tgtgttggag   4020
tttggccata aaaaaggatc gagtatgaaa cgaggataca tatgatagac tagatgtaac   4080
atcggtgcga                                                          4090
```

<210> SEQ ID NO 21
<211> LENGTH: 10452
<212> TYPE: DNA
<213> ORGANISM: Zea mays

<400> SEQUENCE: 21

```
tgcggataga cttcagagga aaggactacc gcacccggtg gtttgtccat tatgtgatca     60
agagcaggaa actatcttgc acctcttgtg ctcttgcagt ttcgctagac aattttggca    120
tgttatattt tcagctttga ggatgggcca tcttacgcct actagagagg cgggctcttt    180
tgtggattgg tgggaaaagg tgcataggag agtccccaaa catatcagaa aaaggttttc    240
atagtctcat tatcctaggg gcctggtgtt tatggctaca tcgcaataag gcggtttttg    300
atggtgtcaa cccttcattg agcaccattc agaggctttt catggatgag gtggaatgct    360
ggtatatggc tggtgcaaag cagctcgaga gtctcggact tctggctgct tttgctagga    420
tcagggctat tcctagtgca tgaggctgta ctatttttcc tttttatttt ttgcctgctt    480
ggctttgtac tttggtccat ttcggacctt tctctctttc aatataatga tgcgcagttt    540
tcctgcgtgt tcgagaaaaa aaaatataaa cttctctcta tagtaaccta gcataagtgc    600
actcaaagaa aatatgtatc agatggtttg tggctcaaaa gagcaagttg tgtcactatt    660
tcaatttctt tttgataaaa ttaccttttg tgagattgtg agaatgaccc tcttttttttg    720
aaagaactac atgaagattt ttatctttaa aggtatcttt agacaccaaa ttattcataa    780
aacattaatt ccattagtaa ctaagaattt atacatataa ttaatagaaa agataccatc    840
tttatgcaag tgccaaacaa acacgttaga ttcttgtttt agcaatttag cttgccatga    900
tttttattta ggtaagattc gaaaaccctt tgttttgggc ctttcctccc taaccacccc    960
cacatacact ccatcatatt tttacttttc caagttttgt ttggtttata aaatagaatg   1020
aaataatctg ccattacttt attcctcaca atctaataat tactactagt aagataagag   1080
ataattgtga ttataccctt cgttggcctt gcaattgtga ttttactctg cattttcaac   1140
tttctaattt tacacctccg ttttaaatac gaagctacca tttgcccttc actctcaaca   1200
tcgttagtga aaatcagaat tagtgattaa aaataaaaaa atgagaaaat aaatgggtga   1260
aaggttcaaa ctaccttttt ctattcttta tgggcacaac cctaataggg gtgaaatcac   1320
```

-continued

```
tattacataa tataacgagg gtaaaatcaa aataaattgc ttgggtattt ttatcttttg   1380
catcaaattt aacattgtta actgcatcta acggcacaag ggtatggcaa ctcttcgttt   1440
tcaaaatgaa gggataaaat atcacaaagt tgaaaaacga tgggtaaaat cacaatttca   1500
agaccagaga gggtataatc acaaataccc tataagataa atagagtcat tatatcattt   1560
tttgtaagat atacttgggg atacatcaac tcatccttag agtttgtttg ggactgtgcg   1620
gctctatatt tcaaccaaac aagtgtagct aaaaaaggtg aagttaaaag agaagtactc   1680
tagaaactct aaattaaatt tagagaaaat tcctggtatg ccatcaaatt ttatactcat   1740
tccttgtgtg ccactgagtg gcatataggt atatttttg gtgtctatga catgtggggt    1800
cagtggcata caaggaatga gtatattttc tagtggcata cagggaattg gcccttaaat   1860
ttatggagta gattttgagg atagatctaa ccaggcttga tgatgacatg tcactgtatt   1920
acaacattga tgaagatctt tcacttgagg aaaatactat tgtgcaacca aacattctat   1980
acaatccaac tatcaaaagt cacaaaaata tttaaaaaat tatacatata tattatttac   2040
tttatcaata tatcatattt aagatcctag attgatttat gctatgttaa tatataattc   2100
attcatctta tataacaagg tatatatttt tggtacagtc tttggagcga aactttgact   2160
atttgtttat ttcaaaatat gctatcaata aaaacataac gagcattaaa ttaaagtaat   2220
ttttgaatac aaatcaagta tataacatgt atatactaaa atatatgctt ttggctgaat   2280
tactagtcaa aagttttaaa acattgagtc tttttttttt aaaatgcagg ccttatttta   2340
cggaattgag ggaatttttt ttatctaatt gaatatattt tttcttttac tattgtataa   2400
atttaaactt aaaattttat aatctaataa agtaaacaat aaattatatt tatatatttt   2460
tagaattttt tatggttttt ggtagtccaa ttatacattg attgtatgca aaacttgctc   2520
tgcggtgggg cgctacaatg gtctggtatg tttgcatatg ggaaaactaa tagcccgttc   2580
ccttggtttt aattcgaaac ggcttttact atttctgtag tgttttggtc tctgtgaatt   2640
gcagctacaa taatctaaac aactgacttt aattcgaagc taacaggcta taagacgctc   2700
tccaacggat cctttcccct ccccttcacg acgtattcgg tgatttcgta catcgagaga   2760
gcttcaacag gtccctctcc tccctcttgt agggtgagag aaggaaaaca ccttgtaaaa   2820
cgagaaagat agaaccctac tcttcactaa ttagtgtttt taactataaa attaatctgc   2880
tataagtttg gttaagtgac aatgtgtatt atgatattat aaatattaaa aactctaaaa   2940
actgatgtag aaaagtcaaa tagcttagtt aaagggtaaa gggagagctg aatagaggga   3000
tgcttggaga ggaggtaaaa tagggaaata atagtgaaga tgaggatatt taaatatgaa   3060
tagaaagtcc aaatgtggga tttgagatgg agaatgattg gagagagcct aataaaatca   3120
agggataatt gtgattatac ccttttctaa tattttaatt gtgattttat cccttctttt   3180
ttaactttgt taccccctctg ttttgaaaac aaagccgttg tttgcaccgc cttatcaacg   3240
ttaataaaaa tcagaattag tgattaaaaa taaaaataag gggtaaaatc acaattgtaa   3300
agtgagagaa ggctataatc acaattaacc ataaaaagtt taatattatt ttcagattaa   3360
ttttgagtat atccttctct tcccttacaa ttatgatttt acccctcatt tttaattttc   3420
gtaatcaata attcacgaag ttgaaaacgt ataatcacag ttgtccttaa aataaatgtg   3480
ctgcccaaca aaatactctc ggactgacag acagtcgcca gtcaagagcc cctcgggcag   3540
caggatcttc cccctcccca aaaccaaacc agctgcctcc gacagcatcc accttttcct   3600
cccccaaacc atggacttct ccaccggcgg gagcgtgagc gggggcggcg gaggcgccag   3660
cgacggcccc gcgcaggcgg agcgctggct ggagatcgcc gagaagctcc tcgcggcgcg   3720
```

```
cgacctcgtc ggctgcaagc gcttcgcgga gcggtcgatg gaggcgaacc cgctcctcgc   3780
tggcgttgac gagctcctcg ccgtcgccga cgtcctcctc gcttcccagt tcatgggccc   3840
ctcgggccag ccggacccgc tcgccatcct ccagctgccg cccggagtca gccccgacca   3900
ggccgccgtg tcccgcgcct tccgccgcct cgcgctcctc ctcggcccca gcaacccgca   3960
cccgggagcc gagatggcgc tccgcctcgt caacgacgcc tacgccttcc tctcggatcc   4020
ctctcgccgc cccccgccgc ccgccgatcc cgccactggt accccttact cctcccagta   4080
tcccgccgcg gccgctcccg cctcggacac cccggagttc tggacggcgt gccccttctg   4140
ctgctacgtg caccagtacc cgcgcagcct gatcgggcgc gccctcaagt gccccaacgc   4200
gggctgccgc cgcggattcg tggcttctga gctcccgacc ccacccaccg ttgtgccggg   4260
cactgaaatg taccactgcg cctgggggtt cttcccccctc ggatttccca acgcggccga   4320
cctgggtgcc aactggaagc cattctacaa gatgtttcct tggaacacgg ctcccagtgg   4380
ccaaggtggt ggtggtagga gtcacggaaa ccatggtggt aggcagccac agaatgacag   4440
tgctcgtggt ggctcttcta gaggtaggat caagaagacg acggcccgca agaaggtcgg   4500
ggtagggctc aggagacgtt ctcttggtgt ggagagtggc attgattctt cgatgctcgg   4560
gcaggaaggc tgggctgggg atgagaacgc tggagatgga agggccgagg aggtgaggag   4620
aattaacata aatgaggcag cacatgctac agatggcact ggtagggtta atgttagcgg   4680
tgctggcgga gttgaagata tcagcaactt tcatatcgat gttgatgcat ctgaggatat   4740
attggggaat ttgcacaaca tgcacttctt gagggtggac aatcttggac ggatgattta   4800
actgttgtta tggtttactg ggctatgat tagccaggcc gaagcagatg tctcagagac   4860
tggctcttgc tgttcaagtg ttcatttgag tgtaattgtt ccatccctgt tatgtaatgt   4920
tgtagttgta gacttgtagt ctacctggta cctgtagtta cttaacatca ggcagggcaa   4980
aatttgtatg ttcattagat ggagatacat gccatttgcc ttagcaaaca cgctttgtgg   5040
aggtttccag tgatgggata atgcttcaca gaggtctggt tggactggca atgcttacca   5100
tgccacttct ggtttcttcc tggcatggtg acacaaaatg ttgttgagat caagtaagtg   5160
aattatgttc tgctttctga gttcggtaaa cttctttggc tacaaaagga ctaatcttag   5220
ttatgataac ttgttgactt ggttgtgatc attgcatcat tctgctgtct gaattgatac   5280
ttaatacctc tgattttta tagcctgctt acaattccat atgttaccta atgagatata   5340
ttccattttc cattgattct gttaacaata ttcataccac ttttgtagtc atatatgtct   5400
acatgtgaag tgaatgatcc tttatcagat acacatgaat tctcatagtg ttgcttgata   5460
tgtcaccgtt taagtttgct cctacagaag ataggattcg atgatgacat gtaacaaaga   5520
ttacttgtga ttttgtctat taattggatc agatattatc ttgaagcaaa aggccatcga   5580
gaaccataaa aaatgggtta atcccacagc agactagtac tgtccgctaa atacaagtgc   5640
ttacctttca tggatcattt aatgtttgaa acacactcag aacttgttat agataatctt   5700
tgcgatatca tggaatataa atcattgact tgggtgctta acatagcaag cacttgacga   5760
ttttgagtta ctcatgtcca tttttgctgc gtatccatat taatgcagac ggccatagtt   5820
catttttgtg tcgttatttt tcattgagaa agaacaaaac agtgacttct cttggggagt   5880
agacttatta ccaacgctgg catcctgtta tctagtttaa tctgaacctg ttcttgaaaa   5940
ctgtgtttca gaaagtcact tgccttggtt tgttctataa tattcttctg tgctatgagc   6000
tattgtaagc aaaatatttc gaattttaaa gcagttttct aaatgatgca aaggcagatt   6060
```

-continued

```
ggtttgagat tgcacatcta cagaattctt ttagctaaca tcttatctta gccaagcagt   6120
agttaagatt aactgtttta ctcaccaagt agaactcttc aaagctcaga ctaagcattt   6180
tgtggtttct tactaacttc tttgtttggc aatccgcagt gggttgtcca tatcatgccc   6240
tgaatgaagc aaagtttctt ggccgattgg cccagcttag tggggatatc agcagctcta   6300
gcctgaaggg ccaattcctt ttactgtttt ttatccctgt tttttgagga agcaaagttc   6360
caacaacaat gttatgaata tgtttgaata aatgatggag acacatgtga cttttcgatt   6420
agaatatgac tacataaaaa attagctgag tctatggata agatcacaaa gggatatctc   6480
ttaacatatg ttttttatgg atgtagtgtt agttgatgaa agctaagcac gagtaaatag   6540
aaaactagag ttgtggtggg agattctaga gtttaaaggt tttggacgat tttggactcg   6600
atcagtagaa ctcaaattga atataaaaga tgtgatttca acactactac atatgaggaa   6660
agacatgtta gtttgaaaaa tcaagtagtg tccaggaagg acatctttag atatttagga   6720
tctatgctac tacatattag gaaagacatg ttagtttgaa aaatcaagta gtgtccatga   6780
aggacatctt tagatattta ggatctatgc tacgtagaga tattgataaa ggtattagtc   6840
aatggatgag gtagcgccaa acatttgata ttctatatga caataggata ccacaaaagt   6900
taaaaagaag ttttatagga tgacaattcg atctgctatg ttgttcggtg caaaatgtta   6960
gtctaaaaaa gacatgttca atacatatgc gctacagaaa tgcatatgtt gtgttggagt   7020
ttggccataa aaaaggatcg agtatgaaac gacgatacat atgatagact agatgtaaca   7080
ccggtgcgaa gaaaacctca tccaacatcg gttgaaatgg tttagacata tcaataaaga   7140
ctttcagatg caccaataat tccttcttcg ctttcctttc ttcctttttt ttatcacaaa   7200
caagttaaag aacacggctc tctttgatcc tctgtattga agctactagt ttgctacgaa   7260
aattgaaaag catcatataa acatgtatgc ttgcgacctt taggtacata agaatgcaac   7320
ctcaataata ccaaacgaat cgcctcacca atcaccacca ccacaggagc aaccagccaa   7380
acatttcttg cagcactctg ggcgacctgg aacgataatc ccggaatgca gcaaatggct   7440
gcttacgcga tacgaaggaa gcggtcctat ccaatgcttt gttctttaac aaattcaccc   7500
cattctaaat ttgtccagct acgccagcac gagcctgcag tgtctcggta cgtttgcttt   7560
tttccatttg ttccaccagc cagtctatgc cagatttgat ccccctcctg caagagccgg   7620
tgtcacattt aaacaatata acagatcttt agaatatcat gcacccagga aacaatataa   7680
cagacgaatg tgtgaatttt tttgtatctt tgagtaaaat tgtcattttt ttcatggcga   7740
gtcaaatttc ctcaggaacc agttgagttt ctgcgctcac ccatcatatg cagatacagc   7800
ctgaaatgta tatgtcctct catccagttc tttatgcaga aatttagcca attcttcctc   7860
atcaatggct ccaggtaaat cctgccaaaa gaaatccaga agcaccctcc aaacatgaga   7920
acaagctaga ggtaaataat aaacaatttg atagaataat gtgtacccag cttaacagaa   7980
acagacagtg catgtagtca ttggtttcca tgtgatcttt tcaggaagtt ttaattgatt   8040
taaaaactac atctggtatt caacctcgca atggcgcata ggcgctttgc aacgtaggaa   8100
tttatatttg tatgcctcac agcatgtgca catgacaaaa acaaaatctt tattttaact   8160
acgatggcaa ctttattgta agcactaaat ctttcaatca taattatgta ctgtggtaca   8220
aaatatagaa agtggaagta aacccttcac ctgtttgttt gcaactatca agagtggtgc   8280
tcctctcaga tgttcatggc gaataacctt ctctgaagta agaaatttag gttaggttct   8340
ctagaatgag ttctcatccc atttaccaga gaggcattgc atcttctgga aagatctagc   8400
aatagaaaca aaccagtact ccctctgttc caagttataa gacgatgttt tagcttttct   8460
```

```
agatatattg ttttaactat gtaccaggac attatatata tttttaatat ttaagtccat   8520
agcaaaattt atttatctag aaaaaggcca aaatgtctta taatttggaa tggatggcgt   8580
agtttataat tgacacaaat aagaacctta cccaaagcag atttggaatc ttcaaatgac   8640
gatgctgtgg cagcgtcaat aacgtacatt atggcatggg cctcttcata gtatttctcc   8700
cagattgttc gtaggctaac ctgccaagca ggcaagtgtg taagaaatac tgaacttggc   8760
atggaagctt aattatcata ctagcaagca gtgatactga agttagtttt acactaattc   8820
ttataacata gcagagaagc tgatgctgtt ctactagcca cccaattcta ttgagtactg   8880
tgaatgttag ccaacagagc atatctttgc tttctgaaaa ttctattgag cattccatat   8940
aactagatta tatatattct gctggaacgc aaaaagatgc taggttaata actaaagcaa   9000
ccacatccta gtaatttgat tttatgacat gtatttccca ggcattagaa accctgatat   9060
agcaccaaac tgacaagact caaatatcaa cgatcgtagg gtggtgccac ggcaacagaa   9120
ggctcacttt actacgtacg taaacgttct tacctgacca cctagatccc agaaaacaag   9180
ttttgccttt gcgtcttcga tgcggccaat gttgagccca actgttggaa cgacacggtc   9240
aggcggaagt ccttcccccct tgagatatat cgatttcaac ttctccagca aagtctatgg   9300
caacggttcc agaaacattg tgtacaggta agtttcatca atttctagtt cagaaaggga   9360
aatatatata tatgaaggct gggagctagc agctaccgtc ttgccagctc tgtcaacacc   9420
aagaatcaga acacggaact cgtccttggc gaacacatac ttccacaggc catagaacaa   9480
ggagaacatt tccgcttata tatatatatc cggcgataag caaccgccag cacgttacgt   9540
cctgaaaaac gaatcatacg ttacaaacat tttctccgat cagtaacagt acgcagccaa   9600
aagcatgtac gccccaaatt gccagacgca aaactaggaa ccatcctcat agtacagggc   9660
cgcagcattt caatccacaa cgaaatggta tcgaccgagt aaaaataagg ggagaggata   9720
taacttaact gaaccatcgg gcgggagagt acaactacag actacagagg ggagaggatg   9780
ttgagatcta gatagctcac cggagcgctc gaaggctcct tgatcgcgcc gcttcagacg   9840
acaccacccg ctcccgtgtg gactggagcg cgggaggctg agggcgggtt ttgagccgcg   9900
cggcggtggg agcgcgccca ccggagttag gaactggggc actcgcctcg ccagtcgcca   9960
cacggcttgg gttcggttga ctcgatgggc gtcacggtgg gcgacttgga actggaaccc  10020
acgcaggagc aggacccgtg ggctatgat cggtgggtcc tgcaggattc tgggacggga  10080
ggccctaccg ctcagtgagg ttatcgtact gccagtggga attcgtgatg tgactgtacc  10140
agtggttgac ccggaaggaa ggcactggct ggcaggaggg ctttgccatt aataaaaaca  10200
taaattattg catctgacaa gtttagtgga gagctaacgg tgccaaatgt tgcgcttgcc  10260
tttctacctg cagtcagtcc tattcagccc agctcattta gcccggtctc ggactctcgg  10320
cccacatggc agcccatacc atgacactct ccacctctcg aaatgtcagc ccataccatg  10380
acattcactt aaggggtgtt tgaatgcact agagctaata gttagtagct aaaattagtt  10440
gagacatcca aa                                                      10452
```

<210> SEQ ID NO 22
<211> LENGTH: 6816
<212> TYPE: DNA
<213> ORGANISM: Zea mays

<400> SEQUENCE: 22

```
tgtcccgcgc ctcccgccgc ctcgcgctcc tcctcggccc cagcaacccg cacccgggag     60
```

-continued

```
ccgagatggc gctccgcctc gtcaacgacg cctacgcctt cctctcggat ccctctcgcc    120
gccccccgcc gcccgccgat cccgccactg gtacccctta ctcctcccag tatcccgccg    180
cggccgctcc cgcctcggac accccggagt tctggacggc gtgccccttc tgctgctacg    240
tgcaccagta cccgcgcagc ctgatcgggc gcgccctcaa gtgccccaac gcgggctgcc    300
gccgcggatt cgtggcttct gcgacgcggg ctgccgccgc ggattcgtgg cttctgagct    360
cccgacccca cccaccgttg tgccgggcac tgaaatgtac cactgcgcct gggggttctt    420
ccccctcgga tttcccaacg cggccgacct gggtgccaac tggaagccat tctacaagat    480
gtttccttgg aacacggctc ccagtggcca aggtggtggt ggtaggagtc acggaaacca    540
tggtggtagg cagccacaga atgacagtgc tcgtggtggc tcttctagag gtaggatcaa    600
gaagacgacg gcccgcaaga aggtcggggt agggctcagg agacgttctc ttggtgtgga    660
gagtggcatt gattcttcga tgctcgggca ggaaggctgg gctggggatg agaacgctgg    720
agatggaagg gccgaggagg tgaggagaat taacataaat gaggcagcac atgctacaga    780
tggcactggt agggttaatg ttagcggtgc tggcggagtt gaagatatca gcaactttca    840
tatcgatgtt gatgcatctg aggatatatt ggggaatttg cacaacatgc acttcttgag    900
ggtggacaat cttggacgga tgatttaact gttgttatgg tttactgggg ctatgattag    960
ccaggccgaa gcagatgtct cagagactgg ctcttgctgt tcaagtgttc atttgagtgt   1020
aattgttcca tccctgttat gtaatgttgt agttgtagac ttgtagtcta cctggtacct   1080
gtagttactt aacatcaggc agggcaaaat ttgtatgttc attagatgga gatacatgcc   1140
atttgcctta gcaaacacgc tttgtggagg tttccagtga tgggataatg cttcacagag   1200
gtctggttgg actggcaatg cttaccatgc cacttctggt ttcttcctgg catggtgaca   1260
caaaatgttg ttgagatcaa gtaagtgaat tatgttctgc tttctgagtt cggtaaactt   1320
ctttggctac aaaaggacta atcttagtta tgataacttg ttgacttggt tgtgatcatt   1380
gcatcattct gctgtctgaa ttgatactta atacctctga ttttttatag cctgcttaca   1440
attccatatg ttacctaatg agatatattc cattttccat tgattctgtt aacaatattc   1500
ataccacttt tgtagtcata tatgtctaca tgtgaagtga atgatccttt atcagataca   1560
catgaattct catagtgttg cttgatatgt caccgtttaa gtttgctcct acagaagata   1620
ggattcgatg atgacatgta acaaagatta cttgtgattt tgtctattaa ttggatcaga   1680
tattatcttg aagcaaaagg ccatcgagaa ccataaaaaa tgggttaatc ccacagcaga   1740
ctagtactgt ccgctaaata caagtgctta cctttcatgg atcatttaat gtttgaaaca   1800
cactcagaac ttgttataga taatctttgc gatatcatgg aatataaatc attgacttgg   1860
gtgcttaaca tagcaagcac ttgacgattt tgagttactc atgtccattt ttgctgcgta   1920
tccatattaa tgcagacggc catagttcat ttttgtgtcg ttatttttca ttgagaaaga   1980
acaaaacagt gacttctctt ggggagtaga cttattacca acgctggcat cctgttatct   2040
agtttaatct gaacctgttc ttgaaaactg tgtttcagaa agtcacttgc cttggtttgt   2100
tctataatat tcttctgtgc tatgagctat tgtaagcaaa atatttcgaa ttttaaagca   2160
gttttctaaa tgatgcaaag gcagattggt ttgagattgc acatctacag aattctttta   2220
gctaacatct tatcttagcc aagcagtagt taagattaac tgttttactc accaagtaga   2280
actcttcaaa gctcagacta agcattttgt ggtttcttac taacttcttt gtttggcaat   2340
ccgcagtggg ttgtccatat catgccctga atgaagcaaa gtttcttggc cgattggccc   2400
agcttagtgg ggatatcagc agctctagcc tgaagggcca attcctttta ctgtttttta   2460
```

```
tccctgtttt ttgaggaagc aaagttccaa caacaatgtt atgaatatgt ttgaataaat   2520

gatggagaca catgtgactt ttcgattaga atatgactac ataaaaaatt agctgagtct   2580

atggataaga tcacaaaggg atatctctta acatatgttt tttatggatg tagtgttagt   2640

tgatgaaagc taagcacgag taaatagaaa actagagttg tggtgggaga ttctagagtt   2700

taaaggtttt ggacgatttt ggactcgatc agtagaactc aaattgaata taaaagatgt   2760

gatttcaaca ctactacata tgaggaaaga catgttagtt tgaaaaatca agtagtgtcc   2820

aggaaggaca tctttagata tttaggatct atgctactac atattaggaa agacatgtta   2880

gtttgaaaaa tcaagtagtg tccatgaagg acatctttag atatttagga tctatgctac   2940

gtagagatat tgataaaggt attagtcaat ggatgaggta gcgccaaaca tttgatattc   3000

tatatgacaa taggatacca caaaagttaa aaagaagttt tataggatga caattcgatc   3060

tgctatgttg ttcggtgcaa aatgttagtc taaaaaagac atgttcaata catatgcgct   3120

acagaaatgc atatgttgtg ttggagtttg gccataaaaa aggatcgagt atgaaacgac   3180

gatacatatg atagactaga tgtaacaccg gtgcgaagaa aacctcatcc aacatcggtt   3240

gaaatggttt agacatatca ataaagactt tcagatgcac caataattcc ttcttcgctt   3300

tcctttcttc cttttttta tcacaaacaa gttaaagaac acggctctct ttgatcctct   3360

gtattgaagc tactagtttg ctacgaaaat tgaaaagcat catataaaca tgtatgcttg   3420

cgacctttag gtacataaga atgcaacctc aataatacca aacgaatcgc ctcaccaatc   3480

accaccacca caggagcaac cagccaaaca tttcttgcag cactctgggc gacctggaac   3540

gataatcccg gaatgcagca aatggctgct tacgcgatac gaaggaagcg gtcctatcca   3600

atgctttgtt ctttaacaaa ttcaccccat tctaaatttg tccagctacg ccagcacgag   3660

cctgcagtgt ctcggtacgt ttgctttttt ccatttgttc caccagccag tctatgccag   3720

atttgatccc cctcctgcaa gagccggtgt cacatttaaa caatataaca gatctttaga   3780

atatcatgca cccaggaaac aatataacag acgaatgtgt gaattttttt gtatctttga   3840

gtaaaattgt catttttttc atggcgagtc aaatttcctc aggaaccagt tgagtttctg   3900

cgctcaccca tcatatgcag atacagcctg aaatgtatat gtcctctcat ccagttcttt   3960

atgcagaaat ttagccaatt cttcctcatc aatggctcca ggtaaatcct gccaaaagaa   4020

atccagaagc accctccaaa catgagaaca agctagaggt aaataataaa caatttgata   4080

gaataatgtg tacccagctt aacagaaaca gacagtgcat gtagtcattg gtttccatgt   4140

gatcttttca ggaagtttta attgatttaa aaactacatc tggtattcaa cctcgcaatg   4200

gcgcataggc gctttgcaac gtaggaattt atatttgtat gcctcacagc atgtgcacat   4260

gacaaaaaca aaatctttat tttaactacg atggcaactt tattgtaagc actaaatctt   4320

tcaatcataa ttatgtactg tggtacaaaa tatagaaagt ggaagtaaac ccttcacctg   4380

tttgtttgca actatcaaga gtggtgctcc tctcagatgt tcatggcgaa taaccttctc   4440

tgaagtaaga aatttaggtt aggttctcta gaatgagttc tcatcccatt taccagagag   4500

gcattgcatc ttctggaaag atctagcaat agaaacaaac cagtactccc tctgttccaa   4560

gttataagac gatgttttag cttttctaga tatattgttt taactatgta ccaggacatt   4620

atatatattt ttaatattta agtccatagc aaaatttatt tatctagaaa aaggccaaaa   4680

tgtcttataa tttggaatgg atggcgtagt ttataattga cacaaataag aaccttaccc   4740

aaagcagatt tggaatcttc aaatgacgat gctgtggcag cgtcaataac gtacattatg   4800
```

```
gcatgggcct cttcatagta tttctcccag attgttcgta ggctaacctg ccaagcaggc   4860

aagtgtgtaa gaaatactga acttggcatg gaagcttaat tatcatacta gcaagcagtg   4920

atactgaagt tagttttaca ctaattctta taacatagca gagaagctga tgctgttcta   4980

ctagccaccc aattctattg agtactgtga atgttagcca acagagcata tctttgcttt   5040

ctgaaaattc tattgagcat tccatataac tagattatat atattctgct ggaacgcaaa   5100

aagatgctag gttaataact aaagcaacca catcctagta atttgatttt atgacatgta   5160

tttcccaggc attagaaacc ctgatatagc accaaactga caagactcaa atatcaacga   5220

tcgtagggtg gtgccacggc aacagaaggc tcactttact acgtacgtaa acgttcttac   5280

ctgaccacct agatcccaga aaacaagttt tgcctttgcg tcttcgatgc ggccaatgtt   5340

gagcccaact gttggaacga cacggtcagg cggaagtcct tccccccttga gatatatcga   5400

tttcaacttc tccagcaaag tctatggcaa cggttccaga aacattgtgt acaggtaagt   5460

ttcatcaatt tctagttcag aaagggaaat atatatatat gaaggctggg agctagcagc   5520

taccgtcttg ccagctctgt caacaccaag aatcagaaca cggaactcgt ccttggcgaa   5580

cacatacttc cacaggccat agaacaagga gaacatttcc gcttatatat atatatccgg   5640

cgataagcaa ccgccagcac gttacgtcct gaaaaacgaa tcatacgtta caaacatttt   5700

ctccgatcag taacagtacg cagccaaaag catgtacgcc ccaaattgcc agacgcaaaa   5760

ctaggaacca tcctcatagt acagggccgc agcatttcaa tccacaacga aatggtatcg   5820

accgagtaaa aataaggga gaggatataa cttaactgaa ccatcgggcg ggagagtaca   5880

actacagact acagagggga gaggatgttg agatctagat agctcaccgg agcgctcgaa   5940

ggctccttga tcgcgccgct tcagacgaca ccacccgctc ccgtgtggac tggagcgcgg   6000

gaggctgagg gcgggttttg agccgcgcgg cggtgggagc gcgcccaccg gagttaggaa   6060

ctggggcact cgcctcgcca gtcgccacac ggcttgggtt cggttgactc gatgggcgtc   6120

acggtgggcg acttggaact ggaacccacg caggagcagg acccgtgggg ctatgatcgg   6180

tgggtcctgc aggattctgg gacgggaggc cctaccgctc agtgaggtta tcgtactgcc   6240

agtgggaatt cgtgatgtga ctgtaccagt ggttgacccg gaaggaaggc actggctggc   6300

aggagggctt tgccattaat aaaaacataa attattgcat ctgacaagtt tagtggagag   6360

ctaacggtgc caaatgttgc gcttgccttt ctacctgcag tcagtcctat tcagcccagc   6420

tcatttagcc cggtctcgga ctctcggccc acatggcagc ccataccatg acactctcca   6480

cctctcgaaa tgtcagccca taccatgaca ttcacttaag ggtgtttga atgcactaga   6540

gctaatagtt agtagctaaa attagttgag acatccaaac actttagtta atagttcaac   6600

tattagctat ttttggtaaa ttagttaata gttagatagt tatttgttag ctagctaatt   6660

ccactaccaa tttttagcca actaactatt agttctagtg cattcaaaca cccccttagc   6720

ctggtcttaa cagagtagaa gagatgtcag caccgacaac ctgaaacctt tgctactcaa   6780

gtgcaattga tggacaagtg ctttccttgt tcttcg                             6816
```

```
<210> SEQ ID NO 23
<211> LENGTH: 3904
<212> TYPE: DNA
<213> ORGANISM: Zea mays

<400> SEQUENCE: 23

tgcggataga cttcagagga aaggactacc gcacccggtg gtttgtccat tatgtgatca     60

agagcaggaa actatcttgc acctcttgtg ctcttgcagt ttcgctagac aattttggca    120
```

```
tgttatattt tcagctttga ggatgggcca tcttacgcct actagagagg cgggctcttt    180

tgtggattgg tgggaaaagg tgcataggag agtccccaaa catatcagaa aaaggttttc    240

atagtctcat tatcctaggg gcctggtgtt tatggctaca tcgcaataag gcggtttttg    300

atggtgtcaa cccttcattg agcaccattc agaggctttt catggatgag gtggaatgct    360

ggtatatggc tggtgcaaag cagctcgaga gtctcggact tctggctgct tttgctagga    420

tcagggctat tcctagtgca tgaggctgta ctatttttcc tttttatttt ttgcctgctt    480

ggctttgtac tttggtccat ttcggacctt tctctctttc aatataatga tgcgcagttt    540

tcctgcgtgt tcgagaaaaa aaaatataaa cttctctcta tagtaaccta gcataagtgc    600

actcaaagaa aatatgtatc agatggtttg tggctcaaaa gagcaagttg tgtcactatt    660

tcaatttctt tttgataaaa ttaccttttg tgagattgtg agaatgaccc tctttttttg    720

aaagaactac atgaagattt ttatctttaa aggtatcttt agacaccaaa ttattcataa    780

aacattaatt ccattagtaa ctaagaattt atacatataa ttaatagaaa agataccatc    840

tttatgcaag tgccaaacaa acacgttaga ttcttgtttt agcaatttag cttgccatga    900

tttttattta ggtaagattc gaaaaccctt tgttttgggc ctttcctccc taaccacccc    960

cacatacact ccatcatatt tttacttttc caagttttgt ttggtttata aaatagaatg   1020

aaataatctg ccattacttt attcctcaca atctaataat tactactagt aagataagag   1080

ataattgtga ttataccctt cgttggcctt gcaattgtga ttttactctg cattttcaac   1140

tttctaattt tacacctccg ttttaaatac gaagctacca tttgcccttc actctcaaca   1200

tcgttagtga aaatcagaat tagtgattaa aaataaaaaa atgagaaaat aaatgggtga   1260

aaggttcaaa ctaccttttt ctattcttta tgggcacaac cctaataggg gtgaaatcac   1320

tattacataa tataacgagg gtaaaatcaa aataaattgc ttgggtattt ttatcttttg   1380

catcaaattt aacattgtta actgcatcta acggcacaag ggtatggcaa ctcttcgttt   1440

tcaaaatgaa gggataaaat atcacaaagt tgaaaaacga tgggtaaaat cacaatttca   1500

agaccagaga gggtataatc acaaataccc tataagataa atagagtcat tatatcattt   1560

tttgtaagat atacttgggg atacatcaac tcatccttag agtttgtttg ggactgtgcg   1620

gctctatatt tcaaccaaac aagtgtagct aaaaaaggtg aagttaaaag agaagtactc   1680

tagaaactct aaattaaatt tagagaaaat tcctggtatg ccatcaaatt ttatactcat   1740

tccttgtgtg ccactgagtg gcatataggt atattttttg gtgtctatga catgtggggt   1800

cagtggcata caaggaatga gtatattttc tagtggcata cagggaattg gcccttaaat   1860

ttatggagta gattttgagg atagatctaa ccaggcttga tgatgacatg tcactgtatt   1920

acaacattga tgaagatctt tcacttgagg aaaatactat tgtgcaacca aacattctat   1980

acaatccaac tatcaaaagt cacaaaaata tttaaaaaat tatacatata tattatttac   2040

tttatcaata tatcatattt aagatcctag attgatttat gctatgttaa tatataattc   2100

attcatctta tataacaagg tatatatttt tggtacagtc tttggagcga aactttgact   2160

atttgtttat ttcaaaatat gctatcaata aaaacataac gagcattaaa ttaaagtaat   2220

ttttgaatac aaatcaagta tataacatgt atatactaaa atatatgctt ttggctgaat   2280

tactagtcaa aagttttaaa acattgagtc tttttttttt aaaatgcagg ccttatttta   2340

cggaattgag ggaatttttt ttatctaatt gaatatattt tttcttttac tattgtataa   2400

atttaaactt aaaattttat aatctaataa agtaaacaat aaattatatt tatatatttt   2460
```

```
tagaatttt tatggtttt ggtagtccaa ttatacattg attgtatgca aaacttgctc   2520
tgcggtgggg cgctacaatg gtctggtatg tttgcatatg ggaaaactaa tagcccgttc   2580
ccttggtttt aattcgaaac ggcttttact atttctgtag tgttttggtc tctgtgaatt   2640
gcagctacaa taatctaaac aactgacttt aattcgaagc taacaggcta taagacgctc   2700
tccaacggat cctttcccct ccccttcacg acgtattcgg tgatttcgta catcgagaga   2760
gcttcaacag gtccctctcc tccctcttgt agggtgagag aaggaaaaca ccttgtaaaa   2820
cgagaaagat agaaccctac tcttcactaa ttagtgtttt taactataaa attaatctgc   2880
tataagtttg gttaagtgac aatgtgtatt atgatattat aaatattaaa aactctaaaa   2940
actgatgtag aaaagtcaaa tagcttagtt aaagggtaaa gggagagctg aatagaggga   3000
tgcttggaga ggaggtaaaa tagggaaata atagtgaaga tgaggatatt taaatatgaa   3060
tagaaagtcc aaatgtggga tttgagatgg agaatgattg gagagagcct aataaaatca   3120
agggataatt gtgattatac ccttttctaa tattttaatt gtgattttat cccttctttt   3180
ttaactttgt taccccctctg ttttgaaaac aaagccgttg tttgcaccgc cttatcaacg   3240
ttaataaaaa tcagaattag tgattaaaaa taaaaataag gggtaaaatc acaattgtaa   3300
agtgagagaa ggctataatc acaattaacc ataaaaagtt taatattatt ttcagattaa   3360
ttttgagtat atccttctct tcccttacaa ttatgatttt acccctcatt tttaattttc   3420
gtaatcaata attcacgaag ttgaaaacgt ataatcacag ttgtccttaa aataaatgtg   3480
ctgcccaaca aaatactctc ggactgacag acagtcgcca gtcaagagcc cctcgggcag   3540
caggatcttc cccctcccca aaaccaaacc agctgcctcc gacagcatcc accttttcct   3600
cccccaaacc atggacttct ccaccggcgg gagcgtgagc gggggcggcg gaggcgccag   3660
cgacggcccc gcgcaggcgg agcgctggct ggagatcgcc gagaagctcc tcgcggcgcg   3720
cgacctcgtc ggctgcaagc gcttcgcgga gcggtcgatg gaggcgaacc cgctcctcgc   3780
tggcgttgac gagctcctcg ccgtcgccga cgtcctcctc gcttcccagt tcatgggccc   3840
ctcgggccag ccggacccgc tcgccatcct ccagctgccg cccggagtca gccccgacca   3900
ggcc                                                                3904
```

```
<210> SEQ ID NO 24
<211> LENGTH: 1191
<212> TYPE: DNA
<213> ORGANISM: Zea mays

<400> SEQUENCE: 24

atggacttct ccaccggcgg gagcgtgagc gggggcggcg gaggcgccag cgacggcccc     60
gcgcaggcgg agcgctggct ggagatcgcc gagaagctcc tcgcggcgcg cgacctcgtc    120
ggctgcaagc gcttcgcgga gcggtcgatg gaggcgaacc cgctcctcgc tggcgttgac    180
gagctcctcg ccgtcgccga cgtcctcctc gcttcccagt tcatgggccc ctcgggccag    240
ccggacccgc tcgccatcct ccagctgccg cccggagtca gccccgacca ggccgccgtg    300
tcccgcgcct tccgccgcct cgcgctcctc ctcggcccca gcaacccgca cccgggagcc    360
gagatggcgc tccgcctcgt caacgacgcc tacgccttcc tctcggatcc ctctcgccgc    420
cccccgccgc ccgccgatcc cgccactggt accccttact cctcccagta tcccgccgcg    480
gccgctcccg cctcggacac cccggagttc tggacggcgt gccccttctg ctgctacgtg    540
caccagtacc cgcgcagcct gatcgggcgc gccctcaagt gccccaacgc gggctgccgc    600
cgcggattcg tggcttctga gctcccgacc ccacccaccg ttgtgccggg cactgaaatg    660
```

```
taccactgcg cctgggggtt cttccccctc ggatttccca acgcggccga cctgggtgcc    720

aactggaagc cattctacaa gatgtttcct tggaacacgg ctcccagtgg ccaaggtggt    780

ggtggtagga gtcacggaaa ccatggtggt aggcagccac agaatgacag tgctcgtggt    840

ggctcttcta gaggtaggat caagaagacg acggcccgca agaaggtcgg ggtagggctc    900

aggagacgtt ctcttggtgt ggagagtggc attgattctt cgatgctcgg gcaggaaggc    960

tgggctgggg atgagaacgc tggagatgga agggccgagg aggtgaggag aattaacata   1020

aatgaggcag cacatgctac agatggcact ggtagggtta atgttagcgg tgctggcgga   1080

gttgaagata tcagcaactt tcatatcgat gttgatgcat ctgaggatat attggggaat   1140

ttgcacaaca tgcacttctt gagggtggac aatcttggac ggatgattta a            1191
```

<210> SEQ ID NO 25
<211> LENGTH: 5776
<212> TYPE: DNA
<213> ORGANISM: Zea mays

<400> SEQUENCE: 25

```
acctagaggg ggtaaataga tgatcctgca aaattagctt taaacaacac aaacttggtt     60

tgtaaaatat gttagtgaga actaaaacca agttaggtta cgaagagagg agaaaagaga    120

actcttcact tgattgctcc tttaaaataa gtattaaagt tagtagcaat attataaata    180

aatatgagaa ttaaatagat aataatcgca ataagcagaa tggtccctct caggccaacc    240

gttccatccg tatccatttc tatcacatca tctctcacgt ctgcatgaac atgtgcacat    300

ggtatttcct tctcaaattt aacccgcgat atgaaaaaca tcgttatcaa tctttcacat    360

ctcaaaataa ctctacataa attttagtat ttgttttatt tagttcaatg agaaaaagat    420

ttgattatat acattgtagt acacctcacg ttctgcttgg acacctctat atatcttcct    480

ctaggcccta tactccctgg cccaattaaa caacacggca tcatgcagta ccaaaagaca    540

aaaacaattt ctagtagtcg agtgcctcct ctctctcctc gataccacat aatatgatat    600

atcacatggc agacggtaga taaagtaggc ggactttgct gggcatagaa aaaaaaaagg    660

atcggcgcca attaccatgg caccgatctt ctgtcacgta gacgccagat cagcgtgaaa    720

gagtgagatc tcgacgccat cttatattgg cgcgcgagac atgcaaactc ggtactaata    780

ataatggcgc cggagtaaag gttcattttt tgaattgaaa cttaaaaaga cgtatttgta    840

ataatcttac aaaaaaatat caaaataaaa aaaaagtcag cgaaacaacg cttcacctat    900

tttaaaacgg gcctcggcgc tcgccctctt ggccacagcg cgcctcacag cgacacccac    960

aagaccacgc ccccggtcgt gcatcatcat catcgctcgc gtcttcgagt tcgaggacat   1020

ggagaggccg cgttgctact ctccgcttgc cctgcacctc ctcctctgcc tcttctcgct   1080

ccgcgcctgt tccgccgcgt ccatcacagc cggcaccccc gacgagtcgg agctgtgggg   1140

gtacgtcgag gtccggccaa gtacgtaaca acccctccct atctcgttgc gcttcagagc   1200

ctctcctcgt cgaaggcgag gtgtcgccgt tgacgacgct ttgccgcctt gtcgcagagg   1260

cgcacctgtt ctggtggtac tacaagagcc cgcagaagac gtcgacgccg tccaagccat   1320

ggcccacggt cctctggctg cagggcggcc cggtaggcag ctgctgcctc gttctctctt   1380

tccctcctca caccaccaca atttctcggc ttcggcacag gagggcatga tccggcctct   1440

gtgcttcatt acgggagcac ggtctagcta cctgatgagc gagagcgagt gatcaaccat   1500

ggttgttttg tccctctcgc agggcgcgtc cggggtcggg ctcggcaact tcctggagat   1560
```

-continued

```
ggggccgctg gacgtggacc tgaagccgcg caactcgacg tggctccaca aggccgacct   1620
catctttgtg gtcagaccag agagcgatag ctgatgcctg atggcggctc tcttctcctc   1680
tcttctgccc cccgctcttc tacacctttc gctgtcgtga tgtcctcgct gaccgacttc   1740
ttccatggcc gggcgcgcgc gcgcaggaca acccggtcgg cacagggtac agctacgtgg   1800
aggacgacag cctgttcgtg accagcgact ggcagcaggc cgcggacatg acgacggtgg   1860
tcagggcgct ggcgaaggag gtgcccaccc tggcgagcag cccgctgttc ctggtcgccg   1920
agtcctacgg cggcaagtac gccgccacgc tcggcgcgtc cattgccagg gccgtccgcg   1980
ctggcgagct caacgtcacg ctcggaggtt cgtaaggtta cttccgttcc atctccgggc   2040
tccgactcga tgaaccaaat cgacgttggg ggagcagagc agctgactcg atgaaattct   2100
cgttccctcc tgctgcaggt gtggcggttg gagatagctg gatctcgccg gaggatttca   2160
cggtgaggtt gaccattcct agtttcgtta gtgcagaaat aaaccacgga cacattacag   2220
agctaatagt tacctgctaa aattagctaa atacatttag tctagctaat aatttaacta   2280
ttagctattt tagtaaacta gcgtatagcc tgtactaata tattatctag ccaaacaata   2340
atttatattg tttgtttacc ctttaactta tttaagtttg attatataat ctagaggata   2400
tccaaaccta taaaactaat agctagaagc taaaactagc tatctcaacc tagctaaaac   2460
cagctaataa gtgattggcg attaaattgc tccgaaccat ttctacctat tagcttatta   2520
gaaaaaggga cgtggatagc ttatcagaat aatctagggt attagcttta gatttagaac   2580
atcctcagct aataatagtt agccagtaac aattagttgt agaggtttgg cttcatctag   2640
actaatgcta ctaaccgaga ctaaattaga ccagtgattt tagtcttgtt ttccatctga   2700
tcgggactaa aagatgaaga cttgttctgt actagtgttc tcttggataa atcacaaatg   2760
atgaatacgc atgtgataat taaagtgagg cctgagtgct gctgcagctt tcctacacac   2820
cgctgcttct gagcgtgtcg aggctggacg acaacgccgg cgacgaagca aacaagtaag   2880
gcagcaacaa cacgcacact gcaccaccac catttgcatg cataaatttc tcttgacgct   2940
tagcgcaccc ccatcacata tatgggcatg cgaatttgag ttcaggaagg cggagacggt   3000
gaaggagcaa atcgtggcgg ggcagtgggc cgcctcgcag aagtcatggg gcagcctgct   3060
agatttcatc gacacaaaga gcggcaacgt cgtaagacta gtttacttat cttcgttctt   3120
atattcaaac ttcactcttc gaacaatata atctacagtg caatctcttt tttttggcag   3180
gacgtttaca atttcatgct cgactccggc atggacccgg tggcactgcc cgtgggttct   3240
tcatcactga tgagcagctt gcaggcgatg aagtactcga cgtacggcca ggactcccag   3300
cctggctcca acaccattga cggcatcatg aatggggtca tcaagcaaaa gctcaagata   3360
atccccaaga acttcacgta tgtcagtcca tagcagtgct catatcgcat cacaagtcac   3420
agccggtttc ctgctgctaa tataatgctg cctgtgacgc tggctgcgct tccaaattaa   3480
acgtctacag gtgggggggag caatccgact cggtctacaa cgcgctggtc aacgatttca   3540
tgaaaccgaa gatcgatgag gtaaacggat cgagcagatc aatgaaaagc gccctcgatc   3600
agtttctgaa atttatccct ctttgttttc ttattcagat tgatgagctg ctgtcttatg   3660
gcattaatgt gacggtgtac aatggccagg tcagtaacag tctgcaactt cttcttacga   3720
tccccagcag ctcaaaacta ctcggagctc gtcatcggtt tttactgcat gcatgcgttc   3780
tgttagttcg attagtatta cactgcctgg catcctatct gctataaagc cgtccactct   3840
ttgtaattaa aaaaaaaaca cagatcatga aaactagaag acagaccagg ataaggtcat   3900
tggatagtgg cttagtgaat gattggcatt gactataata atattcgaag ttgagattat   3960
```

```
tagcatttac taataagact gcattttttt cattactgaa cttgatatat acatgacttt   4020
tcctctatct gaagctcgac gtaatctgct cgaccaacgg agcagaagca tgggttcaga   4080
agctcaagta agtttttttt tgcgacctat tcccttccct ccccttctct ggcaggattt   4140
caacgatgca tctggattgc tcgttttcag atgggatggt ctgaggacct tcctgagcct   4200
gccaaggcag cccctctact gtggcgccag caagggtacc aaggcctttg tcaggtccca   4260
caagaacctg catttctact ggatacttgg agcagggcac tatgtaagtc ccaagtctga   4320
accccaactg tgccgtctca tctgagatct gcttcccatg tctgtgagag tgtgaggttc   4380
ttaggtttgg atgaaccaaa taaaacctta tttgttttct cgtgggatca tctctctgat   4440
tgcattgcag gtgcctgcag accagccctg catcgcgcta agcatgatca gcagcataac   4500
ccagtcgcca gcaagctagt tcactgactc tatgtggtgt atgccaagaa caaaggaggc   4560
gttgaagcag gtagcgcaag gtcccggagg accattcggc gttcttgaag tgcggtatag   4620
gttggatacc tgaaagacga tgcagttgac aaggacattt tttttacaga aaaagatccg   4680
ataaaaacat atatgatcta cgtattacaa aatattgtaa agaggccgga acttgttttt   4740
ttaataatag aaatgtatct ggcttcatcc tggtccaaat aacgtgccaa ataacgtgaa   4800
aaatacattg ccgcattctc tagcttgcgg aatgcctgca acatcggctc ctgctcctca   4860
gacattgtat ttgggcccaa gatccaagcc aatgcattcg actgaaaatg acatacaaga   4920
gattttggtc agcaaagttg tcaaattttg acagcttcgt ttcttgttag ctagatagat   4980
taacagatca cagacgtcat gtccataaaa aatggatctt tgtagggtat taatcattga   5040
aacagttttg gatattcagc ggcggagagg tcttcgtcag ggagaccctc tcttccctat   5100
gttgtttgtg ctgatcatgg acgtgcttag cagtcttttc aggactgctg aatgtagggg   5160
attgctgcac agtttggaaa gggcaagagt ccataacagg ctttctatct atgttgatga   5220
tgtggtcctt tttgttaaac ccattgagga agatctgaaa tgtgttagat tgattctgaa   5280
ttgttttggg tcggcctccg gattggttac caatatgaat aagagttatg ctattcctat   5340
cagatgtgag gagcatgtgg ttcaagaggg ctgcaatatg ctgaggtgca gtgtggcctc   5400
atttccttgt tcttacttgg gtctgccaat ctcagacagg aagctgaagc gagatgatct   5460
taagttgtgg atagataaaa ttgcagacag actccctaac tggaaggctc gtttattgaa   5520
cctagccggg aggacaacat tagtgcggtt tgtcttatcg gtcatcccaa tttatcttct   5580
tattgccatt aaaattccca aatgggttat taaatcaatt gacaagattc gaagagagtt   5640
tctttggaaa gggtgaaagg aggtgaatgg tggaagttgt attgttccct gggaaactgt   5700
gacaaggcca taagtttagg gggtcttggt gttcctaatt tgcaattgaa gagttgggca   5760
ctgcaggcta agtggc                                                    5776
```

<210> SEQ ID NO 26
<211> LENGTH: 1653
<212> TYPE: DNA
<213> ORGANISM: Zea mays

<400> SEQUENCE: 26

```
gtcttcgagt tcgaggacat ggagaggccg cgttgctact ctccgcttgc cctgcacctc     60
ctcctctgcc tcttctcgct ccgcgcctgt tccgccgcgt ccatcacagc cggcaccccc    120
gacgagtcgg agctgtgggg gtacgtcgag gtccggccaa aggcgcacct gttctggtgg    180
tactacaaga gcccgcagaa gacgtcgacg ccgtccaagc catggcccac ggtcctctgg    240
```

```
ctgcagggcg gcccgggcgc gtccggggtc gggctcggca acttcctgga gatggggccg    300

ctggacgtgg acctgaagcc gcgcaactcg acgtggctcc acaaggccga cctcatcttt    360

gtggacaacc cggtcggcac agggtacagc tacgtggagg acgacagcct gttcgtgacc    420

agcgactggc agcaggccgc ggacatgacg acggtggtca gggcgctggc gaaggaggtg    480

cccaccctgg cgagcagccc gctgttcctg gtcgccgagt cctacggcgg caagtacgcc    540

gccacgctcg gcgcgtccat tgccagggcc gtccgcgctg gcgagctcaa cgtcacgctc    600

ggaggtgtgg cggttggaga tagctggatc tcgccggagg atttcacgct ttcctacaca    660

ccgctgcttc tgagcgtgtc gaggctggac gacaacgccg gcgacgaagc aaacaagaag    720

gcggagacgg tgaaggagca aatcgtggcg gggcagtggg ccgcctcgca gaagtcatgg    780

ggcagcctgc tagatttcat cgacacaaag agcggcaacg tcgacgttta caatttcatg    840

ctcgactccg gcatggaccc ggtggcactg cccgtgggtt cttcatcact gatgagcagc    900

ttgcaggcga tgaagtactc gacgtacggc caggactccc agcctggctc caacaccatt    960

gacggcatca tgaatggggt catcaagcaa aagctcaaga taatccccaa gaacttcacg   1020

tggggggagc aatccgactc ggtctacaac gcgctggtca acgatttcat gaaaccgaag   1080

atcgatgaga ttgatgagct gctgtcttat ggcattaatg tgacggtgta caatggccag   1140

ctcgacgtaa tctgctcgac caacggagca gaagcatggg ttcagaagct caaatgggat   1200

ggtctgagga ccttcctgag cctgccaagg cagcccctct actgtggcgc cagcaagggt   1260

accaaggcct ttgtcaggtc ccacaagaac ctgcatttct actggatact tggagcaggg   1320

cactatgtgc ctgcagacca gccctgcatc gcgctaagca tgatcagcag cataacccag   1380

tcgccagcaa gctagttcac tgactctatg tggtgtatgc caagaacaaa ggaggcgttg   1440

aagcaggtag cgcaaggtcc cggaggacca ttcggcgttc ttgaagtgcg gtataggttg   1500

gatacctgaa agacgatgca gttgacaagg acattttttt tacagaaaaa gatccgataa   1560

aaacatatat gatctacgta ttacaaaata ttgtaaagag gccggaactt gttttttttaa  1620

taatagaaat gtatctggct tcatcctggt cca                                1653
```

<210> SEQ ID NO 27
<211> LENGTH: 1800
<212> TYPE: DNA
<213> ORGANISM: Zea mays

<400> SEQUENCE: 27

```
acgtgggaga ccacgccccc ggtcgtgcat catcatcatc gctcgcgtct acgagttcga     60

ggacatggag aggccgcgtt gctactctcc gcttgccctg cacctcctcc tctgcctctt    120

ctcgctccgc gcctgttccg ccgcgtccat cacagccggc acccccgacg agtcggagct    180

gtgggggtac gtcgaggtcc ggccaaaggc gcacctgttc tggtggtact acaagagccc    240

gcagaagacg tcgacgccgt ccaagccatg gcccacggtc ctctggctgc agggcggccc    300

gggcgcgtcc ggggtcgggc tcggcaactt cctggagatg ggccgctgg acgtggacct    360

gaagccgcgc aactcgacgt ggctccacaa ggccgacctc atctttgtgg acaacccggt    420

cggcacaggg tacagctacg tggaggacga cagcctgttc gtgaccagcg actggcagca    480

ggccgcggac atgacgacgg tggtcagggc gctggcgaag gaggtgccca ccctggcgag    540

cagcccgctg ttcctggtcg ccgagtccta cggcggcaag tacgccgcca cgctcggcgc    600

gtccattgcc agggccgtcc gcgctggcga gctcaacgtc acgctcggag gtgtggcggt    660

tggagatagc tggatctcgc cggaggattt cacgctttcc tacacaccgc tgcttctgag    720
```

```
cgtgtcgagg ctggacgaca acgccggcga cgaagcaaac aagaaggcgg agacggtgaa    780
ggagcaaatc gtggcggggc agtgggccgc ctcgcagaag tcatggggca gcctgctaga    840
tttcatcgac acaaagagcg gcaacgtcga aggacaaatt caggctgagc agtgggccgc    900
ctcgcagaag tcaaacggca ccctgcgaac aatataatcg acacagcaag agcggcaacg    960
tggcaggacg tttacaattt catgctcgac tccggcatgg acccggtggc actgcccgtg   1020
ggttcttcat cactgatgag cagcttgcag gcgatgaagt actcgacgta cggccaggac   1080
tcccagcctg gctccaacac cattgacggc atcatgaatg gggtcatcaa gcaaaagctc   1140
aagataatcc ccaagaactt cacgtggggg gagcaatccg actcggtcta caacgcgctg   1200
gtcaacgatt tcatgaaacc gaagatcgat gagattgatg agctgctgtc ttatggcatt   1260
aatgtgacgg tgtacaatgg ccagctcgac gtaatctgct cgaccaacgg agcagaagca   1320
tgggttcaga agctcaaatg ggatggtctg aggaccttcc tgagcctgcc aaggcagccc   1380
ctctactgtg gcgccagcaa gggtaccaag gcctttgtca ggtcccacaa gaacctgcat   1440
ttctactgga tacttggagc agggcactat gtgcctgcag accagccctg catcgcgcta   1500
agcatgatca gcagcataac ccagtcgcca gcaagctagt tcactgactc tatgtggtgt   1560
atgccaagaa caaaggaggc gttgaagcag gtagcgcaag gtcccggagg accattcggc   1620
gttcttgaag tgcggtatag gttggatacc tgaaagacga tgcagttgac aaggacattt   1680
ttttttacag aaaaagatcc gataaaaaca tatatgatct acgtattaca aaatattgta   1740
aagaggccgg aacttgtttt tttaataata gaaatgtatc tggcttcatc ctggtccaaa   1800
```

<210> SEQ ID NO 28
<211> LENGTH: 1150
<212> TYPE: DNA
<213> ORGANISM: Zea mays

<400> SEQUENCE: 28

```
tcacaaatga tgaatacgca tgtgataatt aaagtgaggc ctgagtgctg ctgcagcttt     60
cctacacacc gctgcttctg agcgtgtcga ggctggacga caacgccggc gacgaagcaa    120
acaagaaggc ggagacggtg aaggagcaaa tcgtggcggg gcagtgggcc gcctcgcaga    180
agtcatgggg cagcctgcta gatttcatcg acacaaagag cggcaacgtc gtaagactag    240
tttacttatc ttcgttctta tattcaaact tcactcttcg aacaatataa tctacagtgc    300
aatctctttt ttttggcagg acgtttacaa tttcatgctc gactccggca tggacccggt    360
ggcactgccc gtgggttctt catcactgat gagcagcttg caggcgatga agtactcgac    420
gtacggccag gactcccagc ctggctccaa caccattgac ggcaccatga atggggtcat    480
caagcaaaag ctcaagataa tccccaagaa cttcacgtgg ggggagcaat ccgactcggt    540
ctacaacgcg ctggtcaacg atttcatgaa accgaagatc gatgagattg atgagctgct    600
gtcttatggc attaatgtga cggtgtacaa tggccagctc gacgtaatct gctcgaccaa    660
cggagcagaa gcatgggttc agaagctcaa atgggatggt ctgaggacct tcctgagcct    720
gccaaggcag cccctctact gtggcgccag caagggtacc aaggcctttg tcaggtccca    780
caagaacctg catttctact ggatacttgg agcagggcac tatgtgcctg cagaccagcc    840
ctgcatcgcg ctaagcatga tcagcagcat aacccagtcg ccagcaagct agttcactga    900
ctctatgtgg tgtatgccaa gaacaaagga ggcgttgaag caggtagcgc aaggtcccgg    960
aggaccattc ggcgttcttg aagtgcggta taggttggat acctgaaaga cgatgcagtt   1020
```

gacaaggaca tttttttac agaaaaagat ccgataaaaa catatatgat ctacgtatta 1080
caaaatattg taaagaggcc ggaacttgtt tttttaataa tagaaatgta tctggcttca 1140
tcctggtcca 1150

<210> SEQ ID NO 29
<211> LENGTH: 4215
<212> TYPE: DNA
<213> ORGANISM: Zea mays

<400> SEQUENCE: 29
aaggacatat ttgtaataat ctttccaaaa aagtgtcaaa atacaaaaaa aaaagtcagc 60
gaaacaacgc ttcacctatt ttaaaacggg tctcggcgct cgccctcttg gccacaggcc 120
cacagcgcgc ctcacagcga cacccaccac gcccccggtc gtgcatcatc atcatcactc 180
gcgtcttcga gttcgaggac atggacaggc cgcgttgcta ctccccgctt gccctgcacc 240
tcctcctctg cctcgtctcg ctccgcgcct gttccgccgc gtccatcact gccggcaccc 300
ccgacgagtc ggagctgtgg gggtacgtcg aggtccggcc aagtacgtaa cacccccctcc 360 ctagctcgtt gcgcttcaga gcctctcttc gtcgaaggcg aggtgtcgcc gttgacgacg 420
ctttgccgcc ttgtcgcaga ggcgcacctg ttctggtggt actacaagag cccgcagagg 480
acgtcgacgc cgtccaagcc atggcccacg gtcctctggc tgcagggcgg cccggtaggc 540
agctgctgcc tcgttctctc tttccctcct cacaccacca caatttctcg gcttcggcac 600
aggaggacat gatccggcct ctgtgcttca ttacgggagc acggtctagc tacctgatga 660
gcaagagcga gtaatcaacc atggttgtct tgtccctctc gcagggcgcg tccggggtcg 720
ggctcggcaa cttcctggag atggggccgc tggacgtgga cctgaagccg cgcaactcga 780
cgtggctcca caaggccgac ctcatctttg tggtcagacc agagagcgat agctgatggc 840
ggctctcttc tccgatcctc tcttctgccc cccgctcttc ttctacacct ttcgctgtcg 900
tgatgtcctc actgaccgac ttcttccatg gccgggcgcg cgcgcaggac aacccggtcg 960
gcacagggta cagctacgtg gaggacgaca gcctgttcgt gaccagcgac tggcagcagg 1020
ccgcggacat gacgacggtg gtcagggcgc tggcgaagga ggtgcccacc ctggcgagca 1080
gcccgctgtt cctggtcgcc gagtcctacg gcggcaagta cgccgccacg ctcggcgcgt 1140
ccatcgccag ggccgtccgc gctggcgagc tcaacgtcac gctcggaggt tcgtaaggtt 1200
gcttccgttc catctccggg ctccgactcg atgaaccaaa tcgacgttgg gggagcagag 1260
cagagcagag cagctgactc gatgaaattc tcgttccctc ctgctgcagg tgtggcggtt 1320
ggagatagct ggatctcgcc ggaggatttc acggtgaggt tgaccgttct tagtttcgtt 1380
agtgcagaaa taaactgcgg ctacgttgca gagctaatag ttagctgata aaattagcta 1440
aaaacattta aatagtctag ctaataattt aactattagc tattttagta aactagcgtg 1500
tagcatgtac taatatatta tctaaaagcc aaataataat ctatattgtt tgtttaccct 1560
ttaacttatt taagtttaat tatataatct agaggatatc caaacttata aaattaatag 1620
ctagaagcta aaactagcta tcccaaccta gctaaaacca gctaataagt gattgacgat 1680
taaattgctt cgaaccattt ctacctatta gcttattaga aaaagggacg tggatagctt 1740
atcagaataa tctagggtat tagctttaga tttagaacat cctcaactaa taatagttcc 1800
agtaacaatt agttctagag gtttggcttg atctagacta atgctactaa ccgagactaa 1860
attagaccag tgattttagt cttgtttggt agcttcaatc gagactaatg cttccatctg 1920
atcgggacta aaagatgaag acttgttctg tactagtgtt ctcttggata aatcacaaat 1980

```
gatgaatatg catgtgataa ttaaagtgag gcctgaatgc tgctgcagct ttcctacaca   2040
ccgctgcttc tgagcgtgtc gaggctggac gacaacgccg gcgacgaagc aaacaagtaa   2100
gggggtgttt ggtttctagg gactaatgtt tagtcccttc attttattcc tttttagtgt   2160
ataaattgat aaacatagaa attaaaataa agttttagtt tctatatttg gtaattttgg   2220
accaaaaatg gaataaaatc tagggactaa acattagtcc ctagaaacca aacaccctct   2280
aaggcagcaa caacacgcac actgcaccac caccatttgc atgcataaat ttctcttgac   2340
gcttagcgca cccccatcac atatatgggc atgcgaattt gagttcagga aggcggagac   2400
ggtgaaggag caaatcgtgg cggggcagtg ggccgcctcg cagaagtcat ggagcagcct   2460
gctagatttc atcgacacaa agagcggcaa cgtcgtaagg ctagtttact tatcttcatt   2520
cttatattta aacttcactc ttcgaacaat ataatctaca gtgcaatctc tttttttttgg   2580
caggacgttt acaatttcat gctcgactcc ggcatggacc cggtggcact gctgcccgtg   2640
ggttcttcat cactgatgag cagcttgcag gcgatgaaga agtactcgac gtacggccag   2700
gactcccagc ctggctccaa caccattgac ggcatcatga atggggtcat caagcaaaag   2760
ctcaagataa tccccaagaa cttcacgtat gtcagtccat agcagtgctc atatcgcatc   2820
acaagtcaca gccggtttcc tgctgctaat gtaatgctgc ctgtgacgct ggctgcgctt   2880
ccaaattaaa cgtctacagg tgggggcagc aatccgactc ggtctacaac gcgctggtca   2940
acgatttcat gaaaccgagg atcgatgagg taaactggtc gagcagataa atgaaaagcg   3000
ccctcgatca gtttctgaaa ttaatccctc ttcattttct cattcagatt gatgagctgc   3060
tgtcttatgg cattaatgtg acggtgtaca atggccaggt cagtaacagt ctgcaacttc   3120
aattcttacg atccccagca gctcaaaact actcggaaaa aaatttgctg cagcccggct   3180
gcaaaacagt atgtttacag cccctcacaa aaaggaggat agatctctac tcttttttttt   3240
ctcgaatata caggagacct gcatatctgt tagttcgatt agtattacac tgccatccta   3300
tctgctataa agccgtccac tctttgtaat taaaaaaaac acagatcatg aaaactagaa   3360
gacagaccag gataaggtca ttggatagtg gcttagtgaa tgattggcat tgactaataa   3420
tattcgaagt tgagattgag attattagca tttactaata agactgcatt tttttcatta   3480
ctgaacttga tatatacatg acttttcctc tatctgaagc tcgacgtaat ctgctcgacc   3540
aacggagcag aagcatgggt tcagaagctc aagtaagttt tttttttggc aacctattcc   3600
ctcccattct ctggcaggat ttcaacgatg catctggatt gctcgttttc agatgggatg   3660
gtctgaggac cttcctgagc ctgccaaggc agcccctcta ctgtggcgcc agcaagggca   3720
ccaaggcctt tgtcaggtcc cacaagaacc tgcatttcta ctggattctt ggagcagggc   3780
actatgtaag tcccaagtct gaaccctaac tgtgccgtct catctgagat ctgcttccca   3840
tgtctgtgag agtgggaggt tcttaggttt ggatgaacca aaaccttatt tgttttctcg   3900
tgggatcatc tctctgattg cattgcaggt gcctgcagac cagccctgca tcgcgctaag   3960
catgatcagc agcataaccc agtcgccagc aagctagttg actgactcta tgtggtgtat   4020
gccaaaaaca aaggaggcgt tgaagcaggt agcgcaaggt cccggaggac cattcggcgt   4080
tcttgaagtg cggtataggt tggatacctg aaaaaataca taagattata ttataaaaag   4140
gaagaatata cactaaatgg tagtataatt aattataaaa tgtttgtagt ccttttcttg   4200
cgaagaaaat ctttt                                                    4215
```

<210> SEQ ID NO 30

<211> LENGTH: 5108
<212> TYPE: DNA
<213> ORGANISM: Zea mays

<400> SEQUENCE: 30

```
tataatccga ctacatttaa tacccggaac ggaggttcaa acattcgatg ggacagggac     60
taaattttag cggggtgtaa ccaaacaccc ccttagtagc aatattacaa gtgaatatga    120
gaacttaaga agacaataat cgcaataaga agaatggtcc ctctccggcc aaccgttcca    180
tccatatcca tttctatcac atcatctctc acgtctccat gaacatgtgc acatggtatt    240
tccttctcaa atttttaccc gcgatatgaa aaacatcgtt atcaatcttt cacatctcaa    300
aataactcta ctataaattt ttagtatttg ttatatttag ttcaatgaga aaaggatttg    360
attatataca ttgtagtaca cgtcatgttc tgcttggaca cctctgtata tctccctcta    420
ggctctatac tccctgcccc aattaaacaa cacggcatca tgccaaaaac aatttctagt    480
agtcgagtgc ctactctctc tcctcgttct ctctccccag tggcatcgaa ggaaaagtat    540
atatgattgt acccatgatg tgatatacca tatgacagac ggtagataaa gcaggcggac    600
tttgatgggc atagaaaaca gggtcggcgc caattaccat ggcgccgatc tcatgtcaca    660
tagacgccac atcagcgtga gagagtgaga tctcgacagt cgacgccatc tatattgccg    720
cgcgagacgt gcaaactcgg tactaataat aatggcgccg ggtaaaggtc tattttttta    780
attgaaactt aaaaggacat atttgtaata atctttccaa aaaagtgtca aaatacaaaa    840
aaaaaagtca gcgaaacaac gcttcaccta ttttaaaacg ggtctcggcg ctcgccctct    900
tggccacagg cccacagcgc gcctcacagc gacacccacc acgcccccgg tcgtgcatca    960
tcatcatcac tcgcgtcttc gagttcgagg acatggacag gccgcgttgc tactccccgc   1020
ttgccctgca cctcctcctc tgcctcgtct cgctccgcgc ctgttccgcc gcgtccatca   1080
ctgccggcac ccccgacgag tcggagctgt gggggtacgt cgaggtccgg ccaagtacgt   1140
aacacccccct ccctagctcg ttgcgcttca gagcctctct tcgtcgaagg cgaggtgtcg   1200
ccgttgacga cgctttgccg ccttgtcgca gaggcgcacc tgttctggtg gtactacaag   1260
agcccgcaga ggacgtcgac gccgtccaag ccatggccca cggtcctctg gctgcagggc   1320
ggcccggtag gcagctgctg cctcgttctc tctttccctc ctcacaccac cacaatttct   1380
cggcttcggc acaggaggac atgatccggc ctctgtgctt cattacggga gcacggtcta   1440
gctacctgat gagcaagagc gagtaatcaa ccatggttgt cttgtccctc tcgcagggcg   1500
cgtccggggt cgggctcggc aacttcctgg agatggggcc gctggacgtg gacctgaagc   1560
cgcgcaactc gacgtggctc cacaaggccg acctcatctt tgtggtcaga ccagagagcg   1620
atagctgatg gcggctctct tctccgatcc tctcttctgc cccccgctct tcttctacac   1680
ctttcgctgt cgtgatgtcc tcactgaccg acttcttcca tggccgggcg cgcgcgcagg   1740
acaacccggt cggcacaggg tacagctacg tggaggacga cagcctgttc gtgaccagcg   1800
actggcagca ggccgcggac atgacgacgg tggtcagggc gctggcgaag gaggtgccca   1860
ccctggcgag cagcccgctg ttcctggtcg ccgagtccta cggcggcaag tacgccgcca   1920
cgctcggcgc gtccatcgcc agggccgtcc gcgctggcga gctcaacgtc acgctcggag   1980
gttcgtaagg ttgcttccgt tccatctccg ggctccgact cgatgaacca aatcgacgtt   2040
gggggagcag agcagagcag agcagctgac tcgatgaaat tctcgttccc tcctgctgca   2100
ggtgtggcgg ttggagatag ctggatctcg ccggaggatt tcacggtgag gttgaccgtt   2160
cttagtttcg ttagtgcaga aataaactgc ggctacgttg cagagctaat agttagctga   2220
```

```
taaaattagc taaaaacatt taaatagtct agctaataat ttaactatta gctattttag   2280
taaactagcg tgtagcatgt actaatatat tatctaaaag ccaaataata atctatattg   2340
tttgtttacc ctttaactta tttaagttta attatataat ctagaggata tccaaactta   2400
taaaattaat agctagaagc taaaactagc tatcccaacc tagctaaaac cagctaataa   2460
gtgattgacg attaaattgc ttcgaaccat ttctacctat tagcttatta gaaaaaggga   2520
cgtggatagc ttatcagaat aatctagggt attagcttta gatttagaac atcctcaact   2580
aataatagtt ccagtaacaa ttagttctag aggtttggct tgatctagac taatgctact   2640
aaccgagact aaattagacc agtgatttta gtcttgtttg gtagcttcaa tcgagactaa   2700
tgcttccatc tgatcgggac taaaagatga agacttgttc tgtactagtg ttctcttgga   2760
taaatcacaa atgatgaata tgcatgtgat aattaaagtg aggcctgaat gctgctgcag   2820
ctttcctaca caccgctgct tctgagcgtg tcgaggctgg acgacaacgc cggcgacgaa   2880
gcaaacaagt aagggggtgt ttggtttcta gggactaatg tttagtccct tcattttatt   2940
ccttttagt gtataaattg ataaacatag aaattaaaat aaagttttag tttctatatt   3000
tggtaatttt ggaccaaaaa tggaataaaa tctagggact aaacattagt ccctagaaac   3060
caaacaccct ctaaggcagc aacaacacgc acactgcacc accaccattt gcatgcataa   3120
atttctcttg acgcttagcg cacccccatc acatatatgg gcatgcgaat ttgagttcag   3180
gaaggcggag acggtgaagg agcaaatcgt ggcggggcag tgggccgcct cgcagaagtc   3240
atggagcagc ctgctagatt tcatcgacac aaagagcggc aacgtcgtaa ggctagttta   3300
cttatcttca ttcttatatt taaacttcac tcttcgaaca atataatcta cagtgcaatc   3360
tctttttttt ggcaggacgt ttacaatttc atgctcgact ccggcatgga cccggtggca   3420
ctgctgcccg tgggttcttc atcactgatg agcagcttgc aggcgatgaa gaagtactcg   3480
acgtacggcc aggactccca gcctggctcc aacaccattg acggcatcat gaatggggtc   3540
atcaagcaaa agctcaagat aatccccaag aacttcacgt atgtcagtcc atagcagtgc   3600
tcatatcgca tcacaagtca cagccggttt cctgctgcta atgtaatgct gcctgtgacg   3660
ctggctgcgc ttccaaatta aacgtctaca ggtgggggca gcaatccgac tcggtctaca   3720
acgcgctggt caacgatttc atgaaaccga ggatcgatga ggtaaactgg tcgagcagat   3780
aaatgaaaag cgccctcgat cagtttctga aattaatccc tcttcatttt ctcattcaga   3840
ttgatgagct gctgtcttat ggcattaatg tgacggtgta caatggccag gtcagtaaca   3900
gtctgcaact tcaattctta cgatccccag cagctcaaaa ctactcggaa aaaaatttgc   3960
tgcagcccgg ctgcaaaaca gtatgtttac agcccctcac aaaaaggagg atagatctct   4020
actctttttt ttctcgaata tacaggagac ctgcatatct gttagttcga ttagtattac   4080
actgccatcc tatctgctat aaagccgtcc actctttgta attaaaaaaa acacagatca   4140
tgaaaactag aagacagacc aggataaggt cattggatag tggcttagtg aatgattggc   4200
attgactaat aatattcgaa gttgagattg agattattag catttactaa taagactgca   4260
tttttttcat tactgaactt gatatataca tgacttttcc tctatctgaa gctcgacgta   4320
atctgctcga ccaacggagc agaagcatgg gttcagaagc tcaagtaagt tttttttttg   4380
gcaacctatt ccctcccatt ctctggcagg atttcaacga tgcatctgga ttgctcgttt   4440
tcagatggga tggtctgagg accttcctga gcctgccaag gcagcccctc tactgtggcg   4500
ccagcaaggg caccaaggcc tttgtcaggt cccacaagaa cctgcatttc tactggattc   4560
```

```
ttggagcagg gcactatgta agtcccaagt ctgaacccta actgtgccgt ctcatctgag   4620
atctgcttcc catgtctgtg agagtgggag gttcttaggt ttggatgaac caaaacctta   4680
tttgttttct cgtgggatca tctctctgat tgcattgcag gtgcctgcag accagccctg   4740
catcgcgcta agcatgatca gcagcataac ccagtcgcca gcaagctagt tgactgactc   4800
tatgtggtgt atgccaaaaa caaaggaggc gttgaagcag gtagcgcaag gtcccggagg   4860
accattcggc gttcttgaag tgcggtatag gttggatacc tgaaaaaata cataagatta   4920
tattataaaa aggaagaata tacactaaat ggtagtataa ttaattataa aatgtttgta   4980
gtccttttct tgcgaagaaa atcttttaaa tggcatttgt gtgaagcaca atgtttagag   5040
tcctaaaaat gcaattgtct ctgttgggga cttgctctca aatgctatga atcaagagca   5100
agacaaca                                                            5108
```

```
<210> SEQ ID NO 31
<211> LENGTH: 1659
<212> TYPE: DNA
<213> ORGANISM: Zea mays

<400> SEQUENCE: 31

gtcttcgagt tcgaggacat ggacaggccg cgttgctact ctccgcttgc cctgcacctc     60
ctcctctgcc tcttctcgct ccgcgcctgt tccgccgcgt ccatcacagc cggcaccccc    120
gacgagtcgg agctgtgggg gtacgtcgag gtccggccaa aggcgcacct gttctggtgg    180
tactacaaga gcccgcagaa gacgtcgacg ccgtccaagc catggcccac ggtcctctgg    240
ctgcagggcg gcccgggcgc gtccggggtc gggctcggca acttcctgga gatggggccg    300
ctggacgtgg acctgaagcc gcgcaactcg acgtggctcc acaaggccga cctcatcttt    360
gtggacaacc cggtcggcac agggtacagc tacgtggagg acgacagcct gttcgtgacc    420
agcgactggc agcaggccgc ggacatgacg acggtggtca gggcgctggc gaaggaggtg    480
cccaccctgg cgagcagccc gctgttcctg gtcgccgagt cctacggcgg caagtacgcc    540
gccacgctcg gcgcgtccat tgccagggcc gtccgcgctg gcgagctcaa cgtcacgctc    600
ggaggtgtgg cggttggaga tagctggatc tcgccggagg atttcacgct ttcctacaca    660
ccgctgcttc tgagcgtgtc gaggctggac gacaacgccg gcgacgaagc aaacaagaag    720
gcggagacgg tgaaggagca aatcgtggcg gggcagtggg ccgcctcgca gaagtcatgg    780
ggcagcctgc tagatttcat cgacacaaag agcggcaacg tcgacgttta caatttcatg    840
ctcgactccg gcatggaccc ggtggcactg ctgcccgtgg gttcttcatc actgatgagc    900
agcttgcagg cgatgaagaa gtactcgacg tacggccagg actcccagcc tggctccaac    960
accattgacg gcatcatgaa tggggtcatc aagcaaaagc tcaagataat ccccaagaac   1020
ttcacgtggg gggagcaatc cgactcggtc tacaacgcgc tggtcaacga tttcatgaaa   1080
ccgaagatcg atgagattga tgagctgctg tcttatggca ttaatgtgac ggtgtacaat   1140
ggccagctcg acgtaatctg ctcgaccaac ggagcagaag catgggttca gaagctcaaa   1200
tgggatggtc tgaggacctt cctgagcctg ccaaggcagc ccctctactg tggcgccagc   1260
aagggtacca aggcctttgt caggtcccac aagaacctgc atttctactg gatacttgga   1320
gcagggcact atgtgcctgc agaccagccc tgcatcgcgc taagcatgat cagcagcata   1380
acccagtcgc cagcaagcta gttcactgac tctatgtggt gtatgccaag aacaaaggag   1440
gcgttgaagc aggtagcgca aggtcccgga ggaccattcg gcgttcttga agtgcggtat   1500
aggttggata cctgaaagac gatgcagttg acaaggacat ttttttaca gaaaaagatc   1560
```

```
cgataaaaac atatatgatc tacgtattac aaaatattgt aaagaggccg gaacttgttt   1620

ttttaataat agaaatgtat ctggcttcat cctggtcca                          1659
```

<210> SEQ ID NO 32
<211> LENGTH: 1795
<212> TYPE: DNA
<213> ORGANISM: Zea mays

<400> SEQUENCE: 32

```
agttcatcac taatcacact tattgtgccc tcgacgagta tctatagcta gctcattaat     60

cgattcgggg gtgtgttgtc gaaggcggca atggcgagct actcgtcgcg gcgtccatgc    120

aatacctgta gcacgaaggc gatggccggg agcgtggtcg gcgagcccgt cgtgctgggg    180

cagagggtga cggtgctgac ggtggacggc ggcggcgtcc ggggtctcat cccgggaacc    240

atcctcgcct tcctggaggc caggctgcag gagctggacg gaccggaggc gaggctggcg    300

gactacttcg actacatcgc cggaaccagc accggcggtc tcatcaccgc catgctcacc    360

gcgcccggca aggacaagcg gcctctctac gctgccaagg acatcaacca cttttacatg    420

cagaactgcc cgcgcatctt tcctcagaag tgagtccgat gctgccgcca ttgttcttgc    480

atccatccag catcgtacgt acgtcctcta tacatctgcg gatcatcatg tgcgcatgtt    540

tgtggcatgc atgcatgcat gtgagcagga gcaggcttgc ggccgccatg tccgcgctga    600

ggaagccaaa gtacaacggc aagtgcatgc gcagcctgat taggagcatc ctcggcgaga    660

cgagggtaag cgagacgctg accaacgtca tcatccctgc cttcgacatc aggctgctgc    720

agcctatcat cttctctacc tacgacgtac gtacgtcgtc acgaatgatt catctgtacg    780

tcgtcgcatg cgaatggctg cctacgtacg ccgtgcgcta acatactcag ctctttccta    840

tctgctgcgc caatttgcag gccaagagca cgcctctgaa gaacgctctg ctctcggacg    900

tgtgcattgg cacgtccgcc gcgccgacct acctcccggc gcactacttc cagactgaag    960

acgccaacgg caaggagcgc gaatacaacc tcatcgacgg cggtgtggcg gccaacaacc   1020

cggtaactga ctagctaact ggaaaacgga cgcacagact ccatgtccat ggcggcccac   1080

aaggtcgatg ctaattgttg cttatgtatg tcgcccgatt gcacatgcgt agacgatggt   1140

tgcgatgacg cagatcacca aaaagatgct tgccagcaag gacaaggccg aggagctgta   1200

cccagtgaag ccgtcgaact gccgcaggtt cctggtgctg tccatcggga cggggtcgac   1260

gtccgagcag ggcctctaca cggcgcggca gtgctcccgg tggggtatct gccggtggct   1320

ccgcaacaac ggcatggccc ccatcatcga catcttcatg gcggccagct cggacctggt   1380

ggacatccac gtcgccgcga tgttccagtc gctccacagc gacggcgact acctgcgcat   1440

ccaggacaac tcgctccgtg gcgccgcggc caccgtggac gcggcgacgc cggagaacat   1500

gcggacgctc gtcgggatcg gggagcggat gctggcacag agggtgtcca gggtcaacgt   1560

ggagacaggg aggtacgaac cggtgactgg cgaaggaagc aatgccgatg ccctcggtgg   1620

gctcgctagg cagctctccg aggagaggag aacaaggctc gcgcgccgcg tctctgccat   1680

caacccaaga ggctctagat gtgcgtcgta cgatatctaa gacaagtggc tttactgtca   1740

gtcacatgct tgtaaataag tagactttat tttaataaaa cataaaaata tatat        1795
```

<210> SEQ ID NO 33
<211> LENGTH: 1452
<212> TYPE: DNA
<213> ORGANISM: Zea mays

<400> SEQUENCE: 33

```
agttcatcac taatcacact tattgtgccc tcgacgagta tctatagcta gctcattaat      60
cgattcgggg gtgtgttgtc gaaggcggca atggcgagct actcgtcgcg gcgtccatgc     120
aatacctgta gcacgaaggc gatggccggg agcgtggtcg gcgagcccgt cgtgctgggg     180
cagagggtga cggtgctgac ggtggacggc ggcggcgtcc ggggtctcat cccgggaacc     240
atcctcgcct tcctggaggc caggctgcag gagctggacg gaccggaggc gaggctggcg     300
gactacttcg actacatcgc cggaaccagc accggcggtc tcatcaccgc catgctcacc     360
gcgcccggca aggacaagcg gcctctctac gctgccaagg acatcaacca cttttacatg     420
cagaactgcc cgcgcatctt tcctcagaag agcaggcttg cggccgccat gtccgcgctg     480
aggaagccaa agtacaacgg caagtgcatg cgcagcctga ttaggagcat cctcggcgag     540
acgagggtaa gcgagacgct gaccaacgtc atcatccctg ccttcgacat caggctgctg     600
cagcctatca tcttctctac ctacgacgcc aagagcacgc ctctgaagaa cgctctgctc     660
tcggacgtgt gcattggcac gtccgccgcg ccgacctacc tcccggcgca ctacttccag     720
actgaagacg ccaacggcaa ggagcgcgaa tacaacctca tcgacggcgg tgtggcggcc     780
aacaacccga cgatggttgc gatgacgcag atcaccaaaa agatgcttgc cagcaaggac     840
aaggccgagg agctgtaccc agtgaagccg tcgaactgcc gcaggttcct ggtgctgtcc     900
atcgggacgg ggtcgacgtc cgagcagggc ctctacacgg cgcggcagtg ctcccggtgg     960
ggtatctgcc ggtggctccg caacaacggc atggccccca tcatcgacat cttcatggcg    1020
gccagctcgg acctggtgga catccacgtc gccgcgatgt tccagtcgct ccacagcgac    1080
ggcgactacc tgcgcatcca ggacaactcg ctccgtggcg ccgcggccac cgtggacgcg    1140
gcgacgccgg agaacatgcg gacgctcgtc gggatcgggg agcggatgct ggcacagagg    1200
gtgtccaggg tcaacgtgga gacagggagg tacgaaccgg tgactggcga aggaagcaat    1260
gccgatgccc tcggtgggct cgctaggcag ctctccgagg agaggagaac aaggctcgcg    1320
cgccgcgtct ctgccatcaa cccaagaggc tctagatgtg cgtcgtacga tatctaagac    1380
aagtggcttt actgtcagtc acatgcttgt aaataagtag actttatttt aataaaacat    1440
aaaaatatat at                                                        1452
```

<210> SEQ ID NO 34
<211> LENGTH: 4564
<212> TYPE: DNA
<213> ORGANISM: Zea mays

<400> SEQUENCE: 34

```
aaggaaaggt cacacatcct agctagcttc actggttcta gctccttcca attttgcaaa      60
aaagtcacaa aggataagcc atttttccaa atgatttgtg aaatgcctat gctaaaaagc     120
ctacttttcc gaaaaaccag agctagagcc atttttgaca agtcagaacc ctaccaaata     180
gtccctcagt ttaagcaaag tgaggccata ctgaagctaa attatgccaa attgggccta     240
catctccata ttttcaacca aatgctttag ggtttcttgt aatcgacatg atttgtttct     300
tcataaatag tatatggacc gctccaaaat actccatccg tttcaattta tatttcgttt     360
gatcttttta ccctaaattt gatcgactcg tcttattaaa aaaagttcat aactattaat     420
aatctttact gtgatatcat ttagcatata atatacttta attgtggctt tgattttttt     480
ccgcaaaaat taaatgaaac gacccaatca aacttgataa aaaagtaaaa ctaattataa     540
atttggacag aaggagtagg agggtgtttg aatacactag agttaatagt tagttgcctt     600
```

```
aaaatttgct agtacaatta gctagctaac aaatatttag gtaactatta gctaatttgc    660
taaaaacagc taatagttaa actattagct agactgtttg gatgtattca gctaatttta    720
gcagctaact attagctata gtataatatt caaacacctc ctaattaaaa tggacaaata    780
tctcttccct tggtcccttg cgttagattt ccatatctcc ttatttagta taaaaagaat    840
catcaaaaag tggacaaccc ctagtggaac accattttag tagtggttgc atgaaacctt    900
tcgcgcatca gttactatgt gtcactctaa aaatggggca gcatgtacgc agtgcctata    960
tttatacaag gcatctatcg ttgcctcctc agttcatcac taatcacact tattgttccc   1020
tcgacgagta tctagctagc tcattaatcg atcaatcggg gtgtgcggtc gaaggcggca   1080
atggcgagct actcgtcgcg gcgtccatgc aatacctgta gcacgaaggc gatggccggg   1140
agcgtggtcg gcgagcccgt cgtgctgggg cagagggtga cggtgctgac ggtggacggc   1200
ggcggcgtcc ggggtctcat cccgggaacc atcctcgcct tcctcgaggc caggctgcag   1260
gagctggacg gaccggaggc gaggctggcg gactacttcg actacatcgc cggaaccagc   1320
accggcggtc tcatcaccgc catgctcacc gcgcccggca aggacaagcg gcctctctac   1380
gctgccaagg acatcaacca cttttacatg gagaactgcc cgcgcatctt ccctcagaag   1440
tgagtccgat gctgccgcca ttgttcttgc atccatgcat ccagcatcgt acgtcctcta   1500
tacatctgcg gatgatcatt tgcgcatgtt tgtggcatgc atgcatgtga tgtgagcagg   1560
agcaggcttg cggccgccat gtccgcgctg aggaagccaa agtacaacgg caagtgcatg   1620
cgcagcctga ttaggagcat cctcggcgag acgagggtaa gcgagacgct gaccaacgtc   1680
atcatccctg ccttcgacat caggctgctg cagcctatca tcttctctac ctacgacgta   1740
cgtacgtcgt cacgaatgat tcatctgtac gtcgtcgcat gcgaatggct gcctacgtac   1800
gccgtgcgct aacatactca gctctttcct atctgctgcg ccaatttgca ggccaagagc   1860
acgcctctga agaacgctct gctctcggac gtgtgcattg gcacgtccgc cgcgccgacc   1920
tacctcccgg cgcactactt ccagactgaa gacgccaacg gcaaggagcg cgaatacaac   1980
ctcatcgacg gcggtgtggc ggccaacaac ccggtaactg actagctaac tggaaaacgg   2040
acgcacagac tccatgtcca tggcggccca caaggtcgat gctaattgtt gcttatgtat   2100
gtcgcccgat tgcacatgcg tagacgatgg ttgcgatgac gcagatcacc aaaaagatgc   2160
ttgccagcaa ggacaaggcc gaggagctgt acccagtgaa gccgtcgaac tgccgcaggt   2220
tcctggtgct gtccatcggg acggggtcga cgtccgagca gggcctctac acggcgcggc   2280
agtgctcccg gtggggtatc tgccggtggc tccgcaacaa cggcatggcc cccatcatcg   2340
acatcttcat ggcggccagc tcggacctgg tggacatcca cgtcgccgcg atgttccagt   2400
cgctccacag cgacggcgac tacctgcgca tccaggacaa ctcgctccgt ggcgccgcgg   2460
ccaccgtgga cgcggcgacg ccggagaaca tgcggacgct cgtcgggatc ggggagcgga   2520
tgctggcaca gagggtgtcc agggtcaacg tggagacagg gaggtacgaa ccggtgactg   2580
gcgaaggaag caatgccgat gccctcggtg ggctcgctag gcagctctcc gaggagagga   2640
gaacaaggct cgcgcgccgc gtgtctgcca tcaacccaag aggctctaga tgtgcgtcgt   2700
acgatatcta agacaagtgg ctttactgtc agtcacatgc ttgtaaataa gtagacttta   2760
ttttaataaa acataaaaat atatatatgt tcttgaatat aaaattgata accaaaattc   2820
gaaccatcac ttatacataa ttttacttta ttttttataa aacgtgaacg ggaaggacta   2880
ccatgaatga ctatagaacc aatcatacta gtataaaata tatgatgaca ctacgagaga   2940
```

```
gacaaacttt gtctggcgct aaatattttg ccgagtgtga attcacgggc actaggcaaa   3000
gatcttcttt gccgagtgtt acgctgggca aagtaagaca ctaggtaaat cagtcatttg   3060
ccgagtgtcc gccactaggc aaagcaaaac actggcaaat caaaagttta cctagtgcca   3120
gacactaggc aaaaaaaaac gctcggcaaa tcggaagttt ccctagtgcc agacactaga   3180
caaagaaaaa cacttgataa actagcgtcg tcagctaaca ccatccacca accgttaacg   3240
ttgccgagta tctgacttcg acactcggca aagaaggtct ctttgcctag tgtcggtctg   3300
gaacactagg caaagaggca ctttacctag tgtcgtattt tgacactcag taaaataatt   3360
tttttcttt ctgcttccaa actttttatg atgtgttcct atagcaccta gaactacatg   3420
tcaagttttg gtaaaatttt tgaagttttt gctatattta cttaatttat tttatttaat   3480
tgaatttctt ttgataattc aaatttgaac tcggcaaggt aagaagcgag ggtagcctgg   3540
aaacacactt tgcctagtgt tacactcggt acaggagcct cccctgccta gtgctgcact   3600
cgacaaaaga ttcgcctttg cctagcgctg cactcggcac aggagtcgcc tttgcctagt   3660
gctgcactag gcaaagcctc cgttaccgtg ccttccatcg tcatggaaac ttttcttcgc   3720
cgagtgacgt gtggcactag gcaaagtttt tgccgagtgc ccgagaaatg gcactcggca   3780
aggactcttt gtcgatccct tcgttgccga cttctttttg ccgagtgcaa cactaggcaa   3840
accatttgcc gagtgtaaaa gaggctttgc ctagtgtctg tggcactagg caaagaagac   3900
gagtcctgta gtgaacctag taggccagtg cgggaccatt ccaaaaaata cctataaaaa   3960
taaatttaat attaaattaa acatatggtc cacgtaccaa gatattaaac tcaaaagaac   4020
aattattaca atttatctta gctaaaaggc cgagaaaagt atatgttaaa aaggagtgtg   4080
atcccatttt tatagctcgc tcggtcgatc gcccgtccac ttttaggtaa cgaggtggta   4140
ccatgtagga gtgttgcgtt gcgtgcgact tcctatcatg ttgggcttag gtggcttctc   4200
acgacccaat gataggcgag aagtgtggaa gatgaacaaa cctacttgtt tcgtgcacga   4260
cgcatgtgtt tgaacaacga gttagattag aaaaaaaata taatgacttt ttttttgcaa   4320
aagtgaggat aatgaaaacc agaaaaactg gtgcttcata agagtagaga tttgatggta   4380
aatatagtag taatgcaatg gctatactac acgcgagagt ccaatggcaa gccggtgtgt   4440
tggggcgaag gcgaagacgc tacccttcgc tccaggcctt tgtcaactcg ctgcaccaac   4500
agaggcaaga tgaccggcgc ggcccaccct tcgtcctctt cactgcaaga cgaaggccta   4560
cgac                                                                4564
```

<210> SEQ ID NO 35
<211> LENGTH: 2089
<212> TYPE: DNA
<213> ORGANISM: Zea mays

<400> SEQUENCE: 35

```
caccggcggt ctcatcaccg ccatgctcac cgcgcccggc aaggacaagc ggcctctcta     60
cgctgccaag gacatcaact acttttacat ggagaactgc ccgcgcatct tccctcagaa    120
gtgagtccga tgctgccgcc attgttctcg catccatcca gcatcgtacg tcctctatac    180
atctgcggat gatcatttgc gcatgtttgt ggcatgcatg tgagcaggag caggcttgcg    240
gccgccatgt ccgcgctgag gaagccaaag tacaacggca agtgcatgcg cagcctgatt    300
aggagcatcc tcggcgagac gagggtaagc gagacgctga ccaacgtcat catccctgcc    360
ttcgacatca ggctgctgca gcctatcatc ttctctacct acgacgtacg tacgtcgtca    420
cgaatgattc atctgtacgt cgtcgcatgc gaatggctgc ctacgccgtg cgctaacata    480
```

```
ctcagctctt tccgatctgc tgcgccaatt tgcaggccaa gagcacgcct ctgaagaacg    540
cgctgctctc ggacgtgtgc attggcacgt ccgccgcgcc gacctacctc ccggcgcact    600
acttccagac tgaagacgcc aacggcaagg agcgcgaata caacctcatc gacggcggtg    660
tggcggccaa caacccggta actgactagc taactgcaaa acgaacgcac agactccatg    720
tccatggcgg cccacaaggt cgatgctaat tgttgcttat gtatgtcgcc cgattgcaca    780
tgcgtagacg atggttgcga tgacgcagat caccaaaaag atgcttgcca gcaaggacaa    840
ggccgaggag ctgtacccag tgaacccgtc gaactgccgc aggttcctgg tgctgtccat    900
cgggacgggg tcgacgtccg agcagggcct ctacacggcg cggcagtgct cccggtgggg    960
catctgccgg tggctccgca acaacggcat ggccccatc atcgacatct tcatggcggc   1020
cagctcggac ctggtggaca tccacgtcgc cgcgatgttc cagtcgctcc acagcgacgg   1080
cgactaccta cgcatccagg acaactcgct ccgtggcgcc gcggcaaccg tggacgcggc   1140
gacgccggag aacatgcgga cgctcgtcgg gatcggggag cggatgctgg cacagcgggt   1200
gtccagggtc aacgtggaga cagggagcga ggtacgaacc ggtgaccgga gaaggaagca   1260
atgccgatgc cctcggtggg ctcgctaggc agctctccga ggagaggaga acaaggctcg   1320
cgcgccgcgt ctctgccatc aaccccagaa gctctagatg tgcgccctac gatatctaag   1380
acaagtggct ttactgtcaa tcacatgctt gtaaataagt agactttatt ttaataaaat   1440
ataaatatat atatattctg ataaccaaga ttcgaaccct cacttataca caattttatc   1500
ttatttttta taaaatgaga atggaaagga ctaccgtgaa cgactataga accaatcata   1560
ctagtttaaa atgctcgtaa gctatgacga acctagtagg ccggtgctgg accattccaa   1620
aaaacctata aaaataaatt taatattaaa ttaaacatat ggtctatata tcagatatta   1680
aactcaaaag aataattatt ataatttatc ttagctaaaa ggttgagaaa ggtatgcgtt   1740
aaaaaagagt tttaacccat ttttatagct tatttgatcg cccgtccact tttagggagc   1800
gaggtggtac tatgcagaag tgttgcgctg tgtgcgactt actatcatgt tgggtttagg   1860
tggattctca cgacccaatg atagacgaga agtgtgggag atgaacaaac ctacgcattt   1920
cgcgtacgac acatgtgttt gaacaacgag ttagattgga aaaaatataa tgaccttttt   1980
tgcaaaaatg actacaatga aaaccaggaa aaccggtgct tcataggagt agagatttga   2040
cggtaaattg ttacgatcta ctggtatttg ctgcgaggat gtattcgct               2089
```

<210> SEQ ID NO 36
<211> LENGTH: 3557
<212> TYPE: DNA
<213> ORGANISM: Zea mays

<400> SEQUENCE: 36

```
tgacgtttgg taaaacgact tcttccgaaa aacacccaaa aacccaagat attttatact     60
acgaaggaaa ggtcacacat cctagttagc ttcactggtt ctagctcctt ccaattttgc    120
aaaaaagtca caaaggataa gccatttttt caaatgattt gtgaaatgcc tacgctaaaa    180
agtctacttt tccaaaaaaa ctagagctag agccgttttt ggcaagtcag aaccctacca    240
aatagtccct cagtttaagc aaagtgaggc tatactgaag ctaaattatg ccaaattggg    300
cctacatctc catattttca accaaatgct ttagggtttc ttgtaatcga catgatttgt    360
ttcttcataa atagtatatg gaccgctcca aaatactcca tccgtttcaa tttatattac    420
gtttgatctt tttaccctaa atttgatcga ctcgtcttat taaaaaagtt cataactatt    480
```

```
aataatcttt actgtgatat catttagcat ataatatact ttaagtgtag ctttgatttt    540
ttttttgcaa aaattaaatg aaacgaccca atcaaacttg ataaaaaagt aaaactaatt    600
ataaatttgg acataaggag taggagggtg tttgaataca ctagagttaa tagttagttg    660
tcttaaaatt tgctagtaca attagctagc taacaaatat ttaggtaact attagctaat    720
ttgctaaaaa cagctaatag ttgaactatt agttgaacta ttagctagac tgtttggatg    780
tattcaacta attttagcag ctaactatta gttatagtat aatattcaaa cacctcctaa    840
ttaaaatgga caaatatcta ttcccttggt cccttgcgtt agattttcca tatatcctca    900
tttagtataa aaagaatcat caaaaagtgg acaaccccta gtggaacacc attttagtag    960
tggttgcatg aaacctttcg cgcatcagtt actatgtgtc actctaaaaa tggggcagca   1020
tgtacgcagt gcctatattt atacaaggca tctatcgttg cctcctcagt tcatcactaa   1080
tcacacttat tgtgccctcg acgagtatct agctagctca ttaatcgatc aatcggggtg   1140
tgcggtcgaa ggcggcaatg gcgagctact cgtcgcggcg tccatgcaat acctgtagca   1200
cgaaggcgat ggccgggagc gtggtcggcg agcccgtcgt gctggggcag agggtgacgg   1260
tgctgacggt ggacggcggc ggcgtccggg gtctcatccc gggaaccatc ctcgccttcc   1320
tggaggccag gctgcaggag ctggacggac cggaggcgag gctggcggac tacttcgact   1380
acatcgccgg aaccagcacc ggcggtctca tcaccgccat gctcaccgcg cccggcaagg   1440
acaagcggcc tctctacgct gccaaggaca tcaactactt ttacatggag aactgcccgc   1500
gcatcttccc tcagaagtga gtccgatgct gccgccattg ttctcgcatc catccagcat   1560
cgtacgtcct ctatacatct gcggatgatc atttgcgcat gtttgtggca tgcatgtgag   1620
caggagcagg cttgcggccg ccatgtccgc gctgaggaag ccaaagtaca acggcaagtg   1680
catgcgcagc ctgattagga gcatcctcgg cgagacgagg gtaagcgaga cgctgaccaa   1740
cgtcatcatc cctgccttcg acatcaggct gctgcagcct atcatcttct ctacctacga   1800
cgtacgtacg tcgtcacgaa tgattcatct gtacgtcgtc gcatgcgaat ggctgcctac   1860
gccgtgcgct aacatactca gctctttccg atctgctgcg ccaatttgca ggccaagagc   1920
acgcctctga agaacgcgct gctctcggac gtgtgcattg gcacgtccgc cgcgccgacc   1980
tacctcccgg cgcactactt ccagactgaa gacgccaacg gcaaggagcg cgaatacaac   2040
ctcatcgacg gcggtgtggc ggccaacaac ccggtaactg actagctaac tgcaaaacga   2100
acgcacagac tccatgtcca tggcggccca caaggtcgat gctaattgtt gcttatgtat   2160
gtcgcccgat tgcacatgcg tagacgatgg ttgcgatgac gcagatcacc aaaaagatgc   2220
ttgccagcaa ggacaaggcc gaggagctgt acccagtgaa cccgtcgaac tgccgcaggt   2280
tcctggtgct gtccatcggg acggggtcga cgtccgagca gggcctctac acggcgcggc   2340
agtgctcccg gtggggcatc tgccggtggc tccgcaacaa cggcatggcc cccatcatcg   2400
acatcttcat ggcggccagc tcggacctgg tggacatcca cgtcgccgcg atgttccagt   2460
cgctccacag cgacggcgac tacctacgca tccaggacaa ctcgctccgt ggcgccgcgg   2520
caaccgtgga cgcggcgacg ccggagaaca tgcggacgct cgtcgggatc ggggagcgga   2580
tgctggcaca gcgggtgtcc agggtcaacg tggagacagg gagcgaggta cgaaccggtg   2640
accggagaag gaagcaatgc cgatgccctc ggtgggctcg ctaggcagct ctccgaggag   2700
aggagaacaa ggctcgcgcg ccgcgtctct gccatcaacc ccagaagctc tagatgtgcg   2760
ccctacgata tctaagacaa gtggctttac tgtcaatcac atgcttgtaa ataagtagac   2820
tttattttaa taaaatataa atatatatat attctgataa ccaagattcg aaccctcact   2880
```

```
tatacacaat tttatcttat tttttataaa atgagaatgg aaaggactac cgtgaacgac   2940

tatagaacca atcatactag tttaaaatgc tcgtaagcta tgacgaacct agtaggccgg   3000

tgctggacca ttccaaaaaa cctataaaaa taaatttaat attaaattaa acatatggtc   3060

tatatatcag atattaaact caaaagaata attattataa tttatcttag ctaaaaggtt   3120

gagaaaggta tgcgttaaaa aagagtttta acccattttt atagcttatt tgatcgcccg   3180

tccactttta gggagcgagg tggtactatg cagaagtgtt gcgctgtgtg cgacttacta   3240

tcatgttggg tttaggtgga ttctcacgac ccaatgatag acgagaagtg tgggagatga   3300

acaaacctac gcatttcgcg tacgacacat gtgtttgaac aacgagttag attggaaaaa   3360

atataatgac ctttttgca aaaatgacta caatgaaaac caggaaaacc ggtgcttcat   3420

aggagtagag atttgacggt aaattgttac gatctactgg tatttgctgc gaggatgtat   3480

tcgcttggtg aaaacagaat tacagagtag cagtagcagg gaagacagta gcgagaggag   3540

aagaagaaac ttgagga                                                  3557
```

<210> SEQ ID NO 37
<211> LENGTH: 1382
<212> TYPE: DNA
<213> ORGANISM: Zea mays

<400> SEQUENCE: 37

```
agttcatcac taatcacact tattgtgccc tcgacgagta tctagctagc tcattaatcg     60

atcaatcggg gtgtgcggtc gaaggcggca atggcgagct actcgtcgcg gcgtccatgc    120

aatacctgta gcacgaaggc gatggccggg agcgtggtcg gcgagcccgt cgtgctgggg    180

cagagggtga cggtgctgac ggtggacggc ggcggcgtcc ggggtctcat cccgggaacc    240

atcctcgcct tcctggaggc caggctgcag gagctggacg gaccggaggc gaggctggcg    300

gactacttcg actacatcgc cggaaccagc accggcggtc tcatcaccgc catgctcacc    360

gcgcccggca aggacaagcg gcctctctac gctgccaagg acatcaacta cttttacatg    420

gagaactgcc cgcgcatctt ccctcagaag agcaggcttg cggccgccat gtccgcgctg    480

aggaagccaa agtacaacgg caagtgcatg cgcagcctga ttaggagcat cctcggcgag    540

acgagggcca agagcacgcc tctgaagaac gcgctgctct cggacgtgtg cattggcacg    600

tccgccgcgc cgacctacct cccggcgcac tacttccaga ctgaagacgc caacggcaag    660

gagcgcgaat acaacctcat cgacggcggt gtggcggcca acaacccgac gatggttgcg    720

atgacgcaga tcaccaaaaa gatgcttgcc agcaaggaca aggccgagga gctgtaccca    780

gtgaacccgt cgaactgccg caggttcctg gtgctgtcca tcgggacggg gtcgacgtcc    840

gagcagggcc tctacacggc gcggcagtgc tcccggtggg gcatctgccg gtggctccgc    900

aacaacggca tggcccccat catcgacatc ttcatggcgg ccagctcgga cctggtggac    960

atccacgtcg ccgcgatgtt ccagtcgctc cacagcgacg gcgactacct acgcatccag   1020

gacaactcgc tccgtggcgc cgcggcaacc gtggacgcgg cgacgccgga gaacatgcgg   1080

acgctcgtcg ggatcgggga gcggatgctg gcacagcggg tgtccagggt caacgtggag   1140

acagggagcg aggtacgaac cggtgaccgg agaaggaagc aatgccgatg ccctcggtgg   1200

gctcgctagg cagctctccg aggagaggag aacaaggctc gcgcgccgcg tctctgccat   1260

caaccccaga agctctagat gtgcgcccta cgatatctaa gacaagtggc tttactgtca   1320

atcacatgct tgtaaataag tagactttat tttaataaaa tataaatata tatatattct   1380
```

ga 1382

<210> SEQ ID NO 38
<211> LENGTH: 10843
<212> TYPE: DNA
<213> ORGANISM: Zea mays

<400> SEQUENCE: 38

```
cgcacacact gtctttctct gcctttcttt ccctagcgcc gcgccggcgc cgccattcga     60
tcaggccgct tcgccggcga cagcatattc caggtatgcc gtcccttctg ctccttctgc    120
gagaattcaa acaccccgaa ctccccaaat ctagtatttg tattcggatc tgaccatttt    180
tcactgggcc cgcccctgat tcgcaggtcg gttggttttg gcacttcgga ccggcggcca    240
tggcttccga cggcatcggc cccagaggta taactgtttc atctcttctt tgtgttcaaa    300
cagacagacg tcaaaccgcc gagaggaggt acaaatatag attttgggct atgagcacgc    360
cattgcgctt ccagcgatct gacatattgg gaattcttgt tttttttttg ggtaccttgc    420
aaggccgaaa tttgacgctt ttctgtttaa ttctagtgcc tgtctgcatc cattagggca    480
tcctagctgc tccatgctcg tgatctcgtc cgtttgcttg attgaatcca ttgttttcca    540
aagttcattg ctactgcgaa atacgtttat atgattacca caatttgtgt ttttgccttt    600
tcgggttgca cagagggtac tgccatcatt gttgttttag cgccatttgg aacaagtgat    660
tcactggtac tagtacagta tgtgcttttc atgtgtgttt ggtttgtacc atcagatgga    720
attttgagcg cggtttacaa attagtacta tagatatact gtgaggtgca cactagatgg    780
ttctgctttg ttctacagtc agtaactttt tcttccttgc tcacagatgt atgtgttgtt    840
ggggttgcac gcaccccaat gggcggtttc cttggtgcct tgtctccctt gcctgctacg    900
aaacttggct ctatagtaat tcaaggtgag atccgaatct tctctgcatt tacatccgag    960
ctctgaacat ggtcatggct gggggctgtt agctgctctg gaaagagcaa acgtggatcc   1020
agccctcgtg caggaggtct actttggaaa cgtcttgagt gctaatttgg ggcaagctcc   1080
tgcaaggcaa gctgctctgg gtgccgggat accaaactct gttgtttgca ccactgttaa   1140
caaagtctgt gcatctggca tgaaaggttt gaatcgaatt tatctgtctg tccttgtgta   1200
ctctgctcag agttcacaga agtgagagat tacctgacca tgctcttgtt ttcctttcct   1260
atatgcagct actatgtttg cagcacagtc aattcaattg ggtatcaatg atattgttgt   1320
ggctggtggc atggaaagca tgtccaatgc cccaaagtac attgctgaag ctaggtatgc   1380
aattattact tggtggatat attcaatatc gagctgcata aaccaaatga tagtcttaag   1440
ttatttggta gatacatgca tgcttactta tcttcattgc attttctaaa tttgtttgta   1500
agaaatgttg attcaccagc agcgaggcta ttaacgaagt ggccagtttt gttgtgaaag   1560
tatattctgt tcatgtttaa agtgcatttc aactgcttat aagcttgcta attacaattg   1620
caggaagggg tctcgttttg gtcatgacac acttgttgat gccatgctta aggatgggct   1680
ttgggatgta tacaatgatt gtgccatggg aatgtgtgcc gagctttgtg ctgacaacca   1740
tgccctcaca agagaagacc aggtctctta atacagatag cagtaaatgc tgtttgttat   1800
aatattccca tatttttcaa gatataagtt gtgctataca acatgtcaat gctggcaatt   1860
cttttgagac tgccctggaa tcttcgtgct ttatcttggt catcatcata aatggtctag   1920
agactctaga ccagcatctg cattccttgt ctgatgaact agtaacttgg atcctttcta   1980
gcaatgattt tctgttatgt tgtgacatga ttgatagggt gggcttttat gcatgctctg   2040
ggtctgtgaa ctgaccattc atctgcttcc agagatgaaa gtagatgtgc cacacaaaaa   2100
```

```
tgagcactct tttgtattcc tgttagagct atacaagtat aatctcttaa aagctgctca   2160
tcagtacatg acactagtac cttgatgatt ttactgtatc tgtttatgta atttttttct   2220
taataaattt gatatagtat aattaaaatt gagttgcctt ttaattttca cttatatgtt   2280
gcaatttatt tttgtctata ttgcaataaa tatatttcca atttctggta tatttaattt   2340
tacttattct tgaataggat gcatttgcta tccaaagcaa cgagcgtgga attgctgctc   2400
gtgacagtgg tgcttttgca tgggagatta ttccggtaat tttctccctc attgatgata   2460
ctagacatgc ttttcttggt tttctgatgg tcagtgttgt cacccaggtt caagttcctg   2520
ttggtagagg aaaacccccca acattaattg agagagatga aagcctggat aaggtatttt   2580
ttctgacgtg acaaaatatt tttaacaaaa taaagcttgt agttgatcaa aggcaaaaag   2640
actggcaggc actttgattt attgttcttg cttcctccaa atgcaacgtt ccttgcataa   2700
tgagctttgc tagcagttat ttgtaagatc aatgcatgac agttttattt atgtcttgtg   2760
ctattccttt tgtgtcttag tttgacccag taaaactaaa gaaacttcgc ccaagtttca   2820
aggagaatgg tggtacagtt acagctggaa atgcttctag tataaggtag ctgcttgaaa   2880
tatttctgag gccttttgtc ctacaaagtc tttctgagac cttgtttttc ggccatatgt   2940
tgtttagctg acagatatga aggacaacct atttcattgt tgacagttaa attatattat   3000
tgtattatgc atgcattttt aactgatata ttatgcttgc attttgtcaa cttcattgtt   3060
tctctatttg tttttagact gcttgggtat gctctactcc gttaaataga tggtaatttt   3120
ttctttagat ttggtaccca attggtgtga atgatttatc acaatatcac ataagaaagt   3180
aaaaacattt taaatgcctt attatgccca ttcaaacaac aaaagttgcc ctacctttta   3240
aatttcttca tggttgccct agaccttgtt tgtctcactt tgtactgtgt ctatttttag   3300
ctgacaagta ctgtccggtg tactgcctac tatggcttgt gtagccttct gcaaccagtc   3360
atctaatttg ttttatatgg atcagtgatg gagctgctgc attagtttta gtgagtgggc   3420
agaaggctca agagcttggc cttcaagtcc ttgcaaggat caaaggttat gctgatgcag   3480
ctcaagtaag ccacagaaac aattgttagc tctcctaaga gtagaatgcg cttattctaa   3540
tttacactgt gatctaaata ttttaggata taggaagtta tttttatctg gaacgatttt   3600
atgttactat tttagatatc gaaatttatc aactattgga acttgtgatc tggaatatta   3660
ttttgtaatg tggatgctgt ttatacaggc tccggagctt tttacaacca ctccagcact   3720
tgcaatacca aaggctatcg caaatgctgg attagagtca tcccgtgttg atttctatga   3780
gattaatgaa gccttttcgg tatgcattga gtttctttta ctcacatttt ttgtaagcct   3840
tttgttatgc attgagagtt tattttactt attacttttt ttgtaataat gtctttttta   3900
cttgtcaata taggctgttg cgcttgcaaa tcaaaaactt cttggaattc cttcagtaag   3960
tgtcacctgt attaaactgc cattctttgt ggattttaga agttaaacaa tcactttcag   4020
aaagtacata ttgtctcttt tttgttattt gctatgcagc agcaacgtgt aattgcatta   4080
taacagtatt atctgtacta acagcatatg tgtttgcagg aaaagattaa tgttcatgga   4140
ggagctgtat ccttaggaca tcctctcggg tgcagtggtg ctcgcatttt ggttaccctt   4200
attggtgtaa gttctatctt aagatgcttg ttttaccttt tgagttacaa tccctttttgt   4260
ttaaaaaaaa tgtgcaatgt ttttctagta aaaaaataga tggtctttga gtaaaataatg   4320
aattctgaca tatgttacca tatcatcata gggttcgtga tgaacagtaa gcatcttcac   4380
tattgctact aggtctactt cctctatccc aaattataag acgtcttggg atgttggcat   4440
```

-continued

```
tgttagattt atagctttta ctacgtgtac tgagacataa tgtttatcgc aataaaaact   4500
acaaatctag aaaaagtaaa aacatcttat aatttgaaac atagggagta tgttggatca   4560
agccacccca tccctgcacc aaacactacc ttaggccatg ttcggttaca agtggttcga   4620
gggggattga aggggattaa atccccttct agttaaaatt gaataggagg ggatttaatc   4680
cccctcaatc ccctccaatc ctctcgcaac cgaacaagcc cttagtgatt tccaatgtgc   4740
aaattatctg caaatagaat cttgtataaa gctgcaaatg tagagtttca cattgatatc   4800
ggctcatccc ttgtttcact tgttgctggt gatcaatagt ttctttttct cttcattttc   4860
tttaagcaaa acgttgggca caatatagtg ccatcatgtt gggacatcaa aatatattgt   4920
gcttgaccct cctaatcatt gtttcttgtt aacaggttct cagggcgaag agtggcaaga   4980
tcggagttgc tggtgtctgc aacggtggag gcggagcatc agctcttgtt ctggagctcg   5040
cataagaaat ctagaccttg taagactcaa aacaccgaat atatctcaac tcaaattgat   5100
tcttttacta gctggcagta ggagctaacc agtataaggt gctattatca aactgtaata   5160
tggtcgcata ttcagctagg cctaattaag ttgtattttt tccttttaca actgttgtgc   5220
aatttgacta actgctgcac cttgatattg caggtagtta gcaaaagctc cctgaggtga   5280
tcttgtagtc ttattttccg ttgtagtagt cccatagaac atttcttaat ttaatttggc   5340
aataaagcaa aagctccctg aggagatatt gcttctgttg gttgcatagt agagtatcat   5400
gtaataagag ctacagaaat atttttgata tatttgtgag gatactacag aaatatttta   5460
tatatttgtg atgtgtcttg tacatttatc taggtcacat caactatcct gccgcccggg   5520
atctggaact ccgacagccc gatttcaaat agtttgaaag aacatcagca aacacccaag   5580
gcaaatacaa agatcagaga agctggaggg ttagttacag gagcatcagg ttaccgagaa   5640
tgcaaccatg cacggcaaaa ggcgcctacc ccgcatcaaa atttctgcca gaaacaaaca   5700
agaaacgaaa gaatcacacg cacactatct acatccagaa acgtgatgtt atactagata   5760
gtcagcggca ttcaggaagc cctcgtactg ggtaccgttg agggcgctgt agacctcgtc   5820
ccagttctcg atctgctccg acagcggctt cgtgtgtatc ttcacgtgcc ggctcaccag   5880
cttcctcctc ggcactccga ggaaatccag gacatccaag agcttctgca gtgcagcagc   5940
gatggtaagc gacacaacca acggaaggga acagacaagg gaagggcatc agcgagaacg   6000
cactgttctg ttgcggacga cgtcctcgta gtagacgctc atgtgccggg tgttgtttag   6060
gttctcaaga gcgtcgcgag tgtactcgtc agctcgtttc agctgccata tcagtgacgt   6120
cgtgttgagc ctgggcctgt atcttgccag tatatgggcc tgtggagcga gaacgaacga   6180
cacgtcaaac acagagagag atcagatcag ctcagagact tgctgccata tccgtttctt   6240
agctagcatt actaacctca cgcttcgtgt ggacatgggc cttgtgcgtt ccgtttagtt   6300
gcttaagtaa cctgtcgtgg ttgttcgcta cctgtgatac caactggcgg agcaggttcc   6360
ttctgaaaag aaatatcgca gagactcctc ttcggttgaa gtagtcgact acgtccgcat   6420
ggtttgccac gaggccctga aaacatacac cccaaccccg ttcagaagaa atgctccttt   6480
gtttccactc tctagctaca atgcctgttt tgtttccagt ctctaaacct atgtttggcc   6540
aatattcatg gtttggttag gcaatctgtc taccaggaaa aaagttcgtt ctcgcacaaa   6600
ttagatgaag ccctgaaaca aacatgcttg acatgtagat tataatcagt ctactggaca   6660
cactacagaa tctatcaaat attactccat atgcatttgc agttctcatg catgttcgag   6720
agagagaaaa tttgtctaaa atgcaggatc tgacagcaag tcagaaaact aaactagcta   6780
ccgacagttc cataaggcct tgttcggtta ttcgcatccc acatggattg gaagagattg   6840
```

```
gaaaatttta agaaggattt tgacttctta tggatttaaa ctcatccaat ctcgtccaat   6900
ccacatggat tggcactaaa acgagcaagc cctaaagtgg attcccaaaa aaaaatagtt   6960
acatggactt gaggaaagtt tggcgcaata tgcaataaca tttagcatct acagttgaga   7020
acatgtaggc cgtttaggag actacacata ctaataattg aaacatactg gaactaaatg   7080
gaaaaataaa tgaaaaagga tcatccaaat aaattatcta tactgcatgt tttagtccgc   7140
acctgattta gcatccactt gaagccaata gctgcagtgc actcattctt ggaagcgcta   7200
ctgttccagt ccaaattgta cactttatcc agggtatcta ttatagagga aatgttactc   7260
ctcctttctt ttctagagaa aatttcacca ttggagctaa cattcatgtg gctgttaaga   7320
agtgtttcaa accagccact tccagatcgc tgcgatgata taattgcaaa ggaccggaca   7380
gcattgcact tgcattcctc cctagaaata aaaaattatg cattaggcat taaacaaacg   7440
agattgctca atcttaccac agtgcagatc tcacctgctg taaatatagg aagttatttt   7500
tatctggaac gattttatgt tactatttta gatatcgaaa tttatcaact attggaactt   7560
gtgatctgga atattatttt gtaatgtgga tgctgtttat acaggctccg gagcttttta   7620
caaccactcc agcacttgca ataccaaagg ctatcgcaaa tgctggatta gagtcatccc   7680
gtgttgattt ctatgagatt aatgaagcct tttcggtatg cattgagttt cttttactca   7740
catttttgt aagccttttg ttatgcattg agagtttatt ttacttatta cttttttttgt   7800
aataatgtct tttttacttg tcaatatagg ctgttgcgct tgcaaatcaa aaacttcttg   7860
gaattccttc agtaagtgtc acctgtatta aactgccatt ctttgtggat tttagaagtt   7920
aaacaatcac tttcagaaag tacatattgt ctcttttttg ttatttgcta tgcagcagca   7980
acgtgtaatt gcattataac agtattatct gtactaacag catatgtgtt tgcaggaaaa   8040
gattaatgtt catggaggag ctgtatcctt aggacatcct ctcgggtgca gtggtgctcg   8100
cattttggtt acccttattg gtgtaagttc tatcttaaga tgcttgtttt accttttgag   8160
ttacaatccc ttttgtttaa aaaaaatgtg caatgttttt ctagtaaaaa aatagatggt   8220
ctttgagtaa ataatgaatt ctgacatatg ttaccatatc atcatagggt tcgtgatgaa   8280
cagtaagcat cttcactatt gctactaggt ctacttcctc tatcccaaat tataagacgt   8340
cttgggatgt tggcattgtt agatttatag cttttactac gtgtactgag acataatgtt   8400
tatcgcaata aaaactacaa atctagaaaa agtaaaaaca tcttataatt tgaaacatag   8460
ggagtatgtt ggatcaagcc accccatccc tgcaccaaac actaccttag gccatgttcg   8520
gttacaagtg gttcgagggg gattgaaggg gattaaatcc ccttctagtt aaaattgaat   8580
aggaggggat ttaatccccc tcaatcccct ccaatcctct cgcaaccgaa caagccctta   8640
gtgatttcca atgtgcaaat tatctgcaaa tagaatcttg tataaagctg caaatgtaga   8700
gtttcacatt gatatcggct catcccttgt ttcacttgtt gctggtgatc aatagtttct   8760
ttttctcttc attttcttta agcaaaacgt tgggcacaat atagtgccat catgttggga   8820
catcaaaata tattgtgctt gaccctccta atcattgttt cttgttaaca ggttctcagg   8880
gcgaagagtg gcaagatcgg agttgctggt gtctgcaacg gtggaggcgg agcatcagct   8940
cttgttctgg agctcgcata agaaatctag accttgtaag actcaaaaca ccgaatatat   9000
ctcaactcaa attgattctt ttactagctg gcagtaggag ctaaccagta taaggtgcta   9060
ttatcaaact gtaatatggt cgcatattca gctaggccta attaagttgt attttttcct   9120
tttacaactg ttgtgcaatt tgactaactg ctgcaccttg atattgcagg tagttagcaa   9180
```

```
aagctccctg aggtgatctt gtagtcttat tttccgttgt agtagtccca tagaacattt   9240
cttaatttaa tttggcaata aagcaaaagc tccctgagga gatattgctt ctgttggttg   9300
catagtagag tatcatgtaa taagagctac agaaatattt ttgatatatt tgtgaggata   9360
ctacagaaat attttatata tttgtgatgt gtcttgtaca tttatctagg tcacatcaac   9420
tatcctgccg cccgggatct ggaactccga cagcccgatt tcaaatagtt tgaaagaaca   9480
tcagcaaaca cccaaggcaa atacaaagat cagagaacgr mmgtgagcat caggttaccg   9540
agaatgcaac catgcacggc aaaaggcgcc taccccgcat caaaatttct gccagaaaca   9600
aacaagaaac gaaagaatca cacgcacact atctacatcc agaaacgtga tgttatacta   9660
gatagtcagc ggcattcagg aagccctcgt actgggtacc gttgagggcg ctgtagacct   9720
cgtcccagtt ctcgatctgc tccgacagcg gcttcgtgtg tatcttcacg tgccggctca   9780
ccagcttcct cctcggcact ccgaggaaat ccaggacatc caagagcttc tgcagtgcag   9840
cagcgatggt aagcgacaca accaacggaa gggaacagac aagggaaggg catcagcgag   9900
aacgcactgt tctgttgcgg acgacgtcct cgtagtagac gctcatgtgc cgggtgttgt   9960
ttaggttctc aagagcgtcg cgagtgtact cgtcagctcg tttcagctgc catatcagtg  10020
acgtcgtgtt gagcctgggc ctgtatcttg ccagtatatg ggcctgtgga gcgagaacga  10080
acgacacgtc aaacacagag agagatcaga tcagctcaga gacttgctgc catatccgtt  10140
tcttagctag cattactaac ctcacgcttc gtgtggacat gggccttgtg cgttccgttt  10200
agttgcttaa gtaacctgtc gtggttgttc gctacctgtg ataccaactg gcggagcagg  10260
ttccttctga aaagaaatat cgcagagact cctcttcggt tgaagtagtc gactacgtcc  10320
gcatggtttg ccacgaggcc ctgaaaacat acaccccaac cccgttcaga agaaatgctc  10380
ctttgtttcc actctctagc tacaatgcct gttttgtttc cagtctctaa acctatgttt  10440
ggccaatatt catggtttgg ttaggcaatc tgtctaccag gaaaaaagtt cgttctcgca  10500
caaattagat gaagccctga aacaaacatg cttgacatgt agattataat cagtctactg  10560
gacacactac agaatctatc aaatattact ccatatgcat ttgcagttct catgcatgtt  10620
cgagagagag aaaatttgtc taaaatgcag gatctgacag caagtcagaa aactaaacta  10680
gctaccgaca gttccataag gccttgttcg gttattcgca tcccacatgg attggaagag  10740
attggaaaat tttaagaagg attttgactt cttatggatt taaactcatc caatctcgtc  10800
caatccacat ggattggcac taaaacgagc aagccctaaa gtg                    10843
```

<210> SEQ ID NO 39
<211> LENGTH: 1704
<212> TYPE: DNA
<213> ORGANISM: Zea mays

<400> SEQUENCE: 39

```
gtgttgcgtt ccctacttgc tcttttcttc ctccgcttca acctgtcccg agcgcccccc     60
gcgcacacac tgtctttctc tgcctttctt tccctagcgc cgcgccggcg ccgccattcg    120
atcaggccgc ttcgccggcg acagcatatt ccaggtcggt tggttttggc acttcggacc    180
ggcggccatg gcttccgacg gcatcggccc cagagatgta tgtgttgttg gggttgcacg    240
caccccaatg ggcggtttcc ttggtgcctt gtctcccttg cctgctacga aacttggctc    300
tatagtaatt caaggtgaga tccgaatctt ctctgcattt acatccgagc tctgaacatg    360
gtcatggctg ggggctgtta gctgctctgg aaagagcaaa cgtggatcca gccctcgtgc    420
aggaggtcta ctttggaaac gtcttgagtg ctaatttggg gcaagctcct gcaaggcaag    480
```

```
ctgctctggg tgccgggata ccaaactctg ttgtttgcac cactgttaac aaagtctgtg    540

catctggcat gaaagctact atgtttgcag cacagtcaat tcaattgggt atcaatgata    600

ttgttgtggc tggtggcatg gaaagcatgt ccaatgcccc aaagtacatt gctgaagcta    660

ggaaggggtc tcgttttggt catgacacac ttgttgatgc catgcttaag gatgggcttt    720

gggatgtata caatgattgt gccatgggaa tgtgtgccga gctttgtgct gacaaccatg    780

ccctcacaag agaagaccag gatgcatttg ctatccaaag caacgagcgt ggaattgctg    840

ctcgtgacag tggtgctttt gcatgggaga ttattccggt tcaagttcct gttggtagag    900

gaaaaccccc aacattaatt gagagagatg aaagcctgga taagtttgac ccagtaaaac    960

taaagaaact tcgcccaagt ttcaaggaga atggtggtac agttacagct ggaaatgctt   1020

ctagtataag tgatggagct gctgcattag ttttagtgag tgggcagaag gctcaagagc   1080

ttggccttca agtccttgca aggatcaaag gttatgctga tgcagctcaa gctccggagc   1140

tttttacaac cactccagca cttgcaatac caaaggctat cgcaaatgct ggattagagt   1200

catcccgtgt tgatttctat gagattaatg aagccttttc ggctgttgcg cttgcaaatc   1260

aaaaacttct tggaattcct tcagaaaaga ttaatgttca tggaggagct gtatccttag   1320

gacatcctct cgggtgcagt ggtgctcgca ttttggttac ccttattggt gttctcaggg   1380

cgaagagtgg caagatcgga gttgctggtg tctgcaacgg tggaggcgga gcatcagctc   1440

ttgttctgga gctcgcataa gaaatctaga ccttgtagtt agcaaaagct ccctgaggtg   1500

atcttgtagt cttattttcc gttgtagtag tcccatagaa catttcttaa tttaatttgg   1560

caataaagca aaagctccct gaggagatat tgcttctgtt ggttgcatag tagagtatca   1620

tgtaataaga gctacagaaa tatttttgat atatttgtga ggatactaca gaaatatttt   1680

atatatttgt gatgtgtctt gtac                                          1704
```

<210> SEQ ID NO 40
<211> LENGTH: 1637
<212> TYPE: DNA
<213> ORGANISM: Zea mays

<400> SEQUENCE: 40

```
gtgttgcgtt ccctacttgc tcttttcttc ctccgcttca acctgtcccc agcgcccccc     60

gcgcacacac tgtctttctc tgcctttctt tccctagcgc cgcgccggcg ccgccattcg    120

atcaggccgc ttcgccggcg acagcatatt ccaggtcggt tggttttggc acttcggacc    180

ggcggccatg gcttccgacg gcatcggccc cagagatgta tgtgttgttg gggttgcacg    240

caccccaatg ggcggtttcc ttggtgcctt gtctcccttg cctgctacga aacttggctc    300

tatagtaatt caagctgctc tggaaagagc aaacgtggat ccagccctcg tgcaggaggt    360

ctactttgga aacgtcttga gtgctaattt ggggcaagct cctgcaaggc aagctgctct    420

gggtgccggg ataccaaact ctgttgtttg caccactgtt aacaaagtct gtgcatctgg    480

catgaaagct actatgtttg cagcacagtc aattcaattg ggtatcaatg atattgttgt    540

ggctggtggc atggaaagca tgtccaatgc cccaaagtac attgctgaag ctaggaaggg    600

gtctcgtttt ggtcatgaca cacttgttga tgccatgctt aaggatgggc tttgggatgt    660

atacaatgat tgtgccatgg gaatgtgtgc cgagctttgt gctgacaacc atgccctcac    720

aagagaagac caggatgcat ttgctatcca aagcaacgag cgtggaattg ctgctcgtga    780

cagtggtgct tttgcatggg agattattcc ggttcaagtt cctgttggta gaggaaaacc    840
```

```
cccaacatta attgagagag atgaaagcct ggataagttt gacccagtaa aactaaagaa    900

acttcgccca agtttcaagg agaatggtgg tacagttaca gctggaaatg cttctagtat    960

aagtgatgga gctgctgcat tagttttagt gagtgggcag aaggctcaag agcttggcct   1020

tcaagtcctt gcaaggatca aaggttatgc tgatgcagct caagctccgg agctttttac   1080

aaccactcca gcacttgcaa taccaaaggc tatcgcaaat gctggattag agtcatcccg   1140

tgttgatttc tatgagatta atgaagcctt ttcggctgtt gcgcttgcaa atcaaaaact   1200

tcttggaatt ccttcagaaa agattaatgt tcatggagga gctgtatcct taggacatcc   1260

tctcgggtgc agtggtgctc gcattttggt tacccttatt ggtgttctca gggcgaagag   1320

tggcaagatc ggagttgctg gtgtctgcaa cggtggaggc ggagcatcag ctcttgttct   1380

ggagctcgca taagaaatct agaccttgta gttagcaaaa gctccctgag gtgatcttgt   1440

agtcttattt tccgttgtag tagtcccata gaacatttct taatttaatt tggcaataaa   1500

gcaaaagctc cctgaggaga tattgcttct gttggttgca tagtagagta tcatgtaata   1560

agagctacag aaatattttt gatatatttg tgaggatact acagaaatat tttatatatt   1620

tgtgatgtgt cttgtac                                                  1637
```

<210> SEQ ID NO 41
<211> LENGTH: 1780
<212> TYPE: DNA
<213> ORGANISM: Zea mays

<400> SEQUENCE: 41

```
cagagcacca gctcaccgcc ccaccgattc aaaggcgctc ggatcctctg acgtcgacgt     60

tccctgccag ctcccggctg ccgccctcgc tccttccgcc atctgcgctg ctctgcggcg    120

ccagagccgg cgcccgcccg ctgccgccct cgacggaccg ggacacgggg ccccaccgtt    180

ctctttcctg cgctgcgctg cgcggcggct gtgctgctga tcagttaatg tgcctgtgag    240

gctgtgacag gcggcgtcga gcgagtccga ggcgggctaa ctaaacccgc cgtctctcga    300

ggcggcgccc gcggagggcc aggtggaggg ccgaggaagg tggaggcggt gaggcgatgg    360

ggggcgccaa ggcggaggac aagcccgccg ccgccaccgc tgaagacgat tggtgttacc    420

agtttggaaa caagaatgcg tttgactcga aggccccgaa aaaatcacca cttgcattga    480

gagtggttgt ctttgccatg actgtgttat gtgggatatc tatttggtca atgtgtatga    540

agcagctagg gagtgatggc tggtcaagaa tagtgaagat cgaagttgtg gaacaaccat    600

gtaataagtc tacagttcct ccttctgagg ttcaatttgc gcattaccct caaccgacaa    660

cttacagcag ggaggaatgc aagtgcaatg ctgtccggtt ctttgcgatt atatcatcac    720

agcgatctgg aagtggctgg tttgaaaccc ttcttaacag ccacatgaat gttagctcca    780

acggtgaaat tttctctaga aaagaaagga gaagtaacat ttcctctata atagataccc    840

tggataaagt gtacaatttg gactggaaca gtagcgcttc caagaatgag tgcactgcag    900

ctattggctt caagtggatg ctaaatcagg gcctcgtggc aaaccatgcg gacgtagtcg    960

actacttcaa ccgaagagga gtctctgcga tatttctttt cagaaggaac ctgctccgcc   1020

agttggtatc acaggtagcg aacaaccacg acaggttact taagcaacta aacggaacgc   1080

acaaggccca tgtccacacg aagcgtgagg cccatatact ggcaagatac aggcccaggc   1140

tcaacacgac gtcactgata tggcagctga aacgagctga cgagtacact cgcgacgctc   1200

ttgagaacct aaacaacacc cggcacatga gcgtctacta cgaggacgtc gtccgcaaca   1260

gaacaaagct cttggatgtc ctggatttcc tcggagtgcc gaggaggaag ctggtgagcc   1320
```

```
ggcacgtgaa gatacacacg aagccgctgt cggagcagat cgagaactgg gacgaggtct   1380

acagcgccct caacggtacc cagtacgagg gcttcctgaa tgccgctgac tatctagtat   1440

aacatcacgt ttctggatgt agatagtgtg cgtgtgattc tttcgtttct tgtttgtttc   1500

tggcagaaat tttgatgcgg ggtaggcgcc ttttgccgtg catggttgca ttctcggtaa   1560

cctgatgctc ctgtaactaa ccctccagct tctctgatct ttgtatttgc cttgggtgtt   1620

tgctgatgtt ctttcaaact atttgaaatc gggctgtcgg agttccagat cccgggcggc   1680

aggatagttg atgtgaccta gataaatgta caagacacat cacaaatata taaaatattt   1740

ctgtagtatc ctcaaaaaaa aaaaaaaaaa aaaaaaaag                          1780
```

<210> SEQ ID NO 42
<211> LENGTH: 11900
<212> TYPE: DNA
<213> ORGANISM: Zea mays

<400> SEQUENCE: 42

```
aacgccatgg agaaatcaca catgagacac caattactca aggagtttac ttaattatat     60

tttacttaaa ttgagtatag gattcatcgt actaccaagg ggatccaaaa ataaggttgg    120

tgtttgccaa agctcaagcc tctatattca aaagctattt tttgaaaatc aaaaatctct    180

ttaaaattct atggttgact atggttaggt ttgagaaacc tagagtgttt ttgttgaaaa    240

gcagctgagc ttttcagctg aactaaactt cagctgagtt gagcttcttc agctgcagtt    300

gagcttttca gctgagctaa acttcagctg tgtcgagctt tctcaactcc agttgaactt    360

caacttcaac tggggtccag tcaagttcaa ccggggtcca ggcaggttca accggggtcc    420

aaggcaagtt caaccggggt ccagagaggt tcaactgggg tccaggaaaa gttcaaccgg    480

ggtttagaga ggttcaacca gggatgggct gtacgcaacg cgtctaagaa ttgtacgtgt    540

gttctctcgt aaccagaagc agcctcacct cctttgtata tataaacgag cagagggagg    600

cgaacggata gtaacggtca ccatcagagc tatcattaca gccagccaga aacggacgcc    660

attagtgacg tccgttaata gctgacaagc attataactc gttcgttact atccataaca    720

taggaaacga ccaataacgt acaacagtaa tggacggtca tcactttagg caaaatgtgc    780

aaccgttagg aaggaatatt cggaccaagg tccgatctac cacggccacg gcccggcggc    840

gcgcgcgtgt ggcagtcctt catcattttc tcaacttctc actagatgca ccaaagatcc    900

gcctatttaa gttgattgaa ttgtcccttg tacttccggt atggtactaa agtactagta    960

caccgtagca ttaaagtggg cctttagcat tgactattat tgaatattaa tttgggttag   1020

gccctcatta attcaacagt agcttctagg cctaaccatc ccaccccca aactaagcat    1080

agatgaacta tgtttaggtt gctacaaaaa tattccaaaa aataattccc tccgtcctaa   1140

aatactaacc gttttagcat tttaatagat tcataaaaat atgtcagatc cacaagtcat   1200

acgaggcaac tgtctcgagc atgatggatg gagaaccaat atccccttg taaaatgtct    1260

tcttcctcca cttccaatgc atgcaatcta tactcaatat cataatagaa aatccccttt   1320

ccacctcctt agctaagata agcctaagtc attgacaatg gcatgataat tgtactccgc   1380

cctgaaacat gcaataccac ctctacagaa tagaccaaaa actccactcg taggggaaat   1440

actgccccca cggtaagaag aagcttaatc ggagccctga tcgagaaagg tcacgaaaga   1500

tgtacccctc cccccatgca acatgagagt ccgcccccta taggccagat ctttactcgt   1560

gctttgagcc ctactagccc ttacacgagg atccgcccca taggtcagcc catctcatgt   1620
```

```
gcacacaact agggaaacta gtgagtgacc ttgttaacct cagcctaaaa ttcgctccca   1680
ccgggattca aacttaggac ctgaggagtg ctactcagac gacctaacca acttaactag   1740
ggaccctttc acacagaata gtccaaggca ctctgaggtg gaactttcct cattttgatg   1800
tactcatcga tggagtcagc aatgctacag tacgcaagca tgcttaggcc aattgtgcac   1860
ttctggtggg ggaggaaaca ctgcggttga atgcatcggt tcaaaaagtg aagtatggga   1920
agtgctcacc caatctctct aagatatgaa ggaagagact tctctagatg cggtaacttt   1980
gacaaaagta gagcagtggg tagacacaca ggtcgttgaa atggtcttgc attaaccggt   2040
cgtatgcaac tacatagtcg cagtcaatgt atctctgatg ttgccttggc cacctcatcg   2100
acctaggaga ctcggatcca agctctgacg cctgttgcat tatattttgt tgtaataact   2160
tgaataactc ttttcagtca tattgatgtc caagctgaac gaaaacatca caacaatgct   2220
tgatttgatt gaaacgagtg taagaggatt ataaggggtg gtagagaaat ttgaagtgtg   2280
ggttgtgtga atgagatcaa acactcctct atttatagac caagttctag tttttttatt   2340
tttgaaaaaa aatcaaaata aagcgaagca attagaacct gccacatggc aagaggcgat   2400
cgttatcgac atggccgcaa tagctgttca gtaccaacca gtcagtatcg accgacgcgg   2460
tcccaacacg gtcaatagta accctggcgg ccgatcagta gcctcgacaa ccacaagcga   2520
ggctattagt gctggcacca tgtcgggtga tactgaccat ttggttgtgc cacatgggtg   2580
ggcgggcagt agagccaagc gccggcactc gcctaacatg atctaaaaca atcgataaaa   2640
ctgacagatt ggttgcggtt catgactacc tagacctggt cgaccacaag tagaaaatga   2700
gtcgagccga gcttgactcg gctcgtccat ttcacgagct agagagttag gctcggctca   2760
gctcgaagtc ggctcgcgag ctacaccccg atatatatta tttcattata tagtaaatta   2820
ttaatatata aacataaaat ataaaaatat tattcaccat tatgaattat cttatattta   2880
tcatcaaagg ctaagaaata agccgactat ctataaatta tctaatatct atcattattc   2940
tacatattga ttaatttggt acaactagct cgctcgcaga cgctccgaac ttgatctgac   3000
tcgtgagcct caagtttttt ttctagcctt aaccacatgc ccgcgaggat gattgttcga   3060
ggtgattagc aaacgcaaac gatatcaatt gacatttttt attagtttca ttaggtttag   3120
agataaaatt atatcatgta tgtcactcgt ctagtatctt atttgttatc ataaatgttc   3180
taatcctttt tacgtcaccc gaatacaatt ttttactctt tcatgtcata gtaagggact   3240
aagacataca acattttaca tttaacattt ggccacgaca tgtaagagtg agatattgaa   3300
ttcgagtaac atacgaggta cgatgaataa ggtattacac aaaattacag tggcatatag   3360
tgaattgaat tgttctattt ttactttttt tttgcctaac ataaagccta ttttatttag   3420
tactttctct gattcagctt taatttttat gatttattaa ttttattata tatctatata   3480
ttgtatagat taaaaaataa aataaattat agatttagga aaaattacat tcgggtgatt   3540
tggctgttgg gtgttgcgtt ccctacttgc tcttttcttc ctccgcttca acctgtcccc   3600
agcgcccccc gcgcacacac tgtctttctc tgcctttctt tccctagcgc cgcgccggcg   3660
ccgccattcg atcaggccgc ttcgccggcg acagcatatt ccaggtatgc cgtcccttct   3720
gctccttctg cgagaattca aacaccccga actccccaaa tctagtattt gtattcggat   3780
ctgaccattt ttcactgggc ccgcccctga ttcgcaggtc ggttggtttt ggcacttcgg   3840
accggcggcc atggcttccg acggcatcgg ccccagaggt ataactgttt catctcttct   3900
ttgtgttcaa acagacagac gtcaaaccgc cgagaggagg tacaaatata gattttgggc   3960
tatgagcacg ccattgcgct tccagcgatc tgacatattg ggaattcttg tttttttttt   4020
```

gggtaccttg caaggccgaa atttgacgct tttctgttta attctagtgc ctgtctgcat 4080
ccattagggc atcctagctg ctccatgctc gtgatctcgt ccgtttgctt gattgaatcc 4140
attgttttcc aaagttcatt gctactgcga aatacgttta tatgattacc acaatttgtg 4200
tttttgcctt ttcgggttgc acagagggta ctgccatcat tgttgtttta gcgccatttg 4260
gaacaagtga ttcactggta ctagtacagt atgtgctttt catgtgtgtt tggtttgtac 4320
catcagatgg aattttgagc gcggtttaca aattagtact atagatatac tgtgaggtgc 4380
acactagatg gttctgcttt gttctacagt cagtaacttt ttcttccttg ctcacagatg 4440
tatgtgttgt tggggttgca cgcaccccaa tgggcggttt ccttggtgcc ttgtctccct 4500
tgcctgctac gaaacttggc tctatagtaa ttcaaggtga gatccgaatc ttctctgcat 4560
ttacatccga gctctgaaca tggtcatggc tgggggctgt tagctgctct ggaaagagca 4620
aacgtggatc cagccctcgt gcaggaggtc tactttggaa acgtcttgag tgctaatttg 4680
gggcaagctc ctgcaaggca agctgctctg ggtgccggga taccaaactc tgttgtttgc 4740
accactgtta acaaagtctg tgcatctggc atgaaaggtt tgaatcgaat ttatctgtct 4800
gtccttgtgt actctgctca gagttcacag aagtgagaga ttacctgacc atgctcttgt 4860
tttcctttcc tatatgcagc tactatgttt gcagcacagt caattcaatt gggtatcaat 4920
gatattgttg tggctggtgg catggaaagc atgtccaatg ccccaaagta cattgctgaa 4980
gctaggtatg caattattac ttggtggata tattcaatat cgagctgcat aaaccaaatg 5040
atagtcttaa gttatttggt agatacatgc atgcttactt atcttcattg cattttctaa 5100
atttgtttgt aagaaatgtt gattcaccag cagcgaggct attaacgaag tggccagttt 5160
tgttgtgaaa gtatattctg ttcatgttta aagtgcattt caactgctta taagcttgct 5220
aattacaatt gcaggaaggg gtctcgtttt ggtcatgaca cacttgttga tgccatgctt 5280
aaggatgggc tttgggatgt atacaatgat tgtgccatgg gaatgtgtgc cgagctttgt 5340
gctgacaacc atgccctcac aagagaagac caggtctctt aatacagata gcagtaaatg 5400
ctgtttgtta taatattccc atatttttca agatataagt tgtgctatac aacatgtcaa 5460
tgctggcaat tcttttgaga ctgccctgga atcttcgtgc tttatcttgg tcatcatcat 5520
aaatggtcta gagactctag accagcatct gcattccttg tctgatgaac tagtaacttg 5580
gatcctttct agcaatgatt ttctgttatg ttgtgacatg attgataggg tgggctttta 5640
tgcatgctct gggtctgtga actgaccatt catctgcttc cagagatgaa agtagatgtg 5700
ccacacaaaa atgagcactc ttttgtattc ctgttagagc tatacaagta taatctctta 5760
aaagctgctc atcagtacat gacactagta ccttgatgat tttactgtat ctgtttatgt 5820
aatttttttc ttaataaatt tgatatagta taattaaaat tgagttgcct tttaattttc 5880
acttatatgt tgcaatttat ttttgtctat attgcaataa atatatttcc aatttctggt 5940
atatttaatt ttacttattc ttgaatagga tgcatttgct atccaaagca acgagcgtgg 6000
aattgctgct cgtgacagtg gtgcttttgc atgggagatt attccggtaa ttttctccct 6060
cattgatgat actagacatg cttttcttgg ttttctgatg gtcagtgttg tcacccaggt 6120
tcaagttcct gttggtagag gaaaaccccc aacattaatt gagagagatg aaagcctgga 6180
taaggtattt tttctgacgt gacaaaatat ttttaacaaa ataaagcttg tagttgatca 6240
aaggcaaaaa gactggcagg cactttgatt tattgttctt gcttcctcca aatgcaacgt 6300
tccttgcata atgagctttg ctagcagtta tttgtaagat caatgcatga cagttttatt 6360

```
tatgtcttgt gctattcctt ttgtgtctta gtttgaccca gtaaaactaa agaaacttcg   6420
cccaagtttc aaggagaatg gtggtacagt tacagctgga aatgcttcta gtataaggta   6480
gctgcttgaa atatttctga ggccttttgt cctacaaagt ctttctgaga ccttgttttt   6540
cggccatatg ttgtttagct gacagatatg aaggacaacc tatttcattg ttgacagtta   6600
aattatatta ttgtattatg catgcatttt taactgatat attatgcttg cattttgtca   6660
acttcattgt ttctctattt gtttttagac tgcttgggta tgctctactc cgttaaatag   6720
atggtaattt tttctttaga tttggtaccc aattggtgtg aatgatttat cacaatatca   6780
cataagaaag taaaaacatt ttaaatgcct tattatgccc attcaaacaa caaaagttgc   6840
cctacctttt aaatttcttc atggttgccc tagaccttgt ttgtctcact ttgtactgtg   6900
tctattttta gctgacaagt actgtccggt gtactgccta ctatggcttg tgtagccttc   6960
tgcaaccagt catctaattt gttttatatg gatcagtgat ggagctgctg cattagtttt   7020
agtgagtggg cagaaggctc aagagcttgg ccttcaagtc cttgcaagga tcaaaggtta   7080
tgctgatgca gctcaagtaa gccacagaaa caattgttag ctctcctaag agtagaatgc   7140
gcttattcta atttacactg tgatctaaat attttaggat ataggaagtt atttttatct   7200
ggaacgattt tatgttacta ttttagatat cgaaatttat caactattgg aacttgtgat   7260
ctggaatatt attttgtaat gtggatgctg tttatacagg ctccggagct ttttacaacc   7320
actccagcac ttgcaatacc aaaggctatc gcaaatgctg gattagagtc atcccgtgtt   7380
gatttctatg agattaatga agccttttcg gtatgcattg agtttctttt actcacattt   7440
tttgtaagcc ttttgttatg cattgagagt ttattttact tattactttt tttgtaataa   7500
tgtctttttt acttgtcaat ataggctgtt gcgcttgcaa atcaaaaact tcttggaatt   7560
ccttcagtaa gtgtcacctg tattaaactg ccattctttg tggattttag aagttaaaca   7620
atcactttca gaaagtacat attgtctctt ttttgttatt tgctatgcag cagcaacgtg   7680
taattgcatt ataacagtat tatctgtact aacagcatat gtgtttgcag gaaaagatta   7740
atgttcatgg aggagctgta tccttaggac atcctctcgg gtgcagtggt gctcgcattt   7800
tggttaccct tattggtgta agttctatct taagatgctt gttttacctt ttgagttaca   7860
atccttttg tttaaaaaaa atgtgcaatg tttttctagt aaaaaaatag atggtctttg    7920
agtaaataat gaattctgac atatgttacc atatcatcat agggttcgtg atgaacagta   7980
agcatcttca ctattgctac taggtctact tcctctatcc caaattataa gacgtcttgg   8040
gatgttggca ttgttagatt tatagctttt actacgtgta ctgagacata atgtttatcg   8100
caataaaaac tacaaatcta gaaaaagtaa aaacatctta taatttgaaa catagggagt   8160
atgttggatc aagccacccc atccctgcac caaacactac cttaggccat gttcggttac   8220
aagtggttcg agggggattg aaggggatta aatccccttc tagttaaaat tgaataggag   8280
gggatttaat ccccctcaat cccctccaat cctctcgcaa ccgaacaagc ccttagtgat   8340
ttccaatgtg caaattatct gcaaatagaa tcttgtataa agctgcaaat gtagagtttc   8400
acattgatat cggctcatcc cttgtttcac ttgttgctgg tgatcaatag tttctttttc   8460
tcttcatttt ctttaagcaa aacgttgggc acaatatagt gccatcatgt tgggacatca   8520
aaatatattg tgcttgaccc tcctaatcat tgtttcttgt taacaggttc tcagggcgaa   8580
gagtggcaag atcggagttg ctggtgtctg caacggtgga ggcggagcat cagctcttgt   8640
tctggagctc gcataagaaa tctagacctt gtaagactca aaacaccgaa tatatctcaa   8700
ctcaaattga ttcttttact agctggcagt aggagctaac cagtataagg tgctattatc   8760
```

```
aaactgtaat atggtcgcat attcagctag gcctaattaa gttgtatttt ttccttttac   8820
aactgttgtg caatttgact aactgctgca ccttgatatt gcaggtagtt agcaaaagct   8880
ccctgaggtg atcttgtagt cttattttcc gttgtagtag tcccatagaa catttcttaa   8940
tttaatttgg caataaagca aaagctccct gaggagatat tgcttctgtt ggttgcatag   9000
tagagtatca tgtaataaga gctacagaaa tatttttgat atatttgtga ggatactaca   9060
gaaatatttt atatatttgt gatgtgtctt gtacatttat ctaggtcaca tcaactatcc   9120
tgccgcccgg gatctggaac tccgacagcc cgatttcaaa tagtttgaaa gaacatcagc   9180
aaacacccaa ggcaaataca aagatcagag aagctggagg gttagttaca ggagcatcag   9240
gttaccgaga atgcaaccat gcacggcaaa aggcgcctac cccgcatcaa aatttctgcc   9300
agaaacaaac aagaaacgaa agaatcacac gcacactatc tacatccaga aacgtgatgt   9360
tatactagat agtcagcggc attcaggaag ccctcgtact gggtaccgtt gagggcgctg   9420
tagacctcgt cccagttctc gatctgctcc gacagcggct tcgtgtgtat cttcacgtgc   9480
cggctcacca gcttcctcct cggcactccg aggaaatcca ggacatccaa gagcttctgc   9540
agtgcagcag cgatggtaag cgacacaacc aacggaaggg aacagacaaa gggcatcagc   9600
gagaacgcac tgttctgttg cggacgacat cctcgtagta gacgctcatg tgccgggtgt   9660
tgtttaggtt ctcaagagcg tcgcgagtgt actcgtcagc tcgtttcagc tgccatatca   9720
gtgacgtcgt gttgagcctg ggcctgtatc ttgccagtat atgggcctgt ggagcgagaa   9780
cgaacgacac gtcaaacaca gacagagatc agctcagctc agagacttgc tgtgagagtg   9840
agacattagc cgcgaacacg tttcttagct agcattacta acctcacgct tcgtgtggac   9900
atgggccttg tgcgttccgt ttagttgctt aagtaacctg tcgtgattgt tcgctacttg   9960
tgataccaac tggcggagca ggttccttct gaaaagaaat attgcagaga ctcctcttcg  10020
attgaagtag tcgactacgt ccgcatggtt tgccacgagg ccctgaaaac atacacccca  10080
accccaaccc cgttcagaag aaatgctcct ttgtttccac tctctagcta cagtgcctgt  10140
tttgtttcca gtctctaact ctatgtttgg ccaacattca tggtttggtt aggcaatctg  10200
tctaccagga aaaaagtttg ttctcacaca aattagatga agccctgaaa caaacatgct  10260
tgacatgtag attataatca gtctactgga cacactacag aatctatcaa atattactcc  10320
atatgcattt gcagttctca tgcacgttcg agagaaaaaa attgtctaaa atgcaggatc  10380
tgacagcaag tcacaaaact aaactagcta tccgacagtc ccataaggtt attcgcatcc  10440
cacatagatt ggaagggatt ggaaaatttt aagaaggatt ttgacttctt acggatttaa  10500
acccgttcaa tctcgtccaa tccacatgga ttggcactaa gacgagcaag ccctaaagtg  10560
gattcccaaa aaaaaatagt tccatggact tgaggaaagt ttggagcaat atgcaatact  10620
ggaactaaat ggaaaaataa atgaaaaagg gtcatccaaa taaatctata ctgcatgttt  10680
tagtccgcac ctgatttagc atccacttga agccaatagc tgcagtgcac tcattcttgg  10740
aagcgctact gttccagtcc aaattgtaca ctttatccag ggtatctatt atagaggaaa  10800
tgttactcct cctttctttt ctagagaaaa tttcaccatt ggagctaaca ttcatgtggc  10860
tgttaagaag agtttcaaac cagccacttc cagatcgctg cgatgatata attgcaaagg  10920
accggacagc attgcacttg cattcctccc tagaaattaa aaattatgta ttaggcatta  10980
aacaaacgag attgctcaat cttaccacag ttgcagatct cacctgctgt aagttatcgg  11040
ttgaggatag cgcacaaatt gagcctccga aagaggagca atggacttat tacatggttg  11100
```

```
tcccacaact tcaatcttga caactcttga ccagccatca ctccctagtt gcttcatgca  11160

cattgagcaa atagatatcc cgcataacat agtcatagca aagacaaccg ttctcaacgc  11220

gatcggtgat tttttcgggg gcttcaagtc aaatgcatcc tgcaaacaga tccgaccagt  11280

acaaaaccaa tcagcaggtt gcactgcgca tacgcggttc agtgccagta tatatacatt  11340

gcagcccttt tttgaggtaa gatctgttat tttgtaacct tctgctacag taaaaaaacc  11400

tttcagcaaa caacacaaac attaatgttc aatgtgagct gagaagcatc catttggcta  11460

catctatata agcagaaata aaaagaaata aacaaataaa acttcaaggt ctatctagtc  11520

ctcagggaag ttaaaatgag cacgtactat tcaattcagc tactagcctt tttaccaaca  11580

tggaagacac ggcaagggat gaaaaggccc ttttttgata agttcaagta cattcccata  11640

tattctgtcg cccagctgcc ttagggggcg tttggttgcc ttctccagtg gtgcagctgc  11700

atctacacat gcaaaaagta gtgtttgttt ggttcgttgt atcgcacgag acaggctagc  11760

acggaactta aagcgccgcg agccaggccc ggcagaaacg catcgcgcga ccgcacgcgc  11820

gcggccaggc tccgctcagc cagctcttta ctcgtgcacg catatcgaga cacgttttta  11880

attggttttt tcattatatc                                              11900
```

<210> SEQ ID NO 43
<211> LENGTH: 1411
<212> TYPE: DNA
<213> ORGANISM: Zea mays

<400> SEQUENCE: 43

```
gtgttgcgtt ccctacttgc tcttttcttc ctccgcttca acctgtcccc agcgcccccc    60

gcgcacacac tgtctttctc tgcctttctt tccctagcgc cgcgccggcg ccgccattcg   120

atcaggccgc ttcgccggcg acagcatatt ccaggtcggt tggttttggc acttcggacc   180

ggcggccatg gcttccgacg gcatcggccc cagaggatgt atgtgttgtt ggggttgcac   240

gcaccccaat gggcggtttc cttggtgcct tgtctccctt gcctgctacg aaacttggct   300

ctatagtaat tcaagctgct ctggaaagag caaacgtgga tccagccctc gtgcaggagg   360

tctactttgg aaacgtcttg agtgctaatt tggggcaagc tcctgcaagg caagctgctc   420

tgggtgccgg gataccaaac tctgttgttt gcaccactgt taacaaagtc tgtgcatctg   480

gcatgaaagc tactatgttt gcagcacagt caattcaatt gggtatcaat gatattgttg   540

tggctggtgg catggaaagc atgtccaatg ccccaaagta cattgctgaa gctaggaagg   600

ggtctcgttt tggtcatgac acacttgttg atgccatgct taaggatggg ctttgggatg   660

tatacaatga ttgtgccatg ggaatgtgtg ccgagctttg tgctgacaac catgccctca   720

caagagaaga ccaggatgca tttgctatcc aaagcaacga gcgtggaatt gctgctcgtg   780

acagtggtgc ttttgcatgg gagattattc cggttcaagt tcctgttggt agaggaaaac   840

cccaacatt aattgagaga gatgaaagcc tggataagtt tgacccagta aaactaaaga    900

aacttcgccc aagtttcaag gagaatggtg gtacagttac agctggaaat gcttctagta   960

taagtgatgg agctgctgca ttagttttag tgagtgggca gaaggctcaa gagcttggcc  1020

ttcaagtcct tgcaaggatc aaaggttatg ctgatgcagc tcaagctccg gagcttttta  1080

caaccactcc agcacttgca ataccaaagg ctatcgcaaa tgctggatta gagtcatccc  1140

gtgttgattt ctatgagatt aatgaagcct tttcggctgt tgcgcttgca aatcaaaaac  1200

ttcttggaat tccttcagaa aagattaatg ttcatggagg agctgtatcc ttaggacatc  1260

ctctcgggtg cagtggtgct cgcattttgg ttacccttat tggtgttctc agggcgaaga  1320
```

gtggcaagat cggagttgct ggtgtctgca acggtggagg cggagcatca gctcttgttc 1380
tggagctcgc ataagaaatc tagaccttgt a 1411

<210> SEQ ID NO 44
<211> LENGTH: 5790
<212> TYPE: DNA
<213> ORGANISM: Zea mays

<400> SEQUENCE: 44
gggggcagtc tatactgccc ccttaatagt tagtagagat ttggtacaac tcacgagcta 60
gctcgctcgc agacgctccg aacttgatct gactcgtgag cctcaagttt tttttctagc 120
cttaaccaca tgcccacgag gatgattgtt cgaggtgatt agcaaacgca aacgatatca 180
attgacattt tttattagtt tcattaggtt tagagataaa attatatcat gtatgtcact 240
catctagtat cttatttgtt atcataaatg ttctaatcct ttttacgtca cccgaataca 300
attttttact ctttcatgtc atcgttgatg acatagtaag ggactaagac atacaacatt 360
ttacatttaa catttggcca cgacatgtaa gagtgagata ttgaattcga gtaacatacg 420
aggtacgatg aataaggtat tacacaaaat tacagtggca tatagtgaat tgaattgttc 480
tatttttact tttttttgc ctaacataaa gcctatttta tttagtactt tctctgattc 540
agctttaatt tttatgattt attaatttta ttatatatct atatattgta tagattaaaa 600
aataaaatag attatagatt taggaaaaat tacattcggg tgatttggct gttgggtgtt 660
gcgttcccta cttgctcttt tcttcctccg cttcaacctg tccccagcgc cccccgcgca 720
cacactgtct ttctctgcct ttctttccct agcgccgcgc cggcgacgcc attcgatcag 780
gccgcttcgc cggcgacagc atattccagg tatgccgtcc cttctgctcc ttctgcgaga 840
attcaaacac cccgaactcc ccaaatctag tatttgtatt cggatctgac catttttcac 900
tgggcccgcc cctgattcgc aggtcggttg gttttggcac ttcggaccgg cggccatggc 960
ttccgacggc atcggcccca gaggtattac tgtttcatct cttcttgtgt tcaaacagac 1020
agacgtcaag ccgccgagag gaggtacaaa tatagatttt gggtaatgag cacgccattg 1080
cgcttccagc gatctgacat attgggaatt cttgcttttt tttgggtacc ttgcaaggcc 1140
gaaatttgac gcttttctgt ttaattctag tgcctgtctg catccattag ggcatcctag 1200
ctgctccatg ctcgtgatct cgtccgtttg cttgattgaa tccattgttt tccaaagttc 1260
attgctactg cgaaatacgt ttatatgatt accacaagtt gtgttttttc cttttcgggt 1320
tgcacagagg gtactgccat cattgttgtt atagcgccat ttggaacaag tgattcactg 1380
gtactagtac agtatgtgct tttcatgtgt gtttggtttg taccatcaga tggaattttg 1440
agcgcggttt acaaattagt actatagata tactgtgagg tgcacactag atggttctgc 1500
tttgttctac agtcagtaac tttttcttcc ttgctcacag atgtatgtgt tgttggggtt 1560
gcacgcaccc caatgggcgg tttccttggt gccttgtctc ccttgcctgc tacgaaactt 1620
ggctctatag taattcaagg tgagatccga atcttctctg catttacatc cgagctctga 1680
acatggtcat ggctgggggc tgttagctgc tctggaaaga gcaaacgtgg atccagccct 1740
cgtgcaggag gtctactttg gaaacgtctt gagtgctaat ttggggcaag cgcctgcaag 1800
gcaagctgct ctgggtgccg ggataccaaa ctctgttgtt tgcaccactg ttaacaaagt 1860
ctgtgcatct ggcatgaaag gtttgaatcg aatttatctg tctgtccttg tgtactctgc 1920
tcagagttca cagaagtgag agattacctg accatgctct tgtttccctt tcctatatgc 1980

-continued

```
agctactatg tttgcagcac agtcaattca attgggtatc aatgatattg ttgtggctgg   2040
tggcatggaa agcatgtcca atgccccaaa gtacattgct gaagctaggt atgcaattat   2100
tacttggtgg atatattcaa tatcgagctg cataaaccaa atgatagtct taagttattt   2160
ggtagataca tgcatgctta cttatcttca ttgcattttc taaatttgtt tgtaagaaat   2220
gttgattcac cagcagcgag gctattaacg aagtggccag ttttgttgtg aaagtatatt   2280
ctgttcatgt ttaaagtgca tttcaactgc tttaatccaa taagcttgct acttacaatt   2340
gcaggaaggg gtctcgtttt ggtcatgaca cacttgttga tgccatgctt aaggatgggc   2400
tttgggatgt atacaatgat tgtgccatgg gaatgtgtgc cgagctttgt gctgacaatc   2460
atgccctcac aagagaagac caggtctctt aatacagata gcagtaaatg ctgtttgtta   2520
taatattccc atatttttca agatataagt tgtgctatac aacatgtcaa tgctggcaat   2580
tattttgaga gtgccctgga atcttcgtgc tttatcttgg ttatcatcat aaatggtcta   2640
gagactctag accagcatct gcattccttg tccgatgaac tagtaacttg gatcctttct   2700
ggcaatgatt ttctgttagg ttgtgacatg attgataggg tgggcttatg catgctctgg   2760
gtctgtgaac tgaccattca tttgcttcca gagatgaaag tagatgtgcc acacaaaaat   2820
gagcactctt ttgcattctt gttagagcta tacaagtata atctcttaaa agctgctcat   2880
cagtacatga cactagtacc ttgatgattt tactgtatct gtttatgtaa ttttttttctt   2940
aataaatttg atatagtata attaaaattg agttgccttt gaattttcac ttatatgttg   3000
caatgtattt ttgtctatat tgcaataaat atattcccaa tttctggtat atttacttat   3060
tcttgaatag gatgcatttg ctatccaaag caatgagcgt ggaattgctg ctcgtgacag   3120
tggtgctttt gcatgggaga ttattccggt aattttctcc ctcattgatg atactagaca   3180
tgcttttctt ggttttctga tggtcaatgt tgtcgcccag gttcaagttc ctgttggtag   3240
aggaaaaccc ccaacattaa ttgagagaga tgaaagcctg gataaggttt tttttctgat   3300
ttgacaaaat atttttaaca aaataaagct tgtagttgat caaaggcaaa aagactggca   3360
ggcactttga tttattgttc ttgcttcctc caaatgcaac gttcctcgca taatgagctt   3420
tgctagcagt tatttgtaag atcaatgcat gacagtttta tttatgtctt gtgctattcc   3480
ttttgtgtct tagtttgacc cagtaaaact aaagaaactt cgcccaagtt tcaaggagaa   3540
tgatggtaca gttacagctg gaaatgcttc tagtataagg tagctgcttg aaatatttct   3600
gagacctttt tgtcctacaa agtctttctg agaccttgtt tttcggccat atgttgttta   3660
gctgacagat atgaaggaca acctatttca ttgttgacag ttaaattata ttattgtatt   3720
atgcatgcat ttttaactga tatattatgc ttgcattttg tcaacttcat tgtttctcta   3780
tttgttttta gactgcttgg gtatgctcta ctctgtgaaa tagatggtaa tttttttcttt   3840
agaattggta cccaatcgat gtgaatgatt tatcacataa gaaagtaaaa acattttaaa   3900
tgccttatta tgcccattca aacaacaaaa gttgccctag accttgtctg tctcactttg   3960
tactgtgtct atttttagct gaccagtact gtccggtgta ctgcctacta tggcttgtct   4020
agccttctgc aaccagtcat atctaatttg ttttatatgg atcagtgatg gagctgctgc   4080
attagttttg gtgagtgggc agaaggctca agagcttggc cttcaagtcc ttgcaaggat   4140
caaaggttat gctgatgcag ctcaagtaag ccacagtaac aattgttagc tctcctaaga   4200
gtagaatgcg cttattctaa ttcacattgt gatctaaata ttttaggata taggaagtta   4260
tttttatctg gaacgatttt atgttactat tttagatatc gaaatttatc aactattgga   4320
acttgtgatc tggaatatta ttttgtaatg tggatgctgt ttatacaggc tccggagctt   4380
```

```
tttacaacca ctccagcact tgcaatacca aaggctatcg caaatgctgg attagagtca   4440

tcccatgttg atttctatga gattaatgaa gccttttcgg tatgcattgg gtttctttat   4500

ttgtaagcct tttgttatgc attgagagct tattttactt attacttttt ttttgtaata   4560

atgtcttttt tacttatcaa tataggctgt tgcacttgca aatcaaaagc ttcttggaat   4620

tccttcagta agtgtcacct gtattaaact gccattcttt gtgcatttta gaagttaaaa   4680

catcactttc agaaagtaca tattggccct tttttgttat ttgctatgca gcagcaacat   4740

gtaattgcat tataacagca ttatatgtac taacaacata tgtgtttgca ggaaaagatt   4800

aatgttcatg gaggagctgt atctttagga catcctctcg ggtgcagtgg tgctcgcatt   4860

ttggttaccc ttattggtgt aagttctatc ttaagatgct tgttttatct tttgagttac   4920

aatccctttt gtttaaaaaa atgtgcaatg tttttctagt aaaaaaatag atgatggtct   4980

ttgagtaatt gatgaattct gacatatgtt accgtatcat catagggttc gtgatgaaca   5040

gtaagcatct tcactattgc tactaagtct acttccttag tgttttccaa tgtgcaatgt   5100

ttttcttgta taaagctgca aatgtagagt ttcacttgtt gctggtgatc agtagtttct   5160

cttcattttc tttaagcaaa accttgagaa caatatggtg ccatcatgtt gggacatcaa   5220

atatatggtg cttgaccctc ctaatcattg tttcttgtta acaggttctc agggcgaaga   5280

gtggcaagat cggagttgct ggtgtctgca acggtggagg cggagcatca gctcttgttc   5340

tggagctcgc ataagaaatc tagaccttgt aaggctcaaa acaccgaata tatctcaact   5400

caaattgatt cttttactag ctggcaggag ctaaccagta taaggtgcta ttactgttgt   5460

gcaatttgac taactgctgc aactgatatt gcaggtattt agcaaaagtt ccctgaggtg   5520

atcttgtagt cttattttcc gttgtagtag tcccatagaa catttcttaa tttaatttgg   5580

caataaagcg aagtcgtgct tctgttggtt gcatagtaga gtatcatgta ataagagcaa   5640

tggggatgtt tcatagatat ttttgaggat gctacagaaa tattttatat actagtgagt   5700

gctcgtgcgt tgcaacggga atatataatt ctatgataac ttatatacaa aatgtgtgct   5760

acattgttat aagaaaatgt ttcataatct                                   5790
```

```
<210> SEQ ID NO 45
<211> LENGTH: 5881
<212> TYPE: DNA
<213> ORGANISM: Zea mays

<400> SEQUENCE: 45
```

```
gggcagtcta tactgccccc ttaatagtta gtagagattt ggtacaactc acgagctagc     60

tcgctcgcag acgctccgaa cttgatctga ctcgtgagcc tcaagttttt tttctagcct    120

taaccacatg cccacgagga tgattgttcg aggtgattag caaacgcaaa cgatatcaat    180

tgacattttt tattagtttc attaggttta gagataaaat tatatcatgt atgtcactca    240

tctagtatct tatttgttat cataaatgtt ctaatccttt ttacgtcacc cgaatacaat    300

tttttactct ttcatgtcat cgttgatgac atagtaaggg actaagacat acaacatttt    360

acatttaaca tttggccacg acatgtaaga gtgagatatt gaattcgagt aacatacgag    420

gtacgatgaa taaggtatta cacaaaatta cagtggcata tagtgaattg aattgttcta    480

tttttacttt ttttttgcct aacataaagc ctattttatt tagtactttc tctgattcag    540

ctttaatttt tatgatttat taattttatt atatatctat atattgtata gattaaaaaa    600

taaaatagat tatagattta ggaaaaatta cattcgggtg atttggctgt tgggtgttgc    660
```

```
gttccctact tgctcttttc ttcctccgct tcaacctgtc cccagcgccc cccgcgcaca    720
cactgtcttt ctctgccttt ctttccctag cgccgcgccg gcgacgccat tcgatcaggc    780
cgcttcgccg gcgacagcat attccaggta tgccgtccct tctgctcctt ctgcgagaat    840
tcaaacaccc cgaactcccc aaatctagta tttgtattcg gatctgacca tttttcactg    900
ggcccgcccc tgattcgcag gtcggttggt tttggcactt cggaccggcg gccatggctt    960
ccgacggcat cggccccaga ggtattactg tttcatctct tcttgtgttc aaacagacag   1020
acgtcaagcc gccgagagga ggtacaaata tagattttgg gtaatgagca cgccattgcg   1080
cttccagcga tctgacatat tgggaattct tgcttttttt tgggtacctt gcaaggccga   1140
aatttgacgc ttttctgttt aattctagtg cctgtctgca tccattaggg catcctagct   1200
gctccatgct cgtgatctcg tccgtttgct tgattgaatc cattgttttc caaagttcat   1260
tgctactgcg aaatacgttt atatgattac cacaagttgt gttttttcct tttcgggttg   1320
cacagagggt actgccatca ttgttgttat agcgccattt ggaacaagtg attcactggt   1380
actagtacag tatgtgcttt tcatgtgtgt ttggtttgta ccatcagatg gaattttgag   1440
cgcggtttac aaattagtac tatagatata ctgtgaggtg cacactagat ggttctgctt   1500
tgttctacag tcagtaactt tttcttcctt gctcacagat gtatgtgttg ttggggttgc   1560
acgcacccca atgggcggtt tccttggtgc cttgtctccc ttgcctgcta cgaaacttgg   1620
ctctatagta attcaaggtg agatccgaat cttctctgca tttacatccg agctctgaac   1680
atggtcatgg ctgggggctg ttagctgctc tggaaagagc aaacgtggat ccagccctcg   1740
tgcaggaggt ctactttgga aacgtcttga gtgctaattt ggggcaagcg cctgcaaggc   1800
aagctgctct gggtgccggg ataccaaact ctgttgtttg caccactgtt aacaaagtct   1860
gtgcatctgg catgaaaggt ttgaatcgaa tttatctgtc tgtccttgtg tactctgctc   1920
agagttcaca gaagtgagag attacctgac catgctcttg tttccctttc ctatatgcag   1980
ctactatgtt tgcagcacag tcaattcaat tgggtatcaa tgatattgtt gtggctggtg   2040
gcatggaaag catgtccaat gccccaaagt acattgctga agctaggtat gcaattatta   2100
cttggtggat atattcaata tcgagctgca taaaccaaat gatagtctta agttatttgg   2160
tagatacatg catgcttact tatcttcatt gcattttcta aatttgtttg taagaaatgt   2220
tgattcacca gcagcgaggc tattaacgaa gtggccagtt ttgttgtgaa agtatattct   2280
gttcatgttt aaagtgcatt tcaactgctt taatccaata agcttgctac ttacaattgc   2340
aggaaggggt ctcgttttgg tcatgacaca cttgttgatg ccatgcttaa ggatgggctt   2400
tgggatgtat acaatgattg tgccatggga atgtgtgccg agctttgtgc tgacaatcat   2460
gccctcacaa gagaagacca ggtctcttaa tacagatagc agtaaatgct gtttgttata   2520
atattcccat atttttcaag atataagttg tgctatacaa catgtcaatg ctggcaatta   2580
ttttgagagt gccctggaat cttcgtgctt tatcttggtt atcatcataa atggtctaga   2640
gactctagac cagcatctgc attccttgtc cgatgaacta gtaacttgga tcctttctgg   2700
caatgatttt ctgttaggtt gtgacatgat tgatagggtg ggcttatgca tgctctgggt   2760
ctgtgaactg accattcatt tgcttccaga gatgaaagta gatgtgccac acaaaaatga   2820
gcactctttt gcattcttgt tagagctata caagtataat ctcttaaaag ctgctcatca   2880
gtacatgaca ctagtacctt gatgatttta ctgtatctgt ttatgtaatt tttttcttaa   2940
taaatttgat atagtataat taaaattgag ttgcctttga attttcactt atatgttgca   3000
atgtattttt gtctatattg caataaatat attcccaatt tctggtatat ttacttattc   3060
```

```
ttgaatagga tgcatttgct atccaaagca atgagcgtgg aattgctgct cgtgacagtg   3120
gtgcttttgc atgggagatt attccggtaa ttttctccct cattgatgat actagacatg   3180
cttttcttgg ttttctgatg gtcaatgttg tcgcccaggt tcaagttcct gttggtagag   3240
gaaaaccccc aacattaatt gagagagatg aaagcctgga taaggttttt tttctgattt   3300
gacaaaatat ttttaacaaa ataaagcttg tagttgatca aaggcaaaaa gactggcagg   3360
cactttgatt tattgttctt gcttcctcca aatgcaacgt tcctcgcata atgagctttg   3420
ctagcagtta tttgtaagat caatgcatga cagttttatt tatgtcttgt gctattcctt   3480
ttgtgtctta gtttgaccca gtaaaactaa agaaacttcg cccaagtttc aaggagaatg   3540
atggtacagt tacagctgga aatgcttcta gtataaggta gctgcttgaa atatttctga   3600
gaccttttg tcctacaaag tctttctgag accttgtttt tcggccatat gttgtttagc   3660
tgacagatat gaaggacaac ctatttcatt gttgacagtt aaattatatt attgtattat   3720
gcatgcattt ttaactgata tattatgctt gcattttgtc aacttcattg tttctctatt   3780
tgtttttaga ctgcttgggt atgctctact ctgtgaaata gatggtaatt ttttctttag   3840
aattggtacc caatcgatgt gaatgattta tcacataaga aagtaaaaac attttaaatg   3900
ccttattatg cccattcaaa caacaaaagt tgccctagac cttgtctgtc tcactttgta   3960
ctgtgtctat ttttagctga ccagtactgt ccggtgtact gcctactatg gcttgtctag   4020
ccttctgcaa ccagtcatat ctaatttgtt ttatatggat cagtgatgga gctgctgcat   4080
tagttttggt gagtgggcag aaggctcaag agcttggcct tcaagtcctt gcaaggatca   4140
aaggttatgc tgatgcagct caagtaagcc acagtaacaa ttgttagctc tcctaagagt   4200
agaatgcgct tattctaatt cacattgtga tctaaatatt ttaggatata ggaagttatt   4260
tttatctgga acgattttat gttactattt tagatatcga aatttatcaa ctattggaac   4320
ttgtgatctg gaatattatt ttgtaatgtg gatgctgttt atacaggctc cggagctttt   4380
tacaaccact ccagcacttg caataccaaa ggctatcgca aatgctggat tagagtcatc   4440
ccatgttgat ttctatgaga ttaatgaagc cttttcggta tgcattgggt ttctttattt   4500
gtaagccttt tgttatgcat tgagagctta ttttacttat tacttttttt ttgtaataat   4560
gtcttttta cttatcaata taggctgttg cacttgcaaa tcaaaagctt cttggaattc   4620
cttcagtaag tgtcacctgt attaaactgc cattctttgt gcattttaga agttaaaaca   4680
tcactttcag aaagtacata ttggcccttt tttgttattt gctatgcagc agcaacatgt   4740
aattgcatta taacagcatt atatgtacta acaacatatg tgtttgcagg aaaagattaa   4800
tgttcatgga ggagctgtat ctttaggaca tcctctcggg tgcagtggtg ctcgcatttt   4860
ggttaccctt attggtgtaa gttctatctt aagatgcttg ttttatcttt tgagttacaa   4920
tccctttgt ttaaaaaaat gtgcaatgtt tttctagtaa aaaaatagat gatggtcttt   4980
gagtaattga tgaattctga catatgttac cgtatcatca tagggttcgt gatgaacagt   5040
aagcatcttc actattgcta ctaagtctac ttccttagtg ttttccaatg tgcaatgttt   5100
ttcttgtata aagctgcaaa tgtagagttt cacttgttgc tggtgatcag tagtttctct   5160
tcattttctt taagcaaaac cttgagaaca atatggtgcc atcatgttgg gacatcaaat   5220
atatggtgct tgaccctcct aatcattgtt tcttgttaac aggttctcag ggcgaagagt   5280
ggcaagatcg gagttgctgg tgtctgcaac ggtggaggcg gagcatcagc tcttgttctg   5340
gagctcgcat aagaaatcta gaccttgtaa ggctcaaaac accgaatata tctcaactca   5400
```

```
aattgattct tttactagct ggcaggagct aaccagtata aggtgctatt actgttgtgc   5460

aatttgacta actgctgcaa ctgatattgc aggtatttag caaaagttcc ctgaggtgat   5520

cttgtagtct tattttccgt tgtagtagtc ccatagaaca tttcttaatt taatttggca   5580

ataaagcgaa gtcgtgcttc tgttggttgc atagtagagt atcatgtaat aagagcaatg   5640

gggatgtttc atagatattt ttgaggatgc tacagaaata ttttatatac tagtgagtgc   5700

tcgtgcgttg caacgggaat atataattct atgataactt atatacaaaa tgtgtgctac   5760

attgttataa gaaaatgttt cataatctat acacaaagat gagatttctg caaagaatac   5820

catgccacat cactaaaata tgaatggctc acttatccct tataacagca gccttgtctt   5880

t                                                                   5881
```

```
<210> SEQ ID NO 46
<211> LENGTH: 1628
<212> TYPE: DNA
<213> ORGANISM: Zea mays

<400> SEQUENCE: 46

gtgttgcgtt ccctacttgc tcttttcttc ctccgcttca acctgtcccc agcgcccccc     60

gcgcacacac tgtctttctc tgcctttctt tccctagcgc cgcgccggcg acgccattcg    120

atcaggccgc ttcgccggcg acagcatatt ccaggtcggt tggttttggc acttcggacc    180

ggcggccatg gcttccgacg gcatcggccc cagagatgta tgtgttgttg gggttgcacg    240

caccccaatg ggcggtttcc ttggtgcctt gtctcccttg cctgctacga aacttggctc    300

tatagtaatt caagctgctc tggaaagagc aaacgtggat ccagccctcg tgcaggaggt    360

ctactttgga aacgtcttga gtgctaattt ggggcaagcg cctgcaaggc aagctgctct    420

gggtgccggg ataccaaact ctgttgtttg caccactgtt aacaaagtct gtgcatctgg    480

catgaaagct actatgtttg cagcacagtc aattcaattg ggtatcaatg atattgttgt    540

ggctggtggc atggaaagca tgtccaatgc ccccaaagtac attgctgaag ctaggaaggg    600

gtctcgtttt ggtcatgaca cacttgttga tgccatgctt aaggatgggc tttgggatgt    660

atacaatgat tgtgccatgg gaatgtgtgc cgagctttgt gctgacaatc atgccctcac    720

aagagaagac caggatgcat ttgctatcca aagcaatgag cgtggaattg ctgctcgtga    780

cagtggtgct tttgcatggg agattattcc ggttcaagtt cctgttggta gaggaaaacc    840

cccaacatta attgagagag atgaaagcct ggataagttt gacccagtaa aactaaagaa    900

acttcgccca agtttcaagg agaatgatgg tacagttaca gctggaaatg cttctagtat    960

aagtgatgga gctgctgcat tagttttggt gagtgggcag aaggctcaag agcttggcct   1020

tcaagtcctt gcaaggatca aaggttatgc tgatgcagct caagctccgg agctttttac   1080

aaccactcca gcacttgcaa taccaaaggc tatcgcaaat gctggattag agtcatccca   1140

tgttgatttc tatgagatta atgaagcctt ttcggctgtt gcacttgcaa atcaaaagct   1200

tcttggaatt ccttcagaaa agattaatgt tcatggagga gctgtatctt taggacatcc   1260

tctcgggtgc agtggtgctc gcattttggt tacccttatt ggtgttctca gggcgaagag   1320

tggcaagatc ggagttgctg gtgtctgcaa cggtggaggc ggagcatcag ctcttgttct   1380

ggagctcgca taagaaatct agaccttgta tttagcaaaa gttccctgag gtgatcttgt   1440

agtcttattt tccgttgtag tagtcccata gaacatttct taatttaatt tggcaataaa   1500

gcgaagtcgt gcttctgttg gttgcatagt agagtatcat gtaataagag caatggggat   1560

gtttcataga tatttttgag gatgctacag aaatatttta tatactagtg agtgctcgtg   1620
```

cgttgcaa 1628

<210> SEQ ID NO 47
<211> LENGTH: 1714
<212> TYPE: DNA
<213> ORGANISM: Zea mays

<400> SEQUENCE: 47
aagagcccct cgggcagcag gatcttcccc ctccccaaaa ccaaaccagc tgcctccgac 60
agcatccacc ttttcctccc ccaaaccatg gacttctcca ccggcgggag cgtgagcggg 120
ggcggcggag gcgccagcga cggccccgcg caggcggagc gctggctgga gatcgccgag 180
aagctcctcg cggcgcgcga cctcgtcggc tgcaagcgct tcgcggagcg gtcggtggag 240
gcgaacccgc tcctcgccgg cgttgacgaa ctcctcgccg tcgccgacgt cctcctcgct 300
tcccagttca tgggcacctc gggccagccg gacccgctcg ccatcctcca gctgccgccc 360
ggagtcagcc ccgaccaggc cgccgtgtcc cgcgccttcc gccgcctcgc gctcctcctc 420
ggtcccagca acccgcaccc gggagccgag atggcgctcc gcctcgtcaa cgacgcctac 480
gccttcctct cggatccctc tcgccgcccc ccgccgcccg ccgatcccgc cactggtacc 540
ccttactcct cccagtatcc cgccgcggcc gctcccgcct ccgacacccc ggagttctgg 600
acggcgtgcc ccttctgctg ctacgtgcac cagtacccgc gcagcctgat cgggcgcgcc 660
ctcaagtgcc ccaacgcggg ctgccgccgc ggattcgtgg cttctgagct cccgacccca 720
cccacggttg tgccgggcac tgaaatgtac cactgcgcct gggggttctt ccccctcgga 780
tttcccaacg cggccgacct gggtgccaac tggaagccat tctacaagat gttcccttgg 840
aacacggctc ccagtggcca aggtggtggt ggtaggagtc acggaaacca tggtggtagg 900
cagccacaga atgacagtgc tcgtggtggc tcttctagag gtaggatcaa gaagacgacg 960
gcccgcaaga aggtcggggt agggctcagg agacgttctc ttggtgtgga gagtggcatt 1020
gattcttcga tgctcgggca ggaaggctgg gctggggatg agaacgctgg agatggaagg 1080
gccgaggagg tgaggagaat taacataaat gaggcagcac atgctacaga tggcactggt 1140
agggttaatg ttagcggtgc tggcggagtt gaagatatcg gcaactttca tatcgatgtt 1200
gatgcatccg aggatatatt ggggaatttg cacaacatgc acttcttgag ggtggacaat 1260
cttggacgga tgatttaact gttgttatgg tttactgggg ctatgattag ccaggccgac 1320
tcttgctgtt caagtgttca tttgagtgta attgttccat ccctgttatg taatgttgta 1380
gttgtagact tgtagtctac ctggtacctg tagttactta acatcaggca gggaaaaatt 1440
tgtatgttca ttagatggag atacatgcca tttgccttag caaacacact ttgtggaggt 1500
ttccagtgat gggataatgc ttcgcagagg tgtggttgga ctggcaatgc ttaccatgcc 1560
acttctggtt tytttcctggc atggtgacac aaaatgttgt tgagatcaag taagtgaatt 1620
atgttctgct ttctgagttc ggtaaacttc tttggctaca aaaggactaa gcttagttat 1680
gctaacttgt tgatttggtt gtgatcattg catc 1714

<210> SEQ ID NO 48
<211> LENGTH: 9828
<212> TYPE: DNA
<213> ORGANISM: Zea mays

<400> SEQUENCE: 48
tggcctcagc atgtttgcaa aatgaatcag taaggaaaaa gaacacggct gcatcatcta 60

```
tatgatacct ccaagtgaac ataaaggaca acatcatcga ccaatttaat ataaatccaa    120
agcaaaccac atgaaaatca aactcgcagc aggtataaca tgaacaacac actgtaccaa    180
accctaactc atgaagcatg aaccagaaaa tagaacgatt gggggttgat ttcaccttgg    240
ggtcaaggtc gtagcaacgg agacggagca gacctagaag tataggaagc aaatcgacca    300
gagacgaagc gacgaagcag atgcccaacg ccacggagtc ctggcaccag gcggagctgg    360
acgcagccgc gacgcacagc cactcgccgc cggtctctca cgagggaggg agggggtgga    420
agaagaacga gcagcgagag gaggggaaaa ggagggtgca ccgtcgccat atatagccgc    480
aagaggattc accggagcgc tccttcccgc gcgcgcgaaa acctcaccat tcccgcgcga    540
gcccgcgcga gctcccgcca gccacctcgc ccgccgccac attccgccag tgcgccgcgc    600
gcagccgagc tcccaggaaa cgaaccctag ccgcgtttcc tgggagccac ccaggaaaca    660
ggctgttttc agccaggctg cgaaacgggc caaccttgca aacaaggtta gttgtagccc    720
acgggcacaa tcgggctact gggccatcct ccgaaacacg cccttggtga tctctggtgg    780
cgaagcgata cgatacgatg gccggccgta gtacgtcccg tgggtggccg ctgacgtgac    840
gagaaacagt cggtcggcgg ccagccagta acgtgacact cgccatctgc ttccatcttt    900
tgtggttttt tcttctctag acttgactgc atgcagccaa gaaccagaaa ccggacgacc    960
gaccgacgac ggcgacgggt cgtcgtgcac cgccacacgg gggtcatacg atacgacacg   1020
acacgttccg ccgcgagatc gaggtcgatg agtccgaggc tctcggctcc caagtcccaa   1080
caagctgcac cggctcgacg aggacgacgt actgtacgaa cagaacaaca gccagaggcc   1140
ggccggccgg acgaccgacg gtcgccgtcg tgcaccgtgc acggtgcacc acgtctcatg   1200
ccgtctggcg tgtgggtgac gaatcactga aactgaaagg gtaggcagca cagcacatcc   1260
acacacatgt tctttgccta tcacacgctc tttgtaaaat tttagtacac tggtgacaat   1320
aggcggaccg agtccaacat caacaaaaaa atatatatat actggacgtt cgttagccgg   1380
gaccattttt cccccaaaag gaaccaacta cagcaggctg aaataaacgt tcctccctct   1440
atgccaaaat aaaattcgta ttagtaaatt agtggttcat ataacatttg atgtatgtgt   1500
tttgtatata tatacatgcc tatatttatt aacatttatt tgaatataga tataaaaaca   1560
cagagctaaa acgattacta ataaagttaa cttgacgctg cagtgttgtt tttttttata   1620
aactctgttc aagttagaga aatctgattt gtagcagctc ttgacttcaa cagagggatc   1680
agaataacta taaagctcca gtaaatagat tacagaatac agcttccctg tttctttcaa   1740
caatacggca gtttagaatt ttttatgtaa caaagctaga gagtttgtgt tttatgtaac   1800
taagccaaag tgtgggtaag tgatatacga taaagtagca tgacacacgg aagttccact   1860
catggaatgg ctttgttcgt ttacaccaat cccgctctag attagcatgg attggaatta   1920
aatccatgcc tcaatccatg ccccaaaata atccatgact acttaatttt ttttattcgg   1980
ttaaacccat catggaatat aacccaaagg tttgggaatt ttttaaacta tggaagacat   2040
ggattctatc catagcccat taggtatgga acaaatccat gagatattgc acaagtttac   2100
attagaattc atggatcaaa agaataacta gctttgaaag tcacatggat ttgttgatgg   2160
atttaatccc accatgggat taggtgtgag atatggattc acccaatcca tacccagatt   2220
aaatccatgg tgggattata tcccatataa ccgaacaaga ccttatgtgg aaatataact   2280
aaataggagg acaacaagct tacttctatt caagcacagc tctagcaagg gactatgaca   2340
atacagataa accaagatat agtaaggtag gacacaatag cattccaggg tgcaccacga   2400
gcgctatgct ttaacaaata gacctaacat catggagtac atagattagg gataaaaaca   2460
```

```
ggtacccgaa ctcttaaaac aaatctaata ttttaaaata gatatgtata aaatttaatc   2520
ataatctttc cttctgttat aagcacacta ttatatataa gaataaattt tacatagatt   2580
gttttataca ttatttactc tttacaacaa aaagatgaaa aaatgtttgt atccgtatcc   2640
gaatgctacc caaattttat atctatcatt ttaaaaaata tgataaattt gatgtttatt   2700
ttttataaat ctttacaagt tcaatgctaa aaacaagaat attaatttgt ctagcagatt   2760
ctatatcata tttattcact atcaaagaaa aaaataccaa aaaactggta tgcgaatagg   2820
tacccgtttt catccctaca taggatggac atggttgtca ccaccttcca actatcatta   2880
actatttaga ggcctaacca cattccggta cccggtagag taaacaccac tgaaaggccc   2940
tagtttgatt ttggtaaccg agtgacaacc taggtggact aatatatttt ctatgttgag   3000
atacacaggt gattagtcca caagtagact agtttgagat acttaaatca tgatggtgaa   3060
atgcttggat ttattgtaaa cctcaactag gtgtatgtga gacatcacat ggtgtcttgt   3120
ggataggtgc aggcagtggc ggagccagga tttctgtaag tgtagggcca atataacact   3180
aacaaatatt tatatcagct agaaaatctt aaatcatgca aatgtataga taatgacaca   3240
tatgaccatg aacggattat acaaattctc tcattccttc agaacatatt tgggtcccta   3300
gcaatttttc ggctcaagag tagggcccaa gccctaatgg ccctatgcct gtctccgcca   3360
ctgggtgtag gatatcaaga gacatggttt gggtatgaag gactgattgt aaaagtgatt   3420
gacaagttag atactttgag gcgatggacc acatgtggca gagaagcttg agcaaggact   3480
tggcaccgat cgaccaagga aacaataaag accaaatgaa gttgcgataa ataaagtaat   3540
gaggccacaa tggtaacatg aagtggacca tatcattcaa agaagatcaa gccaattgtt   3600
tattcatgtt gatggtcaag tggcttgatg aagtatgatg gaggaacttc atgatatggt   3660
taatgatcaa aggtagcatg gttggctaca tctatggatg atcattgccc atcatgtgat   3720
gaggttggat gcttgtataa catcatcaac attaagatga aatggaatgt gcaagacaaa   3780
ggtattgtcc aagattgttc tgtagtgatt atgcaggtat gtcacgagat cgagagcata   3840
gtgattatgt aggtatttca cgagatcgat agcatatata gtgattatac gggatatgtc   3900
atgggatcga gagctaaagg ttagggcatg agagacatga ggatttatac atgtttggac   3960
tctcaatgtc agacaatact ttttgtcttg tgtgtgttgt tatatgttcg gaacgatcac   4020
agagttttcc cgtccctctt tttatattct aaggagggat agatgttaca cggtaagcat   4080
agagccgatt atcaagttca tgatggaatc aagtcaattg ccaagttgta cacaagtcca   4140
atttacggct tatctcatat tcagttgaga tctttaaaat ctatcctagt ttaatcattg   4200
attctttgga cttatggccg gacgcatagg tccttctgct tagcctcttc tttataaagc   4260
ttgatttagg tactcatgca tattattgac aatagcttca gactttgttt gacgataaaa   4320
aagactctct atatatgaga gcatccatac aaggttttga ccactttagg acgaaacttg   4380
aagatggaga gatatgagaa aatacaatgt cgtttccatc tctactcaca gccgtgagtc   4440
catacacgag ttgtttttat gttcaatttc cacggtcatg tccctgtatt taaatgataa   4500
aaaaactaaa attatattta aatataagat atgacatatg gatgttggct ataaacctat   4560
attcacacac ctaactcatg gttctatagt cgtcgtgcat caccccttctc attcccgttt   4620
atgcaaaaat aaagagaaaa tatgcatgat tggggatttg aactttagtt gtaggatcta   4680
agttcatacc ctcctatcca acagagcaca tatattttta tgtttcatta aaaacaaagt   4740
atactcatgt cttatataaa aaccgtttca acgaatgaac atctcattag tgatatttaa   4800
```

```
aaactatagc aatgcataag caactaacta ctcaaaaaaa tgcaacctga atacttcctt   4860
tgcttctcca cacatgaaat gaaagaaact gaaataagaa acgggcaaac ggcgctgcaa   4920
aagcgggaaa tccctttcc ttgctgatag tgatacccgg tcaaaaccca ccgagacggc   4980
gagacgcggg gagcgggtac atacacactg acacacctca cgcgagccga gacgcccagc   5040
tcaccgcccc accgagtccc acagtctcag aggccacctc gagcccccc tgccccgcaa   5100
gccgcacccg ccgctccctc cgccatctgc gctgcgctgc tctgctctgc ggtgccaggc   5160
tgccagccag tgccggcgcg cgcccgctgc cgccccgacg ggcccaccgt tctcttctct   5220
ccgcgctgcg cgccggctgg gctgcaggtc agttaatgcg cccgtgacag gcggcgtcgg   5280
ggaggccaag ggcggtgccg ggttaatccc gccgtctctc gaggcggcgc ccgcggagga   5340
ccaggcggga gggggagacg gtgaggcgcg gccatggggg gcgccaaggc ggaggacaaa   5400
cccgccgccg ccgctgcaga agattggtgc taccaatttg gaaacaaggt tcgatttctt   5460
caccatttgc actcctctgc aagactggga cacgtttccg ggtttcgttc tgcctgggcg   5520
gcgacaaatc tcatggcaaa ttgcctttgt ggggctcatt ccctgggttc acactccaaa   5580
tccttccttg cgaccttctc tcagccgtcg cgctttccgt ggcaagcctt ttggaaccct   5640
gatctgaagt gtcactcaga tcaatgcagt cgcattgatt ctattcgttt cctgtttccg   5700
tttcccctt ttaacgtgtc tgctagttcc aagtcccgag cgttttccgt tctctgtttc   5760
agaattgaag cttgttaagt tctgttttt ttacaatcct tcgtttttgt cccagtcctt   5820
tctattcctg gagaagttag gaatctgttg ttctcctgtt ccatttctcc tttctattcc   5880
tggagaagtt aggaatctgt tgttctcctg ttccatttct cggtgcagta ttagttgcag   5940
aacaggaatc cacttgattt gtcagtttaa ttatgcttgt gtcacctcag atgtgtcata   6000
ttgattatga ctgcattttt gtcagctgta atatgcgtgt tggcttgcat ttgtttctct   6060
ctttattagt actaccagca ttttcggtca gtatttttg tcttccttgc tgaagaatga   6120
gaaggaaagc tgtcatactc ctcgtcggga tagcttcatt tattaaggca gctgggcgac   6180
agaatatatg ggaatgtact tgaacttcac aaaaaagggc cttttcatcc cttgccgtgt   6240
cttccatgtt ggtaaaaagg ctagtagctg aattgaatag tacgtgctca ttttaactac   6300
cctgaggact agatagatct tgaagtttta tttgtttatt tctttttatt tctgcttata   6360
tagatgtagg atgtagccaa atggatgctt ctcagctcac attgaacatt aatgtttgtg   6420
ttgtttgctg aaaggttttt tactgtagca gaaggttaca aaataacaga tcttacctca   6480
aaaaagggct gcaatgtata tatactggca ctgaaccgcg tatgcgcagt gcaacctgct   6540
gattggtttt gtactggtcg gatctgtttg caggatgcat ttgacttgaa gcccccgaaa   6600
aaatcaccga tcgcgttgag aacggttgtc ttcgctatga ctatgttatg cgggatatct   6660
atttgctcaa tgtgcatgaa gcaactaggg agtgatggct ggtcaagagt tgtcaagatt   6720
gaagttgtgg aacaaccatg taataagtcc attgctcctc tttcggaggc tcaatttgtg   6780
cgctatcctc aaccgataac ttacagcagg tgagatctgc actgtggtaa gattgagcaa   6840
tctcgtttgt ttaatgccta atgcataatt ttttatttct agggaggaat gcaagtgcaa   6900
tgctgtccgg tcctttgcaa ttatatcatc gcagcgatct ggaagtggct ggtttgaaac   6960
acttcttaac agccacatga atgttagctc caatggtgaa attttctcta gaaaagaaag   7020
gaggagtaac atttcctcta taatagatac cctggataaa gtgtacaatt tggactggaa   7080
cagtagcgct tccaagaatg agtgcactgc agctattggc ttcaagtgga tgctaaatca   7140
ggtgcggact aaaacatgca gtatagataa tttatttgga tgatcctttt tcatttattt   7200
```

```
ttccatttag ttccagtatg tttcaattat tagtatgtgt agtctcctaa acggcctaca   7260
tgttctcaac tgtagatgct aaatgttatt gcatattgcg ccaaactttc ctcaagtcca   7320
tgtaactatt ttttttggg aatccacttt agggcttgct cgttttagtg ccaatccatg   7380
tggattggac gagattggat gagtttaaat ccataagaag tcaaaatcct tcttaaaatt   7440
ttccaatctc ttccaatcca tgtgggatgc gaataaccga acaaggcctt atggaactgt   7500
cggtagctag tttagttttc tgacttgctg tcagatcctg cattttagac aaattttctc   7560
tctctcgaac atgcatgaga actgcaaatg catatggagt aatatttgat agattctgta   7620
gtgtgtccag tagactgatt ataatctaca tgtcaagcat gtttgtttca gggcttcatc   7680
taatttgtgc gagaacgaac tttttcctg gtagacagat tgcctaacca aaccatgaat   7740
attggccaaa cataggttta gagactggaa acaaaacagg cattgtagct agagagtgga   7800
aacaaaggag catttcttct gaacggggtt ggggtgtatg ttttcagggc ctcgtggcaa   7860
accatgcgga cgtagtcgac tacttcaacc gaagaggagt ctctgcgata tttcttttca   7920
gaaggaacct gctccgccag ttggtatcac aggtagcgaa caaccacgac aggttactta   7980
agcaactaaa cggaacgcac aaggcccatg tccacacgaa gcgtgaggtt agtaatgcta   8040
gctaagaaac ggatatggca gcaagtctct gagctgatct gatctctctc tgtgtttgac   8100
gtgtcgttcg ttctcgctcc acaggcccat atactggcaa gatacaggcc caggctcaac   8160
acgacgtcac tgatatggca gctgaaacga gctgacgagt acactcgcga cgctcttgag   8220
aacctaaaca acacccggca catgagcgtc tactacgagg acgtcgtccg caacagaaca   8280
gtgcgttctc gctgatgccc ttcccttgtc tgttcccttc cgttggttgt gtcgcttacc   8340
atcgctgctg cactgcagaa gctcttggat gtcctggatt tcctcggagt gccgaggagg   8400
aagctggtga gccggcacgt gaagatacac acgaagccgc tgtcggagca gatcgagaac   8460
tgggacgagg tctacagcgc cctcaacggt acccagtacg agggcttcct gaatgccgct   8520
gactatctag tataacatca cgtttctgga tgtagatagt gtgcgtgtga ttctttcgtt   8580
tcttgtttgt ttctggcaga aattttgatg cggggtaggc gccttttgcc gtgcatggtt   8640
gcattctcgg taacctgatg ctcctgtaac taaccctcca gcttctctga tctttgtatt   8700
tgccttgggt gtttgctgat gttctttcaa actatttgaa atcgggctgt cggagttcca   8760
gatcccgggc ggcaggatag ttgatgtgac ctagataaat gtacaagaca catcacaaat   8820
atataaaata tttctgtagt atcctcacaa atatatcaaa aatatttctg tagctcttat   8880
tacatgatac tctactatgc aaccaacaga agcaatatct cctcagggag cttttgcttt   8940
attgccaaat taaattaaga aatgttctat gggactacta caacggaaaa taagactaca   9000
agatcacctc agggagcttt tgctaactac ctgcaatatc aaggtgcagc agttagtcaa   9060
attgcacaac agttgtaaaa ggaaaaaata caacttaatt aggcctagct gaatatgcga   9120
ccatattaca gtttgataat agcaccttat actggttagc tcctactgcc agctagtaaa   9180
agaatcaatt tgagttgaga tatattcggt gttttgagtc ttacaaggtc tagatttctt   9240
atgcgagctc cagaacaaga gctgatgctc cgcctccacc gttgcagaca ccagcaactc   9300
cgatcttgcc actcttcgcc ctgagaacct gttaacaaga aacaatgatt aggagggtca   9360
agcacaatat attttgatgt cccaacatga tggcactata ttgtgcccaa cgttttgctt   9420
aaagaaaatg aagagaaaaa gaaactattg atcaccagca acaagtgaaa caagggatga   9480
gccgatatca atgtgaaact ctacatttgc agctttatac aagattctat ttgcagataa   9540
```

```
tttgcacatt ggaaatcact aagggcttgt tcggttgcga gaggattgga ggggattgag   9600

ggggattaaa tcccctccta ttcaatttta actagaaggg gatttaatcc ccttcaatcc   9660

ccctcgaacc acttgtaacc gaacatggcc taaggtagtg tttggtgcag ggatggggtg   9720

gcttgatcca acatactccc tatgtttcaa attataagat gtttttactt tttctagatt   9780

tgtagttttt attgcgataa acattatgtc tcagtacacg tagtaaaa                9828
```

<210> SEQ ID NO 49
<211> LENGTH: 11900
<212> TYPE: DNA
<213> ORGANISM: Zea mays

<400> SEQUENCE: 49

```
gatataatga aaaaaccaat taaaaacgtg tctcgatatg cgtgcacgag taaagagctg     60

gctgagcgga gcctggccgc gcgcgtgcgg tcgcgcgatg cgtttctgcc gggcctggct    120

cgcggcgctt taagttccgt gctagcctgt ctcgtgcgat acaacgaacc aaacaaacac    180

tactttttgc atgtgtagat gcagctgcac cactggagaa ggcaaccaaa cgccccctaa    240

ggcagctggg cgacagaata tatgggaatg tacttgaact tatcaaaaaa gggccttttc    300

atcccttgcc gtgtcttcca tgttggtaaa aaggctagta gctgaattga atagtacgtg    360

ctcattttaa cttccctgag gactagatag accttgaagt tttatttgtt tatttctttt    420

tatttctgct tatatagatg tagccaaatg gatgcttctc agctcacatt gaacattaat    480

gtttgtgttg tttgctgaaa ggttttttta ctgtagcaga aggttacaaa ataacagatc    540

ttacctcaaa aaagggctgc aatgtatata tactggcact gaaccgcgta tgcgcagtgc    600

aacctgctga ttggttttgt actggtcgga tctgtttgca gratgcattt gacttgaagc    660

ccccgaaaaa atcaccgatc gcgttgagaa cggttgtctt tgctatgact atgttatgcg    720

ggatatctat ttgctcaatg tgcatgaagc aactagggag tgatggctgg tcaagagttg    780

tcaagattga agttgtggaa caaccatgta ataagtccat tgctcctctt tcggaggctc    840

aatttgtgcg ctatcctcaa ccgataactt acagcaggtg agatctgcaa ctgtggtaag    900

attgagcaat ctcgtttgtt taatgcctaa tacataattt ttaatttcta gggaggaatg    960

caagtgcaat gctgtccggt cctttgcaat tatatcatcg cagcgatctg gaagtggctg   1020

gtttgaaach cttcttaaca gccacatgaa tgttagctcc aatggtgaaa ttttctctag   1080

aaaagaaagg aggagtaaca tttcctctat aatagatacc ctggataaag tgtacaattt   1140

ggactggaac agtagcgctt ccaagaatga gtgcactgca gctattggct tcaagtggat   1200

gctaaatcag gtgcggacta aaacatgcag tatagattta tttggatgac cctttttcat   1260

ttatttttcc atttagttcc agtattgcat attgctccaa actttcctca agtccatgga   1320

actatttttt tttgggaatc cactttaggg cttgctcgtc ttagtgccaa tccatgtgga   1380

ttggacgaga ttgaacgggt ttaaatccgt aagaagtcaa aatccttctt aaaattttcc   1440

aatcccttcc aatctatgtg ggatgcgaat aaccttatgg gactgtcgga tagctagttt   1500

agttttgtga cttgctgtca gatcctgcat tttagacaat ttttttctct cgaacgtgca   1560

tgagaactgc aaatgcatat ggagtaatat ttgatagatt ctgtagtgtg tccagtagac   1620

tgattataat ctacatgtca agcatgtttg tttcagggct tcatctaatt tgtgtgagaa   1680

caaacttttt tcctggtaga cagattgcct aaccaaacca tgaatgttgg ccaaacatag   1740

agttagagac tggaaacaaa acaggcactg tagctagaga gtggaaacaa aggagcattt   1800

cttctgaacg gggttggggt tggggtgtat gttttcaggg cctcgtggca aaccatgcgg   1860
```

```
acgtagtcga ctacttcaac cgaagaggag tctctgcgat atttcttttc agaaggaacc   1920
tgctccgcca gttggtatca caggtagcga acaaccacga caggttactt aagcaactaa   1980
acggaacgca caaggcccat gtccacacga agcgtgaggt tagtaatgct agctaagaaa   2040
cgtgttcgcg gctaatgtct cactctcaca gcaagtctct gagctgagct gatctctgtc   2100
tgtgtttgac gtgtcgttcg ttctcgctcc acaggcccat atactggcaa gatacaggcc   2160
caggctcaac acgacgtcac tgatatggca gctgaaacga gctgacgagt acactcgcga   2220
cgctcttgag aacctaaaca acacccggca catgagcgtc tactacgagg acgtcgtccg   2280
caacagaaca gtgcgttctc gctgatgccc tttgtctgtt cccttccgtt ggttgtgtcg   2340
cttaccatcg ctgctgcact gcagaagctc ttggatgtcc tggatttcct cggagtgccg   2400
aggaggaagc tggtgagccg gcacgtgaag atacacacga agccgctgtc ggagcagatc   2460
gagaactggg acgaggtcta cagcgccctc aacggtaccc agtacgaggg cttcctgaat   2520
gccgctgact atctagtata acatcacgtt tctggatgta gatagtgtgc gtgtgattct   2580
ttcgtttctt gtttgtttct ggcagaaatt ttgatgcggg gtaggcgcct tttgccgtgc   2640
atggttgcat tctcggtaac ctgatgctcc tgtaactaac cctccagctt ctctgatctt   2700
tgtatttgcc ttgggtgttt gctgatgttc tttcaaacta tttgaaatcg ggctgtcgga   2760
gttccagatc ccgggcggca ggatagttga tgtgacctag ataaatgtac aagacacatc   2820
acaaatatat aaaatatttc tgtagtatcc tcamaaatat atcaaaaata tttctgtagc   2880
tcttattaca tgatactcta ctatgcaacc aacagaagca atatctcctc agggagcttt   2940
tgctttattg ccaaattaaa ttaagaaatg ttctatggga ctactacaac ggaaaataag   3000
actacaagat cacctcaggg agcttttgct aactacctgc aatatcaagg tgcagcagtt   3060
agtcaaattg cacaacagtt gtaaaaggaa aaaatacaac ttaattaggc ctagctgaat   3120
atgcgaccat attacagttt gataatagca ccttatactg gttagctcct actgccagct   3180
agtaaaagaa tcaatttgag ttgagatata ttcggtgttt tgagtcttac aaggtctaga   3240
tttcttatgc gagctccaga acaagagctg atgctccgcc tccaccgttg cagacaccag   3300
caactccgat cttgccactc ttcgccctga gaacctgtta acaagaaaca atgattagga   3360
gggtcaagca caatatattt tgatgtccca acatgatggc actatattgt gcccaacgtt   3420
ttgcttaaag aaaatgaaga gaaaaagaaa ctattgatca ccagcaacaa gtgaaacaag   3480
ggatgagccg atatcaatgt gaaactctac atttgcagct ttatacaaga ttctatttgc   3540
agataatttg cacattggaa atcactaagg gcttgttcgg ttgcgagagg attggagggg   3600
attgaggggg attaaatccc ctcctattca attttaacta gaaggggatt taatcccctt   3660
caatccccct cgaaccactt gtaaccgaac atggcctaag gtagtgtttg gtgcagggat   3720
ggggtggctt gatccaacat actccctatg tttcaaatta taagatgttt ttactttttc   3780
tagatttgta gtttttattg cgataaacat tatgtctcag tacacgtagt aaaagctata   3840
aatctaacaa tgccaacatc ccaagacgtc ttataatttg ggatagagga agtagaccta   3900
gtagcaatag tgaagatgct tactgttcat cacgaaccct atgatgatat ggtaacatat   3960
gtcagaattc attatttact caaagaccat ctattttttt actagaaaaa cattgcacat   4020
tttttttaaa caaaagggat tgtaactcaa aaggtaaaac aagcatctta agatagaact   4080
tacaccaata agggtaacca aaatgcgagc accactgcac ccgagaggat gtcctaagga   4140
tacagctcct ccatgaacat taatcttttc ctgcaaacac atatgctgtt agtacagata   4200
```

```
atactgttat aatgcaatta cacgttgctg ctgcatagca aataacaaaa aagagacaat   4260
atgtactttc tgaaagtgat tgtttaactt ctaaaatcca caaagaatgg cagtttaata   4320
caggtgacac ttactgaagg aattccaaga agtttttgat ttgcaagcgc aacagcctat   4380
attgacaagt aaaaaagaca ttattacaaa aaaagtaata agtaaaataa actctcaatg   4440
cataacaaaa ggcttacaaa aaatgtgagt aaaagaaact caatgcatac cgaaaaggct   4500
tcattaatct catagaaatc aacacgggat gactctaatc cagcatttgc gatagccttt   4560
ggtattgcaa gtgctggagt ggttgtaaaa agctccggag cctgtataaa cagcatccac   4620
attacaaaat aatattccag atcacaagtt ccaatagttg ataaatttcg atatctaaaa   4680
tagtaacata aaatcgttcc agataaaaat aacttcctat atcctaaaat atttagatca   4740
cagtgtaaat tagaataagc gcattctact cttaggagag ctaacaattg tttctgtggc   4800
ttacttgagc tgcatcagca taacctttga tccttgcaag gacttgaagg ccaagctctt   4860
gagccttctg cccactcact aaaactaatg cagcagctcc atcactgatc catataaaac   4920
aaattagatg actggttgca gaaggctaca caagccatag taggcagtac accggacagt   4980
acttgtcagc taaaaataga cacagtacaa agtgagacaa acaaggtcta gggcaaccat   5040
gaagaaattt aaaaggtagg gcaacttttg ttgtttgaat gggcataata aggcatttaa   5100
aatgttttta ctttcttatg tgatattgtg ataaatcatt cacaccaatt gggtaccaaa   5160
tctaaagaaa aaattaccat ctatttaacg gagtagagca tacccaagca gtctaaaaac   5220
aaatagagaa acaatgaagt tgacaaaatg caagcataat atatcagtta aaaatgcatg   5280
cataatacaa taatataatt taactgtcaa caatgaaata ggttgtcctt catatctgtc   5340
agctaaacaa catatggccg aaaaacaagg tctcagaaag actttgtagg acaaaaggcc   5400
tcagaaatat ttcaagcagc taccttatac tagaagcatt tccagctgta actgtaccac   5460
cattctcctt gaaacttggg cgaagtttct ttagttttac tgggtcaaac taagacacaa   5520
aaggaatagc acaagacata aataaaactg tcatgcattg atcttacaaa taactgctag   5580
caaagctcat tatgcaagga acgttgcatt tggaggaagc aagaacaata aatcaaagtg   5640
cctgccagtc tttttgcctt tgatcaacta caagctttat tttgttaaaa atattttgtc   5700
acgtcagaaa aaatacctta tccaggcttt catctctctc aattaatgtt gggggttttc   5760
ctctaccaac aggaacttga acctgggtga caacactgac catcagaaaa ccaagaaaag   5820
catgtctagt atcatcaatg agggagaaaa ttaccggaat aatctcccat gcaaaagcac   5880
cactgtcacg agcagcaatt ccacgctcgt tgctttggat agcaaatgca tcctattcaa   5940
gaataagtaa aattaaatat accagaaatt ggaaatatat ttattgcaat atagacaaaa   6000
ataaattgca acatataagt gaaaattaaa aggcaactca attttaatta tactatatca   6060
aatttattaa gaaaaaaatt acataaacag atacagtaaa atcatcaagg tactagtgtc   6120
atgtactgat gagcagcttt taagagatta tacttgtata gctctaacag gaatacaaaa   6180
gagtgctcat ttttgtgtgg cacatctact ttcatctctg gaagcagatg aatggtcagt   6240
tcacagaccc agagcatgca taaaagccca ccctatcaat catgtcacaa cataacagaa   6300
aatcattgct agaaaggatc caagttacta gttcatcaga caaggaatgc agatgctggt   6360
ctagagtctc tagaccattt atgatgatga ccaagataaa gcacgaagat tccagggcag   6420
tctcaaaaga attgccagca ttgacatgtt gtatagcaca acttatatct tgaaaaatat   6480
gggaatatta taacaaacag catttactgc tatctgtatt aagagacctg gtcttctctt   6540
gtgagggcat ggttgtcagc acaaagctcg gcacacattc ccatggcaca atcattgtat   6600
```

```
acatcccaaa gcccatcctt aagcatggca tcaacaagtg tgtcatgacc aaaacgagac   6660
cccttcctgc aattgtaatt agcaagctta taagcagttg aaatgcactt taaacatgaa   6720
cagaatatac tttcacaaca aaactggcca cttcgttaat agcctcgctg ctggtgaatc   6780
aacatttctt acaaacaaat ttagaaaatg caatgaagat aagtaagcat gcatgtatct   6840
accaaataac ttaagactat catttggttt atgcagctcg atattgaata tatccaccaa   6900
gtaataattg catacctagc ttcagcaatg tactttgggg cattggacat gctttccatg   6960
ccaccagcca caacaatatc attgataccc aattgaattg actgtgctgc aaacatagta   7020
gctgcatata ggaaaggaaa acaagagcat ggtcaggtaa tctctcactt ctgtgaactc   7080
tgagcagagt acacaaggac agacagataa attcgattca aacctttcat gccagatgca   7140
cagactttgt taacagtggt gcaaacaaca gagtttggta tcccggcacc cagagcagct   7200
tgccttgcag gagcttgccc caaattagca ctcaagacgt ttccaaagta gacctcctgc   7260
acgagggctg gatccacgtt tgctctttcc agagcagcta acagccccca gccatgacca   7320
tgttcagagc tcggatgtaa atgcagagaa gattcggatc tcaccttgaa ttactataga   7380
gccaagtttc gtagcaggca agggagacaa ggcaccaagg aaaccgccca ttggggtgcg   7440
tgcaacccca acaacacata catctgtgag caaggaagaa aaagttactg actgtagaac   7500
aaagcagaac catctagtgt gcacctcaca gtatatctat agtactaatt tgtaaaccgc   7560
gctcaaaatt ccatctgatg gtacaaacca aacacacatg aaaagcacat actgtactag   7620
taccagtgaa tcacttgttc caaatggcgc taaaacaaca atgatggcag taccctctgt   7680
gcaacccgaa aaggcaaaaa cacaaattgt ggtaatcata taaacgtatt tcgcagtagc   7740
aatgaacttt ggaaaacaat ggattcaatc aagcaaacgg acgagatcac gagcatggag   7800
cagctaggat gccctaatgg atgcagacag gcactagaat taaacagaaa agcgtcaaat   7860
ttcggccttg caaggtaccc aaaaaaaaaa caagaattcc caatatgtca gatcgctgga   7920
agcgcaatgg cgtgctcata gcccaaaatc tatatttgta cctcctctcg gcggtttgac   7980
gtctgtctgt ttgaacacaa agaagagatg aaacagttat acctctgggg ccgatgccgt   8040
cggaagccat ggccgccggt ccgaagtgcc aaaaccaacc gacctgcgaa tcaggggcgg   8100
gcccagtgaa aaatggtcag atccgaatac aaatactaga tttggggagt tcggggtgtt   8160
tgaattctcg cagaaggagc agaagggacg gcatacctgg aatatgctgt cgccggcgaa   8220
gcggcctgat cgaatggcgg cgccggcgcg gcgctaggga aagaaaggca gagaaagaca   8280
gtgtgtgcgc ggggggcgct ggggacaggt tgaagcggag gaagaaaaga gcaagtaggg   8340
aacgcaacac ccaacagcca aatcacccga atgtaatttt tcctaaatct ataatttatt   8400
ttattttta atctatacaa tatatagata tataataaaa ttaataaatc ataaaaatta   8460
aagctgaatc agagaaagta ctaaataaaa taggctttat gttaggcaaa aaaaaagtaa   8520
aaatagaaca attcaattca ctatatgcca ctgtaatttt gtgtaatacc ttattcatcg   8580
tacctcgtat gttactcgaa ttcaatatct cactcttaca tgtcgtggcc aaatgttaaa   8640
tgtaaaatgt tgtatgtctt agtcccttac tatgacatga aagagtaaaa aattgtattc   8700
gggtgacgta aaaaggatta gaacatttat gataacaaat aagatactag acgagtgaca   8760
tacatgatat aattttatct ctaaacctaa tgaaactaat aaaaaatgtc aattgatatc   8820
gtttgcgttt gctaatcacc tcgaacaatc atcctcgcgg gcatgtggtt aaggctagaa   8880
aaaaaacttg aggctcacga gtcagatcaa gttcggagcg tctgcgagcg agctagttgt   8940
```

-continued

```
accaaattaa tcaatatgta gaataatgat agatattaga taatttatag atagtcggct   9000
tatttcttag cctttgatga taaatataag ataattcata atggtgaata atatttttat   9060
attttatgtt tatatattaa taatttacta tataatgaaa taatatatat cggggtgtag   9120
ctcgcgagcc gacttcgagc tgagccgagc ctaactctct agctcgtgaa atggacgagc   9180
cgagtcaagc tcggctcgac tcattttcta cttgtggtcg accaggtcta ggtagtcatg   9240
aaccgcaacc aatctgtcag ttttatcgat tgttttagat catgttaggc gagtgccggc   9300
gcttggctct actgcccgcc cacccatgtg gcacaaccaa atggtcagta tcacccgaca   9360
tggtgccagc actaatagcc tcgcttgtgg ttgtcgaggc tactgatcgg ccgccagggt   9420
tactattgac cgtgttggga ccgcgtcggt cgatactgac tggttggtac tgaacagcta   9480
ttgcggccat gtcgataacg atcgcctctt gccatgtggc aggttctaat tgcttcgctt   9540
tattttgatt ttttttcaaa aataaaaaaa ctagaacttg gtctataaat agaggagtgt   9600
ttgatctcat tcacacaacc cacacttcaa atttctctac caccccttat aatcctctta   9660
cactcgtttc aatcaaatca agcattgttg tgatgttttc gttcagcttg gacatcaata   9720
tgactgaaaa gagttattca agttattaca acaaaatata atgcaacagg cgtcagagct   9780
tggatccgag tctcctaggt cgatgaggtg gccaaggcaa catcagagat acattgactg   9840
cgactatgta gttgcatacg accggttaat gcaagaccat ttcaacgacc tgtgtgtcta   9900
cccactgctc tacttttgtc aaagttaccg catctagaga agtctcttcc ttcatatctt   9960
agagagattg ggtgagcact tcccatactt cactttttga accgatgcat tcaaccgcag  10020
tgtttcctcc cccaccagaa gtgcacaatt ggcctaagca tgcttgcgta ctgtagcatt  10080
gctgactcca tcgatgagta catcaaaatg aggaaagttc cacctcagag tgccttggac  10140
tattctgtgt gaaagggtcc ctagttaagt tggttaggtc gtctgagtag cactcctcag  10200
gtcctaagtt tgaatcccgg tgggagcgaa ttttaggctg aggttaacaa ggtcactcac  10260
tagtttccct agttgtgtgc acatgagatg ggctgaccta tggggcggat cctcgtgtaa  10320
gggctagtag ggctcaaagc acgagtaaag atctggccta tagggggcgg actctcatgt  10380
tgcatggggg gaggggtaca tctttcgtga cctttctcga tcagggctcc gattaagctt  10440
cttcttaccg tgggggcagt atttccccta cgagtggagt ttttggtcta ttctgtagag  10500
gtggtattgc atgtttcagg gcggagtaca attatcatgc cattgtcaat gacttaggct  10560
tatcttagct aaggaggtgg aaaggggatt ttctattatg atattgagta tagattgcat  10620
gcattggaag tggaggaaga agacatttta caagggggat attggttctc catccatcat  10680
gctcgagaca gttgcctcgt atgacttgtg gatctgacat atttttatga atctattaaa  10740
atgctaaaac ggttagtatt ttaggacgga gggaattatt ttttggaata tttttgtagc  10800
aacctaaaca tagttcatct atgcttagtt tggggggtgg gatggttagg cctagaagct  10860
actgttgaat taatgagggc ctaacccaaa ttaatattca ataatagtca atgctaaagg  10920
cccactttaa tgctacggtg tactagtact ttagtaccat accggaagta caagggacaa  10980
ttcaatcaac ttaaataggc ggatctttgg tgcatctagt gagaagttga gaaaatgatg  11040
aaggactgcc acacgcgcgc gccgccgggc cgtggccgtg gtagatcgga ccttggtccg  11100
aatattcctt cctaacggtt gcacattttg cctaaagtga tgaccgtcca ttactgttgt  11160
acgttattgg tcgtttccta tgttatggat agtaacgaac gagttataat gcttgtcagc  11220
tattaacgga cgtcactaat ggcgtccgtt tctggctggc tgtaatgata gctctgatgg  11280
tgaccgttac tatccgttcg cctccctctg ctcgtttata tatacaaagg aggtgaggct  11340
```

```
gcttctggtt acgagagaac acacgtacaa ttcttagacg cgttgcgtac agcccatccc  11400

tggttgaacc tctctaaacc ccggttgaac ttttcctgga ccccagttga acctctctgg  11460

accccggttg aacttgcctt ggaccccggt tgaacctgcc tggaccccgg ttgaacttga  11520

ctggacccca gttgaagttg aagttcaact ggagttgaga aagctcgaca cagctgaagt  11580

ttagctcagc tgaaaagctc aactgcagct gaagaagctc aactcagctg aagtttagtt  11640

cagctgaaaa gctcagctgc ttttcaacaa aaacactcta ggtttctcaa acctaaccat  11700

agtcaaccat agaattttaa agagattttt gattttcaaa aaatagcttt tgaatataga  11760

ggcttgagct ttggcaaaca ccaaccttat ttttggatcc ccttggtagt acgatgaatc  11820

ctatactcaa tttaagtaaa atataattaa gtaaactcct tgagtaattg gtgtctcatg  11880

tgtgatttct ccatggcgtt                                               11900
```

<210> SEQ ID NO 50
<211> LENGTH: 3571
<212> TYPE: DNA
<213> ORGANISM: Zea mays
<220> FEATURE:
<221> NAME/KEY: misc_feature
<222> LOCATION: (1933)..(1933)
<223> OTHER INFORMATION: n is a, c, g, or t

<400> SEQUENCE: 50

```
ggagggggag acggtgaggc gcggccatgg ggggcgccaa ggcggaggac aaaccggccg     60

ccgctgcaga agattggtgc taccaatttg gaaacaaggt tcgatttctt caccatttgc    120

actcctctgc aagactggga cacgtttccg ggtttcgttc tgcctgggcg gcgacaaatc    180

tcatggcaaa ttgcctttgg ggggctcatt ccctgggttc acactccaaa tccttccttg    240

cgaccttctc tcagccgtcg cgctttccgt ggcaagcctt ttggaaccct gatctgaagt    300

gtcactcaga tcaatgcagt cgcattgatt ctattcgttt cctgtttccg tttcccccctt   360

ttaacgtgtc tgctagttcc aagtcccgag cgttttccgt tctctgtttc agaattgaag    420

cttgttaagt tctgtttttt tttacaatcc ttcgtttttg tcccagtcct ttctattcct    480

ggagaagtta ggaatctgtt gttctcctgt tccatttctc ggtgcagtat tagttgcaga    540

acaggaatcc acttgatttg tcagtttaat tatgcttgtg tcacctcaga tgtgtcatat    600

tgatgatgac tgcatttttt tttcagctgt aatatgcgtg ttggcttgca tttgtttctc    660

tctttattag tactaccagc attttcggtc agtatttttt gtcttccttg ctgaagaatg    720

agaaggaaag ctgtcatact cctcgtcggg atagcttcat ttattatggc agctgggcga    780

cagaatatat gggaatgtac ttgaacttca caaaaaaggg ccttttcatc ccttgccgtg    840

tcttccatgt tggtaaaaag gctagtagct gaattgaata gtacgtgctc attttaacta    900

ccctgaggac tagatagatc ttgaagtttt atttgtttat ttctttttac ttctgcttat    960

atagatgtag ccaaatatat gcttcttcag ctcacgttga acattaatgt ttgtgttgtt   1020

tgctgaaagg ttttttactg tagcagaagg ttacaaaata acagatctta cctcaaaaaa   1080

gggctgcaat gcatatatac tggcactgaa ccgcgtatgc gcagtgcaac ctgctgattg   1140

gttttgtact ggtcggatct gtttgcagga tgcatttgac ttgaagcccc cgaaaaaatc   1200

accgatcgcg ttgagaacgg ttgtctttgc tatgactatg ttatgcggga tatctatttg   1260

ctcaatgtgc atgaagcaac tagggagtga tggctggtca agagttgtca agattgaagt   1320

tgtggaacaa ccatgtaata agtccattgc tcctctttcg gaggctcaat ttgtgcgcta   1380
```

```
tcctcaaccg ataacttaca gcaggtgaga tttgcactgt ggtaagattg agcaatctcg   1440
tttgtttaat gcctaatata taatttttaa tttctaggga ggaatgcaag tgcaatgctg   1500
tccggtcctt tgcaattata tcatcgcagc gatctggaag tggctggttt gaaacacttc   1560
ttaacagcca catgaatgtt agctccaatg gtgaaatttt ctctagaaaa gaaaggagga   1620
gtaacatttc ctctatagta gataccctgg ataaagtgta caatttggac tggaatagta   1680
gtgcttccaa gaatgagtgc actgcagcta ttggcttcaa gtggatgctg aatcaggtgc   1740
ggactaaaac atgcagtata gataatttat ttggatgatc ctttttcatt tattgttcca   1800
tttagttcca gtatgtttca attattacta tctgtagtct cctaaacggc ctacatgttc   1860
tcaactgtag atgctagatg ttattgcata ttgcgccaaa ctttcctcaa gaccatggaa   1920
cttttttttt ttnttttttt ttttggaaac cactttaggg cttgttcgtt ttagtgccaa   1980
tccatatgga ttggatgggt ttaaatacat aagaagtcaa aatccttctt aaaatttttc   2040
aatctcttcc aatccatgtg ggtgggatgc gattccaatc catgtgggat gcgaataacc   2100
gaacaaggcc ttataggact gtcgaatagc tagtttagtt ttctgacttg ctgtcagatc   2160
ctgcatttta gacaatttct ctctctcgaa catgcatgag aactgcaaat gcatatggag   2220
taatatttga tagattctgt agtgtgtcca gtagactgat tataatctac atgtcaagca   2280
tgtttgtttc agggcttcat ctaatttgtg cgagaacaaa ctttttttcct ggtagacaga   2340
ttgcctaacc aaaccatgaa tattggccaa acagagagtt agagactgga aacaaaaacag   2400
gcactctagc tagggagtgg aaacaaagga gcatttcttc tgaacggggt tggggttggg   2460
gtgtatgttt tcagggcctc gtggcaaacc atgcggacgt agtcgactac ttcaaccgaa   2520
gaggagtctc tgcaatattt cttttcagaa ggaacctgct ccgtcagttg gtatcacaag   2580
tagcgaacaa tcacgacagg ttacttaagc aactaaacgg aacgcacaag gcccatgtcc   2640
acacgaagcg tgaggttagt aatgctagct aagaaacgtg ttcgcggcta atgtctcact   2700
ctcacagcaa gtctctgagc tgagctgatc tctgtctgtg tttgacgtgt cgttcgttct   2760
cgctccacag gcccatatac tggcaagata caggcccagg ctcaacacga cgtcactgat   2820
atggcagctg aaacgagctg acgagtacac tcgcgacgct cttgagaacc taaacaacac   2880
ccggcacatg agcgtctact acgaggacgt cgtccgcaac agaacagtgc gttctcgctg   2940
atgccctttg tctgttccct tccgttggtt gtatcgctta ccatcgctgc tgcactgcag   3000
aagctcttgg atgtcctgga tttcctcgga gtgccgagga ggaagctggt gagccggcac   3060
gtgaagatac acacgaagcc gctgtcggag cagatcgaga actgggacga ggtctacagc   3120
gccctcaacg gtacccagta cgagggcttc ctgaatgccg ctgactatct agtataacat   3180
cacgtttctg gatgtagata gtgtgcgtgt gattctttcg tttcttgttt gtttctggca   3240
gaaattttga tgcggggtag gcgccttttg ccgtgcatgg ttgcattctc ggtaacctga   3300
tgctcctgta actaaccctc cagcttctct ggtctttgta tttgccttgg gtgtttgctg   3360
atgttctttc aaactatttg aaatcgggct gtcggagttc cagatcacgg gcggcaggat   3420
aggtgatgtg acctagataa atgtacgaga cacatgacaa atctatacta cttattaaaa   3480
gtgtaatagc agtctgccgt tctgccatcc tgcaacctca accgtccatt ccattgttct   3540
gcaatttcaa ccgttcgatc ccacccacca g                                  3571
```

<210> SEQ ID NO 51
<211> LENGTH: 1896
<212> TYPE: DNA
<213> ORGANISM: Zea mays

<400> SEQUENCE: 51

```
ccaaggcgga ggacaaaccg gccgccgctg cagaagattg gtgctaccaa tttggaaaca     60
aggttcgatt tcttcaccat ttgcactcct ctgcaagact gggacacgtt tccgggtttc    120
gttctgcctg ggcggcgaca aatctcatgg caaattgcct ttggggggct cattccctgg    180
gttcacactc caaatccttc cttgcgacct tctctcagcc gtcgcgcttt ccgtggcaag    240
ccttttggaa ccctgatctg aagtgtcact cagatcaatg cagtcgcatt gattctattc    300
gtttcctgtt tccgtttccc ccttttaacg tgtctgctag ttccaagtcc cgagcgtttt    360
ccgttctctg tttcagaatt gaagcttgtt aagttctgtt tttttttaca atccttcgtt    420
tttgtcccag tcctttctat tcctggagaa gttaggaatc tgttgttctc ctgttccatt    480
tctcggtgca gtattagttg cagaacagga atccacttga tttgtcagtt taattatgct    540
tgtgtcacct cagatgtgtc atattgatga tgactgcatt tttttttcag ctgtaatatg    600
cgtgttggct tgcatttgtt tctctcttta ttagtactac cagcattttc ggtcagtatt    660
ttttgtcttc cttgctgaag aatgagaagg aaagctgtca tactcctcgt cgggatagct    720
tcatttatta tggcagctgg gcgacagaat atatgggaat gtacttgaac ttcacaaaaa    780
agggcctttt catcccttgc cgtgtcttcc atgttggtaa aaaggctagt agctgaattg    840
aatagtacgt gctcatttta actaccctga ggactagata gatcttgaag ttttatttgt    900
ttatttcttt ttacttctgc ttatatagat gtagccaaat atatgcttct tcagctcacg    960
ttgaacatta atgtttgtgt tgtttgctga aaggtttttt actgtagcag aaggttacaa   1020
aataacagat cttacctcaa aaaagggctg caatgcatat atactggcac tgaaccgcgt   1080
atgcgcagtg caacctgctg attggttttg tactggtcgg atctgtttgc aggatgcatt   1140
tgacttgaag cccccgaaaa aatcaccgat cgcgttgaga acggttgtct ttgctatgac   1200
tatgttatgc gggatatcta tttgctcaat gtgcatgaag caactaggga gtgatggctg   1260
gtcaagagtt gtcaagattg aagttgtgga acaaccatgt aataagtcca ttgctcctct   1320
ttcggaggct caatttgtgc gctatcctca accgataact tacagcaggt gagatttgca   1380
ctgtggtaag attgagcaat ctcgtttgtt taatgcctaa tatataattt ttaatttcta   1440
gggaggaatg caagtgcaat gctgtccggt cctttgcaat tatatcatcg cagcgatctg   1500
gaagtggctg gtttgaaaca cttcttaaca gccacatgaa tgttagctcc aatggtgaaa   1560
ttttctctag aaaagaaagg aggagtaaca tttcctctat agtagatacc ctggataaag   1620
tgtacaattt ggactggaat agtagtgctt ccaagaatga gtgcactgca gctattggct   1680
tcaagtggat gctgaatcag gtgcggacta aaacatgcag tatagataat ttatttggat   1740
gatccttttt catttattgt tccatttagt tccagtatgt ttcaattatt actatctgta   1800
gtctcctaaa cggcctacat gttctcaact gtagatgcta gatgttattg catattgcgc   1860
caaactttcc tcaagaccat ggaacttttt tttttt                             1896
```

<210> SEQ ID NO 52
<211> LENGTH: 1371
<212> TYPE: DNA
<213> ORGANISM: Zea mays

<400> SEQUENCE: 52

```
agttcatcac taatcacact tattgtgccc tcgacgagta tctatagcta gctcattaat     60
cgattcgggg gtgtgttgtc gaaggcggca atggcgagct actcgtcgcg gcgtccatgc    120
```

```
aatacctgta gcacgaaggc gatggccggg agcgtggtcg gcgagcccgt cgtgctgggg    180

cagagggtga cggtgctgac ggtggacggc ggcggcgtcc ggggtctcat cccgggaacc    240

atcctcgcct tcctggaggc caggctgcag gagctggacg gaccggaggc gaggctggcg    300

gactacttcg actacatcgc cggaaccagc accggcggtc tcatcaccgc catgctcacc    360

gcgcccggca aggacaagcg gcctctctac gctgccaagg acatcaacca cttttacatg    420

cagaactgcc cgcgcatctt tcctcagaag agcaggcttg cggccgccat gtccgcgctg    480

aggaagccaa agtacaacgg caagtgcatg cgcagcctga ttaggagcat cctcggcgag    540

acgagggcca agagcacgcc tctgaagaac gctctgctct cggacgtgtg cattggcacg    600

tccgccgcgc cgacctacct cccggcgcac tacttccaga ctgaagacgc caacggcaag    660

gagcgcgaat acaacctcat cgacggcggt gtggcggcca acaacccgac gatggttgcg    720

atgacgcaga tcaccaaaaa gatgcttgcc agcaaggaca aggccgagga gctgtaccca    780

gtgaagccgt cgaactgccg caggttcctg gtgctgtcca tcgggacggg gtcgacgtcc    840

gagcagggcc tctacacggc gcggcagtgc tcccggtggg gtatctgccg gtggctccgc    900

aacaacggca tggcccccat catcgacatc ttcatggcgg ccagctcgga cctggtggac    960

atccacgtcg ccgcgatgtt ccagtcgctc cacagcgacg gcgactacct gcgcatccag   1020

gacaactcgc tccgtggcgc cgcggccacc gtggacgcgg cgacgccgga gaacatgcgg   1080

acgctcgtcg ggatcgggga gcggatgctg gcacagaggg tgtccagggt caacgtggag   1140

acagggaggt acgaaccggt gactggcgaa ggaagcaatg ccgatgccct cggtgggctc   1200

gctaggcagc tctccgagga gaggagaaca aggctcgcgc gccgcgtctc tgccatcaac   1260

ccaagaggct ctagatgtgc gtcgtacgat atctaagaca agtggcttta ctgtcagtca   1320

catgcttgta aataagtaga ctttatttta ataaaacata aaaatatata t            1371
```

<210> SEQ ID NO 53
<211> LENGTH: 1458
<212> TYPE: DNA
<213> ORGANISM: Zea mays

<400> SEQUENCE: 53

```
agttcatcac taatcacact tattgtgccc tcgacgagta tctagctagc tcattaatcg     60

atcaatcggg gtgtgcggtc gaaggcggca atggcgagct actcgtcgcg gcgtccatgc    120

aatacctgta gcacgaaggc gatggccggg agcgtggtcg gcgagcccgt cgtgctgggg    180

cagagggtga cggtgctgac ggtggacggc ggcggcgtcc ggggtctcat cccgggaacc    240

atcctcgcct tcctggaggc caggctgcag gagctggacg gaccggaggc gaggctggcg    300

gactacttcg actacatcgc cggaaccagc accggcggtc tcatcaccgc catgctcacc    360

gcgcccggca aggacaagcg gcctctctac gctgccaagg acatcaacta cttttacatg    420

gagaactgcc cgcgcatctt ccctcagaag agcaggcttg cggccgccat gtccgcgctg    480

aggaagccaa agtacaacgg caagtgcatg cgcagcctga ttaggagcat cctcggcgag    540

acgagggtaa gcgagacgct gaccaacgtc atcatccctg ccttcgacat caggctgctg    600

cagcctatca tcttctctac ctacgacgcc aagagcacgc ctctgaagaa cgcgctgctc    660

tcggacgtgt gcattggcac gtccgccgcg ccgacctacc tcccggcgca ctacttccag    720

actgaagacg ccaacggcaa ggagcgcgaa tacaacctca tcgacggcgg tgtggcggcc    780

aacaacccga cgatggttgc gatgacgcag atcaccaaaa agatgcttgc cagcaaggac    840

aaggccgagg agctgtaccc agtgaacccg tcgaactgcc gcaggttcct ggtgctgtcc    900
```

```
atcgggacgg ggtcgacgtc cgagcagggc ctctacacgg cgcggcagtg ctcccggtgg    960

ggcatctgcc ggtggctccg caacaacggc atggccccca tcatcgacat cttcatggcg   1020

gccagctcgg acctggtgga catccacgtc gccgcgatgt tccagtcgct ccacagcgac   1080

ggcgactacc tacgcatcca ggacaactcg ctccgtggcg ccgcggcaac cgtggacgcg   1140

gcgacgccgg agaacatgcg gacgctcgtc gggatcgggg agcggatgct ggcacagcgg   1200

gtgtccaggg tcaacgtgga gacagggagc gaggtacgaa ccggtgaccg gagaaggaag   1260

caatgccgat gccctcggtg ggctcgctag gcagctctcc gaggagagga gaacaaggct   1320

cgcgcgccgc gtctctgcca tcaaccccag aagctctaga tgtgcgccct acgatatcta   1380

agacaagtgg ctttactgtc aatcacatgc ttgtaaataa gtagacttta ttttaataaa   1440

atataaatat atatatat                                                 1458
```

<210> SEQ ID NO 54
<211> LENGTH: 401
<212> TYPE: PRT
<213> ORGANISM: Zea mays

<400> SEQUENCE: 54

```
Met Ala Ser Tyr Ser Ser Arg Arg Pro Cys Asn Thr Cys Ser Thr Lys
1               5                   10                  15

Ala Met Ala Gly Ser Val Val Gly Glu Pro Val Val Leu Gly Gln Arg
            20                  25                  30

Val Thr Val Leu Thr Val Asp Gly Gly Gly Val Arg Gly Leu Ile Pro
        35                  40                  45

Gly Thr Ile Leu Ala Phe Leu Glu Ala Arg Leu Gln Glu Leu Asp Gly
    50                  55                  60

Pro Glu Ala Arg Leu Ala Asp Tyr Phe Asp Tyr Ile Ala Gly Thr Ser
65                  70                  75                  80

Thr Gly Gly Leu Ile Thr Ala Met Leu Thr Ala Pro Gly Lys Asp Lys
                85                  90                  95

Arg Pro Leu Tyr Ala Ala Lys Asp Ile Asn His Phe Tyr Met Gln Asn
            100                 105                 110

Cys Pro Arg Ile Phe Pro Gln Lys Ser Arg Leu Ala Ala Ala Met Ser
        115                 120                 125

Ala Leu Arg Lys Pro Lys Tyr Asn Gly Lys Cys Met Arg Ser Leu Ile
    130                 135                 140

Arg Ser Ile Leu Gly Glu Thr Arg Ala Lys Ser Thr Pro Leu Lys Asn
145                 150                 155                 160

Ala Leu Leu Ser Asp Val Cys Ile Gly Thr Ser Ala Ala Pro Thr Tyr
                165                 170                 175

Leu Pro Ala His Tyr Phe Gln Thr Glu Asp Ala Asn Gly Lys Glu Arg
            180                 185                 190

Glu Tyr Asn Leu Ile Asp Gly Gly Val Ala Ala Asn Asn Pro Thr Met
        195                 200                 205

Val Ala Met Thr Gln Ile Thr Lys Lys Met Leu Ala Ser Lys Asp Lys
    210                 215                 220

Ala Glu Glu Leu Tyr Pro Val Lys Pro Ser Asn Cys Arg Arg Phe Leu
225                 230                 235                 240

Val Leu Ser Ile Gly Thr Gly Ser Thr Ser Glu Gln Gly Leu Tyr Thr
                245                 250                 255

Ala Arg Gln Cys Ser Arg Trp Gly Ile Cys Arg Trp Leu Arg Asn Asn
            260                 265                 270
```

```
Gly Met Ala Pro Ile Ile Asp Ile Phe Met Ala Ala Ser Ser Asp Leu
        275                 280                 285

Val Asp Ile His Val Ala Ala Met Phe Gln Ser Leu His Ser Asp Gly
    290                 295                 300

Asp Tyr Leu Arg Ile Gln Asp Asn Ser Leu Arg Gly Ala Ala Ala Thr
305                 310                 315                 320

Val Asp Ala Ala Thr Pro Glu Asn Met Arg Thr Leu Val Gly Ile Gly
                325                 330                 335

Glu Arg Met Leu Ala Gln Arg Val Ser Arg Val Asn Val Glu Thr Gly
            340                 345                 350

Arg Tyr Glu Pro Val Thr Gly Glu Gly Ser Asn Ala Asp Ala Leu Gly
        355                 360                 365

Gly Leu Ala Arg Gln Leu Ser Glu Glu Arg Arg Thr Arg Leu Ala Arg
    370                 375                 380

Arg Val Ser Ala Ile Asn Pro Arg Gly Ser Arg Cys Ala Ser Tyr Asp
385                 390                 395                 400

Ile


<210> SEQ ID NO 55
<211> LENGTH: 428
<212> TYPE: PRT
<213> ORGANISM: Zea mays

<400> SEQUENCE: 55

Met Ala Ser Tyr Ser Ser Arg Arg Pro Cys Asn Thr Cys Ser Thr Lys
1               5                   10                  15

Ala Met Ala Gly Ser Val Val Gly Glu Pro Val Val Leu Gly Gln Arg
            20                  25                  30

Val Thr Val Leu Thr Val Asp Gly Gly Gly Val Arg Gly Leu Ile Pro
        35                  40                  45

Gly Thr Ile Leu Ala Phe Leu Glu Ala Arg Leu Gln Glu Leu Asp Gly
    50                  55                  60

Pro Glu Ala Arg Leu Ala Asp Tyr Phe Asp Tyr Ile Ala Gly Thr Ser
65                  70                  75                  80

Thr Gly Gly Leu Ile Thr Ala Met Leu Thr Ala Pro Gly Lys Asp Lys
                85                  90                  95

Arg Pro Leu Tyr Ala Ala Lys Asp Ile Asn His Phe Tyr Met Gln Asn
            100                 105                 110

Cys Pro Arg Ile Phe Pro Gln Lys Ser Arg Leu Ala Ala Ala Met Ser
        115                 120                 125

Ala Leu Arg Lys Pro Lys Tyr Asn Gly Lys Cys Met Arg Ser Leu Ile
    130                 135                 140

Arg Ser Ile Leu Gly Glu Thr Arg Val Ser Glu Thr Leu Thr Asn Val
145                 150                 155                 160

Ile Ile Pro Ala Phe Asp Ile Arg Leu Leu Gln Pro Ile Ile Phe Ser
                165                 170                 175

Thr Tyr Asp Ala Lys Ser Thr Pro Leu Lys Asn Ala Leu Leu Ser Asp
            180                 185                 190

Val Cys Ile Gly Thr Ser Ala Ala Pro Thr Tyr Leu Pro Ala His Tyr
        195                 200                 205

Phe Gln Thr Glu Asp Ala Asn Gly Lys Glu Arg Glu Tyr Asn Leu Ile
    210                 215                 220

Asp Gly Gly Val Ala Ala Asn Asn Pro Thr Met Val Ala Met Thr Gln
225                 230                 235                 240
```

```
Ile Thr Lys Lys Met Leu Ala Ser Lys Asp Lys Ala Glu Glu Leu Tyr
                245                 250                 255

Pro Val Asn Pro Ser Asn Cys Arg Arg Phe Leu Val Leu Ser Ile Gly
            260                 265                 270

Thr Gly Ser Thr Ser Glu Gln Gly Leu Tyr Thr Ala Arg Gln Cys Ser
        275                 280                 285

Arg Trp Gly Ile Cys Arg Trp Leu Arg Asn Asn Gly Met Ala Pro Ile
    290                 295                 300

Ile Asp Ile Phe Met Ala Ala Ser Ser Asp Leu Val Asp Ile His Val
305                 310                 315                 320

Ala Ala Met Phe Gln Ser Leu His Ser Asp Gly Asp Tyr Leu Arg Ile
                325                 330                 335

Gln Asp Asn Ser Leu Arg Gly Ala Ala Ala Thr Val Asp Ala Ala Thr
            340                 345                 350

Pro Glu Asn Met Arg Thr Leu Val Gly Ile Gly Glu Arg Met Leu Ala
        355                 360                 365

Gln Arg Val Ser Arg Val Asn Val Glu Thr Gly Arg Tyr Glu Pro Val
    370                 375                 380

Thr Gly Glu Gly Ser Asn Ala Asp Ala Leu Gly Gly Leu Ala Arg Gln
385                 390                 395                 400

Leu Ser Glu Glu Arg Arg Thr Arg Leu Ala Arg Arg Val Ser Ala Ile
                405                 410                 415

Asn Pro Arg Gly Ser Arg Cys Ala Ser Tyr Asp Ile
            420                 425
```

<210> SEQ ID NO 56
<211> LENGTH: 372
<212> TYPE: PRT
<213> ORGANISM: Zea mays

<400> SEQUENCE: 56

```
Met Ala Ser Tyr Ser Ser Arg Arg Pro Cys Asn Thr Cys Ser Thr Lys
1               5                   10                  15

Ala Met Ala Gly Ser Val Val Gly Glu Pro Val Val Leu Gly Gln Arg
            20                  25                  30

Val Thr Val Leu Thr Val Asp Gly Gly Gly Val Arg Gly Leu Ile Pro
        35                  40                  45

Gly Thr Ile Leu Ala Phe Leu Glu Ala Arg Leu Gln Glu Leu Asp Gly
    50                  55                  60

Pro Glu Ala Arg Leu Ala Asp Tyr Phe Asp Tyr Ile Ala Gly Thr Ser
65                  70                  75                  80

Thr Gly Gly Leu Ile Thr Ala Met Leu Thr Ala Pro Gly Lys Asp Lys
                85                  90                  95

Arg Pro Leu Tyr Ala Ala Lys Asp Ile Asn Tyr Phe Tyr Met Gln Asn
            100                 105                 110

Cys Pro Arg Ile Phe Pro Gln Lys Ser Arg Leu Ala Ala Ala Met Ser
        115                 120                 125

Ala Leu Arg Lys Pro Lys Tyr Asn Gly Lys Cys Met Arg Ser Leu Ile
    130                 135                 140

Arg Ser Ile Leu Gly Glu Thr Arg Ala Lys Ser Thr Pro Leu Lys Asn
145                 150                 155                 160

Ala Leu Leu Ser Asp Val Cys Ile Gly Thr Ser Ala Ala Pro Thr Tyr
                165                 170                 175

Leu Pro Ala His Tyr Phe Gln Thr Glu Asp Ala Asn Gly Lys Glu Arg
```

```
            180                 185                 190

Glu Tyr Asn Leu Ile Asp Gly Gly Val Ala Ala Asn Asn Pro Thr Met
        195                 200                 205

Val Ala Met Thr Gln Ile Thr Lys Lys Met Leu Ala Ser Lys Asp Lys
    210                 215                 220

Ala Glu Glu Leu Tyr Pro Val Asn Pro Ser Asn Cys Arg Arg Phe Leu
225                 230                 235                 240

Val Leu Ser Ile Gly Thr Gly Ser Thr Ser Glu Gln Gly Leu Tyr Thr
                245                 250                 255

Ala Arg Gln Cys Ser Arg Trp Gly Ile Cys Arg Trp Leu Arg Asn Asn
            260                 265                 270

Gly Met Ala Pro Ile Ile Asp Ile Phe Met Ala Ala Ser Ser Asp Leu
        275                 280                 285

Val Asp Ile His Val Ala Ala Met Phe Gln Ser Leu His Ser Asp Gly
    290                 295                 300

Asp Tyr Leu Arg Ile Gln Asp Asn Ser Leu Arg Gly Ala Ala Ala Thr
305                 310                 315                 320

Val Asp Ala Ala Thr Pro Glu Asn Met Arg Thr Leu Val Gly Ile Gly
                325                 330                 335

Glu Arg Met Leu Ala Gln Arg Val Ser Arg Val Asn Val Glu Thr Gly
            340                 345                 350

Ser Glu Val Arg Thr Gly Asp Arg Arg Arg Lys Gln Cys Arg Cys Pro
        355                 360                 365

Arg Trp Ala Arg
    370


<210> SEQ ID NO 57
<211> LENGTH: 399
<212> TYPE: PRT
<213> ORGANISM: Zea mays

<400> SEQUENCE: 57

Met Ala Ser Tyr Ser Ser Arg Arg Pro Cys Asn Thr Cys Ser Thr Lys
1               5                   10                  15

Ala Met Ala Gly Ser Val Val Gly Glu Pro Val Val Leu Gly Gln Arg
            20                  25                  30

Val Thr Val Leu Thr Val Asp Gly Gly Gly Val Arg Gly Leu Ile Pro
        35                  40                  45

Gly Thr Ile Leu Ala Phe Leu Glu Ala Arg Leu Gln Glu Leu Asp Gly
    50                  55                  60

Pro Glu Ala Arg Leu Ala Asp Tyr Phe Asp Tyr Ile Ala Gly Thr Ser
65                  70                  75                  80

Thr Gly Gly Leu Ile Thr Ala Met Leu Thr Ala Pro Gly Lys Asp Lys
                85                  90                  95

Arg Pro Leu Tyr Ala Ala Lys Asp Ile Asn Tyr Phe Tyr Met Gln Asn
            100                 105                 110

Cys Pro Arg Ile Phe Pro Gln Lys Ser Arg Leu Ala Ala Ala Met Ser
        115                 120                 125

Ala Leu Arg Lys Pro Lys Tyr Asn Gly Lys Cys Met Arg Ser Leu Ile
    130                 135                 140

Arg Ser Ile Leu Gly Glu Thr Arg Val Ser Glu Thr Leu Thr Asn Val
145                 150                 155                 160

Ile Ile Pro Ala Phe Asp Ile Arg Leu Leu Gln Pro Ile Ile Phe Ser
                165                 170                 175
```

```
Thr Tyr Asp Ala Lys Ser Thr Pro Leu Lys Asn Ala Leu Leu Ser Asp
            180                 185                 190

Val Cys Ile Gly Thr Ser Ala Ala Pro Thr Tyr Leu Pro Ala His Tyr
        195                 200                 205

Phe Gln Thr Glu Asp Ala Asn Gly Lys Glu Arg Glu Tyr Asn Leu Ile
    210                 215                 220

Asp Gly Gly Val Ala Ala Asn Asn Pro Thr Met Val Ala Met Thr Gln
225                 230                 235                 240

Ile Thr Lys Lys Met Leu Ala Ser Lys Asp Lys Ala Glu Glu Leu Tyr
                245                 250                 255

Pro Val Asn Pro Ser Asn Cys Arg Arg Phe Leu Val Leu Ser Ile Gly
            260                 265                 270

Thr Gly Ser Thr Ser Glu Gln Gly Leu Tyr Thr Ala Arg Gln Cys Ser
        275                 280                 285

Arg Trp Gly Ile Cys Arg Trp Leu Arg Asn Asn Gly Met Ala Pro Ile
    290                 295                 300

Ile Asp Ile Phe Met Ala Ala Ser Ser Asp Leu Val Asp Ile His Val
305                 310                 315                 320

Ala Ala Met Phe Gln Ser Leu His Ser Asp Gly Asp Tyr Leu Arg Ile
                325                 330                 335

Gln Asp Asn Ser Leu Arg Gly Ala Ala Ala Thr Val Asp Ala Ala Thr
            340                 345                 350

Pro Glu Asn Met Arg Thr Leu Val Gly Ile Gly Glu Arg Met Leu Ala
        355                 360                 365

Gln Arg Val Ser Arg Val Asn Val Glu Thr Gly Ser Glu Val Arg Thr
    370                 375                 380

Gly Asp Arg Arg Arg Lys Gln Cys Arg Cys Pro Arg Trp Ala Arg
385                 390                 395
```

<210> SEQ ID NO 58
<211> LENGTH: 2088
<212> TYPE: DNA
<213> ORGANISM: Zea mays

<400> SEQUENCE: 58

```
tatttgtact cattccatgt ctcataaact ttgggcacca tccatccaac acatccaatc      60

taaacacacc aaacgatggg gaatggaaag agcagtattc gattcaacaa tggcaaacaa     120

atatcactga attagaccaa gaataaacct aattagacaa cgacctccca accatcattc     180

gtcaggctgt aaagaagata aagctgcctt ggggcatgga tcaagcagaa caccagagat     240

gaatccaaac acacagaaaa tcacgcgcgc tgtctacaat gacaacaagc cccacatttc     300

attgcagtac actgggctac aaaggcacgt acaacaaaga gctagggaaa cattgcggag     360

ggcacgagag agcagctaac ttgacaatat agcagactga gcttgcactg ttagcaggcg     420

aggaagggaa tcatggggac ggagaatggg gtccatgccc gcgaaggaga aggcggacgc     480

cgccacggtg gcaccggcgc acgcgcacac agggaacccg cacaggcagc caaggatgct     540

gcctcgccat tgcgccggtc gtctctgcca cgctcctctc tctctcccgc tgcatcgccg     600

tggatggggc aagcagagag cagggactgc gacgatctgg gcggaggact cgccttggag     660

agcgcggacg cagacgggat tctagggaga gagcgaagac ggggcgcgcg cggcgctcgc     720

gcggcgtggt ggcggcgaga ttagcggggg tggggggagg gcggagccgt ggtgagggtg     780

tggacgccct ccttaccctc ttaagtagta gtagagatat aatccgttcc aaaatatcca     840

tccgttcaat ttatatttcg tttgatcttt ttaccctaaa tttgattgac tcatcttatt     900
```

```
aaaaaagttc ataactatta ttaatcttta ttgagatatc atttagcata taatatactt    960
taagtgtggt tttagatttt ttttaaaaaa aaaaattcgc aaaaattaaa tgaaacgacc   1020
caatcaaact tgaaaagtaa aactaattat aaatttgaac ggaaggagta agaggatgtt   1080
tgaatgtact agagctaata gttggttgct ttaaaatttg ctagtagaat tagctagcta   1140
ataaatatct agataactat tagctaattt gctaaaacag ctaatagttg aactattagc   1200
tagattgttt ggatgtattc ggctaatttt aatggctaac tattagctat agtacaatat   1260
tcaaacacct cctaattaaa atggacaaat atctcttctt ttggtccctt gcgttagatt   1320
tttcatatct ccttatttag tataaaagaa tcatcaaaaa gtggacaacc cctagtggaa   1380
caccatttta gtagtggttg catgaaacct ttcgcgcacc agtttctatg tgtcactcta   1440
aaaatgggac agcatgtacg tagtgcctat atatatacaa gtcatctatc gttgcctcct   1500
cagttcatca ctaatcacac ttattgtgcc ctcgacgagt atctatagct agctcattaa   1560
tcgattcggg ggtgtgttgt cgaaggcggc attggcgagc tactcgtcgc ggcgtccaag   1620
caatacctgt agcacgaagg cgatcgccgg gagcgtggtc ggcgagcccg tcgtgctggg   1680
gcagagggtg acggtgctga cggtggacgg cggcggcgtc cggggtctca tcccgggaac   1740
catcctcgcc ttcctggagg ccaggctgca ggagctggac gcaccggagg cgaggctggc   1800
ggactacttc gactacatcg ccggaaccag caccggcggt ctcatcaccg ccttgctgac   1860
cgcgcccggc aaggacaagc ggcctctcta ggctgccaag gacatcaacc acttttacat   1920
ccataactgc ccgcgcatct ttcctcagaa gtgagtccga tgctgccgcc attgttcttg   1980
catccatcca gcatcgtacg tacgtcctct atacatctgc ggatcatcat gtgcgcatgt   2040
ttgtggcatg catgcatgca tgtgagcagg agcaggcttg cgaaaacc                2088
```

<210> SEQ ID NO 59
<211> LENGTH: 996
<212> TYPE: DNA
<213> ORGANISM: Zea mays

<400> SEQUENCE: 59

```
gacaagtggc tttactgtca gtcacatgct tgtaaataag tagactttat tttaataaaa     60
cataaaaata tatatatgtt cttgaatata aaattgataa ccaaattaaa attcgaacca    120
tcacttatac ataattttac tttatttttt ataaaacgtg aacgggaagg actaccgtga    180
atgactatag aaccaatcat actagtataa aatatatgat gacactacgg gagagacaaa    240
ctttgtctgg cgctaaatat tttgccgagt gtgaattcac gggcactagg caaagatctt    300
ctttgccgag tgttacgctg ggcaaagtaa gacactaggt aaatcagtca tttgccgagt    360
gtccgccact aggcaaagca aaacactggc aaatcaaaag tttacctagt gccagacact    420
aggcaaaaaa aaaacgctcg gcaaatcgga agtttcccta gtgccagaca ctagacaaag    480
aaaaacactt gataaactag cgtcgtcagc taacaccatc caccaaccgt taacgttgcc    540
gagtatctga cttcgacact cggcaaagaa ggtctctttg cctagtgtcg gtctggaaca    600
ctaggcaaag aggcacttta cctagtgtcg tattttgaca ctcagtaaaa taattttttt    660
tctttctgct tccaaacttt ttatgatgtg ttcctatagc acctagaact acatgtcaag    720
ttttggtaaa atttttgaag tttttgctat atttacttaa tttattttat ttaattgaat    780
ttcttttgat aattcaaatt tgaactcggc aaggtaagaa gcgagggtag cctggaaaca    840
cactttgcct agtgttacac tcggtacagg agcctcccct gcctagtgct gcactcgaca    900
```

```
aaagattcgc ctttgcctag cgctgcactc ggcacaggag tcgcctttgc ctagtgctgc    960

actaggcaaa gcctccgtta ccgtgccttc catcgt                              996


<210> SEQ ID NO 60
<211> LENGTH: 1089
<212> TYPE: DNA
<213> ORGANISM: Artificial Sequence
<220> FEATURE:
<223> OTHER INFORMATION: Synthetic

<400> SEQUENCE: 60

ttgcgatggc gcagatcacc aaaaagatgc ttgccaacaa ggacaaggcc gaggagctgt     60

acccagtgaa gccgtcgaac tgccgcaggt tcctggtgct gtccatcggg acggggtcga    120

cgtccgagca gggcctctac acggcgcggc agtgctcccg gtggggtatc tgccggtggc    180

tccgcgtcga ctcgggagca tgccctttgt gcttatgcct ccgttctgcc ttctgacgaa    240

tttggtactg gaagcagatg agttttggtt cactatcatt ctgaatttac acctgcgctt    300

gctgtcagac taggcaacca agtgactttt gtgactttga tcatgttcag tgtgtttcca    360

agtcctaatc aatcaaaaag aaaaacagtt tgttaacgat tgtttgccat gtctatataa    420

taaagttgct tttatagtag cttagaattc aatcggccaa ctttatctcg tacgctgaca    480

gtaaaggtac atttaaaagg tgacaatgga tagtctaata cttgaactga caatagagac    540

acattacatg tcagttgatt aagtttgtaa cagaaaaata aacaatacta cataattgca    600

aagtttcttt gatgtctttc tttcaagaaa cacaaatata tcaatgctac agtattgctg    660

atgaatttat ccatgttgag atgtttttct ggtttctgat ctgatcagtc tcaattggtg    720

tgctgtttca ttttcatttg ctgatgatcg tccgagtagt taattcttac taatatttag    780

ataatttggc atacaagcga atcacgtaga acatgatact tttgaatgaa tttatcaaag    840

ttttatcact tggtgagttg tttcatggtt ttcctactga tgtctcttct tcagatttct    900

cgaggcggag ccaccggcag ataccccacc gggagcactg ccgcgccgtg tagaggccct    960

gctcggacgt cgaccccgtc ccgatggaca gcaccaggaa cctgcggcag ttcgacggct   1020

tcactgggta cagctcctcg gccttgtcct tgctggcaag catctttttg gtgatctgcg   1080

tcatcgcaa                                                           1089


<210> SEQ ID NO 61
<211> LENGTH: 915
<212> TYPE: DNA
<213> ORGANISM: Artificial Sequence
<220> FEATURE:
<223> OTHER INFORMATION: Synthetic

<400> SEQUENCE: 61

gaacaggctt gcggccgccg tgtccgcgct gaggaagcca aagtacaacg gcaagtgcat     60

gcgcagcctg attaggagca tcctcggcga gacgaggggt cgactcggga gcatgccctt    120

tgtgcttatg cctccgttct gccttctgac gaatttggta ctggaagcag atgagttttg    180

gttcactatc attctgaatt tacacctgcg cttgctgtca gactaggcaa ccaagtgact    240

tttgtgactt tgatcatgtt cagtgtgttt ccaagtccta atcaatcaaa aagaaaaaca    300

gtttgttaac gattgtttgc catgtctata taataaagtt gcttttatag tagcttagaa    360

ttcaatcggc caactttatc tcgtacgctg acagtaaagg tacatttaaa aggtgacaat    420

ggatagtcta atacttgaac tgacaataga gacacattac atgtcagttg attaagtttg    480

taacagaaaa ataaacaata ctacataatt gcaaagtttc tttgatgtct ttctttcaag    540
```

```
aaacacaaat atatcaatgc tacagtattg ctgatgaatt tatccatgtt gagatgtttt    600

tctggtttct gatctgatca gtctcaattg gtgtgctgtt tcattttcat ttgctgatga    660

tcgtccgagt agttaattct tactaatatt tagataattt ggcatacaag cgaatcacgt    720

agaacatgat acttttgaat gaatttatca aagttttatc acttggtgag ttgtttcatg    780

gttttcctac tgatgtctct tcttcagatt tctcgagccc tcgtctcgcc gaggatgctc    840

ctaatcaggc tgcgcatgca cttgccgttg tactttggct tcctcagcgc ggacatggcg    900

gccgcaagcc tgctc                                                      915
```

<210> SEQ ID NO 62
<211> LENGTH: 1452
<212> TYPE: DNA
<213> ORGANISM: Zea mays

<400> SEQUENCE: 62

```
atatatattt ttatgtttta ttaaaataaa gtctacttat ttacaagcat gtgactgaca     60

gtaaagccac ttgtcttaga tatcgtacga cgcacatcta gagcctcttg ggttgatggc    120

agagacgcgg cgcgcgagcc ttgttctcct ctcctcggag agctgcctag cgagcccacc    180

gagggcatcg gcattgcttc cttcgccagt caccggttcg tacctccctg tctccacgtt    240

gaccctggac accctctgtg ccagcatccg ctccccgatc ccgacgagcg tccgcatgtt    300

ctccggcgtc gccgcgtcca cggtggccgc ggcgccacgg agcgagttgt cctggatgcg    360

caggtagtcg ccgtcgctgt ggagcgactg gaacatcgcg gcgacgtgga tgtccaccag    420

gtccgagctg gccgccatga agatgtcgat gatgggggcc atgccgttgt tgcggagcca    480

ccggcagata ccccaccggg agcactgccg cgccgtgtag aggccctgct cggacgtcga    540

ccccgtcccg atggacagca ccaggaacct gcggcagttc gacggcttca ctgggtacag    600

ctcctcggcc ttgtccttgc tggcaagcat ctttttggtg atctgcgtca tcgcaaccat    660

cgtcgggttg ttggccgcca caccgccgtc gatgaggttg tattcgcgct ccttgccgtt    720

ggcgtcttca gtctggaagt agtgcgccgg gaggtaggtc ggcgcggcgg acgtgccaat    780

gcacacgtcc gagagcagag cgttcttcag aggcgtgctc ttggcgtcgt aggtagagaa    840

gatgataggc tgcagcagcc tgatgtcgaa ggcagggatg atgacgttgg tcagcgtctc    900

gcttaccctc gtctcgccga ggatgctcct aatcaggctg cgcatgcact tgccgttgta    960

ctttggcttc ctcagcgcgg acatggcggc cgcaagcctg ctcttctgag gaaagatgcg   1020

cgggcagttc tgcatgtaaa agtggttgat gtccttggca gcgtagagag gccgcttgtc   1080

cttgccgggc gcggtgagca tggcggtgat gagaccgccg gtgctggttc cggcgatgta   1140

gtcgaagtag tccgccagcc tcgcctccgg tccgtccagc tcctgcagcc tggcctccag   1200

gaaggcgagg atggttcccg ggatgagacc ccggacgccg ccgccgtcca ccgtcagcac   1260

cgtcaccctc tgccccagca cgacgggctc gccgaccacg ctcccggcca tcgccttcgt   1320

gctacaggta ttgcatggac gccgcgacga gtagctcgcc attgccgcct tcgacaacac   1380

acccccgaat cgattaatga gctagctata gatactcgtc gagggcacaa taagtgtgat   1440

tagtgatgaa ct                                                        1452
```

<210> SEQ ID NO 63
<211> LENGTH: 1382
<212> TYPE: DNA
<213> ORGANISM: Zea mays

<400> SEQUENCE: 63

```
tcagaatata tatatattta tattttatta aaataaagtc tacttattta caagcatgtg     60
attgacagta aagccacttg tcttagatat cgtagggcgc acatctagag cttctggggt    120
tgatggcaga gacgcggcgc gcgagccttg ttctcctctc ctcggagagc tgcctagcga    180
gcccaccgag ggcatcggca ttgcttcctt ctccggtcac cggttcgtac ctcgctccct    240
gtctccacgt tgaccctgga cacccgctgt gccagcatcc gctccccgat cccgacgagc    300
gtccgcatgt tctccggcgt cgccgcgtcc acggttgccg cggcgccacg gagcgagttg    360
tcctggatgc gtaggtagtc gccgtcgctg tggagcgact ggaacatcgc ggcgacgtgg    420
atgtccacca ggtccgagct ggccgccatg aagatgtcga tgatgggggc catgccgttg    480
ttgcggagcc accggcagat gccccaccgg gagcactgcc gcgccgtgta gaggccctgc    540
tcggacgtcg accccgtccc gatggacagc accaggaacc tgcggcagtt cgacgggttc    600
actgggtaca gctcctcggc cttgtccttg ctggcaagca tctttttggt gatctgcgtc    660
atcgcaacca tcgtcgggtt gttggccgcc acaccgccgt cgatgaggtt gtattcgcgc    720
tccttgccgt tggcgtcttc agtctggaag tagtgcgccg ggaggtaggt cggcgcggcg    780
gacgtgccaa tgcacacgtc cgagagcagc gcgttcttca gaggcgtgct cttggccctc    840
gtctcgccga ggatgctcct aatcaggctg cgcatgcact tgccgttgta ctttggcttc    900
ctcagcgcgg acatggcggc cgcaagcctg ctcttctgag ggaagatgcg cgggcagttc    960
tccatgtaaa agtagttgat gtccttggca gcgtagagag gccgcttgtc cttgccgggc   1020
gcggtgagca tggcggtgat gagaccgccg gtgctggttc cggcgatgta gtcgaagtag   1080
tccgccagcc tcgcctccgg tccgtccagc tcctgcagcc tggcctccag gaaggcgagg   1140
atggttcccg ggatgagacc ccggacgccg ccgccgtcca ccgtcagcac cgtcaccctc   1200
tgccccagca cgacgggctc gccgaccacg ctcccggcca tcgccttcgt gctacaggta   1260
ttgcatggac gccgcgacga gtagctcgcc attgccgcct tcgaccgcac accccgattg   1320
atcgattaat gagctagcta gatactcgtc gagggcacaa taagtgtgat tagtgatgaa   1380
ct                                                                  1382
```

<210> SEQ ID NO 64
<211> LENGTH: 19
<212> TYPE: DNA
<213> ORGANISM: Zea mays

<400> SEQUENCE: 64

```
tacgccgtgc gctaacata                                                  19
```

<210> SEQ ID NO 65
<211> LENGTH: 20
<212> TYPE: DNA
<213> ORGANISM: Zea mays

<400> SEQUENCE: 65

```
gtacctcgct ccctgtctcc                                                 20
```

<210> SEQ ID NO 66
<211> LENGTH: 18
<212> TYPE: DNA
<213> ORGANISM: Zea mays

<400> SEQUENCE: 66

```
gtacgccgtg cgctaaca                                                   18
```

```
<210> SEQ ID NO 67
<211> LENGTH: 20
<212> TYPE: DNA
<213> ORGANISM: Zea mays

<400> SEQUENCE: 67

tcgtacctcc ctgtctccac                                        20
```

HAPLOID INDUCTION COMPOSITIONS AND METHODS FOR USE THEREFOR

STATEMENT OF PRIORITY

This application is a divisional of, and claims the benefit under 35 U.S.C. § 120, of pending U.S. patent application Ser. No. 15/586,649, which is a divisional of U.S. patent application Ser. No. 14/212,504, now U.S. Pat. No. 9,677,082, which claims the benefit, under 35 U.S.C. § 119 (e), of U.S. Provisional Application No. 61/852,428, filed on Mar. 15, 2013. The entire contents of each of these documents is incorporated herein by reference.

STATEMENT REGARDING ELECTRONIC FILING OF A SEQUENCE LISTING

A Sequence Listing in ASCII text format, submitted under 37 C.F.R. § 1.821, entitled 80225_USDIV2_ST25.txt, 287 kilobytes in size, generated on Dec. 12, 2018 and filed via EFS-Web, is provided in lieu of a paper copy. This Sequence Listing is hereby incorporated herein by reference into the specification for its disclosures.

TECHNICAL FIELD

The presently disclosed subject matter relates to the diagnostic detection of haploid induction (HI) or its absence and/or presence in plants which are, or are not haploid inducers. More particularly, the presently disclosed subject matter relates to nucleic acids that can be employed for inducing HI in plants and/or the biological activities which can be modified in order to produce or prevent HI in either a plant that would otherwise exhibit HI or in a plant that would otherwise not exhibit HI. Even more particularly, the presently disclosed subject matter relates to a nucleic acid molecule that encodes a biologically active molecule as well as methods for using the same to regulate HI in plants.

BACKGROUND

Maize breeders have been crossing inbred parent lines, one acting as a male and one as a female to form hybrid seed. The process of developing inbred parent lines which are substantially homozygous usually required a hybrid cross to be selected and self-pollinated (selfed) for numerous generations to become nearly homozygous. This was a time consuming and expensive process. To shorten the time to develop homozygous inbreds in maize, maize breeders have been using a process of using a haploid inducer line to induce haploid seed on a hybrid parent. The chromosomes of the haploid plants are doubled to form double haploid homozygous inbred lines.

A high haploid induction rate allows a higher frequency of haploid seeds to be formed on the parent plant of interest. The parent plants can be pre-screened with genetic markers associated with desired traits or phenotypic observed traits to enrich the genetic potential of the parent plants. When these desired parent plants are pollinated by a haploid inducer that has a higher haploid induction rate, a higher potential of desired doubled haploids can be obtained with the desired genotype and phenotype.

Although the doubled haploid process resulted in faster production of homozygous inbreds, the volume of doubled haploid inbreds that could be produced was limited. The inducer lines had a low frequency of induction of haploids. A number of known haploid-inducing maize lines exist including but not limited to: stock 6, MHI (Moldovian Haploid Inducer), indeterminate gametophyte (ig) mutation, KEMS, RWK, ZEM, ZMS, KMS. The standard inducer lines such as Stock 6 were inducing only 1-3% haploid seeds. Induction of haploids was a rate limiting step in the process of producing doubled haploid lines.

Haploid induction (HI) is a class of plant phenomena characterized by loss of the male inducer chromosomes during embryo development. WO2012/030893 describes a slightly different region of chromosome (1) that is found responsible for haploid induction. The identified markers in the region responsible for haploid induction and increased haploid induction was described as being between 48,249,509-51,199,249 which is associated with a public marker umc1169 that has the physical position of (60/213,661). This region apparently aligns with the Haploid Induction region in Stock 6. Dong et al. (2013) Theor. Appl. Genet. 126: 1713-1720 describe a QTL located in bin 1.04 which explains up to 66% of the genotypic variance for haploid induction rate.

Haploid induction has been observed in numerous plant species, such as sorghum, rice, and other grasses. The HI appears to be a result of rearrangements of, mutations in, and/or recombinations, insertion, or deletions within a region of chromosome 1. Purported HI-lines have been studied and roughly identified. However, experimental evidence demonstrating a causative genetic agent of HI in maize has not been presented. Nor have the markers listed herein that associate with this trait been previously identified.

The presently disclosed subject matter provides isolated cDNA. In some embodiments, the isolated cDNA are selected from the group consisting of: (a) a nucleic acid having at least 90% identity to SEQ ID NO: 33, SEQ ID NO: 37, SEQ ID NO: 52 or SEQ ID NO: 53, optionally wherein the percent identity is calculated over the entire length of SEQ ID NO: 33, SEQ ID NO: 37, SEQ ID NO: 52 or SEQ ID NO: 53; (b) a nucleic acid having at least 95% identity over nucleotides 91-1452 of SEQ ID NO: 33; (c) a nucleic acid that is the reverse complement of either of (a) or (b); and (d) a nucleic acid that encodes a polypeptide comprising an amino acid sequence that is at least 95% identical to SEQ ID NO: 54, or SEQ ID NO: 55, or SEQ ID NO: 56, or SEQ ID NO: 57 optionally wherein the percent identity is calculated over the entire length of SEQ ID NO: 54, or SEQ ID NO: 55, or SEQ ID NO: 56, or SEQ ID NO: 57.

In other embodiments, a synthetic hairpin nucleic acid construct comprising between 15 and 1000 nucleotides from SEQ II) NO. 33, 37, 52 or 53 and the antisense-complement thereof, such that the first and the second polynucleotide sequences hybridize when transcribed into a ribonucleic acid to form the hairpin-like double stranded ribonucleotide molecule. In further embodiments, the synthetic hairpin nucleic acid construct is selected from the group consisting of SEQ ID NO: 60 and SEQ ID NO: 61.

In other embodiments, an expression cassette for RNAi comprises a promoter operably linked to the synthetic hairpin. In further embodiments, the promoter is a constitutive promoter, optionally a maize ubiquitin-1 promoter, a rice actin-1 promoter, a rice ubiquitin-3 promoter, a rice alpha tubulin (tubA1) promoter, a cauliflower mosaic virus (CaMV) 35S promoter, a cestrum yellow leaf curling virus (CmYLCV) CMP promoter, a super MAS promoter, a sorghum ubiquitin-3 promoter, or a sugarcane ubiquitin-4 promoter. In other embodiments, the promoter is a stamen-, anther-, and/or pollen-specific promoter, optionally selected from the group consisting of SEQ ID NO: 58, a *Triticum*

*aestivum* P19 promoter, a maize B200 promoter, a maize prCDPK-01 promoter, a maize prCDPK-02 promter, a rice alpha-N-acetylglucosaminidase (prOsANG) promoter, a rice MADS box gene promoter (optionally a prOsMADS1 promoter, a prOsMADS2 promoter, a prOsMADS6 promoter, a prOsMADS14 promoter, or a prOsMADS16 promoter), a rice anther specific-promoter (optionally a prRA8 promoter or a prOsG6 promoter). In other embodiments, the expression vector may optionally comprise a terminator. In further embodiments, the terminator may be SEQ ID NO: 59. In some embodiments consist of a plant comprising hairpin nucleic acid construct of the previous embodiments. This plant could be a monocot such as a maize plant.

Some embodiments consist of a method of creating a new haploid inducer plant with a silenced patatin-like phospholipase 2A, comprising transcribing a polynucleotide sequence capable of silencing the patatin-like phospholipase 2A, wherein said polynucleotide sequence is selected from the group consisting of: a polynucleotide sequence comprising the nucleic acid sequence set forth in SEQ ID NOs 33, 37, 52, 53 or the complement thereof, a functional fragment comprising at least 15 contiguous bases of any one of SEQ ID NOs 33, 37, 52, 53 or the complement thereof, a polynucleotide sequence having at least 95% sequence identity as determined using the BLASTN alignment tool to the nucleic acid sequence set forth in any one of SEQ ID NOs 33, 37, 52, 53 or the complement thereof, and a double-stranded ribonucleotide sequence produced from the expression of a polynucleotide sequence of any one of the above polynucleotide sequences, wherein silencing of the patatin-like phospholipase 2A creates a new haploid inducer plant.

Other embodiments are a plant made by the above method. The plant may be a maize plant or other monocot. Other embodiments are a method of inducing haploid embryos by using the pollen of the plant made by the above method to fertilize another plant, wherein the fertilization induces haploid embryos. Other embodiments are a method of identifying a maize plant that comprises a genotype associated with an increased haploid induction phenotype, comprising: isolating DNA from a maize plant, providing a reaction mixture comprising the DNA from a maize plant, the pair of primers comprising SEQ ID NO: 64 and SEQ ID NO 65 wherein the first primer is complementary to a sequence on the first strand of the target DNA and the second primer is complementary to a sequence on the second strand of the target DNA, Taq polymerase, and a plurality of free nucleotides comprising adenine, thymine, cytosine and guanine; heating the reaction mixture to a first predetermined temperature for a first predetermined time to separate the strands of the target DNA from each other; cooling the reaction mixture to a second predetermined temperature for a second predetermined time under conditions to allow the first and second primers to hybridize with their complementary sequences on the first and second strands of the target DNA, and to allow the Taq polymerase to extend the primers; and repeating steps (b) and (c) at least 20 times, wherein an amplification product of about 822 nucleotides indicates a maize plant that comprises a genotype associated with an increased haploid induction phenotype.

Some embodiments consist of an expression cassette for expression of a fertility restoring polypeptide in a plant, the expression cassette comprising an isolated nucleic acid of SEQ ID NO. 33 or 52 operably linked to a promoter that regulates transcription of the isolated nucleic acid of SEQ ID NO. 33 or 52 in a plant cell and/or tissue of interest, wherein the isolated cDNA of claim 1 encodes an amino acid sequence that is at least 95% identical to SEQ ID NO: 54 or 55, optionally wherein the percent identity is calculated over the entire length of SEQ ID NO: 54 or 55.

Other embodiments consist of a kit for detecting the presence of absence of a HI-inducing allele in a plant, the kit comprising one or more nucleic acid- and/or amino acid-based reagents derived from the maize HI locus or from a locus linked thereto wherein the one or more nucleic acid- and/or amino acid-based reagents are designed to be employed in a nucleic acid- and/or amino acid-based assay for the presence or absence in the plant of: a nucleic acid having at least 90% identity to SEQ ID NO: 33, SEQ ID NO: 37, SEQ ID NO: 52 or SEQ ID NO: 53, optionally wherein the percent identity is calculated over the entire length of SEQ ID NO: 33; a nucleic acid having at least 95% identity over nucleotides 91-1452 of SEQ ID NO: 33; a nucleic acid that is the reverse complement of either of (a) or (b); and/or a nucleic acid that encodes a polypeptide comprising an amino acid sequence that is at least 95% identical to SEQ ID NO: 54, SEQ ID NO: 55, SEQ ID NO: 56 or SEQ ID NO: 57 optionally wherein the percent identity is calculated over the entire length of SEQ ID NO: 54, SEQ ID NO: 55, SEQ ID NO: 56 or SEQ ID NO: 57, or nucleic acid comprising nucleotides 1230-1233 of SEQ ID NO: 53.

In some embodiments, the isolated nucleic acids are selected from the group consisting of: a sequence having at least 90% identity to the listed SEQ ID NOs which comprise at least one sequence evidencing an association with a haploid inducing trait by its presence or absence selected from the group consisting of genes identified as GRMZM2G305400, GRMZM2G082836, GRMZM2G382717, GRMZM2G120587, GRMZM2G471240, GRMZM2G866758, and GRMZM2G003530.

The presently disclosed subject matter also provides expression cassettes for expression of the gene products made by the gene which is absent in HI plants. In some embodiments, an expression cassette of the presently disclosed subject matter comprises a nucleic acid sequence as described herein as a synthetic hairpin nucleic acid construct comprising between 15 and 1000 nucleotides from SEQ ID NO: 33, SEQ ID NO: 37, SEQ ID NO: 52 or SEQ ID NO: 53 (such as, but not limited to SEQ ID NO: 60 or 61) operably linked to a promoter that regulates transcription of the isolated nucleic acid in a plant cell and/or tissue of interest, and/or an organelle or subcellular structure thereof. In some embodiments, the isolated nucleic acid present in the expression cassette encodes an amino acid sequence that is at least 95% identical to SEQ ID NO: 54, SEQ ID NO: 55, SEQ ID NO: 56 or SEQ ID NO: 57, optionally wherein the percent identity is calculated over the entire length of SEQ ID NO: 54, SEQ ID NO: 55, SEQ ID NO: 56 or SEQ ID NO: 57. In some embodiments, the promoter is a native promoters associated with the genes within this haploid induction region (such as, but not limited to SEQ ID NO: 58). In some embodiments, constitutive promoter, which can optionally be selected from the group consisting of the native promoter, a constitutive promoter such as ZmUbi1, ZmUbi158, ZmUbi361, SbUbiCh3, SbUbiCh4, a maize ubiquitin-1 promoter, a rice actin-1 promoter, a rice ubiquitin-3 promoter, a cauliflower mosaic virus (CaMV) 35S promoter, a sorghum ubiquitin-3 promoter, or a sugarcane ubiquitin-4 promoter, or a promoter that is pollen specific. Examples of pollen promoters are shown in the art in pollen-specific expression cassettes. Pollen-specific genes have been described for maize (Lopez I, Anthony, R. G., Maciver, S. K., Jaing, C.-J., Khan, S., Weeds, A. G., Hussey, P. J. (1996). Pollen specific expression of maize genes encoding actin depolymerizing factor-like proteins. Proc Natl Acad Sci USA 93:7415-7420.) Such information can be used to identify other maize pollen-specific genes, and promoters and produce pollen-specific expression cassettes. In some embodiments, the expression cassette further comprises a transcription terminator operably linked to the promoter and/or coding sequence. Some embodiments are a promoter for anther, stamen or pollen specific expression comprising SEQ ID NO:58.

In some embodiments, the plant cell and/or tissue of interest is selected from the group consisting of a stamen cell, a microspore, a meiotic cell, a cell that differentiates into a stamen cell or a progeny cell thereof, an anther cell, a cell that differentiates into an anther cell or a progeny cell thereof. In some embodiments, the organelle or subcellular structure of the plant cell and/or tissue of interest is a microspore. Thus, in some embodiments, the promoter is a stamen-, anther-, and/or pollen-specific promoter, which in some embodiments is selected from the group consisting of a *Triticum aestivum* P19 promoter, a maize B200 promoter, a maize prCDPK-01 and prCDPK-02 promoter, a rice α-N-acetylglucosaminidase (prOsANG) promoter, a rice MADS box gene promoter (including, but not limited to a prOsMADS1 promoter, a prOsMADS2 promoter, a prOsMADS6 promoter, prOsMADS7 promoter a prOsMADS14 promoter, or a prOsMADS16 promoter), a rice anther-specific promoter (such as, but not limited to a prRA8 promoter or a prOsG6 promoter), a rice stamen-specific promoter (such as, but not limited to the promoters disclosed in U.S. Pat. No. 5,639,948); and a corn stamen-specific promoter (such as, but not limited to the promoters disclosed in U.S. Pat. No. 5,589,610). In some embodiments, the promoter is a promoter that is transcriptionally active in a plant mitochondrion. Exemplary such promoters include, but are not limited to those disclosed in Fey & Maréchal-Drouard, 1999 and Binder et al., 1996.

In some embodiments, the expression cassette further comprises a transcription terminator, optionally a Nos or ags terminator.

In some embodiments, the expression cassette further comprises a targeting peptide (TP) coding sequence that is operably linked to and in frame with a sequence that encodes an amino acid sequence that is at least 95% identical to SEQ ID NO: 54, SEQ ID NO: 55, SEQ ID NO: 56 or SEQ ID NO: 57.

The presently disclosed subject matter also provides vectors comprising an expression cassette as disclosed herein.

The presently disclosed subject matter also provides transgenic plant cells comprising the presently disclosed expression cassettes, as well as plants, plant parts, and seeds comprising or derived from the presently disclosed transgenic plant cells.

The presently disclosed subject matter also provides isolated polypeptides comprising amino acid sequences that are at least 95% identical to SEQ ID NO: 54, SEQ ID NO: 55, SEQ ID NO: 56 or SEQ ID NO: 57. In some embodiments, wherein the percent identity is calculated over the entire length of SEQ ID NO: 54, SEQ ID NO: 55, SEQ ID NO: 56 or SEQ ID NO: 57. In some embodiments, the isolated polypeptides comprise amino acid sequences that comprise all or substantially all of amino acids 1-429 of SEQ ID NO: 54 locus.

The presently disclosed subject matter also provides subsequences, amplicons, and informative fragments of SEQ ID NO: 33, SEQ ID NO: 37, SEQ ID NO: 52 or SEQ ID NO: 53, as well as allelic variations thereof, wherein the subsequences, amplicons, informative fragments, and/or allelic variations can be used to identify the presence or absence of an allele associated with HI in a plant, or plant tissue, or plant cell.

The presently disclosed subject matter also provides compositions comprising amplification primer pairs capable of amplifying plant nucleic acid templates to generate marker amplicons, wherein the marker amplicons correspond to markers comprising informative subsequences of any of SEQ ID NO: 33, SEQ ID NO: 37, SEQ ID NO: 52 or SEQ ID NO: 53, or of the listed SEQ ID NOs. from this 0.6 MB region which comprise at least one sequence evidencing an association with a haploid inducing trait in this by its presence or absence selected from the group consisting of genes identified as GRMZM2G305400, GRMZM2G082836, GRMZM2G382717, GRMZM2G120587, GRMZM2G471240 (two), GRMZM2G003530, and GRMZM2G866758 (two) wherein the informative subsequences permit identification of the presence or absence of an allele associated with HI in plants. In some embodiments, the amplification primers are designed to amplify a subsequence of SEQ ID NO: 33, SEQ ID NO: 37, SEQ ID NO: 52 or SEQ ID NO: 53 (exemplary primers, but not limited to SEQ ID NO: 64, SEQ ID NO: 65, SEQ ID NO: 66 or SEQ ID NO: 67). The presently disclosed subject matter also provides methods for producing plants that exhibit a new or increased HI trait. In some embodiments, the methods comprise (a) transforming a plant cell with an expression cassette comprising a nucleic acid as disclosed herein to produce a transformed plant cell; and (b) generating a plant from the transformed plant cell.

The presently disclosed subject matter also provides methods for identifying the presence or absence of allele associated with HI in plants. In some embodiments, the methods comprise (a) obtaining a sample from the plant comprising genomic and/or nuclear DNA and/or an RNA product derived therefrom; (b) contacting the sample with a pair of primers that, when used in a nucleic acid amplification reaction with a nucleic acid sample from the plant, produces an amplicon that can be used to identify the presence or absence of an allele associated with HI; (c) amplifying a fragment from said sample using the primer pair of (b), wherein the primer pair is complementary and binds to the nucleotide sequence of (b); and (d) detecting an amplicon that can be used to identify the presence or absence of an allele associated with HI in the plant.

The presently disclosed subject matter also provides methods for introgressing HI-inducing nucleotide sequences or haplotypes into plants. In some embodiments, the methods comprise crossing a first plant with a second plant to produce a third plant, wherein the genome of the first plant or the second plant comprises a nucleic acid sequence (in some embodiments a recombinant nucleic acid sequence) encoding a HI-associated gene product of the presently disclosed subject matter and selecting those plants that do not exhibit production of the gene product, or a gene product at substantially reduced levels. In some embodiments, the methods further comprise assaying the genome of the third plant for the presence or absence of the nucleic acid sequence (in some embodiments, the recombinant nucleic acid sequence) encoding the HI-associated gene product. A HI-associated gene product, can be a negative or positive association. In this instance the association is a negative association, i.e. the presence of the gene product is associated with the absence of the haploid induction trait. In some embodiments, the recombinant nucleic acid comprises SEQ ID NO: 33, SEQ ID NO: 37, SEQ ID NO: 52 or SEQ ID NO: 53, and/or encodes a polypeptide that is at least 95% identical to SEQ ID NO: 54, SEQ ID NO: 55, SEQ ID NO: 56 or SEQ ID NO: 57. In some embodiments, the genome of the third plant that is assayed is the third plant's genome.

The presently disclosed subject matter also provides methods for selecting $F_0$ parental plants predicted to produce haploid inducing plants that exhibit inducible HI traits. In some embodiments, the methods comprise identifying in the genome of an $F_0$ plant the present or absence of a nucleic acid comprising a nucleotide sequence selected from the group consisting of: (a) a nucleic acid having at least 90% identity to SEQ ID NO: 33, SEQ ID NO: 37, SEQ ID NO: 52 or SEQ ID NO: 53, optionally wherein the percent identity is calculated over the entire length of SEQ ID NO: 33, SEQ ID NO: 37, SEQ ID NO: 52 or SEQ ID NO: 53; (b) a nucleic acid having at least 95% identity over nucleotides 1-1452 of SEQ ID NO: 33; (c) a nucleic acid that is the reverse complement of either of (a) or (b); and (d) a nucleic acid that encodes a polypeptide comprising an amino acid sequence that is at least 95% identical to SEQ ID NO: 54, SEQ ID NO: 55, SEQ ID NO: 56 or SEQ ID NO: 57, optionally wherein the percent identity is calculated over the entire length of SEQ ID NO: 54, SEQ ID NO: 55, SEQ ID NO: 56 or SEQ ID NO: 57.

In some embodiments, the methods comprise identifying in the genome of an $F_0$ plant the present or absence of a nucleic acid comprising a nucleotide sequence selected from the group consisting of the listed SEQ ID NOs. 3, 9-46 from this 0.6 MB region which comprise at least one sequence evidencing an association with a haploid inducing trait in this by its presence or absence selected from the group consisting of genes identified as GRMZM2G305400, GRMZM2G082836, GRMZM2G382717, GRMZM2G120587, GRMZM2G471240 (two), and GRMZM2G866758 (two) wherein the nucleic acid has at least 90% identity to the selected SEQ ID NO. optionally wherein the percent identity is calculated over the entire length of the selected SEQ ID NO.

Thus, it is an object of the presently disclosed subject matter to identify and/or introgress and/or provide nucleic acids for inducing and/or inhibiting the HI trait in a plant.

BRIEF DESCRIPTION OF THE SEQUENCE LISTING

SEQ ID NO: 1 is a cDNA nucleotide sequence from the maize NIL-genome of SEQ ID NO:3

SEQ ID NO: 2 is an amino acid sequence of a polypeptide encoded by SEQ ID NO: 1 which is a cDNA from the NIL-genome designated GRMZM2G062320-B SEQ ID NO: 3 is the NIL-genome genomic nucleotide sequence SEQ ID NO: 4 is the sequence of ZmABP2-GRMZM2G062320.

SEQ ID NOs: 5-8 are amino acid sequences for maize GRMZM2G062320-A, GRMZM2G062320-C, GRMZM2G062320-D, GRMZM2G062320-E SEQ ID NO: 9 GRMZM2G305400 gDNA (from B73 genome)

SEQ ID NO: 10 GRMZM2G305400 cDNA (from B73 genome)

SEQ ID NO: 11 GRMZM2G082836 gDNA (from the B73 genome)

SEQ ID NO: 12 GRMZM2G082836 cDNA1 (from the B73 genome)

SEQ ID NO: 13 GRMZM2G082836 cDNA2 (from the B73 genome)

SEQ ID NO: 14 GRMZM2G082836 cDNA3 (from the B73 genome)

SEQ ID NO: 15 GRMZM2G082836 gDNA (from the NIL genome)

SEQ ID NO: 16 GRMZM2G082836 gDNA (from the Stock 6 genome)

SEQ ID NO: 17 GRMZM2G082836 gDNA (from the RWK genome)

SEQ ID NO: 18 GRMZM2G382717 gDNA (from B73 genome)

SEQ ID NO: 19 GRMZM2G382717 cDNA2 (from B73 genome)

SEQ ID NO: 20 GRMZM2G382717 gDNA (from NIL genome)

SEQ ID NO: 21 GRMZM2G382717 gDNA (from RWK genome)

SEQ ID NO: 22 GRMZM2G382717 gDNA (991832 from Stock 6 genome)

SEQ ID NO: 23 GRMZM2G382717 gDNA (989131 from Stock 6 genome)

SEQ ID NO: 24 GRMZM2G382717 protein coding sequence (from RWK genome)

SEQ ID NO: 25 GRMZM2G120587 gDNA (from the B73 genome)

SEQ ID NO: 26 GRMZM2G120587 cDNA1 (from the B73 genome)

SEQ ID NO: 27 GRMZM2G120587 cDNA2 (from the B73 genome)

SEQ ID NO: 28 GRMZM2G120587 cDNA3 (from the B73 genome)

SEQ ID NO: 29 GRMZM2G120587 GDNA (from the Stock 6 genome)

SEQ ID NO: 30 GRMZM2G120587 GDNA (from the RWK genome)

SEQ ID NO: 31 GRMZM2G120587 GDNA (from the Stock 6/RWK genome)

SEQ ID NO: 32 GRMZM2G471240 gDNA (from the B73 genome)

SEQ ID NO: 33 GRMZM2G471240 cDNA long splice variant (from the B73 genome)

SEQ ID NO: 34 GRMZM2G471240 gDNA (from the NIL genome)

SEQ ID NO: 35 GRMZM2G471240 gDNA (from the maize Stock 6 genome)

SEQ ID NO: 36 GRMZM2G471240 gDNA (from the maize RWK genome)

SEQ ID NO: 37 GRMZM2G471240 cDNA short splice variant (from the Stock6/RWK genome)

SEQ ID NO: 38 GRMZM5G866758 gDNA (from the B73 genome)

SEQ ID NO: 39 GRMZM5G866758 cDNA1 (from the B73 genome)

SEQ ID NO: 40 GRMZM5G866758 cDNA2 (from the B73 genome)

SEQ ID NO: 41 GRMZM5G866758 cDNA-1780 (from the B73 maize genome)

SEQ ID NO: 42 GRMZM5G866758 gDNA (from the NIL maize genome)

SEQ ID NO: 43 GRMZM5G866758 cDNA (from the NIL genome)

SEQ ID NO: 44 GRMZM5G866758 gDNA (from the Stock 6 genome)

SEQ ID NO: 45 GRMZM5G866758 gDNA (from the RWK genome)

SEQ ID NO: 46 GRMZM5G866758 gDNA (from the Stock 6/RWK genome)

SEQ ID NO: 47 GRMZM2G382717 cDNA1 (from B73 genome).

SEQ ID NO: 48 GRMZM2G003530 gDNA (from B73 genome).

SEQ ID NO: 49 GRMZM2G003530 gDNA (from NIL genome).

SEQ ID NO: 50 GRMZM2G003530 gDNA (from RWK genome).

SEQ ID NO: 51 GRMZM2G003530 gDNA (from Stock 6 genome).

SEQ ID NO: 52 GRMZM2G471240 cDNA short splice variant (from the B73 genome)

SEQ ID NO: 53 GRMZM2G471240 cDNA long splice variant (from the RWK genome)

SEQ ID NO: 54 is an amino acid sequence of a polypeptide encoded by SEQ ID NO: 33

SEQ ID NO: 55 is an amino acid sequence of a polypeptide encoded by SEQ ID NO: 52

SEQ ID NO: 56 is an amino acid sequence of a polypeptide encoded by SEQ ID NO: 37

SEQ ID NO: 57 is an amino acid sequence of a polypeptide encoded by SEQ ID NO: 53

SEQ ID NO: 58 is the promoter of the GRMZM2G471240 gene

SEQ ID NO: 59 is the terminator of the GRMZM2G471240 gene

SEQ ID NO: 60 is a synthetic hairpin designed to SEQ ID NO 33 nt 450-547 with 2 mismatches, a spacer sequence and the reverse compliment of SEQ ID NO 33 nt 450-547

SEQ ID NO: 61 is a synthetic hairpin designed to SEQ ID NO 33 nt 797-987 with 2 mismatches, a spacer sequence and the reverse compliment of SEQ ID NO 33 nt 797-987

SEQ ID NO: 62 is the reverse compliment of SEQ ID NO 33

SEQ ID NO: 63 is the reverse compliment of SEQ ID NO 52

SEQ ID NO: 64 is primer rwk.F1

SEQ ID NO: 65 is primer rwk.R1

SEQ ID NO: 66 is primer nil.F1

SEQ ID NO: 67 is primer nil.R1

DETAILED DESCRIPTION

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques and/or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. For example, the phrase "a cell" refers to one or more cells, and in some embodiments can refer to a tissue and/or an organ. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to all whole number values between 1 and 100 as well as whole numbers greater than 100.

Unless otherwise indicated, all numbers expressing quantities of ingredients, reaction conditions, and so forth used in the specification and claims are to be understood as being modified in all instances by the term "about". The term "about", as used herein when referring to a measurable value such as an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods and/or employ the discloses compositions, nucleic acids, polypeptides, etc. Accordingly, unless indicated to the contrary, the numerical parameters set forth in this specification and attached claims are approximations that can vary depending upon the desired properties sought to be obtained by the presently disclosed subject matter.

As used herein, the term "allele" refers to a variant or an alternative sequence form at a genetic locus. In diploids, a single allele is inherited by a progeny individual separately from each parent at each locus. The two alleles of a given locus present in a diploid organism occupy corresponding places on a pair of homologous chromosomes, although one of ordinary skill in the art understands that the alleles in any particular individual do not necessarily represent all of the alleles that are present in the species.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D (e.g., AB, AC, AD, BC, BD, CD, ABC, ABD, and BCD). In some embodiments, one of more of the elements to which the "and/or" refers can also individually be present in single or multiple occurrences in the combinations(s) and/or subcombination(s).

As used herein, the phrase "associated with" refers to a recognizable and/or assayable relationship between two entities. For example, the phrase "associated with HI" refers to a trait, locus, gene, allele, marker, phenotype, etc., or the expression thereof, the presence or absence of which can influence an extent and/or degree at which a plant or its progeny exhibits HI. As such, a marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with HI" refers to a marker whose presence or absence can be used to predict whether and/or to what extent a plant will display haploid induction.

The term "comprising", which is synonymous with "including", "containing", and "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, or ingredient not specifically recited. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter.

With respect to the terms "comprising", "consisting essentially of", and "consisting of", where one of these three terms is used herein, the presently disclosed and claimed subject matter can include in some embodiments the use of either of the other two terms. For example, if a subject matter relates in some embodiments to nucleic acids that encode polypeptides comprising amino acid sequences that are at least 95% identical to a SEQ ID NO: 55. It is understood that the disclosed subject matter thus also encompasses nucleic acids that encode polypeptides that in some embodiments consist essentially of amino acid sequences that are at least 95% identical to that SEQ ID NO: 55 as well as nucleic acids that encode polypeptides that in some embodiments consist of amino acid sequences that are at least 95% identical to that SEQ ID NO: 55. Similarly, it is also understood that in some embodiments the methods for the disclosed subject matter comprise the steps that are disclosed herein, in some embodiments the methods for the presently disclosed subject matter consist essentially of the steps that are disclosed, and in some embodiments the methods for the presently disclosed subject matter consist of the steps that are disclosed herein.

As used herein, the term "gene" refers to a hereditary unit including a sequence of DNA that occupies a specific location on a chromosome and that contains the genetic instruction for a particular characteristic or trait in an organism.

A "genetic map" is a description of genetic linkage relationships among loci on one or more chromosomes within a given species, generally depicted in a diagrammatic or tabular form. For each genetic map, distances between loci are measured by the recombination frequencies between them. Recombination events between loci can be detected using a variety of markers. A genetic map is a product of the mapping population, types of markers used, and the polymorphic potential of each marker between different populations. The order and genetic distances between loci can differ from one genetic map to another.

As used herein, the phrase "genetic marker" refers to a nucleic acid sequence (e.g., a polymorphic nucleic acid sequence) that has been identified as associated with a locus or allele of interest and that is indicative of the presence or absence of the locus or allele of interest in a cell or organism. Examples of genetic markers include, but are not limited to genes, DNA or RNA-derived sequences, promoters, any untranslated regions of a gene, microRNAs, siRNAs, QTLs, SNPs, transgenes, mRNAs, ds RNAs, transcriptional profiles, and methylation patterns.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) and/or haplotype(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome (in some embodiments, including the nuclear genome, the mitochondrial genome, plastid genome or all three). Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety, or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants can be grown, as well as plant parts, such as leafs, stems, pollen, or cells that can be cultured into a whole plant.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the terms "informative fragment" and "informative subsequence" refer to nucleotide sequences comprising a fragment of a larger nucleotide sequence, wherein detecting of the presence of absence of the fragment allows for the detecting of the presence of absence of the larger nucleotide sequence. For example, an informative fragment of the nucleotide sequence of SEQ ID NO: 33 comprises a fragment of the nucleotide sequence of SEQ ID NO: 33 that permits the accurate identification of whether or not SEQ ID NO: 33 is present in a sample. This non HI locus lacks the 4 nucleotide insertion that is present in the HI germplasm as found in SEQ ID NO: 53 nucleotides 1230-1233. In some embodiments, an informative fragment of SEQ ID NO: 53 allows identification of the presence or absence of the HI locus. In some embodiments, informative fragments of SEQ ID NO: 53 containing nucleotides 1230-1233 allow identification of the presence or absence of the HI locus.

As used herein, the term "isolated" refers to a nucleotide sequence that is free of sequences that normally flank one or both sides of the nucleotide sequence in a plant genome. Thus, isolated nucleic acids include, without limitation, a recombinant DNA that exists as a separate molecule with no flanking sequences present, as well as a recombinant DNA that is incorporated into a vector, an autonomously replicating plasmid, or into the genomic DNA of a plant as part of a hybrid or fusion nucleic acid molecule.

As used herein, the term "linkage" refers to a phenomenon wherein alleles on the same chromosome tend to be transmitted together more often than expected by chance if their transmission were independent. Thus, two alleles on the same chromosome are said to be "linked" when they segregate from each other in the next generation in some embodiments less than 50% of the time, in some embodiments less than 25% of the time, in some embodiments less than 20% of the time, in some embodiments less than 15% of the time, in some embodiments less than 10% of the time, in some embodiments less than 9% of the time, in some embodiments less than 8% of the time, in some embodiments less than 7% of the time, in some embodiments less than 6% of the time, in some embodiments less than 5% of the time, in some embodiments less than 4% of the time, in some embodiments less than 3% of the time, in some embodiments less than 2% of the time, and in some embodiments less than 1% of the time.

As such, "linkage" typically implies and can also refer to physical proximity on a chromosome. Thus, two loci are linked if they are within in some embodiments 20 centiMorgans (cM), in some embodiments 15 cM, in some embodiments 12 cM, in some embodiments 10 cM, in some embodiments 9 cM, in some embodiments 8 cM, in some embodiments 7 cM, in some embodiments 6 cM, in some embodiments 5 cM, in some embodiments 4 cM, in some embodiments 3 cM, in some embodiments 2 cM, and in some embodiments 1 cM of each other. Similarly, a HI locus of the presently disclosed subject matter is linked to a marker (e.g., a genetic marker) if it is in some embodiments within 20, 15, 12, 10, 9, 8, 7, 6, 5, 4, 3, 2, or 1 cM of the marker.

Thus, the term "linkage" refers to the degree with which one marker locus is associated with another marker locus or some other locus (for example, a locus associated with HI). The linkage relationship between a molecular marker and a phenotype can be given as a "probability" or "adjusted probability." Linkage can be expressed as a desired limit or range. For example, in some embodiments, any marker is linked (genetically and physically) to any other marker when the markers are separated by less than about 50, 40, 30, 25, 20, or 15 map units (or cM).

As used herein, the term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and, by definition, are separated by less than 50 cM on the same chromosome). As used herein, linkage can be between two markers, or alternatively between a marker and a phenotype. A marker locus can be "associated with" (linked to) a trait, e.g., HI. The degree of linkage of a molecular marker to a phenotypic trait is measured, e.g., as a statistical probability of co-segregation of that molecular marker with the phenotype. As used herein, the term "linkage equilibrium" describes a situation where two markers independently segregate, i.e., sort among progeny randomly. Markers that show linkage equilibrium are considered unlinked (whether or not they lie on the same chromosome). As such, the phrase "linkage disequilibrium" is defined as change from the expected relative frequency of gamete types in a population of many individuals in a single generation such that two or more loci act as genetically linked loci. If the frequency in a population of allele S is x, s is x', B is y, and b is y', then the expected frequency of genotype SB is xy, that of Sb is xy', that of sB is x'y, and that of sb is x'y', and any deviation from these frequencies is an example of disequilibrium. Linkage disequilibrium is most commonly assessed using the measure r2, which is calculated using the formula described by Hill & Robertson, 1968. When r2=1, complete linkage disequilibrium exists between the two marker loci, meaning that the markers have not been separated by recombination and have the same allele frequency. In some embodiments, values for r2 above 0.33 indicate sufficiently strong linkage disequilibrium to be useful for mapping. See Ardlie et al., 2002. Hence, alleles are in linkage disequilibrium when r2 values between pairwise marker loci are greater than or equal to about 0.33, 0.4, 0.5, 0.6, 0.7, 0.8, 0.9, or 1.0.

As used herein, the terms "marker", "genetic marker", and 'molecular marker" are used interchangeably to refer to an identifiable position on a DNA molecule (e.g., a chromosome or a nuclear genome) the inheritance of which can be monitored and/or a reagent that is used in methods for visualizing differences in nucleic acid sequences present at such identifiable positions on a DNA molecule. Thus, in some embodiments a marker comprises a known or detectable nucleic acid sequence. As such, a marker can comprise a nucleotide sequence that has been associated with an allele or alleles of interest and that is indicative of the presence or absence of the allele or alleles of interest in a cell or organism and/or to a reagent that is used to visualize differences in the nucleotide sequence at such an identifiable position or positions. A marker can be, but is not limited to, an allele, a gene, a haplotype, a restriction fragment length polymorphism (RFLP), a simple sequence repeat (SSR), random amplified polymorphic DNA (RAPD), cleaved amplified polymorphic sequences (CAPS; Rafalski & Tingey, 1993), an amplified fragment length polymorphism (AFLP; Vos et al., 1995), a single nucleotide polymorphism (SNP) (Brookes, 1993), a sequence-characterized amplified region (SCAR; Paran & Michelmore, 1993), a sequence-tagged site (STS; Onozaki et al., 2004), a single-stranded conformation polymorphism (SSCP; Orita et al., 1989), an inter-simple sequence repeat (ISSR; Blair et al., 1999), an inter-retrotransposon amplified polymorphism (IRAP), a retrotransposon-microsatellite amplified polymorphism (REMAP; Kalendar et al., 1999) or an RNA cleavage product (such as a Lynx tag). A marker can be present in genomic (including but not limited to nuclear genomic and/or 1 genomic) or expressed nucleic acids (e.g., ESTs). In some embodiments, a marker is an informative fragment of SEQ ID NO: 33, SEQ ID NO: 37, SEQ ID NO: 52 or SEQ ID NO: 53 that permits the specific identification of nucleic acids comprising or lacking SEQ ID NO: 33, SEQ ID NO: 37, SEQ ID NO: 52 or SEQ ID NO: 53 in samples.

The term marker can also refer to nucleic acids used as probes or primers (e.g., primer pairs) for use in amplifying, hybridizing to, and/or detecting nucleic acid molecules according to methods well known in the art. In some embodiments, a nucleic acid marker that can be employed to detect the presence or absence of SEQ ID NO: 33, SEQ ID NO: 37, SEQ ID NO: 52 or SEQ ID NO: 53 is a primer pair that comprises a forward primer that comprises a subsequence of nucleotides of SEQ ID NO: 33, SEQ ID NO: 37, SEQ ID NO: 52 or SEQ ID NO: 53 and a reverse primer that is the reverse complement of a subsequence of nucleotides of SEQ ID NO: 33, SEQ ID NO: 37, SEQ ID NO: 52 or SEQ ID NO: 53 and/or is an amplicon that is generated by using such a primer pair to amplify a subsequence of SEQ ID NO: 33, SEQ ID NO: 37, SEQ ID NO: 52 or SEQ ID NO: 53 (i.e., the subsequence of SEQ ID NO: 33, SEQ ID NO: 37, SEQ ID NO: 52 or SEQ ID NO: 53 that comprises nucleotides, optionally including 1, 2, 3, 4, 5, 6, 7, 8, 9, 10, or more nucleotides of SEQ ID NO: 33, SEQ ID NO: 37, SEQ ID NO: 52 or SEQ ID NO: 53 that are 5' to and/or 3' to nucleotides selected nucleotides from the positions listed in the Table on Fine Mapping in Example 3 and a part of SEQ ID NO: 1-47).

As used herein, the terms "marker probe" and "probe" refer to a nucleotide sequence or nucleic acid molecule that can be used to detect the presence or absence of sequence within SEQ ID NO: 33, SEQ ID NO: 37, SEQ ID NO: 52 or SEQ ID NO: 53 (e.g., a nucleic acid probe that is complementary to all of or a portion of the marker or marker locus, through nucleic acid hybridization). Marker probes comprising about 8, 10, 15, 20, 30, 40, 50, 60, 70, 80, 90, 100 or more contiguous nucleotides can be used for nucleic acid hybridization.

As used herein, the term "molecular marker" can be used to refer to a genetic marker, as defined above, or an encoded product thereof (e.g., a protein) used as a point of reference when identifying the presence/absence of a HI-associated locus. A molecular marker can be derived from genomic nucleotide sequences or from expressed nucleotide sequences (e.g., from an RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution (e.g., according to Watson-Crick base pairing rules). This term also refers to the genetic markers that indicate a trait by the absence of the nucleotide sequences complementary to or flanking the marker sequences, such as nucleotide sequences used as probes and/or primers capable of amplifying the marker sequence.

As used herein, the terms "nucleotide sequence", "polynucleotide", "nucleic acid sequence", "nucleic acid molecule", and "nucleic acid fragment" refer to a polymer of RNA or DNA that is single- or double-stranded, optionally containing synthetic, non-natural, and/or altered nucleotide bases. A "nucleotide" is a monomeric unit from which DNA or RNA polymers are constructed and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

As used herein, the term "nucleotide sequence identity" refers to the presence of identical nucleotides at corresponding positions of two polynucleotides. Polynucleotides have "identical" sequences if the sequence of nucleotides in the two polynucleotides is the same when aligned for maximum correspondence (e.g., in a comparison window). Sequence comparison between two or more polynucleotides is generally performed by comparing portions of the two sequences over a comparison window to identify and compare local regions of sequence similarity. The comparison window is generally from about 20 to 200 contiguous nucleotides. The "percentage of sequence identity" for polynucleotides, such as about 50, 55, 60, 65, 70, 75, 80, 85, 90, 95, 98, 99 or 100 percent sequence identity, can be determined by comparing two optimally aligned sequences over a comparison window, wherein the portion of the polynucleotide sequence in the comparison window can include additions or deletions (i.e., gaps) as compared to the reference sequence for optimal alignment of the two sequences. In some embodiments, the percentage is calculated by: (a) determining the number of positions at which the identical nucleic acid base occurs in both sequences; (b) dividing the number of matched positions by the total number of positions in the window of comparison; and (c) multiplying the result by 100. Optimal alignment of sequences for comparison can also be conducted by computerized implementations of known algorithms, or by visual inspection. Readily available sequence comparison and multiple sequence alignment algorithms are, respectively, the Basic Local Alignment Search Tool (BLAST) and ClustalW/ClustalW2/Clustal Omega programs available on the Internet (e.g., the website of the EMBL-EBI). Other suitable programs include, but are not limited to, GAP, BestFit, Plot Similarity, and FASTA, which are part of the Accelrys GCG Package available from Accelrys, Inc. of San Diego, Calif., United States of America. See also Smith & Waterman, 1981; Needleman & Wunsch, 1970; Pearson & Lipman, 1988; Ausubel et al., 1988; and Sambrook & Russell, 2001.

One example of an algorithm that is suitable for determining percent sequence identity and sequence similarity is the BLAST algorithm, which is described in Altschul et al., 1990. In some embodiments, a percentage of sequence identity refers to sequence identity over the full length of one of the gDNA, cDNA, or the predicted protein sequences in the largest ORF of SEQ ID No: 33 being compared (e.g., the full length of any of SEQ ID NOs. 1-47 respectively). In some embodiments, a calculation to determine a percentage of nucleic acid sequence identity does not include in the calculation any nucleotide positions in which either of the compared nucleic acids includes an "N" (i.e., where any nucleotide could be present at that position).

The term "open reading frame" (ORF) refers to a nucleic acid sequence that encodes a polypeptide. In some embodiments, an ORF comprises a translation initiation codon, a translation termination (i.e., stop) codon, and the nucleic acid sequence there between that encodes the amino acids present in the polypeptide. The terms "initiation codon" and "termination codon" refer to a unit of three adjacent nucleotides ('codon') in a coding sequence that specifies initiation and chain termination, respectively, of protein synthesis (mRNA translation).

As used herein, the terms "phenotype," "phenotypic trait" or "trait" refer to one or more traits of a plant or plant cell. The phenotype can be observable to the naked eye, or by any other means of evaluation known in the art, e.g., microscopy, biochemical analysis, or an electromechanical assay. In some cases, a phenotype is directly controlled by a single gene or genetic locus (i.e., corresponds to a "single gene trait"). In the case of haploid induction use of color markers, such as R Navajo, and other markers including transgenes visualized by the presences or absences of color within the seed evidence if the seed is an induced haploid seed. The use of R Navajo as a color marker and the use of transgenes is well known in the art as means to detect induction of haploid seed on the female plant. In other cases, a phenotype is the result of interactions among several genes, which in some embodiments also results from an interaction of the plant and/or plant cell with its environment.

As used herein, the term "plant" can refer to a whole plant, any part thereof, or a cell or tissue culture derived from a plant. Thus, the term "plant" can refer to any of: whole plants, plant components or organs (e.g., leaves, stems, roots, etc.), plant tissues, seeds and/or plant cells.

A plant cell is a cell of a plant, taken from a plant, or derived through culture from a cell taken from a plant. Thus, the term "plant cell" includes without limitation cells within seeds, suspension cultures, embryos, meristematic regions, callus tissue, leaves, shoots, gametophytes, sporophytes, pollen, and microspores. The phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like.

As used herein, the term "primer" refers to an oligonucleotide which is capable of annealing to a nucleic acid target (in some embodiments, annealing specifically to a nucleic acid target) allowing a DNA polymerase and/or reverse transcriptase to attach thereto, thereby serving as a point of initiation of DNA synthesis when placed under conditions in which synthesis of a primer extension product is induced (e.g., in the presence of nucleotides and an agent for polymerization such as DNA polymerase and at a suitable temperature and pH). In some embodiments, one or more pluralities of primers are employed to amplify plant nucleic acids (e.g., using the polymerase chain reaction; PCR).

As used herein, the term "probe" refers to a nucleic acid (e.g., a single stranded nucleic acid or a strand of a double stranded or higher order nucleic acid, or a subsequence thereof) that can form a hydrogen-bonded duplex with a complementary sequence in a target nucleic acid sequence. Typically, a probe is of sufficient length to form a stable and sequence-specific duplex molecule with its complement, and as such can be employed in some embodiments to detect a sequence of interest present in a plurality of nucleic acids.

As used herein, the terms "progeny" and "progeny plant" refer to a plant generated from a vegetative or sexual reproduction from one or more parent plants. In haploid induction the seed on the female parent is haploid, thus not a progeny of the inducing haploid line. The progeny of the haploid seed is what is the desired progeny. There is also the HI seed and subsequent plant and seed progeny of the haploid inducing plant. Both the haploid seed and the HI seed can be progeny. A progeny plant can be obtained by cloning or selfing a single parent plant, or by crossing two or more parental plants. For instance, a progeny plant can be obtained by cloning or selfing of a parent plant or by crossing two parental plants and include selfings as well as the $F_1$ or $F_2$ or still further generations. An $F_1$ is a first-generation progeny produced from parents at least one of which is used for the first time as donor of a trait, while progeny of second generation ($F_2$) or subsequent generations ($F_3$, $F_4$, and the like) are specimens produced from selfings, intercrosses, backcrosses, and/or other crosses of $F_1$s, $F_2$s, and the like. An $F_1$ can thus be (and in some embodiments is) a hybrid resulting from a cross between two true breeding parents (i.e., parents that are true-breeding are each homozygous for a trait of interest or an allele thereof), while an $F_2$ can be (and in some embodiments is) a progeny resulting from self-pollination of the $F_1$ hybrids.

As used herein, the phrase "recombination" refers to an exchange of DNA fragments between two DNA molecules or chromatids of paired chromosomes (a "crossover") over in a region of similar or identical nucleotide sequences. A "recombination event" is herein understood to refer in some embodiments to a meiotic crossover.

As used herein, the term "reference sequence" refers to a defined nucleotide sequence used as a basis for nucleotide sequence comparison. In some embodiments, any of SEQ ID NOs: 1 and 3 can serve as a reference sequence for comparing to other sequences obtained from plants.

As used herein, the term "regenerate", and grammatical variants thereof, refers to the production of a plant from tissue culture.

As used herein, the phrase "stringent hybridization conditions" refers to conditions under which a polynucleotide hybridizes to its target subsequence, typically in a complex mixture of nucleic acids, but to essentially no other sequences. Stringent conditions are sequence-dependent and can be different under different circumstances.

Longer sequences typically hybridize specifically at higher temperatures. An extensive guide to the hybridization of nucleic acids is found in Sambrook & Russell, 2001. Generally, stringent conditions are selected to be about 5-10° C. lower than the thermal melting point ($T_m$) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Exemplary stringent conditions are those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides).

Stringent conditions can also be achieved with the addition of destabilizing agents such as formamide. Additional exemplary stringent hybridization conditions include 50% formamide, 5×SSC, and 1% SDS incubating at 42° C.; or SSC, 1% SDS, incubating at 65° C.; with one or more washes in 0.2×SSC and 0.1% SDS at 65° C. For PCR, a temperature of about 36° C. is typical for low stringency amplification, although annealing temperatures can vary between about 32° C. and 48° C. (or higher) depending on primer length. Additional guidelines for determining hybridization parameters are provided in numerous references (see e.g., Ausubel et al., 1999).

As used herein, the term "trait" refers to a phenotype of interest, a gene that contributes to a phenotype of interest, as well as a nucleic acid sequence associated with a gene that contributes to a phenotype of interest. For example, a "HI trait" refers to a haploid induction phenotype as well as a gene that contributes to a haploid induction and a nucleic acid sequence (e.g., a HI-associated gene product) that is associated with the presence or absence of the haploid induction phenotype.

As used herein, the term "transgene" refers to a nucleic acid molecule introduced into an organism or one or more of its ancestors by some form of artificial transfer technique. The artificial transfer technique thus creates a "transgenic organism" or a "transgenic cell". It is understood that the artificial transfer technique can occur in an ancestor organism (or a cell therein and/or that can develop into the ancestor organism) and yet any progeny individual that has the artificially transferred nucleic acid molecule or a fragment thereof is still considered transgenic even if one or more natural and/or assisted breedings result in the artificially transferred nucleic acid molecule being present in the progeny individual.

Maize haploid inducer plants produce pollen which when crossed onto non-inducer germplasm results in the gynogenic development of haploid seeds. Unfortunately, this process often yields a low frequency of haploid kernels. Inefficient haploid induction frequency is a limiting factor in maize doubled haploid breeding programs. The present invention identifies a locus that identifies haploid induction in a plant; and a four nucleotide insertion at positions 1230-1233 of SEQ ID NO: 53 the presence or absence of which distinguishes haploid inducer germplasm from non-inducer germplasm. This locus or the presence or absence of the four nucleotide insertion at positions 1230-1233 of SEQ ID NO: 53 can be employed for selecting, and/or introgressing, and/or transforming the haploid inducing trait into plants.

More specifically, the present invention produces new maize haploid-inducing lines. A number of known haploid—inducing maize lines exist including but not limited to: stock 6, MHI (Moldovian Haploid Inducer), indeterminate gametophyte (ig) mutation, KEMS, ZEM, LMS, KMS, RWS and RWK.—The present invention relates to a method of identifying, and/or selecting germplasm which can or cannot induce haploids. The present invention also relates to increasing and further development of the selected haploid inducing germplasm. The invention further relates to a method of improving haploid inducing germplasm to increase the induction of haploids on the seed producing parent.

The initial step in the production of haploid seeds from a hybrid or segregating maternal parent plant derives from the pollination with pollen from a haploid inducer on to the ear from a seed producing plant. A result of this hybridization process is the production of diploid and maternal haploid (1n) kernels. The induced haploid (1n) kernels are often distinguished from the diploid seed by the use of color markers which indicate embryo ploidy. The diploid seeds are generally discarded, while haploid kernels or embryos are often subjected to chromosome doubling processes to produce doubled haploid plants.

More specifically, the haploid genetic material is treated with one or more mitotic arrest agents to allow the haploid (1n) chromosome complement in one or more cells to produce homolog pairs. After the chemical treatment procedure, the chromosome doubling chemical(s) are removed. The now-doubled haploid maize is allowed to mature and the resulting doubled haploid seeds when planted will produce homozygous plants (also called inbred plant or lines). These inbred lines are the materials that breeders utilize to pursue their hybrid development programs.

The locus for the haploid induction trait was fine mapped. Although a major QTL on chromosome 1 responsible for haploid induction has been mapped and published, Dong et al. Theor. Appl. Genet (2013) 126: 1713-1720, the exact gene/genetic element responsible for the induction process has not been identified until now. The haploid induction locus is fine-mapped to be within a small region of 0.60 Mb (between the markers SM2363 (Chromosome 1, 67851018 nt Maize genome assembly version 3) and SM2712 (Chromosome 1, 68453157 nt Maize genome assembly version 3)). By comparing inducer and non-inducer germplasm, it was determined that a four nucleotide insertion present in haploid inducers which shifts the frame for amino acid coding of GRMZM2G471240 is not present in non-inducer germplasm. Therefore, the present invention has identified a gene with a frameshift mutation in inducer germplasm as being responsible for maize haploid induction. The candidate gene corresponding to gene model GRMZM2G471240 encodes a patatin-like phospholipase 2A.

Also notable are several secondary candidate genes identified as GRMZM2G305400, GRMZM2G082836, GRMZM2G382717, GRMZM2G120587, GRMZM2G062320, and GRMZM2G866758 that also may show differences between inducer and non-inducer lines. The secondary candidate genes may themselves be responsible for improved efficiency in HI. Crossing different HI inducers with these secondary candidate genes such as Stock 6 and RWK lines (each of which lack the candidate gene) can unexpectedly increase haploid induction, which may imply other genetic factors are also contributing to the HI trait. However, improved haploid induction germplasm can be difficult to maintain because it also results in significant seed abortion upon self-pollination and thus, makes HI line maintenance difficult.

DNA sequence was generated for each candidate gene from the two inducer lines and one non-inducer line. In addition, the public B73 genome data was used as a second non-inducer line. Gene model information was compared to EST/cDNA data to confirm the structure of each gene. The annotated sequence data were compared to catalog differences between the four alleles of each gene. The notable exceptions included GRMZM2G305400 which is only identified in the B73 genome and GRMZM2G062320 which is only detected in this study in the NIL and B73 genomes. PCR experiments show that it is present in RWK and Stock 6.

The sequence comparisons revealed that B73 and NIL alleles were similar to each other, and RWK and. Stock 6 alleles were similar to each other. Most sequence differences were single nucleotide polymorphisms that do not alter protein coding sequence. There were some insertions and some deletions, most of which are in non-protein coding sequence.

The exceptional sequence difference identified by the method used to generate the sequence data is in GRMZM2G471240, which contains a four nucleotide insertion in RWK and Stock 6. GRMZM2G471240 (annotated as a patatin-like phospholipase 2A protein) has a frame-shift mutation in the RWK and Stock6 lines resulting from a four base pair insertion in the fourth (and last) exon. When the nucleotide sequence is translated, the mutation shifts the coding frame by one base pair, changing the amino acid (AA) identity for each codon after the mutation. This results in 20 incorrect AA followed by a new, premature stop codon. The entire protein lesion thus constitutes a 30 AA truncation of the protein from the C-terminus, in addition to 20 AA of incorrect sequence between the mutation and the premature stop codon.

The presently disclosed subject matter provides the isolated nucleic acids, the genomic sequence and the protein sequence, the presence or absence, showed an association with HI, as well as any subsequences and informative fragments therefrom. In some embodiments, The presently disclosed subject matter provides isolated cDNA selected from the group consisting of: (a) a nucleic acid having at least 90% identity to SEQ ID NO: 33, SEQ ID NO: 37, SEQ ID NO: 52 or SEQ ID NO: 53, optionally wherein the percent identity is calculated over the entire length of SEQ ID NO: 33, SEQ ID NO: 37, SEQ ID NO: 52 or SEQ ID NO: 53; (b) a nucleic acid having at least 95% identity over nucleotides 91-1452 of SEQ ID NO: 33; (c) a nucleic acid that is the reverse complement of either of (a) or (b); and (d) a nucleic acid that encodes a polypeptide comprising an amino acid sequence that is at least 95% identical to SEQ ID NO: 54, or SEQ ID NO: 55, or SEQ ID NO: 56, or SEQ ID NO: 57 optionally wherein the percent identity is calculated over the entire length of SEQ ID NO: 54, or SEQ ID NO: 55, or SEQ ID NO: 56, or SEQ ID NO: 57.

Comparisons of an amino acid sequence encoded thereby (i.e., SEQ ID NO: 54, SEQ ID NO: 55, SEQ ID NO: 56 and SEQ ID NO: 57) to sequences present in the GENBANK® biosequence database indicated the following this was a patatin-like phospholipase 2A protein. The table below lists gene identities in the interval shown in the tables below. This information is from chromosome 1, and lists a short description of the other encoded proteins from the genes within the haploid inducing locus.

TABLE SHOWING INFORMATION ON CHROMOSOME 1

| gene_id | transcript_start | transcript_end | Query length | Subject length | Score | Identity | Similarity | Align length | Short_description |
|---|---|---|---|---|---|---|---|---|---|
| GRMZM2G305400 | 67991172 | 67994092 | 308 | 362 | 385 | 33.3 | 53.33752 | 314 | Cyclin D2;1 |
| GRMZM2G082836 | 68107606 | 68110989 | 202 | 205 | 729 | 71.2 | 83.33333 | 198 | GTP-binding protein 1 |
| GRMZM2G382717 | 68113455 | 68115168 | 396 | 464 | 489 | 38.77 | 53.17371 | 314 | Chaperone DnaJ-domain superfamily protein |
| GRMZM2G120587 | 68133178 | 68136953 | 458 | 461 | 1329 | 55 | 71.23894 | 452 | serine carboxypeptidase-like 51 |
| GRMZM2G471240 | 68240862 | 68242656 | 428 | 407 | 1049 | 51.5 | 72.36181 | 398 | phospholipase A 2A |
| GRMZM2G471240 | 68240862 | 68242656 | 401 | 407 | 961 | 50.15 | 70.0938 | 395 | phospholipase A 2A |
| GRMZM2G062320 | 68318898 | 68321409 | 335 | 334 | 1064 | 73.3 | 84.21053 | 285 | Phosphoglycerate mutase family protein |
| GRMZM5G866758 | 68430654 | 68436197 | 401 | 403 | 1678 | 80.4 | 90.45226 | 398 | acetoacetyl-CoA thiolase 2 |
| GRMZM5G866758 | 68430654 | 68436197 | 303 | 403 | 1248 | 78.4 | 89.40397 | 302 | acetoacetyl-CoA thiolase 2 |
| GRMZM2G003530 | 68435670 | 68439997 | 360 | 344 | 1063 | 60.5 | 76.41791 | 335 | P-loop containing nucleoside triphosphate hydrolases superfamily protein |
| GRMZM2G077991 | 68543246 | 68546264 | 94 | 95 | 424 | 79.7 | 91.48936 | 94 | Zinc-binding ribosomal protein family protein |
| GRMZM2G077991 | 68543694 | 68546264 | 94 | 95 | 424 | 79.7 | 91.48936 | 94 | Zinc-binding ribosomal protein family protein |
| GRMZM2G077991 | 68543805 | 68546269 | 147 | 95 | 419 | 79.5 | 91.39785 | 93 | Zinc-binding ribosomal protein family protein |
| GRMZM2G077960 | 68554980 | 68559182 | 438 | 428 | 1422 | 65.3 | 79.80998 | 421 | Protein phosphatase 2C family protein |
| GRMZM2G077897 | 68561209 | 68565155 | 784 | 807 | 1561 | 48.1 | 65.69848 | 723 | Plant protein of unknown function (DUF827) |
| GRMZM2G347583 | 68660278 | 68665995 | 1651 | 2156 | 1201 | 41.37 | 55.70954 | 1375 | |
| GRMZM2G173030 | 68668900 | 68671460 | 626 | 2156 | 858 | 35.6 | 48.30299 | 586 | |
| GRMZM2G022061 | 68876150 | 68882226 | 203 | 556 | 618 | 64.9 | 79.89691 | 194 | |
| GRMZM2G022061 | 68876150 | 68882226 | 322 | 556 | 1004 | 66 | 77.47748 | 333 | |
| GRMZM2G022061 | 68876150 | 68882226 | 142 | 556 | 547 | 79.6 | 89.84375 | 128 | |
| GRMZM2G022061 | 68876150 | 68882226 | 322 | 556 | 1004 | 66 | 77.47748 | 333 | |
| GRMZM2G022061 | 68876150 | 68882226 | 534 | 556 | 1802 | 67.7 | 79.81651 | 545 | |
| GRMZM2G340286 | 68928213 | 68929600 | 378 | 403 | 570 | 37.83 | 55.75713 | 407 | |
| GRMZM2G340279 | 68934652 | 68937080 | 746 | 937 | 3095 | 29.34 | 50.31745 | 2517 | Tetratricopeptide repeat (TPR)-like superfamily protein |
| GRMZM2G347808 | 69005208 | 69012612 | 589 | 455 | 1115 | 50.4 | 66.60178 | 423 | S-adenosyl-L-methionine-dependent methyltransferases superfamily protein |

RNA interference (RNAi) occurs when an organism recognizes double-stranded RNA (dsRNA) molecules and hydrolyzes them. The resulting hydrolysis products are small RNA fragments of about 19-24 nucleotides in length, called small interfering RNAs (siRNAs). The siRNAs then diffuse or are carried throughout the organism, including across cellular membranes, where they hybridize to mRNAs (or other RNAs) and cause hydrolysis of the RNA. Interfering RNAs are recognized by the RNA interference silencing complex (RISC) into which an effector strand (or "guide strand") of the RNA is loaded. This guide strand acts as a template for the recognition and destruction of the duplex sequences. This process is repeated each time the siRNA hybridizes to its complementary-RNA target, effectively preventing those mRNAs from being translated, and thus "silencing" the expression of specific genes from which the mRNAs were transcribed. Most plant miRNAs show extensive base pairing to, and guide cleavage of their target mRNAs (Jones-Rhoades et al. (2006) Annu. Rev. Plant Biol. 57, 19-53; Llave et al. (2002) Proc. Natl. Acad. Sci. USA 97, 13401-13406). In other instances, interfering RNAs may bind to target RNA molecules having imperfect complementarity, causing translational repression without mRNA degradation. The majority of the animal miRNAs studied so far appear to function in this manner.

Conveniently, the dsRNA can be produced from a single open reading frame in a recombinant host cell, wherein the sense and anti-sense sequences are flanked by an unrelated sequence which enables the sense and anti-sense sequences to hybridize to form the dsRNA molecule with the unrelated sequence forming a loop structure. Alternatively, the sense strand and antisense strand can be made without an open reading frame to ensure that no protein will be made in the transgenic host cell. The two strands can also be expressed separately as two transcripts, one encoding the sense strand and one encoding the antisense strand. RNA duplex formation can be initiated either inside or outside the cell. The dsRNA can be partially or fully double-stranded. The RNA can be enzymatically or chemically synthesized, either in vitro or in vivo.

The dsRNA need not be full length relative to either the primary transcription product or fully processed RNA. Generally, higher identity can be used to compensate for the use of a shorter sequence. Furthermore, the dsRNA can comprise single stranded regions as well, e.g., the dsRNA can be partially or fully double stranded. The double stranded region of the dsRNA can have a length of at least about 18 to about 25 base pairs, optionally a sequence of about 18 to about 50 base pairs, optionally a sequence of about 50 to about 100 base pairs, optionally a sequence of about 100 to about 200 base pairs, optionally a sequence of about 200 to about 500, and optionally a sequence of about 500 to about 1000 or more base pairs, up to molecule that is double stranded for its full length, corresponding in size to a full length target RNA molecule.

The dsDNA can contain known nucleotide analogs or modified backbone residues or linkages, which are synthetic, naturally occurring, and non-naturally occurring. Examples of such analogs include, without limitation, phosphorothioates, phosphoramidates, methyl phosphonates, chiralmethyl phosphonates and 2-O-methyl ribonucleotides.

As used herein, the term "specifically reduce the level of a target RNA and/or the production of a target protein encoded by the RNA", and variations thereof, refers to the sequence of a portion of one strand of the dsRNA being sufficiently identical to the target RNA such that the presence of the dsRNA in a cell reduces the steady state level and/or the production of said RNA. In many instances, the target RNA will be mRNA, and the presence of the dsRNA in a cell producing the mRNA will result in a reduction in the production of said protein. Preferably, this accumulation or production is reduced at least 10%, more preferably at least 50%, even more preferably at least 75%, yet even more preferably at least 95% and most preferably 100%, when compared to a wild-type cell.

The consequences of inhibition can be confirmed by examination of the outward properties of the cell or organism or by biochemical techniques such as, but not limited to, Northern hybridization, reverse transcription, gene expression monitoring with a microarray, antibody binding, enzyme linked immunosorbent assay (ELISA), Western blotting, radioimmunoassay (RIA), and other immunoassays.

MicroRNAs (miRNAs) are non-protein coding RNAs, generally of between about 18 to about 25 nucleotides in length (commonly about 20-24 nucleotides in length in plants). These miRNAs direct cleavage in trans of target transcripts, negatively regulating the expression of genes involved in various regulation and development pathways (Bartel, Cell, 116:281-297 (2004); Zhang et al. Dev. Biol. 289:3-16 (2006)). As such, miRNAs have been shown to be involved in different aspects of plant growth and development as well as in signal transduction and protein degradation. In addition, small endogenous mRNAs including miRNAs may also be involved in biotic stress responses such as pathogen attack. Since the first miRNAs were discovered in plants (Reinhart et al. Genes Dev. 16:1616-1626 (2002), Park et al. Curr. Biol. 12:1484-1495 (2002)) many hundreds have been identified. Furthermore, many plant miRNAs have been shown to be highly conserved across very divergent taxa. (Floyd et al. Nature 428:485-486 (2004); Zhang et al. Plant J. 46:243-259 (2006)). Many microRNA genes (MIR genes) have been identified and made publicly available in a data base (miRBase; microrna.sanger.ac.uk/sequences). miRNAs are also described in U.S. Patent Publications 2005/0120415 and 2005/144669A1, the entire contents of which are incorporated by reference herein.

Genes encoding miRNAs yield primary miRNAs (termed a "pri-miRNA") of 70 to 300 bp in length that can form imperfect stem-loop structures. A single pri-miRNA may contain from one to several miRNA precursors. In animals, pri-miRNAs are processed in the nucleus into shorter hairpin RNAs of about 65 nt (pre-miRNAs) by the RNaselll enzyme Drosha and its cofactor DGCR8/Pasha. The pre-miRNA is then exported to the cytoplasm, where it is further processed by another RNaselll enzyme, Dicer, releasing a miRNA/miRNA* duplex of about 22 nt in size. In contrast to animals, in plants, the processing of pri-miRNAs into mature miRNAs occurs entirely in the nucleus using a single RNaselll enzyme, DCL1 (Dicer-like 1). (Zhu. Proc. Natl. Acad. Sci. 105:9851-9852 (2008)). Many reviews on microRNA biogenesis and function are available, for example, see, Bartel Cell 116:281-297 (2004), Murchison et al. Curr. Opin. Cell Biol. 16:223-229 (2004), Dugas et al. Curr. Opin. Plant Biol. 7:512-520 (2004) and Kim Nature Rev. Mol. Cell Biol. 6:376-385 (2005).

The term "plant microRNA precursor molecule" as used herein describes a small (~70-300 nt) non-coding RNA sequence that is processed by plant enzymes to yield a ~19-24 nucleotide product known as a mature microRNA sequence. The mature sequences have regulatory roles through complementarity to messenger RNA. The term "artificial plant microRNA precursor molecule" describes the non-coding miRNA precursor sequence prior to processing that is employed as a backbone sequence for the delivery of a siRNA molecule via substitution of the endogenous native miRNA/miRNA* duplex of the miRNA precursor molecule with that or a non-native, heterologous miRNA (amiRNA/amiRNA*; e.g. siRNA/siRNA*) that is then processed into the mature miRNA sequence with the siRNA sequence.

A "coding sequence" is a nucleic acid sequence that is transcribed into RNA such as mRNA, rRNA, (RNA, snRNA, sense RNA or antisense RNA. Preferably the RNA is then translated in an organism to produce a protein.

As used herein, "complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. For example, the sequence "A-G-T" binds to the complementary sequence "T-C-A." It is understood that two polynucleotides may hybridize to each other even if they are not completely complementary to each other, provided that each has at least one region that is substantially complementary to the other.

The terms "complementary" or "complementarity," as used herein, refer to the natural binding of polynucleotides under permissive salt and temperature conditions by base-pairing. Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

As used herein, the terms "substantially complementary" or "partially complementary mean that two nucleic acid sequences are complementary at least a bout 50%, 60%, 70%, 80% or 90% of their nucleotides. In some embodiments, the two nucleic acid sequences can be complementary at least at 85%, 90%, 95%, 96%, 97%, 98%, 99% or more of their nucleotides. The terms "substantially complementary" and "partially complementary" can also mean that two nucleic acid sequences can hybridize under high stringency conditions and such conditions are well known in the art In some embodiments, the dsRNA molecule can comprise, consist essentially of or consist of from at least 18 to a bout 25 consecutive nucleotides (e.g. 18, 19, 20, 21, 22, 23, 24 or 25) to at least about 400 consecutive nucleotides. In some embodiments the dsRNA molecule can comprise, consist essentially of or consist of about 500, or about 50 or about 543 consecutive nucleotides. Additional nucleotides can be added at the 3' end, the 5' end or both the 3' and 5' ends to facilitate manipulation of the dsRNA molecule but that do not materially affect the basic characteristics or function of the dsRN A molecule in RNA interference (RNAi).

In some embodiments, the portion of the mRNA polynucleotide transcribable from a GRMZM2G471240 gene that the antisense strand is complementary to comprises at least 18 consecutive nucleotides of SEQ ID NO:33, SEQ ID NO:37, SEQ ID NO:52 or SEQ ID NO:53. In other embodiments, the portion of mRNA comprises, consists essentially of or consists of at least from 19, 20 or 21 consecutive nucleotides to at least 400 consecutive nucleotides of SEQ ID NO:33, SEQ ID NO:37, SEQ ID NO:52 or SEQ ID NO:53. In other embodiments, the portion of mRNA comprises, consists essentially of or consists of at least about 500, or at least about 98 or at least about 185 consecutive nucleotides of SEQ ID NO:33.

In other embodiments, the portion of the mRNA polynucleotide that is complementary to the antisense strand of a dsRNA of the invention comprises any 19-mer subsequence of SEQ ID NO:33 (GRMZM2G471240) consisting of N to N+18 nucleotides, wherein N is nucleotide 1 to 1452 of SEQ ID NO:33. In other words, the portion of the mRNA that is targeted comprises any of the 1452 19 consecutive nucleotide subsequences (i.e. 19-mer) of SEQ ID NO:33, for example, bases 1-19 (5'-AGTTCATCACTAATCACAC-3'), bases 2-20 (5'-GTTCATCACTAATCACACT-3'), bases 3-21 (5'-TTCATCACTAATCACACTT-3') and so forth to bases 1434-1452 (5'-AAAACATAAAAATATATAT-3').

In other embodiments, the nucleotide sequence of the antisense strand can consist essentially of the nucleotide sequence of any 19-mer subsequence of SEQ TD NO:62 consisting of N to N+18 nucleotides, wherein N is nucleotide 1 to nucleotide 1452 of SEQ ID NO:62. In other words, the antisense strand consists essentially of the nucleotide sequence of any of the 1452 19 consecutive nucleotide subsequences (i.e. 19-mer) of SEQ II) NO:62, for example, bases 1-19 (5'-ATATATATTTTTATGTTTT-3'), bases 2-20 (5'-TATATATTTTTATGTTTTA-3'), bases 3-21 (5'-ATATATTTTTATGTTTTAT-3') and so forth to bases 1434-1452 (5'-GTGTGATTAGTGATGAACT-3').

It would be understood that the deletion of the one nucleotide or the addition of up to six nucleotides do not materially affect the basic characteristics or function of the double stranded RNA molecule of the invention. Such additional nucleotides can be nucleotides that extend the complementarity of the antisense strand along the target sequence and/or such nucleotides can be nucleotides that facilitate manipulation of the RNA molecule or a nucleic acid molecule encoding the RNA molecule, as would be known to one of ordinary skill in the art. For example, a TT overhang at the 3; end may be present, which is used to stabilize the siRNA duplex and does not affect the specificity of the siRNA.

In some embodiments of this invention, the antisense strand of the double stranded RNA molecule can be fully complementary to the target RNA polynucleotide or the antisense strand can be substantially complementary or partially complementary to the target RNA polynucleotide. By substantially or partially complementary is meant that the antisense strand and the target RNA polynucleotide can be mismatched at about 1, 2, 3, 4, 5, 6, 7, 8, 9, or 10 nucleotide pairings. Such mismatches can be introduced into the antisense strand sequence, e.g., near the 3' end, to enhance processing of the double stranded RNA molecule by Dicer, to duplicate a pattern of mismatches in a siRNA molecule inserted into a chimeric nucleic acid molecule or artificial microRNA precursor molecule of this invention, and the like, as would be known to one of skill in the art. Such modification will weaken the base pairing at one end of the duplex and generate strand asymmetry, therefore enhancing the chance of the antisense strand, instead of the sense strand, being processed and silencing the intended gene (Deng and Ding "Double-mismatched siRNAs enhance selective gene silencing of a mutant ALS-causing Andel" Acta Pharmacol. Sin. 29:211-216 (2008); Schwarz et al. "Asymmetry in the assembly of the RNAi enzyme complex" Cell 115:199-208 (2003)). Other such mismatches can be introduced into the antisense strand due to eliminating fortuitous open reading frames created in making dsRNA encoding expression cassettes. Such open reading frames are eliminated by making point mutations in the dsRNA encoding nucleotide sequence thus creating some mismatches in the dsRNA compared to the target gene. In some embodiments of this invention, the dsRNA molecule of the invention is a short hairpin RNA (shRNA) molecule. Expression of shRNA in cells is typically accomplished by delivery of plasmids or recombinant vectors, for example in transgenic plants such as transgenic corn.

The invention encompasses a nucleic acid molecule encoding at least one strand of a dsRNA molecule of the invention. The invention further encompasses a nucleic acid construct comprising at least one strand of a dsRNA molecule of the invention or comprising the nucleic acid molecule encoding the at least one strand of a dsRNA molecule of the invention. In one embodiment of the invention, the nucleic acid molecule encodes a short hairpin RNA. In another embodiment, the nucleic acid molecule that encodes the short hairpin RNA comprises SEQ NO:62 or SEQ ID NO:63

The invention further encompasses chimeric nucleic acid molecules comprising an antisense strand of a dsRNA of the invention operably linked with a plant microRNA precursor molecule. In some embodiments, the chimeric nucleic acid molecule comprises an antisense strand having the nucleotide sequence of any of the 19-mer subsequences of SEQ ID NO:33, SEQ ID NO:37, SEQ ID NO:52 or SEQ ID NO:53 operably linked with a plant microRNA precursor molecule. In some embodiments, the plant microRNA precursor molecule is a maize microRNA precursor.

In some embodiments, the invention encompasses an artificial plant microRNA precursor molecule comprising an antisense strand of a dsRNA molecule of the invention. In other embodiments, the artificial plant microRNA precursor molecule comprises an antisense strand having the nucleotide sequence of any of the 19-mer subsequences of SEQ ID NO:62, or SEQ ID NO:63. The use of artificial plant microRNAs to deliver a nucleotide sequence of interest (e.g an artificial miRNA; siRNA/siRNA*) into a plant is known in the art (see, e.g., Schwab et al. 2006. The Plant Cell 18:1121-1133 and Examples section herein). In the invention, the artificial microRNAs are chimeric or hybrid molecules, having a plant microRNA precursor backbone and an insect (i.e. animal) siRNA sequence inserted therein. As would be understood by one of ordinary skill in the art, it is typically desirable to maintain mismatches that normally occur in the plant microRNA precursor sequence in any nucleotide sequence that is substituted into the plant microRNA precursor backbone. In still other embodiments, the artificial plant microRNA precursor comprises portions of a corn microRNA precursor molecule. Any corn microRNA (miRNA) precursor is suitable for the compositions and methods of the invention. Nonlimiting examples include miR156, miR159, miR160, miR162, miR164, miR166, miR167, miR168, miR169, miR171, miR172, miR319, miR390, miR393, miR394, miR395, miR396, miR397, miR398, miR399, miR408, miR482, miR528, miR529, miR827, miR1432, as well as any other plant miRNA precursors now known or later identified.

In some embodiments, the invention encompasses nucleic acid constructs, nucleic acid molecules or recombinant vectors comprising at least one strand of a dsRNA molecule of the invention, or comprising a chimeric nucleic acid molecule of the invention, or comprising an artificial plant microRNA of the invention. In some embodiments the nucleic acid construct comprises a nucleic acid molecule of the invention. In other embodiments, the nucleic acid construct is a recombinant expression vector.

In some embodiments, the invention encompasses compositions comprising two or more dsRNA molecules of the invention wherein the two or more RNA molecules each comprise a different antisense strand. In some embodiments the two or more dsRNA molecules are present on the same nucleic acid construct, on different nucleic acid constructs or any combination thereof. In other embodiments, the composition comprises an RNA molecule comprising an antisense strand consisting essentially of the nucleotide sequence of SEQ ID NO:62 and an RNA molecule comprising an antisense strand consisting essentially of the nucleotide sequence of SEQ ID NO:63. In other embodiments, the composition comprises two or more nucleic acid constructs, two or more nucleic acid molecules, two or more chimeric nucleic acid molecules, two or more artificial plant microRNA precursors of the invention, wherein the two or more nucleic acid constructs, two or more nucleic acid molecules, two or more chimeric nucleic acid molecules, or two or more artificial plant microRNA precursors, each comprise a different antisense strand.

RNA interference (RNAi) can be used to produce genetically modified plants that are tolerant or resistant to abiotic and biotic stresses. In the past decade, RNAi has been described and characterized in organisms as diverse as plants, fungi, nematodes, hydra, and humans. Zamore and Haley (2005) Science 309, 1519-24. RNA interference in plants is commonly referred to as post-transcriptional gene silencing or RNA silencing and is referred to as quelling in fungi. The process of post-transcriptional gene silencing is thought to be an evolutionarily conserved cellular defense mechanism used to prevent the expression of foreign genes and is commonly shared by diverse flora and phyla. Fire (1999) Trends Genet. 15, 358-363.

RNA interference occurs when an organism recognizes double-stranded. RNA molecules and hydrolyzes them. The resulting hydrolysis products are small RNA fragments of 19-24 nucleotides in length, called small interfering RNAs (siRNAs) or microRNAs (miRNAs). The siRNAs then diffuse or are carried throughout the organism, including across cellular membranes, where they hybridize to mRNAs (or other RNAs) and cause hydrolysis of the RNA. Most plant miRNAs show extensive base pairing to, and guide cleavage of their target mRNAs. Jones-Rhoades et al. (2006) Annu. Rev. Plant Viol 57, 19-53; Llave et al. (2002) Proc. Natl. Acad. Sci. USA 97, 13401-10406. In other instances, interfering RNAs may bind to target RNA molecules having imperfect complementarity, causing translational repression without mRNA degradation.

The mode of action for silencing a plant gene generally includes a double stranded RNA (dsRNA) that associates with a dicer enzyme that cuts the dsRNA into ds fragments 19-24 bps in length (siRNA). There may be more than one dicer enzyme, depending on the organism. Meister and Tuschl, 2004). The siRNA is typically degraded into two single stranded RNAs (ssRNAs), referred to as the passenger strand and the guide strand. A RNA-interference silencing complex (RISC complex) loads the guide strand. The RISC complex associates with a target mRNA that has partial or complete homology to the guide strand. The catalytic RISC component agronaute causes cleavage of the target mRNA preventing it from being used as a translation template. Ahlquist P (2002) RNA-dependent RNA polymerases, viruses, and RNA silencing, Science 296 (5571): 1270-3. The RNAi pathway is exploited in plants by using recombinant technology, which entails transforming a plant with a vector comprising DNA that when expressed produces a dsRNA homologous or nearly homologous to a gene target. The gene target can be homologous to a endogenous plant gene or an insect gene. If the target is an insect gene, the insect eats the plant thereby ingesting the dsRNA, at which the RNAi RISC complex of the insect causes cleavage and targeting of the homologous mRNA, causing disruption of a vital insect process.

To date, plant recombinant technology is the vehicle for delivering gene silencing of target genes, either endogenous plant target genes or target genes of a plant pest organism. In general, a plant is transformed with DNA that is incorporated into the plant genome, and when expressed produces a dsRNA that is complementary to a gene of interest, which can be an endogenous plant gene or an essential gene of a plant pest. Plant recombination techniques to generate transgene and beneficial plant traits require significant investments in research and development, and pose significant regulatory hurdles. Methods and formulations for delivering dsRNA into plant cells by exogenous application to exterior portions of the plant, such as leaf, stem, and/or root surfaces for regulation of endogenous gene expression are not known in the art. Such methods and formulations represent a significant development for gene silencing technology. Known methods for delivering exogenous dsRNA into plant cells are via particle bombardment or viral RNA infection through wounding the plant tissue (e.g. tobacco and rice leaf tissues). Application by spray or brush of RNA molecules, or other non-tissue evasive techniques, resulting in assimilation of the exogenous RNA molecules into plant tissue, thereby causing endogenous and/or pest gene silencing, has not been reported.

The present invention is directed to methods and formulations to incorporate exogenous RNA, by application to external tissue surface(s) of plants, into the plant cells causing silencing of plant endogenous target gene(s) or of the target genes of plant pests.

The present invention is not directed to any particular RNAi mechanism or mode of action of gene silencing, and should not be construed as limited to any such mechanisms, known or unknown.

The terms "silencing" and "suppression" are used interchangeably to generally describe substantial and measurable reductions of the amount of the target mRNA available in the cell for binding and decoding by ribosomes. The transcribed RNA can be in the sense orientation to effect what is referred to as co-suppression, in the anti-sense orientation to effect what is referred to as anti-sense suppression, or in both orientations producing a double-stranded RNA to effect what is referred to as RNA interference. A "silenced" gene includes within its definition a gene that is subject to silencing or suppression of the mRNA encoded by the gene.

MicroRNAs are encoded by genes that are transcribed but not translated into protein (non-coding DNA), although some miRNAs are encoded by sequences that overlap protein-coding genes. By way of background, miRNAs are processed from primary transcripts known as pri-miRNAs to short stem loop structures called pre-miRNAs that are further processed by action of dicer enzyme(s) creating functional siRNAs/miRNAs. Typically, a portion of the precursor miRNA is cleaved to produce the final miRNA molecule. The stem-loop structures may range from, for example, about 50 to about 80 nucleotides, or about 60 nucleotides to about 70 nucleotides (including the miRNA residues, those pairing to the miRNA, and any intervening segments). The secondary structure of the stem-loop structure is not fully base-paired; mismatches, bulges, internal loops, non-WatsonCrick base pairs (i.e., G-U wobble base pairs), and other features are frequently observed in pre-miRNAs and such characteristics are thought to be important for processing. Mature miRNA molecules are partially complementary to one or more mRNA molecules, and they function to regulate gene expression. siRNAs of the present invention have structural and functional properties of endogenous miRNAs (e.g., gene silencing and suppressive functions). Thus, in various aspects of the invention, siRNAs of the invention can derived from miRNAs, from target gene sequence information, or can be produced synthetically based on predictive models known in the art. The phrases "target-specific small interfering RNAs," "target-specific siRNAs," "target-specific microRNAs," "target-specific miRNAs," "target-specific amiRNAs," and "target-specific nucleotide sequence" refer to interfering RNAs that have been designed to selectively hybridize with nucleic acids in a target organism, but not in a non-target organism, such as a host organism (the organism expressing or producing the miRNA) or a consumer of the host organism. Consequently, "target-specific siRNAs" only produce phenotypes in target organisms and do not produce phenotypes in non-target organisms. In the present invention, the target-specific siRNAs selectively hybridize to nucleic acids that are endogenous to the host organism, which are plants. MicroRNAs (miRNAs) are non-protein coding RNAs, generally of between about 19 to about 25 nucleotides (commonly about 20-24 nucleotides in plants), miRNAs direct cleavage in trans of target transcripts, regulating the expression of genes involved in various regulation and development pathways (Bartel, Cell, 116:281-297 (2004); Zhang et al. Dev. Biol, 289:3-16 (2006)). miRNAs have been shown to be involved in different aspects of plant growth and development as well as in signal transduction and protein degradation. In addition, growing evidence indicates that small endogenous mRNAs including miRNAs may also be involved in biotic stress responses such as parasite attack. Since the first miRNAs were discovered in plants (Reinhart et al. Genes Dev. 16:1616-1626 (2002), Park et al. Curr. Biol. 12:1484-1495 (2002)), many hundreds have been identified. Further, many plant miRNAs have been shown to be highly conserved across very divergent taxa. (Floyd et al. Nature 428:485-486 (2004); Zhang et al. Plant J. 46:243-259 (2006)). Many microRNA genes (MIR genes) have been identified and made publicly available in a database ("miRBase," available on line at microrna.sanger.ac.uk/sequences). miRNAs are also described in U.S. Patent Publications 2005/0120415 and 2005/144669A1, the entire contents of which are incorporated by reference herein.

Further encompassed within the presently disclosed subject matter are expression cassettes according to the embodiments of the presently disclosed subject matter as well as expression vectors comprising the same. Also encompassed are plant cells comprising expression cassettes according to the present disclosure, and plants comprising these plant cells. In some embodiments, the plant is a dicot. In some embodiments, the plant is a monocot. In some embodiments, the monocot is a cereal. The plant can be, for example, rice, maize, grass, wheat, maize, barley, brome, oats, rye, millet, sorghum, triticale, secale, einkorn, spelt, emmer, teff, milo, flax, gramma grass, Tripsacum, or teosinte.

Thus, the compositions of the presently disclosed subject matter can comprise nucleic acid sequences for transformation and expression in a plant of interest. The expression is of the primary candidate gene and HI trait is desired the expression may also be for down regulated expression or induced expression in some or all of the female portion of the plant and no expression in the male flowering plant parts. The nucleic acid sequences can be present in DNA constructs or expression cassettes. "Expression cassette" as used herein means a nucleic acid molecule capable of directing expression of a particular nucleotide sequence, or iRNA in an appropriate host cell, comprising a promoter operatively linked to the sequence of interest (e.g., a sequence encoding a gene product or iRNA associated with HI) which is optionally also operatively linked to termination signals. It also typically comprises sequences required for proper translation of the nucleotide sequence. The coding region usually codes for a protein of interest but can also code for a functional RNA of interest, for example antisense RNA or a nontranslated RNA such as, but not limited to a siRNA, in the sense or antisense direction. The expression cassette comprising the nucleotide sequence of interest can be chimeric, meaning that at least one of its components is heterologous with respect to at least one of its other components. The expression cassette can also be one that is naturally occurring but has been obtained in a recombinant form useful for heterologous expression. In some embodiments, the expression cassette is heterologous with respect to the host (i.e., the particular DNA sequence of the expression cassette, or a subsequence thereof, does not occur naturally in the host cell and must have been introduced into the host cell or an ancestor of the host cell by a transformation event). The expression of the nucleotide sequence in the expression cassette can be under the control of a constitutive promoter, a tissue specific promoter, and/or an inducible promoter that initiates transcription only when the host cell is exposed to some particular external stimulus, a minimal promoter, etc. Additionally, the promoter can also be specific to a particular cell type, tissue, organ, and/or stage of development. In some embodiments, an expression cassette is present in a vector that permits replication of the expression cassette in a host cell.

The present presently disclosed subject matter encompasses the transformation of plants with expression cassettes capable of expressing a polynucleotide of interest (e.g., a polynucleotide encoding a gene product or iRNA associated with HI) alone or in combination with one or more additional nucleic acid molecules encoding polypeptides that confer desirable traits. However, if the polynucleotide is the primary gene, GRMZM2G062320, it maybe preferred that the cassette is adapted to down regulate or knock out the gene in nonhaploid inducing material. Or expressed in an inducible matter so that the pollen used to self the HI plant is expressing the gene product that occurs in B73 and other non haploid inducing material. In some embodiments, the expression cassette includes at least the following basic elements oriented in the 5'-3' direction of transcription: a transcriptional and translational initiation region (i.e., a promoter) and a polynucleotide of interest. The expression cassette can optionally comprise a transcriptional and translational termination region (e.g., termination region) functional in plants. In some embodiments, the expression cassette comprises a selectable marker gene to allow for selection for stable transformants.

In some embodiments, the regulatory sequences of the expression construct are operably linked to the polynucleotide of interest. By "operably linked" is intended a functional linkage between a first sequence (e.g., a promoter) and a second sequence (e.g., a coding sequence), wherein the first sequence influences a biological event (e.g., transcription, transcription, replication, etc.) that occurs with respect to the second sequence. Generally, operably linked means that the nucleotide sequences being linked are contiguous in a single molecule.

Any promoter capable of driving expression in the plant of interest can be used in the practice of the presently disclosed subject matter. In some embodiments, the expression cassette is expressed throughout the plant. In some embodiments, the expression cassette is expressed in a specific location and/or tissue of a plant, or at a certain time during the development of the plant. In some embodiments, the location and/or tissue includes, but is not limited to, anther, ovule, plastid, pollen, mitochondrion, chloroplast, epidermis, root, vascular tissue, meristem, cambium, cortex, pith, leaf, flower, and combinations thereof. In another embodiment, the location and/or tissue is a seed.

The promoter can be native or analogous, or can be heterologous or exogenous, to the plant or plant cell in which it is intended to be active. The terms "heterologous" and "exogenous" when used herein to refer to a nucleic acid sequence (e.g., a DNA or RNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, in some embodiments the terms refer to a DNA segment that is foreign or heterologous to the cell, or homologous to the cell but in a position within the host cell nucleic acid in which the element is not ordinarily found. In some embodiments, an exogenous DNA segment is expressed to yield an exogenous polypeptide in a cell or tissue type of interest. In some embodiments, a heterologous or exogenous nucleic acid is referred to herein as a transgene.

A "homologous" nucleic acid (e.g., DNA) sequence is a nucleic acid (e.g., DNA or RNA) sequence that is naturally associated with a host cell into which it is introduced. As such, and by way of example and not limitation, a nucleic acid that is derived from (i.e., isolated from with or without subsequent modification) a plant cell or tissue could be considered a homologous nucleic acid when reintroduced into a plant cell or tissue of the same species, but could be considered heterologous or exogenous when introduced into a cell or tissue of a plant other than the plant species from which it was derived. In some embodiments, a homologous nucleic acid can also be referred to herein as a heterologous or a transgene when the homologous nucleic acid is operatively linked to a nucleotide sequence to which it is not naturally operatively linked.

The choice of promoters to be included depends in some embodiments upon several factors, including, but not limited to, efficiency, selectability, inducibility, desired expression level, and/or cell- or tissue-preferential and/or -specific expression. It is a routine matter for one of skill in the art to modulate the expression of a sequence by appropriately selecting and positioning promoters and other regulatory regions relative to that sequence. The promoters that are used for expression of the transgene(s) can be in some embodiments a strong plant promoter, in some embodiments a viral promoter, and in some embodiments a chimeric promoter comprising such basic transcriptional regulatory elements such as but not limited to a TATA box from any gene (or synthetic, based on analysis of plant gene TATA boxes), optionally fused to the region 5' to the TATA box of plant promoters (which direct tissue and temporally appropriate gene expression), optionally fused to one or more enhancers (such as the 35S enhancer, FMV enhancer, CMP enhancer, etc.).

For example, the selection of the promoter used in expression cassettes can determine the spatial and temporal expression pattern of the transgene in the transgenic plant. Selected promoters can express transgenes in specific cell types and/or in specific tissues or organs, and the selection can reflect the desired location for accumulation of the gene product. Alternatively, the selected promoter can drive expression of the gene under various inducing conditions. Promoters vary in their strength; i.e., their abilities to promote transcription. Depending upon the host cell system utilized, any one of a number of suitable promoters can be used, including the gene's native promoter. The following are non-limiting examples of promoters that can be used in expression cassettes.

Promoters which are directing expression of the gene are referred to herein as "constitutive" promoters and are active under most environmental conditions and states of development or cell differentiation. Examples of constitutive promoters include the 1'- or 2'-promoter derived from T-DNA of *Agrobacterium tumefaciens*, and other transcription initiation regions from various plant genes known to those of ordinary skill in the art. Such genes include, but are not limited to, the inducible promoters of AP2 gene; ACT11 from *Arabidopsis* (Huang et al., 1996); Cat3 from *Arabidopsis* (GENBANK® Accession No. U43147; Zhong et al., 1996); the gene encoding stearoyl-acyl carrier protein desaturase from *Brassica napus* (GENBANK® Accession No. X74782; Solocombe et al., 1994); GPc1 from maize (GENBANK® Accession No. X15596; Martinez et al., 1989); and Gpc2 from maize (GENBANK® Accession No. U45855; Manjunath et al., 1997). Additional non-limiting examples of constitutive promoters include, for example, the core promoter of the Rsyn7 promoter and other constitutive promoters disclosed in PCT International Patent Application Publication No. WO 1999/43838 and U.S. Pat. No. 6,072,050; various ubiquitin promoters (see e.g., U.S. Pat. Nos. 5,641,876 and 8,168,859; Christensen et al., 1989; Christensen et al., 1992; Wei et al., 2003; Lu et al., 2008); the core CaMV 35S promoter (Odell et al., 1985; Benfey & Chua, 1990); the CaMV 19S promoter; the figwort mosaic virus (FMV) promoter; the rice actin-1 promoter (McElroy et al., 1990); the rice alpha tubulin (tubA1) promoter (Fiume et al., 2004); pEMU (Last et al., 1991); the Cestrum yellow leaf curling virus (CmYLCV) CMP promoter (Hohn et al., 2007; U.S. Pat. No. 7,166,770); the MAS promoter (Velten et al., 1984); the Super MAS promoter (Ni et al., 1995; Lee et al., 2007); the ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142; and 6,177,611.

The present invention shows a frame shift mutation in GRMZM2G471240 in the Haploid inducing material, thus RNAi silencing of GRMZM2G471240 will create a HI line. The silencing can be accomplished in numerous ways including expression of a hairpin or artificial mircoRNA to target GRMZM2G471240. The down regulated expression transformants will allow various types of germplasm to act as HI lines.

It should also be possible to compensate the defect in a HI line. Transgenic material with the non-haploid inducing sequence when expressed (SEQ ID NO: 33) should if joined with an inducible promoter make the HI line switchable between being a HI line and a non-HI line. Therefore, transformation methods, cassettes, vectors and transgenic plant with the non-HI sequence are described herein.

Appropriate plant or chimeric promoters are useful for applications such as expression of transgenes and/or other heterologous or homologous nucleic acids in certain tissues, while minimizing expression (including but not limited to a level of expression that is below detection using routine techniques) in other tissues, in some embodiments such as but not limited to seeds and/or female reproductive tissues. In some embodiments, expression of a nucleic acid designed to silence a gene product associated with HI of the current presently disclosed subject matter can optionally be localized to seed, or fruit tissues and preferably no expression in the anther or pollen or very downregulated expression if this gene product is present at all in the anther or pollen. The data suggests that expression of the expression is most likely important in early reproductive structures, particularly female structures. Exemplary cell type- or tissue-preferential (in some embodiments, tissue-specific) promoters drive expression preferentially (or in some embodiments essentially specifically) in the target tissue, but can also lead to some expression in other cell types or tissues as well. Methods for identifying and characterizing promoter regions in plant genomic DNA include, for example, those described in the following references: Green et al., 1988; Bustos et al., 1989; Jordano et al., 1989; Meier et al., 1991; and Zhang et al., 1996.

Alternatively, the plant promoter can direct expression of the nucleic acid molecules of the presently disclosed subject matter in a specific tissue or can be otherwise under more precise environmental or developmental control. Examples of environmental conditions that can effect transcription by inducible promoters include anaerobic conditions, elevated temperature, or the presence of light. Such promoters are referred to herein as "inducible", "cell type-specific", or "tissue-specific" promoters. Those of ordinary skill in the art will recognize that a tissue-specific promoter can drive expression of operatively linked sequences in tissues other than the target tissue. Thus, as used herein a "tissue-specific" promoter is one that drives expression preferentially in the target tissue, but can also lead to some expression in other tissues as well.

Examples of promoters under developmental control include promoters that initiate transcription preferentially or exclusively in certain tissues, such as pollen, anthers, fruit, seeds, or flowers. Promoters that direct expression of nucleic acids in pollen, anthers, and the like and possibly in ovules, flowers, or seeds are particularly useful in the presently disclosed subject matter. As used herein a seed-specific promoters are active in cells destined to produce the ovule and tend to direct expression specifically or preferentially in the seed tissues. And reproduction specific promoters are promoters that are active in cells destined to produce the male parts such as the anther, pollen and microspores and the female parts such as the ovule, silks, embryo, and seed. And male Reproductive specific promoters are promoters that are active in cells destined to produce the male parts like pollen.

Seed specific promoters can be, for example, ovule-specific, embryo-specific, endosperm-specific, integument-specific, seed coat-specific, or some combination thereof. Examples include a promoter from the ovule-specific BEL1 gene described in Reiser et al., 1995 (GENBANK® Accession No. U39944). Non-limiting examples of seed specific promoters are derived from the following genes: MAC1 from maize (Sheridan et al., 1996); Cat3 from maize (GENBANK® Accession No. L05934; Abler et al., 1993); the gene encoding oleosin 18 kD from maize (GENBANK® Accession No. J05212; Lee & Huang, 1994); vivparous-1 from *Arabidopsis* (GENBANK® Accession No. U93215); the gene encoding oleosin from *Arabidopsis* (GENBANK® Accession No. Z17657); Atmycl from *Arabidopsis* (Urao et al., 1996); the 2s seed storage protein gene family from *Arabidopsis* (Conceicao et al., 1994); the gene encoding oleosin 20 kD from *Brassica napus* (GENBANK® Accession No. M63985); napA from *Brassica napus* (GENBANK® Accession No. J02798; Josefsson et al., 1987); the napin gene family from *Brassica napus* (Sjodahl et al., 1995); the gene encoding the 2S storage protein from *Brassica napus* (Dasgupta et al., 1993); the genes encoding oleosin A (GENBANK® Accession No. U09118) and oleosin B (GENBANK® Accession No. U09119) from soybean; and the gene encoding low molecular weight sulfur rich protein from soybean (Choi et al., 1995). Additional cell type- and/or tissue-specific promoters include, but are not limited to the *Triticum aestivum* pistil specific P19 promoter (see Japanese Patent Application JP 2001512988-A/13); the maize silk promoter prB200 (see Japanese Patent Application JP 001512988-A/13), the maize prCDPK-01 and prCDPK-02 promoters (Estruch et al., 1994); the rice α-N-acetylglucosaminidase (prOsANG) promoter (U.S. Pat. No. 7,550,578); the rice MADS box gene promoters prOsMADS1, prOsMADS2, prOsMADS6, prOsMADS7, prOsMADS14; and prOsMADS16 (U.S. Patent Application Publication Nos. 2007/0006344, 2010/0205692 A1, and 2012/0021506 A1); the rice anther-specific promoter prRA8 (see Japanese Patent Application JP 2001512988-A/13); the rice prOsG6 promoter (Tsuchiya et al., 1994); the whole seed-specific promoter disclosed in U.S. Patent Application Publication No. 2012/0036595; and the endosperm promoter disclosed in U.S. Patent Application Publication No. 2012/0036593.

Additional promoters that can be employed with the presently disclosed subject matter include, but are not limited to those described in U.S. Pat. No. 7,151,201; the PsEND1 promoter described in Roque et al., 2007; the corn stamen-specific promoters described in PCT International Patent Application Publication No. WO 1992/013957; and the *APETALA*3 promoter described in U.S. Pat. No. 7,253,340.

In some embodiments, an inducible promoter might be desired. Inducible promoters drive transcription in response to external stimuli such as chemical agents or environmental stimuli. For example, inducible promoters can confer transcription in response to hormones such as gibberellic acid or ethylene, or in response to light, heat or drought.

In some embodiments, an expression construct further comprises a transcription terminator operably linked to the nucleic acid of interest. These are responsible for the termination of transcription beyond the transgene and/or correct mRNA polyadenylation. A variety of transcriptional terminators are available for use in expression cassettes. The termination region can be native with respect to the transcriptional initiation region/promoter (i.e., the promoter and transcription terminator can be derived from the same genetic locus), can be native with the operably linked DNA sequence of interest, can be native with the plant host, and/or can be derived from another source (e.g., can be foreign or heterologous to the promoter, the DNA sequence of interest, the plant host, or any combination thereof). Exemplary transcriptional terminators are those that are known to function in plants and include the CAMV 35S terminator, the tml terminator, the nopaline synthase (Nos) terminator, and the pea rbcs E9 terminator. These can be used in both monocotyledons and dicotyledons. In addition, a gene's native transcription terminator can be used.

In some embodiments, an expression cassette comprises a selectable marker gene for the selection of transformed cells.

Additionally, various sequences have been found to enhance gene expression from within the transcriptional unit, and in some embodiments these sequences are used in conjunction with the nucleic acids of the presently disclosed subject matter to increase their expression in transgenic plants. For example, certain intron sequences have been shown to enhance expression, particularly in monocotyledonous cells. For example, the introns of the maize Adhl gene have been found to significantly enhance the expression of the wild type gene under its cognate promoter when introduced into maize cells. Intron 1 was found to be particularly effective and enhanced expression in fusion constructs with the chloramphenicol acetyltransferase gene (Callis et al., 1987). In the same experimental system, the intron from the maize bronze 1 gene had a similar effect in enhancing expression of an operably linked nucleic acid sequence. Intron sequences have been routinely incorporated into plant transformation vectors, typically within the non-translated leader.

Expression constructs of the presently disclosed subject matter can also comprise a leader sequence and/or a sequence allowing for inducible expression of the polynucleotide of interest. See e.g., Guo et al., 2003; Chen et al., 2003 for examples of sequences allowing for inducible expression.

A number of non-translated leader sequences derived from viruses are also known to enhance expression of operably linked nucleic acid sequences, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (see e.g., Gallie et al., 1987; Skuzeski et al., 1990). Other leader sequences known in the art include, but are not limited to, picornavirus leaders (e.g., the EMCV leader (the encephalomyocarditis 5'-noncoding region); Elroy-Stein et al., 1989); potyvirus leaders (e.g., the Tobacco Etch Virus (TEV) leader; Allison et al., 1986); the Maize Dwarf Mosaic Virus (MDMV) leader (see GENBANK® Accession No. NC_003377); the human immunoglobulin heavy-chain binding protein (BiP) leader (Macejak & Samow, 1991); the untranslated leader from the coat protein mRNA of alfalfa mosaic virus (AMV RNA 4; Jobling & Gehrke, 1987); the tobacco mosaic virus leader (TMV) leader (Gallie et al., 1989); and the Maize Chlorotic Mottle Virus (MCMV) leader (Lommel et al., 1991). See also, Della-Cioppa et al., 1987.

Alternatively or in addition, an expression construct of the present invention can include a presequence that directs the localization polypeptide encoded by the expression construct to an organelle within a plant cell. A nucleotide sequence encoding a presequence can be introduced in frame at the 5' end of a coding sequence in order to target the polypeptide encoded by the presequence/coding sequence hybrid to the target area. In some embodiments, the coding sequence encodes a subsequence or the entire sequence set forth in SEQ ID NO: 54. In some embodiments 454 amino acids of SEQ ID NO: 54 or a subsequence thereof that comprised amino acids non HI trait or less consecutive amino acids or more consecutive amino acids or an amino acid sequence that is 95% identical thereto can be fused to any presequence using standard molecular cloning techniques.

The transformation of non HI; or HI germplasm can include transformants in monocots and dicots which may be for example orthologs. Species that have orthologues to this sequence can readily be employed in the transformation process these include but are not limited to the species: *Sorghum bicolor*, maize, wheat, millet, *Setaria Italica, Oryza brachyantha, Oryza indica, Oryza glaberrima, Hordeum vulgare, Oryza sativa, Solanum lycopersicum* (tomato), and *Brachypodium distachyon.*

In some embodiments, the presently disclosed subject matter provides markers for detecting and/or assaying for the presence or absence of gene products associated with HI in a plant cell or other source of biomolecules. In some embodiments, a marker is intended to detect the presence of a nucleic acid molecule that includes the deletion junction where the maize HI sequences show an insertion in the sequence in SEQ ID NO. 53 to allow for the specific detection of the presence or absence of a chimeric nucleic acid comprising SEQ ID NO: 33, SEQ ID NO: 37, SEQ ID NO: 52 or SEQ ID NO: 53 in a sample. The number of nucleotides 5' and/or 3' of the deletion junction that allow for specific detection of the presence of absence of a chimeric nucleic acid comprising SEQ ID NO: 53 in a sample can vary based on the identification method employed, but can be in some embodiments at least about 5 nucleotides, in some embodiments at least about 10 nucleotides, in some embodiments at least about 15 nucleotides, in some embodiments at least about 20 nucleotides, in some embodiments at least about 25 nucleotides, and in some embodiments at least about 50 nucleotides 5' and/or 3' to the insertion junction on either side of nucleotides 1230-1233 in SEQ ID NO: 53 should have fit within the HI Locus and does appear in the nonHI locus at this position. In some embodiments, an informative fragment of SEQ ID NO: 33, SEQ ID NO: 37, SEQ ID NO: 52 or SEQ ID NO: 53 can be a marker as defined herein below. A marker which tracks the lesion which causes the phenotype will be superior to any marker which is meerly linked because the marker to the causative lesion will never disassociate from the phenotype. Linked markers can and become disassociated by a recombination event.

The presently disclosed subject matter also provides reagents for use in detecting and/or assaying for the presence of gene products associated with HI in a plant cell or other source of biomolecules. Such reagents can include in some embodiments an amplification primer pair capable of amplifying a plant nucleic acid template to generate a marker amplicon, wherein the marker amplicon corresponds to a marker comprising an informative subsequence of SEQ ID NO: 33, SEQ ID NO: 37, SEQ ID NO: 52 or SEQ ID NO: 53, wherein the informative subsequence permits identification of the presence or absence of an allele associated with HI in a plant. By way of example and not limitation, such a amplification primer pair can be designed with a forward primer that is located 5' to the fusion junction and a reverse primer that is located 3' to the fusion junction present in SEQ ID NO: 53. Such an amplification primer pair would not be expected to amplify a gene product derived from a wildtype maize non HI locus.

In some embodiments, one or more amplification primer pairs of the presently disclosed subject matter are provided in the form of a kit, wherein the kit further comprises one or more positive and/or negative amplification primer pairs (such as but not limited to an amplification primer pair designed to amplify a wild type (HI) gene product), instructions for employing the amplification primer pairs, and/or one or more additional reagents necessary for performing an amplification reaction (e.g., a DNA polymerase, a reverse transcriptase, a buffer solution, etc.).

Thus, in some embodiments, a method for detecting and/or assaying for the presence of gene products associated with HI in a plant cell or other source of biomolecules can employ the polymerase chain reaction (PCR) using appropriately designed primers to detect the presence in a plant cell or other source of biomolecules of a gene product associated with HI (including, but not limited to a gene product comprising SEQ ID NO: 33, SEQ ID NO: 37, SEQ ID NO: 52 or SEQ ID NO: 53 or an informative fragment thereof. It is understood that other molecular biological techniques can also be employed for this purpose including, but not limited to TAQMAN® assays, KASPAR™ assays, ILLUMINA® GOLDENGATE® assays, etc.

In some embodiments, the presently disclosed subject matter provides methods for diagnostic determination of whether a plant having such DNA will or will not exhibit HI and/or producing plants that exhibit HI. In some embodiments, the methods comprise (a) transforming a plant cell with an expression cassette as disclosed herein to produce a transformed plant cell; and (b) generating a plant from the transformed plant cell.

In some embodiments, a plant cell is stably transformed with an expression cassette of the presently disclosed subject matter. "Stable transformation" or "stably transformed" is intended to mean that a polynucleotide, for example, an expression cassette as described herein, introduced into a plant integrates into the genome of the plant and is capable of being inherited by the progeny thereof, more particularly, by the progeny of multiple successive generations.

Numerous transformation vectors available for plant transformation are known to those of ordinary skill in the plant transformation arts, and the nucleic acids pertinent to the presently disclosed subject matter can be used in conjunction with any such vectors. The selection of a vector will depend upon the transformation technique to be employed and the target species for transformation. For certain target species, different antibiotic or herbicide selection markers might be preferred. Selection markers used routinely in transformation include the nptII gene, which confers resistance to kanamycin and related antibiotics (Viera & Messing, 1982; Bevan et al., 1983); the pat and bar genes, which confer resistance to the herbicide glufosinate (also called phosphinothricin; see White et al., 1990; Spencer et al., 1990; and U.S. Pat. Nos. 5,561,236 and 5,276,268); the hph gene, which confers resistance to the antibiotic hygromycin (Blochinger & Diggelmann, 1984), and the dhfr gene, which confers resistance to methatrexate (Bourouis & Jarry, 1983); the EPSPS gene, which confers resistance to glyphosate (U.S. Pat. Nos. 4,940,935 and 5,188,642); the glyphosate N-acetyltransferase (GAT) gene, which also confers resistance to glyphosate (Castle et al., 2004; U.S. Patent Application Publication Nos. 2005/0060767, 2005/0246798, and 2007/0004912); and the mannose-6-phosphate isomerase gene, which provides the ability to metabolize mannose (U.S. Pat. Nos. 5,767,378 and 5,994,629), the gene encoding a mutant D-amino acid oxidase which can be derived from *Rhodotorula gracilis*, with a lysine at position 58 rather than a phenylalanine which interacts with D-phosphinothricin to produce a toxin (U.S. Pat. No. 7,939,709).

Thus, in some embodiments the presently disclosed subject matter relates to inducing HI in a plant. In some embodiments, a general technique for producing plants that exhibit HI comprises transforming a plant cell with an expression cassette to produce a transformed plant cell, wherein the expression cassette encodes an RNAi construct targeted to a gene associated with HI; and (b) generating a plant from the transformed plant cell. After a plant cell is transformed with an expression vector or expression cassette encodes an RNAi construct targeted to a gene associated with HI, a whole plant or plant tissue can be regenerated, if desired. Methods for regeneration of plants are also well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

Many vectors are available for transformation using *Agrobacterium tumefaciens*. These typically carry at least one T-DNA border sequence and include vectors such as pBIN19

(Bevan, 1984). For the construction of vectors useful in *Agrobacterium* transformation, see e.g., U.S. Patent Application Publication No. 2006/0260011. See also Lee & Glevin, 2008.

Transformation without the use of *Agrobacterium tumefaciens* circumvents the requirement for T-DNA sequences in the chosen transformation vector and consequently vectors lacking these sequences can be utilized in addition to vectors such as the ones described above which contain one or more T-DNA sequences. Transformation techniques that do not rely on *Agrobacterium* include transformation via particle bombardment, protoplast uptake (e.g., PEG and electroporation), whiskering, and microinjection. The choice of vector depends largely on the chosen selection for the species being transformed. For the construction of such vectors, see e.g., U.S. Patent Application Publication No. 2006/0260011.

For expression of a nucleotide sequence of the presently disclosed subject matter in plant plastids, plastid transformation vector pPH143 (PCT International Patent Application Publication No. WO 1997/32011, example 36) can be used. The nucleotide sequence is inserted into pPH143 thereby replacing the PROTOX coding sequence.

Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, and/or microinjection. Examples of these techniques are described by Paszkowski et al., 1984; Potrykus et al., 1985; Reich et al., 1986; and Klein et al., 1987. In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium* transformation typically involves the transfer of the binary vector carrying the foreign DNA of interest (e.g., pCIB200 or pCIB2001) to an appropriate *Agrobacterium* strain which may depend of the complement of vir genes carried by the host *Agrobacterium* strain either on a co-resident Ti plasmid or chromosomally (e.g., strain CIB542 for pCIB200 and pCIB2001 (Uknes et al., 1993). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Hofgen & Willmitzer, 1988).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. Variations of this technique are disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium, or a bacteriophage, each containing DNA sought to be introduced) can also be propelled into plant cell tissue.

Transformation of most monocotyledon species has now also become routine. Exemplary techniques include direct gene transfer into protoplasts using PEG or electroporation techniques, and particle bombardment into callus tissue. Transformations can be undertaken with a single DNA species or multiple DNA species (i.e., co-transformation), and both of these techniques are suitable for use with the presently disclosed subject matter. Co-transformation can have the advantage of avoiding complete vector construction and of generating transgenic plants with unlinked loci for the gene of interest and the selectable marker, thereby permitting the removal of the selectable marker in subsequent generations, should this be regarded desirable. However, a disadvantage of the use of co-transformation can be the less than 100% frequency with which separate DNA species are integrated into the genome (Schocher et al. Biotechnology 4: 1093-1096 (1986)).

European Patent Applications EP 0 292 435 and EP 0 392 225, and PCT International Patent Application Publication No. WO 1993/07278 describe techniques for the preparation of callus and protoplasts from an elite inbred line of maize, transformation of protoplasts using PEG or electroporation, and the regeneration of maize plants from transformed protoplasts. Gordon-Kamm et al., 1990) and Fromm et al., 1990 have published techniques for transformation of A188-derived maize line using particle bombardment. Furthermore, PCT International Patent Application Publication No. WO 1993/07278 and Koziel et al., 1993 describe techniques for the transformation of elite inbred lines of maize by particle bombardment. This technique utilizes immature maize embryos of 1.5-2.5 mm length excised from a maize ear 14-15 days after pollination and a BIOLISTIC® PDS-1000/He (Bio-Rad Laboratories, Hercules, Calif., United States of America) device for bombardment.

Transformation of rice can also be undertaken by direct gene transfer techniques utilizing protoplasts or particle bombardment. Protoplast-mediated transformation has been described for Japonica-types and Indica-types (Zhang et al., 1988; Shimamoto et al., 1989; Datta et al., 1990). Both types are also routinely transformable using particle bombardment (Christou et al., 1991). Furthermore, PCT International Patent Application Publication No. WO 1993/21335 describes techniques for the transformation of rice via electroporation.

European Patent Application EP 0 332 581 describes techniques for the generation, transformation and regeneration of *Pooideae* protoplasts. These techniques allow the transformation of *Dactylis* and wheat. Furthermore, wheat transformation has been described by Vasil et al., 1992 using particle bombardment into cells of type C long-term regenerable callus, and also by Vasil et al., 1993 and Weeks et al., 1993 using particle bombardment of immature embryos and immature embryo-derived callus. An exemplary technique for wheat transformation, however, involves the transformation of wheat by particle bombardment of immature embryos and includes either a high sucrose or a high maltose step prior to gene delivery. Prior to bombardment, any number of embryos (0.75-1 mm in length) are plated onto MS medium with 3% sucrose (Murashige & Skoog, 1962) and 3 mg/l 2,4-D for induction of somatic embryos, which is allowed to proceed in the dark. On the chosen day of bombardment, embryos are removed from the induction medium and placed onto the osmoticum (i.e., induction medium with sucrose or maltose added at the desired concentration, typically 15%). The embryos are allowed to plasmolyze for 2-3 hours and are then bombarded. Twenty embryos per target plate is typical, although not critical. An appropriate gene-carrying plasmid (such as pCIB3064 or pSOG35) is precipitated onto micrometer size gold particles using standard procedures. Each plate of embryos is shot with the DuPont BIOLISTICS® helium device using a burst pressure of about 1000 psi using a standard 80 mesh screen. After bombardment, the embryos are placed back into the dark to recover for about 24 hours (still on osmoticum). After 24 hours, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Transformation of monocotyledons using *Agrobacterium* has also been described. See e.g., PCT International Patent Application Publication No. WO 1994/00977 and U.S. Pat. No. 5,591,616. See also Negrotto et al., Plant Cell Reports 19: 798-803 (2000), incorporated herein by reference.

For example, rice (*Oryza sativa*) can be used for generating transgenic plants. Various rice cultivars can be used (Hiei et al., 1994; Dong et al., 1996; Hiei et al., 1997). Also, the various media constituents described below can be either varied in quantity or substituted. Embryogenic responses are initiated and/or cultures are established from mature embryos by culturing on MS-CIM medium (MS basal salts, 4.3 g/liter; B5 vitamins (200×), 5 ml/liter; Sucrose, 30 g/liter; proline, 500 mg/liter; glutamine, 500 mg/liter; casein hydrolysate, 300 mg/liter; 2,4-D (1 mg/ml), 2 ml/liter; adjust pH to 5.8 with 1 N KOH; PHYTAGEL™ plant tissue culture reagent, 3 g/liter). Either mature embryos at the initial stages of culture response or established culture lines are inoculated and co-cultivated with the *Agrobacterium tumefaciens* strain LBA4404 (*Agrobacterium*) containing the desired vector construction. *Agrobacterium* is cultured from glycerol stocks on solid YPC medium (100 mg/L spectinomycin and any other appropriate antibiotic) for about 2 days at 28° C. *Agrobacterium* is resuspended in liquid MS-CIM medium. The *Agrobacterium* culture is diluted to an $OD_{600}$ of 0.2-0.3 and acetosyringone is added to a final concentration of 200 μM. Acetosyringone is added before mixing the solution with the rice cultures to induce *Agrobacterium* for DNA transfer to the plant cells. For inoculation, the plant cultures are immersed in the bacterial suspension. The liquid bacterial suspension is removed and the inoculated cultures are placed on co-cultivation medium and incubated at 22° C. for two days. The cultures are then transferred to MS-CIM medium with Ticarcillin (400 mg/liter) to inhibit the growth of *Agrobacterium*. For constructs utilizing the PMI selectable marker gene (Reed et al., 2001), cultures are transferred to selection medium containing Mannose as a carbohydrate source (MS with 2% Mannose, 300 mg/liter Ticarcillin) after 7 days, and cultured for 3-4 weeks in the dark. Resistant colonies are then transferred to regeneration induction medium (MS with no 2,4-D, 0.5 mg/liter IAA, 1 mg/liter zeatin, 200 mg/liter timentin, 2% Mannose, and 3% Sorbitol) and grown in the dark for 14 days. Proliferating colonies are then transferred to another round of regeneration induction media and moved to the light growth room. Regenerated shoots are transferred to GA7 containers with GA7-1 medium (MS with no hormones and 2% Sorbitol) for 2 weeks and then moved to the greenhouse when they are large enough and have adequate roots. Plants are transplanted to soil in the greenhouse (To generation) grown to maturity, and the Ti seed is harvested.

The plants obtained via transformation with a nucleic acid sequence of interest in the presently disclosed subject matter can be any of a wide variety of plant species, including those of monocots and dicots. The plants used in the methods of the presently disclosed subject matter are in some embodiments selected from the list of agronomically important target crops set forth elsewhere herein. The expression of a nucleic acid of the presently disclosed subject matter in combination with other characteristics important for production and quality can be incorporated into plant lines through breeding. Breeding approaches and techniques are known in the art. See e.g., Welsh, 1981; Wood, 1983; Mayo, 1987; Singh, 1986; and Wricke & Weber, 1986.

For the transformation of plastids, seeds of *Nicotiana tabacum* c.v. "Xanthienc" are germinated seven per plate in a 1" circular array on T agar medium and bombarded 12-14 days after sowing with 1 um tungsten particles (M10, Biorad Laboratories, Hercules, Calif., United States of America) coated with DNA from plasmids pPH143 and pPH145 essentially as described in Svab & Maliga, 1993. Bombarded seedlings are incubated on T medium for two days after which leaves are excised and placed abaxial side up in bright light (350-500 μmol photons/$m^2$/s) on plates of RMOP medium (see Svab et al., 1990) containing 500 μg/ml spectinomycin dihydrochloride (Sigma, St. Louis, Mo., United States of America). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (see Sambrook & Russell, 2001). BamHI/EcoRI-digested total cellular DNA (Mettler, 1987) is separated on 1% Tris-borate (TBE) agarose gels, transferred to nylon or nitrocellulose membranes, and probed with $^{32}P$-labeled random-primed DNA sequences corresponding to a 0.7 kb BamHI/HindIII DNA fragment from pC8 containing a portion of the rps 7/12 plastid targeting sequence. Homoplasmic shoots are rooted aseptically on spectinomycin-containing MS/IBA medium (McBride et al., 1994) and transferred to the greenhouse.

To test the haploid induction capacity of newly created lines, the pollen from each line is to be crossed onto an ear to induce fertilization, and the resulting progeny of the cross subjected to ploidy analysis. Ploidy analysis can be defined in this case as any experimental test where the ploidy level of an individual plant is determined. In crosses between two non-inducing lines, the resulting progeny should be almost exclusively diploid, or 2N. However, if a haploid induction line is the male parent, the resulting progeny will be a mixed population of haploids (1N), diploids (2N), aneuploids (somewhere between 1N and 2N), and chimeras (containing tissues with mixed ploidy). The determination of haploid induction capacity can be made binary by setting a cutoff value for the haploid induction rate, which is defined as the number of haploid embryos over the total number of viable embryos. The rate should be at least greater than 0.5%, and for high stringency, a good cutoff off is greater than 1% haploids. This is because a natural 'background' haploid induction rate of around 0.1% exists in maize. Because haploidy is only induced through the male parent during in vivo maize haploid induction, the female simply serves as a "tester" and thus, the female germplasm could be any number of lines. The female tester could be the inducer line itself (and the cross would thus be a self hybridization), or the tester could be any inbred, hybrid, or backcrossed maize line. The ploidy analysis can involve different methods, as described below.

One method of plant ploidy analysis is to evaluate the phenotypic characteristics of the plant, paying attention to those characteristics associated with haploidy, including but not limited to short plant stature, altered phylotaxy, smaller leaf width, low overall body mass, and male sterility. Plants could be given a score on each characteristic and then the scores could be added together and compared to known haploid and diploid controls. In another embodiment, the embryos resulting from a haploid induction cross may be extracted mechanically from immature kernels anytime between day 9 and day 20 after pollination, and then subjected to ploidy analysis by a ploidy analyzer (Partec) which uses DAPI stain combined with flow cytometry to quantify the total DNA amount per cell. In one embodiment, embryonic and/or scutellar tissue is used for processing; in another embodiment, adult plant tissues including roots, leaves, stems, or flowers are used. In one embodiment, the selected tissues are chopped up with a razor blade, incubated in an extraction buffer, filtered through a nylon mesh filter and then incubated in a DAPI stain before loading into the ploidy analyzer. In another embodiment, embryonic or adult tissue including those described above is first digested into protoplasts using a combination of cellulose and maceroenzyme in a buffer solution, then filtered and incubated in DAPI.

In yet another method of ploidy analysis, microscopic imaging of mature, juvenile, or embryonic plant tissues can be used to identify the ploidy by counting the number of chromosomes in certain cells that are undergoing mitosis. The DNA in this case may be stained with DAPI or any other common DNA stain such as propidium iodide. In maize a diploid plant will have 20 chromosomes per cell while a haploid plant will have 10 per cell. In such an approach, the embryos can be incubated on media for anywhere from zero to fourteen days, during which many embryos may germinate and grow small rootlets.

Alone or in combination with any of the ploidy analysis methods described above, the putative novel haploid induction line may be first crossed to a marker line, including but not limited to lines that contain the R1-navajo (R1-nj) or R1-scutellum2 (R1-Scm2) markers, or any line having DNA that encode for protein products that confer a visual identifier, such as a color visible to the human eye (e.g. anthocyanin) or a fluorescence-based marker visible only via fluorescent microscopy. Such markers, having been introgressed into the putative haploid inducer line, can serve as evidence of the existence of the paternal genome in progeny indicating a diploid state, with absence indicating a haploid state. The presence or absence of the marker may be detected using a visual test or microscopy.

The presently disclosed subject matter also provides methods for identifying the presence or absence of an allele associated with HI in a plant. In some embodiments, the methods comprise (a) obtaining a sample from the plant comprising genomic and/or nuclear DNA and/or an RNA product derived therefrom; (b) contacting the sample with a pair of primers that, when used in a nucleic-acid amplification reaction with a nucleic acid sample from the plant, produces an amplicon that can be used to identify the presence or absence of an allele associated with HI; (c) amplifying a fragment from said sample using the primer pair of (b), wherein the primer pair is complementary and binds to the nucleotide sequence of (b); and (d) detecting an amplicon that can be used to identify the presence or absence of an allele associated with HI in the plant.

The presently disclosed subject matter also provides methods for introgressing HI-inducing nucleotide sequences into plants. In some embodiments, the methods comprise crossing a first plant with a second plant to produce a third plant, wherein the genome of the first plant or the second plant comprises a recombinant nucleic acid sequence encoding a HI-associated gene product of the presently disclosed subject matter. In some embodiments, the methods further comprise assaying the genome of the third plant for the presence of the recombinant nucleic acid sequence encoding the HI-associated gene product. In some embodiments, the recombinant nucleic acid comprises (a) a nucleic acid having at least 90% identity to SEQ ID NO: 33, optionally wherein the percent identity is calculated over the entire length of SEQ ID NO: 33; (b) a nucleic acid having at least 95% identity over nucleotides 91-1452 of SEQ ID NO: 33; (c) a nucleic acid that is the reverse complement of either of (a) or (b); (d) a nucleic acid that encodes a polypeptide comprising an amino acid sequence that is at least 95% identical to SEQ ID NO: 54, SEQ ID NO: 55, SEQ ID NO: 56 or SEQ ID NO: 57 optionally wherein the percent identity is calculated over the entire length of SEQ ID NO: 54, SEQ ID NO: 55, SEQ ID NO: 56 or SEQ ID NO: 57 respectively; and, (e) a sequence having at least 90% identity to SEQ ID NO: 32, optionally wherein the percent identity is calculated over the entire length of SEQ ID NO: 32; (f) a sequence having at least 95% identity over nucleotides 1-1795 of SEQ ID NO: 32; (g) a nucleic acid sequence that is the reverse complement of either of (e) or (f). In some embodiments, the recombinant nucleic acid encodes an amino acid sequence that comprises all or substantially all of amino acids 1-454 of SEQ ID NO: 54.

The presently disclosed subject matter also provides methods for selecting $F_0$ parental plants that are predicted to produce subsequent (e.g., $F_1$, $F_2$, $F_3$, etc.) generations with plants that exhibit HI. In some embodiments, the methods comprise identifying in the absence of sequence in the genome of an $F_0$ plant a nucleic acid comprising a sequence selected from the group consisting of The presently disclosed subject matter also provides kits for detecting the presence or absence of a HI-inducing allele in a plant. In some embodiments, the kits comprise one or more nucleic acid- and/or amino acid-based reagents derived from the maize HI locus or from a locus linked thereto, wherein the one or more nucleic acid- and/or amino acid-based reagents are designed to be employed in a nucleic acid- and/or amino acid-based assay for the presence or absence in the plant (a) a nucleic acid having at least 90% identity to SEQ ID NO: 33, optionally wherein the percent identity is calculated over the entire length of SEQ ID NO: 33; (b) a nucleic acid having at least 95% identity over nucleotides 91-1452 of SEQ ID NO: 33; (c) a nucleic acid that is the reverse complement of either of (a) or (b); (d) a nucleic acid that encodes a polypeptide comprising an amino acid sequence that is at least 95% identical to SEQ ID NO: 54, SEQ ID NO: 55, SEQ ID NO: 56 or SEQ ID NO: 57 optionally wherein the percent identity is calculated over the entire length of SEQ ID NO: 54, SEQ ID NO: 55, SEQ ID NO: 56 or SEQ ID NO: 57 respectively; and, (e) a sequence having at least 90% identity to SEQ ID NO: 32, optionally wherein the percent identity is calculated over the entire length of SEQ ID NO: 32; (f) a sequence having at least 95% identity over nucleotides 1-1795 of SEQ ID NO: 32; (g) a nucleic acid sequence that is the reverse complement of either of (e) or (f). In some embodiments, the recombinant nucleic acid encodes an amino acid sequence that comprises all or substantially all of amino acids 1-454 of SEQ ID NO: 54.

In some embodiments, the one or more nucleic acid- and/or amino acid-based reagents derived from the maize HI locus or from a locus linked thereto comprise one or more oligonucleotide primers that are diagnostic of the presence in the plant of in the plant of the nucleic acid having at (a) a nucleic acid having at least 90% identity to SEQ ID NO: 33, optionally wherein the percent identity is calculated over the entire length of SEQ ID NO: 33; (b) a nucleic acid having at least 95% identity over nucleotides 91-1452 of SEQ ID NO: 33; (c) a nucleic acid that is the reverse complement of either of (a) or (b); (d) a nucleic acid that encodes a polypeptide comprising an amino acid sequence that is at least 95% identical to SEQ ID NO: 54, SEQ ID NO: 55, SEQ ID NO: 56 or SEQ ID NO: 57 optionally wherein the percent identity is calculated over the entire length of SEQ ID NO: 54, SEQ ID NO: 55, SEQ ID NO: 56 or SEQ ID NO: 57 respectively; and, (e) a sequence having at least 90% identity to SEQ ID NO: 32, optionally wherein the percent identity is calculated over the entire length of SEQ ID NO: 32; (f) a sequence having at least 95% identity over nucleotides 1-1795 of SEQ ID NO: 32; (g) a nucleic acid sequence that is the reverse complement of either of (e) or (f). In some embodiments, the recombinant nucleic acid encodes an amino acid sequence that comprises all or substantially all of amino acids 1-454 of SEQ ID NO: 54.

As used herein, a "nucleic acid- or amino acid-based reagent" of the presently disclosed subject matter refers to any nucleic acid, peptide, or polypeptide that can be used to detect the presence or absence of SEQ ID NO: 33, SEQ ID NO: 37, SEQ ID NO: 52 or SEQ ID NO: 53 or an informative fragment thereof in a plant in any type of assay. By way of example and not limitation, a nucleic acid-based reagent of the presently disclosed subject matter can be an oligonucleotide primer pair that is designed to flank the deletion junction such that an amplification product will occur only if (a) a nucleic acid having at least 90% identity to SEQ ID NO: 33, optionally wherein the percent identity is calculated over the entire length of SEQ ID NO: 33; (b) a nucleic acid having at least 95% identity over nucleotides 91-1452 of SEQ ID NO: 33; (c) a nucleic acid that is the reverse complement of either of (a) or (b); (d) a nucleic acid that encodes a polypeptide comprising an amino acid sequence that is at least 95% identical to SEQ ID NO: 54, SEQ ID NO: 55, SEQ ID NO: 56 or SEQ ID NO: 57 optionally wherein the percent identity is calculated over the entire length of SEQ ID NO: 54, SEQ ID NO: 55, SEQ ID NO: 56 or SEQ ID NO: 57 respectively; and, (e) a sequence having at least 90% identity to SEQ ID NO: 32, optionally wherein the percent identity is calculated over the entire length of SEQ ID NO: 32; (f) a sequence having at least 95% identity over nucleotides 1-1795 of SEQ ID NO: 32; (g) a nucleic acid sequence that is the reverse complement of either of (e) or (f). In some embodiments, the recombinant nucleic acid encodes an amino acid sequence that comprises all or substantially all of amino acids 1-454 of SEQ ID NO: 54.

Similarly, an amino acid-based reagent of the presently disclosed subject matter can be, but is not limited to, an antibody that binds to a polypeptide having SEQ ID NO: 54, SEQ ID NO: 55, SEQ ID NO: 56 or SEQ ID NO: 57 or an informative fragment thereof. In some embodiments, an antibody that binds to both a polypeptide of SEQ ID NO: 54, SEQ ID NO: 55, SEQ ID NO: 56 or SEQ ID NO: 57 and a maize HI gene product can be employed, wherein in an appropriate assay (e.g., a Western blot or an SDS-PAGE gel), the polypeptide of SEQ ID NO: 54, SEQ ID NO: 55, SEQ ID NO: 56 or SEQ ID NO: 57 and its absence or presence shows the maize HI gene product can be distinguished. In some embodiments, the kit further comprises a set of instructions for performing an assay with the nucleic acid- or amino acid-based reagent. In some embodiments, the kit further comprises one or more additional reagents that can be employed in the performance of the assay with the nucleic acid- or amino acid-based reagent.

EXAMPLES

The following Examples provide illustrative embodiments of the presently disclosed subject matter. In light of the present disclosure and the general level of skill in the art, those of skill will appreciate that the following examples are intended to be exemplary only and that numerous changes, modifications, and alterations can be employed without departing from the scope of the presently disclosed subject matter.

Example 1

QTL Mapping Material Choices

Two mapping populations involving a haploid inducer inbred (RWK) and two non-inducer inbreds (NP2391, NP2460) were generated. RWK was selected because of its high haploid induction ability compared to stock 6. The two non-inducer lines were selected due to existence of extensive data relevant to them. The recombinant inbred populations were backcross populations (BC1) such that the theoretical allele content was 75% RWK and 25% NP2391 for the first population (138 RILs, Recombinant Inbred Lines) and 75% RWK and 25% NP2460 for the second population (123 RILs). The mapping populations were self-pollinated two generations to make the BC1F3. The subsequent BC1F4 plants were testcrossed onto eight plants in two tester rows. The testcrosses were harvested and bulk shelled. Approximately 500 kernels of testcross seed were planted for each entry to observe the number of haploid and diploid plants and thereby determine the haploid induction rate of each recombinant inbred entry within that population.

QTL analysis was performed for both the populations using a version of "QTL Cartographer" software by combining the testcross induction rates with the SNP genotyping data of RILs. QTLs were declared when the LOD score is higher than 2. In total about ~70% variation in haploid induction rate was explained by QTL Bin 1.04. A number of other QTLs were also detected but these accounted for less of the variation. The two important values in QTL studies are the LOD (logarithm of odds) and the $R^2$. A high LOD value represents greater statistical evidence for the present of a QTL, and a higher $R^2$ indicates that the particular QTL has more effect on the trait of interest. The major QTL detected was on Chromosome 1, in a somewhat different region of Chromosome 1 than what was previously indicated by a patent application publication. Additional information about the fine mapping is provided in the subsequent examples.

Breeding—Mapping Strategy

| Season | What | Result |
|---|---|---|
| Year 0 | F1 | Two non-inducers inbreds (NP2391; P2460) were crossed with RWK |
| Year 0 | F1 -> BC1 | Both F1 backcrossed to RWK |
| Year 1 | BC1F1 -> BC1F2 | |
| Year 1 | BC1F2 -> BC1F3 | |
| Year 1 | BC1F4 testcrosses made X 2 Two testers | mapping Populations x two testers |
| Year 1 | BC1F4 testcrosses phenotyped | QTL Bin 1.04 identified, ~70% variation explained |
| Year 1 | BC2 made | |
| Year 2 | BC3 made | |
| Year 2 | BC3F2 made | |
| Year 2 | BC3F3 testcrosses made X 2 testers | Two fine mapping Populations X two testers |
| Year 3 | BC3F3 testcrosses phenotyped | First fine mapping completed |
| Year 3 | BC3F4 testcrosses made X 2 testers | |
| Year 3 | BC3F4 testcrosses phenotyped | Second fine mapping completed |
| Year 4 | BC3F5 testcrosses made X 2 testers | |
| Year 5 | BC3F5 testcrosses phenotyped | Fine mapping completed |
| Year 5 | RWK, RWK-NIL, Stock 6 gemones sequences | Annotations |

Example 2

Development of Near Isogenic Lines

To accurately position and fine-map the QTL for Haploid induction, near isogenic lines (NIL's) are created by back-crossing to RWK for three generations and followed by selfing for another 3 generations. During this process several NIL's were created in RWK background with regions from NP2391 and NP2460 in the target QTL region. This particular strategy was utilized to create NIL's because, haploid induction efficiency can change with the background and also to keep the rest of the RWK genome mostly uniform while focusing on the small non-inducer chromosome regions that were back-crossed into RWK.

Example 3

Fine Mapping

When the experiment was initiated, the haploid induction locus was localized in a region of 3.3 MB containing approximately 90 putative genes within that interval. The fine mapping process reduced the haploid induction locus to a 0.88 MB region with twenty five annotated genes. Additional fine mapping reduced the haploid induction locus to a 0.60 region.

The BC3F3 plants described in the above examples, which were heterozygous at the region of interest were selfed to create additional recombinations. These BC3F4 recombinants were testcrossed with two different testers and phenotypic information was gathered by measuring their haploid induction (HI) ability. The genotypic information from this localized haploid induction region and the phenotypic information taken concerning these line's haploid induction ability were correlated to fine-map the haploid induction locus to a 0.60 MB region with fewer than 7 annotated genes.

TABLE ON FINE MAPPING

| Old interval | New Confidence interval | Refined interval | Gene_ID | transcript_start | transcript_end | transcript_strand |
|---|---|---|---|---|---|---|
| x | x | x | GRMZM2G305400 | 67991172 | 67994092 | −1 |
| x | x | x | GRMZM2G082836 | 68107606 | 68110989 | 1 |
| x | x | x | GRMZM2G382717 | 68113455 | 68115168 | −1 |
| x | x | x | GRMZM2G120587 | 68133178 | 68136953 | −1 |
| x | x | x | GRMZM2G471240 | 68240862 | 68242656 | 1 |
| x | x | x | GRMZM2G471240 | 68240862 | 68242656 | 1 |
| x | x | x | GRMZM2G062320 | 68318898 | 68321409 | 1 |
| x | x | | GRMZM5G866758 | 68430654 | 68436197 | 1 |
| x | x | | GRMZM5G866758 | 68430654 | 68436197 | 1 |
| x | x | | GRMZM2G003530 | 68435670 | 68439997 | −1 |
| x | | | GRMZM2G077991 | 68543246 | 68546264 | −1 |
| x | | | GRMZM2G077991 | 68543694 | 68546264 | −1 |
| x | | | GRMZM2G077991 | 68543805 | 68546269 | −1 |
| x | | | GRMZM2G077960 | 68554980 | 68559182 | 1 |
| x | | | GRMZM2G077897 | 68561209 | 68565155 | −1 |
| x | | | GRMZM2G347583 | 68660278 | 68665995 | 1 |
| x | | | GRMZM2G173030 | 68668900 | 68671460 | 1 |
| x | | | GRMZM2G022061 | 68876150 | 68882226 | 1 |
| x | | | GRMZM2G022061 | 68876150 | 68882226 | 1 |
| x | | | GRMZM2G022061 | 68876150 | 68882226 | 1 |
| x | | | GRMZM2G022061 | 68876150 | 68882226 | 1 |
| x | | | GRMZM2G022061 | 68876150 | 68882226 | 1 |
| x | | | GRMZM2G340286 | 68928213 | 68929600 | 1 |
| x | | | GRMZM2G340279 | 68934652 | 68937080 | −1 |
| x | | | GRMZM2G347808 | 69005208 | 69012612 | 1 |

Example 4

Markers for Refining Fine Mapping

The Table shown in example four shows the marker or locus name on the far left of the table. The limiting factor for further refining the locus was the availability of markers and not the maize line recombinants. Thus additional taqman assays were developed for gathering genotypic information from the haploid induction region. The Table shows the SNPs and their map positions. Each of these markers identifies an allele. The desirable nucleotides for a haploid inducing allele in the RWK (haploid inducing line) are also listed. These markers can be utilized in a marker assisted breeding program to select for or against the haploid induction ability in germplasm.

MARKER TABLE

| Marker or Locus Name | Chromosome | Map Position | RWK Allele |
|---|---|---|---|
| SM0262A | 1 | 45441103 | G/G |
| SM0390D | 1 | 45514003 | G/G |
| SM0657AQ | 1 | 56221199 | A/A |
| SM0103A | 1 | 60144794 | A/A |
| SM2317 | 1 | 60806574 | G/G |
| SM2318 | 1 | 60808690 | A/A |
| SM2315 | 1 | 60834691 | A/A |
| SM2322 | 1 | 61019467 | G/G |
| SM1994CQ | 1 | 61940683 | C/C |
| SM1994AQ | 1 | 61948232 | A/A |
| SM2014DQ | 1 | 62141179 | A/A |
| SM2014CQ | 1 | 62141297 | G/G |
| SM1208A | 1 | 62890212 | C/C |
| SM1208BQ | 1 | 62890343 | C/C |
| SM2332 | 1 | 62890343 | C/C |
| SM2331 | 1 | 62918261 | C/C |
| SM2542 | 1 | 65086371 | A/A |
| SM2543 | 1 | 65086379 | A/A |
| SM2547 | 1 | 65086882 | C/C |
| SM2548 | 1 | 65087687 | G/G |
| SM2359 | 1 | 65222457 | C/C |
| SM2366 | 1 | 65223245 | C/C |
| SM2333 | 1 | 65657736 | G/G |
| SM2338 | 1 | 66955942 | C/C |
| SM2340 | 1 | 67130654 | G/G |
| SM2339 | 1 | 67130683 | A/A |
| SM2356 | 1 | 67645465 | A/A |
| SM2357 | 1 | 67645486 | G/G |
| SM2361 | 1 | 67850657 | G/G |
| SM2363 | 1 | 67851018 | A/A |
| SM2587 | 1 | 68128675 | A/A |
| SM2589 | 1 | 68128928 | G/G |
| SM2593 | 1 | 68129217 | G/G |
| SM2594 | 1 | 68129237 | C/C |
| SM2602 | 1 | 68130522 | A/A |
| SM2607 | 1 | 68424731 | A/A |
| SM2608 | 1 | 68428500 | A/A |
| SM2365 | 1 | 68431623 | G/G |
| SM2362 | 1 | 68431768 | C/C |
| SM2712 | 1 | 68453157 | A/A |
| SM2709 | 1 | 68454360 | G/G |
| SM2706 | 1 | 68455010 | A/A |
| SM2710 | 1 | 68565361 | C/C |
| SM2707 | 1 | 68658060 | G/G |
| SM2550 | 1 | 68670604 | C/C |
| SM2551 | 1 | 68670713 | C/C |
| SM2708 | 1 | 68678452 | A/A |
| SM2610 | 1 | 69012158 | A/A |
| SM2613 | 1 | 69158347 | A/A |
| SM2552 | 1 | 69543214 | A/A |
| SM2553 | 1 | 69587711 | G/G |
| SM2554 | 1 | 69881293 | C/C |
| SM2556 | 1 | 69887955 | A/A |
| SM2557 | 1 | 69889226 | G/G |
| SM2558 | 1 | 70155695 | A/A |
| SM2616 | 1 | 70158847 | A/A |
| SM2617 | 1 | 70159265 | A/A |
| SM2559 | 1 | 70162230 | A/A |
| SM2621 | 1 | 70164485 | A/A |
| SM2624 | 1 | 70213152 | A/A |
| SM2626 | 1 | 70244705 | A/A |
| SM2560 | 1 | 70251144 | A/A |
| SM2628 | 1 | 70347954 | A/A |
| SM2629 | 1 | 70512212 | G/G |
| SM2013BQ | 1 | 71020438 | C/C |
| SM2573 | 1 | 71066077 | C/C |
| SM2575 | 1 | 71541039 | A/A |
| SM2576 | 1 | 71590349 | A/A |
| SM2579 | 1 | 71794881 | G/G |
| SM2580 | 1 | 71794974 | C/C |
| SM2581 | 1 | 72013466 | A/A |
| SM2347 | 1 | 72233113 | G/G |
| SM2349 | 1 | 72233448 | G/G |
| SM2368 | 1 | 73246562 | G/G |
| SM2352 | 1 | 73379493 | A/A |
| SM2369 | 1 | 73380804 | C/C |
| SM2351 | 1 | 73635946 | G/G |
| SM2354 | 1 | 73966550 | G/G |
| SM2353 | 1 | 73966557 | G/G |
| SM2345 | 1 | 73967645 | A/A |
| SM0118A | 1 | 75203350 | G/G |
| SM0251A | 1 | 82575679 | G/G |
| SM0241C | 1 | 147159831 | A/A |
| SM0201B | 1 | 178008426 | A/A |
| SM1990AQ | 1 | 184012848 | G/G |
| SM0376B | 1 | 195332392 | G/G |

Example 5

New Interval Developed with Fine Mapping

As indicated in Example 4, the limiting factor for further refinement of the haploid induction QTL region was resolved with the development of additional markers for the haploid induction region on Chromosome 1. The recombinants were screened with these newly developed markers. The original haploid induction locus was reduced from a starting interval containing ~64 genes, which was then reduced its size to 17-25 genes. Further fine mapping resolved the region to 0.60 MB with 8 genes in the interval. The eight genes include two genes GRMZ2G471240, and GRMZ2G866758 which appear twice because expression data suggests alternative transcripts. Each of the genes are listed in the Table below and are identified by the public Gene ID with the transcript start and end identified. The new refined haploid induction locus is indicated in the new confidence level. With the data from a single recombinant, a subset of approximately 8 genes were identified to be highly likely to have impact on the haploid induction trait. These are indicated by the highlighted section of the third column from the left of the Haploid Interval Table below.

TABLE

Describing Haploid Induction QTL Interval

| New Confidence interval | Refined interval | Sequencing data analysis | gene_id |
|---|---|---|---|
| x | x | Appears to be missing from all three lines | GRMZM2G305400 |

TABLE-continued

Describing Haploid Induction QTL Interval

| New Confidence interval | Refined interval | Sequencing data analysis | gene_id |
|---|---|---|---|
| x | x | NIL and B73 gDNAs align in coding region. RWK/Stock 6 gDNAs are very similar. All protein coding sequences appear similar. | GRMZM2G082836 |
| x | x | NIL/B73 are identical. RWK differs at several bases and three AA residues. It also has a 21 base insert just downstream of the stop codon. Stock 6 data not so good at amino terminus, but suggests its similar to RWK at the carboxy terminus. | GRMZM2G382717 |
| x | x | Stock 6, RWK and NIL differ from B73 outside protein coding region. RWK and Stock 6 have 2 additional amino acids | GRMZM2G120587 |
| x | x | NIL and B73 are virtually identical. Stock 6 and RWK are identical and a frame shift results in 20 incorrect AA followed by a new, premature stop codon | GRMZM2G471240 |
| | x | | GRMZM2G471240 |
| x | x | Not present in Stock 6/RWK. NIL/B73 are virtually identical. Some evidence this is a transcribed gene. | GRM2M2G062320 |
| x | | NIL and B73 are virtually identical. Stock 6 and RWK are identical. The pairs differ slightly at the protein level and outside the coding region. | GRMZM5G866758 |
| x | | | GRMZM5G866758 |
| x | | NIL is 97-98% identical to B73; RWK/Stock 6 95-99% similar to B73. Adjacent to GRMZM5G866758 but transcribed from opposite strand. All 4 encode the same protein. | GRMZM2G003530 |

Example 6

Sequence Analysis of Inducer and Non-Inducer Genomes

The maize haploid induction locus was understood to be present in a 2.2 Mb QTL located on Chromosome 1. This QTL represents approximately 70% of the variation associated with the haploid induction trait, and is therefore required for haploid induction. To date, no one has identified the genetic element responsible for haploid induction. As indicated in the earlier examples the haploid induction QTL was fine-mapped to reduce its size to 0.60 Mb In order to further identify the genes in this Haploid Induction region, the genomes of two haploid inducer lines, Stock 6 and RWK, and an RWK-NIL line were sequenced. Stock 6 is a maize haploid inducer line which is available from the Maize Genetics Stock Center in Champaign Ill. RWK is a maize line which is a haploid inducer line available from the University of Hohenhiem in Germany. B73 is a stiff stalk maize line produced and is broadly available from many sources including the Iowa State University in Ames, Iowa Genomic DNA from the leaf tissue of RWK, RWK-NIL, and Stock 6, was prepared and fragmented to produce two short-insert paired end (SIPE) libraries and one long-insert paired end (LIPE) library. Sufficient DNA sequence data were generated for 50× coverage of each genome, as indicated in the table below. The raw data were trimmed and compiled into sequence contigs. B73 sequence data for the Haploid Induction QTL on Chromosome 1 was used as a scaffold to enrich and refine contigs corresponding to this region from each genome.

Sequence Coverage

| | SIPE data | | LIPE data | | | | |
|---|---|---|---|---|---|---|---|
| | total Mb | Coverage | total Mb | coverage | total cov | % SIPE | % LIPE |
| Stock6 | 185,117 | 74.0 | 47,301 | 18.9 | 93.0 | 80% | 20% |
| NIL | 117,060 | 46.8 | 17,649 | 7.1 | 53.9 | 87% | 13% |
| RNK | 215,666 | 86.3 | 28,108 | 11.2 | 97.5 | 88% | 12% |

Total = total Mb of sequence data
coverage = average depth of sequence coverage (based on maize genome estimate of 2.5 Gb)
SIPE = short insert paired end library data (average insert size ~330 bp)
LIPE = long insert paired end library data (average insert size ~5000 bp)
Sequencing target was >= 50x coverage, >=10% of data from LIPE reads The contigs were assembled and analyzed. The process produced ~300 contigs. These were then BLASTed against the 25 genes found within the HI interval. The candidate sequence from each line was annotated and compared. Expression was verified by cDNA/EST analysis, and the annotation was verified by cDNA/gDNA alignment. The differences between the lines were noted and distinguished. (see Tables in earlier examples.)

Example 7

Sequence Analysis of Inducer and Non-Inducer Genomes

The assembled Stock 6, RWK and NIL (RWK-NIL) sequence contigs were compared to corresponding B73 sequence data. Gene models for each candidate gene were confirmed with additional sequence data from public and proprietary databases. The sequence data for each gene in the reduced HI interval were compared.

Structural Variants in Haploid Induction Interval

| Gene | structural variants? | # SNPs altering protein sequence | annotation |
|---|---|---|---|
| GRMZM2G120587 | No | 3 | Serine carboxypeptidase |
| GRMZM2G471240 | No | 4 | Patatin-like phospholipase |
| GRMZM2G062320 | Yes | 1 | Histidine phosphatase superfamily, Phosphoglycerate mutase family |
| AC213048.3 | No | 0 | pseudogene/hypothetical protein |
| GRMZM5G866758 | Yes | 2 | acetyl-CoA acetyltransferase, cytosolic 1 [Zea mays] |
| GRMZM2G003530 | Yes | 2 | Putative uncharacterized protein |
| GRMZM2G077991 | Yes | 2 | Ribosomal protein L37e |
| GRMZM2G077960 | No | 0 | Protein phosphatase 2C family protein |
| GRMZM2G077897 | No | 15 | Plant protein of unknown function, paramyosin, |

-continued

| Gene | structural variants? | # SNPs altering protein sequence | annotation |
|---|---|---|---|
| GRMZM2G347583 | No | 2 | uncharacterized protein |
| GRMZM2G173030 | No | 0 | hypothetical protein |
| GRMZM2G031591 | Yes | 0 | hypothetical protein |
| GRMZM2G070462 | Yes | 0 | FHA domain-containing protein |
| GRMZM2G022061 | No | 5 | hypothetical protein LOC100279962 (L0C100279962 |
| GRMZM2G340286 | No | 4 | uncharacterized protein |
| GRMZM2G340279 | Yes | 8 | pentatricopeptide repeat-containing protein |
| GRMZM2G347808 | No | 4 | uncharacterized protein |

The experiment did not find DNA sequence evidence that GRMZM2G305400 is present in the Stock 6, RWK or Nil genomes.

The gene GRMZM2G062320 is encoding a phosphoglycerate mutase and is absent in RWK and Stock 6 but present in NIL and B73. This result will be tested by PCR. This gene product has expression in most plant tissues and stages of development. The gene product can be classified as a phosphoglycerate mutase and has sequence that places it in the histidine phosphatase superfamily.

We noted that other genes in the refined HI interval differ in sequence between the various genomes we examined. GRMZM2G471240 encodes a phospholipase that is exclusively expressed in meiotic anthers, and has a four nucleotide insertion resulting in 20 incorrect AA followed by a new, premature stop codon.

GRMZM2G120587 encodes a serine carboxypeptidase-like 51 (SCPL51) that is expressed in anthers and is a good candidate for a haploid induction because proteolysis has been shown to contribute towards centromere-specific localization of CENH3 proteins. The proteins encoded by RWK and Stock 6 have 2 additional amino acids.

GRMZM2G305400 encodes a cyclin and this gene was not present in the inducers or NIL, but it was present in B73.

GRMZM2G082836 gDNAs in Stock 6 and RWK are more similar to each other, and the GRMZM2G082836 gDNAs in NIL and B73 gene are more similar to each other. However the GRMZM2G082836 protein coding sequences of Stock 6, RWK, NIL and B73 are identical. This gene encodes a GTP-binding protein 1.

GRMZM2G382717 gDNAs in the NIL and B73 lines are identical. Sequence coverage for Stock 6 was not complete, but the available data align precisely to the RWK sequence data. RWK differs from NIL/B73 at several bases and at three amino acids, and there is an additional 21 base pair insertion in RWK downstream of the translation stop codon. This gene encodes a chaperone DnaJ-domain superfamily protein.

GRMZM5G866758 gDNAs from the B73 and NIL lines are virtually identical. GRMZM5G866758 gDNAs from the inducer lines, RWK and Stock 6, are identical. The data indicate some sequence differences between RWK/stock 6 and B73/NIL at the protein level and outside the protein coding sequence. This gene encodes an acetoacetyl-CoA thiolase 2.

Example 8

A Method to Knock Out GRMZM2G062320 Expression in Pollen

Any unique GRMZM2G062320 transcript sequence ranging from 200-500 contiguous bases can be used to make an RNAi molecule targeting this gene. Sequences comprising the double stranded RNA can separate by an intron, or other DNA strand that doesn't constrain formation of the GRMZM2G062320 double-strand RNA. Any number of constitutive promoters could be selected. A short list of some constitutive promoters include ZmUbi1, ZmUbi158, ZmUbi361, SbUbiCh3, SbUbiCh4. Pollen specific: Pollen-specific genes have been described for maize (Lopez I, Anthony, R. G., Maciver, S. K., Jaing, C.-J., Khan, S., Weeds, A. G., Hussey, P. J. (1996) Pollen specific expression of maize genes encoding actin depolymerizing factor-like proteins. Proc Natl Acad Sci USA 93:7415-7420.) Such information can be used to identify other maize pollen-specific genes and produce pollen-specific expression cassettes. A general expression cassette design strategy is given in U.S. Pat. No. 812,958. Use of the NOS, AGS terminator components in the design is optional. The gene regulatory sequences are derived from the ZmABP2 gene (Lopez I, Anthony, R. G., Maciver, S. K., Jaing, C.-J., Khan, S., Weeds, A. G., Hussey, P. J. (1996) Pollen specific expression of maize genes encoding actin depolymerizing factor-like proteins. Proc Natl Acad Sci USA 93:7415-7420.).

Example 9

Example Demonstrating Conservation of GRMZM2G062320 Protein Sequence in Maize Syngenta's Maize Solexa Association panel is a collection of RNA-seq data derived from 790 lines. Lines in this collection were chosen based on their phenotypic and genotypic diversity from a larger collection of maize germplasm. Seedling leaf tissue was used to generate the data. The largest open reading frame for each cDNA was translated to the encoded protein for each line. The proteins were then compared to establish diversity across all lines. This evidence shows that there are five GRMZM2G062320 variants in this collection. Sequence analysis of these 790 diverse maize lines showed that version A, SEQ ID NO: 5 is present in 784 lines, version B, SEQ ID NO: 2 is present in 3 lines and versions C SEQ ID NO: 6, D SEQ ID NO: 7, and E SEQ ID NO: 8 are present in one line each. The protein sequences are derived from RNA-seq data. The evidence suggests the GRMZM2G062320 protein is highly conserved.

SEQ ID NO: 5

GRMZM2G062320-A

MAGAISHHALAFSQSHWCSAKNSRFGKRTGNARLVYLKGRCGSGSRKLGL

MWASSSQSSVMEPTHLPSDGNSSHTPKKSSESALILIWHGESLWNEKNLF

TGCIDVPLTPKGVEEAIEAGKRICNIPIDVIYTSSLICAQMTAMLAMMQH

RRKKIPVITHNESEQAHRWSQIYSEETMKQSIPVITAWQLNERMYGELQG

LNKQETVDRFGKEQVHEWHRSYDIPPPNGESLEKCAERAVAYFKDQIIPQ

LVAGKHVMVAAHGNSLRSIIMHLDKLTSQKVISLELSTGIPMLYIFKEGK

FIRRGTPVGPSEASVYAYTRTKRFAEHITFQNKLA

SEQ ID NO: 2

GRMZM2G062320-B

MAGAISHHALAFSQSHWCSAKNSRFGKRTGNARLVYLKGRCGSGSRKLGL

MWASSSQSSVMEPTHLPSDGNSSHTPKKSSESALILIWHGESLWNEKNLF

PGCIDVPLTPKGVEEAIEAGKRICNIPIDVIYTSSLICAQMTAMLAMMQH

RRKKILVITHNESEQAHRWSQIYSEETMKQSIPVITAWQLNERMYGELQG

-continued

```
LNKQETVDRFGKEQVHEWRRSYDIPPPNGESLEKCAERAVAYFKDQIIPQ

LVAGKHVMVAAHGNSLRSIIMHLDKLTSQKVISLELSTGIPMLYIFKEGK

FIRRGTPVGPSEASVYAYTRTKRFAEHITFQNKLA

                                      SEQ ID NO: 6
GRMZM2G062320-C
MAGAISHHALAFSQSHWCSAKNSRFGKRTGNARLVYLKGRCGSGSRKLGL

MWASSSQSSVMEPTHLPSDGNSSHTPKKSSESALILIWHGESLWNEKNLF

PGCIDVPLTPKGVEEAIEAGKRICNIPIDVIYTSSLICAQMTAMLAMMQH

RRKKIPVITHNESEQAHRWSQIYSEETMKQSIPVITAWQLNERMYGELQG

LNKQETVDRFGKEQVHEWHRSYDIPPPNGESLEKCAERAVAYFKDQIIPQ

LVAGKHVMVAAHGNSLRSIIMHLDKLTSQKVISLELSTGIPMLYIFKEGK

FIRRGTPVGPSEASVYAYTRTKRFAEHITFQNKLA

                                      SEQ ID NO: 7
GRMZM2G062320-D
MAGAISHHALAFSQSHWCSAKNSRFGKRTGNARLVYLKGRCGSGSRKLGL

MWASSSQSSVMEPTHLPSDGNSSHTPKKSSESALILIWHGESLWNEKNLF

TGCIDVPLTPKGVEEAIEAGKRICNIPIDVIYTSSLICAQMTSMLAMMQH

RRKKIPVITHNESEQAHRWSQIYSEETMKQSIPVITAWQLNERMYGELQG

LNKQETVDRFGKEQVHEWHRSYDIPPPNGESLEKCAERAVAYFKDQIIPQ

LVAGKHVMVAAHGNSLRSIIMHLDKLTSQKVISLELSTGIPMLYIFKEGK

FIRRGTPVGPSEASVYAYTRTKRFAEHITFQNKLA

                                      SEQ ID NO: 8
GRMZM2G062320-E
MAGAISHHALAFSQSHWCSAKNSRFGKRTGNARLVYLKGRCGSGSRKLGL

MWASSSQSSVMEPTHLPSDGNSSHTPKKSSESALILIWHGESLWNEKNLF

TGCIDVPLTPKGVEEAIEAGKRICNIPIDVIYTSSLICAQMTSMLAMMQH

RRKKIPVITHNESEQAHRWSQIYSEETMKQSIPVITAWQLNERMYGELQG

LNKQETVDRFGKEQVHEWRRSYDIPPPNGESLEKCAERAVAYFKDQIIPQ

LVAGKHVMVAAHGNSLRSIIMHLDKLTSQKVISLELSTGIPMLYIFKEGK

FIRRGTPVGPSEASVYAYTRTKRFAEHITFQNKLA
```

Example 10

PCR Experiments to Determine the Presence or Absence of GRMZM2G062320 in the Haploid Inducer Lines These pairs worked as expected on NIL, RWK, and Stock6 DNA: NIL gDNA only amplified the NIL primer pair. RWK and Stock6 gDNA only amplified the RWK/Stock6 primer pair, which specifically detects the frame-shift allele. The PCR products were sequenced and the sequences were identical to that from whole genome sequencing. The primer pairs are “nil.F1/R1” and “rwk.F1/R1”.

Three PCR reactions spanning all but the first two exons of the gene model amplified in RWK and Stock6, and the amplicons had the correct size PCR gel band. These bands were excised from the gel, sub-cloned and sequenced, and were found to be nearly identical in sequence to the B73 and NIL amplicons, except for a few single nucleotide polymorphisms (SNPs). These SNPs may represent normal genetic drift because none of them caused non-conservative amino acid substitutions. The 5' end of the gene model could not be detected by PCR in RWK, Stock6, or NIL DNA samples. After multiple rounds of PCR and primer redesign, the 5' end was never amplified or cloned in any of the lines. Overall, this data contradicts the genome assemblies, suggesting that at least part of the gene model exists in RWK and Stock6 inducers.

One primer pair, designed to amplify an approximately 400 bp amplicon spanning exons 6-8, not only amplified in all lines tested, but the DNA sequence also matched B73 with 100% nucleotide identity. This primer pair was used to query a panel of high, low, and non-inducer maize plants. The high inducers all give greater than 7% haploid embryos upon outcrossing through the male (>7% haploid induction rate (HIR)). The low inducers have a HIR between 1 and 3%, and the non-inducers have a HIR of <0.1%. All of the high and low inducer lines were derived from the original Stock6 line, and thus it is assumed that the lesion responsible for haploid induction should be present in all high and low inducers, and absent in non-inducers.

When the exon 6-8 PCR primers were tested on these DNA samples, a band of the correct size and sequence was found in 9/9 non-inducers, 8/12 high inducers, and 6/7 low inducers. No band was present in 4/12 high inducers and 1/7 low inducers (Table 1). This indicates that, contrary to the sequencing data, this gene does exist in RWK and Stock6, but in various other induction lines, there may be presence/absence variation but it does not correlate with induction capacity. This makes it difficult to explain how GRMZM2G062320 is responsible for haploid induction.

| GRMZM2G062320 PCR test for presence of amplicon exon 6-8 | Induction Rate | Band present? |
|---|---|---|
| Controls: | | |
| Stock 6 (low) | 2.50% | + |
| RWK (high) | 12% | + |
| RWK-NIL (non) | <1% | + |
| High Inducers: | | |
| ZMS | 7% | − |
| Z19-PR | 7% | − |
| RWS-Z86 | 10% | + |
| K13 | 9% | + |
| (ID3002/Z22)B > 29-5 > 2-5-1-B- | 7% | − |
| Z-19-//AF4031PR//Z-19-)1-1-2-3-1-3-B- | 9.5% | + |
| ZR86 | 12% | + |
| ZR53 | 12% | − |
| ZR75 | 13% | + |
| (Z21/RWS)B(GS)-75-1-2-3-B- | ~8% | + |
| AX5707 inducer-good | ~9% | + |
| Poor Inducers: | | |
| Stock6 R1-nj | 2.5% | + |
| (Z21/RWS//[RWS]B$)33-5- | <2% | + |
| (K-13-/(ZMS/SEW-PR)B > 2 > B-9//K-13-)2-4-1- | <2% | + |
| (K-13-/(ZMS/SEW-PR)B > 2 > B-9//K-13-)6-1-2- | <2% | + |
| (ZMS/SEW-PR)B > 2 > B-7-2-1-2- | <2% | − |
| AX5707 inducer-low | ~3% | + |
| Non-inducers: | | |
| Stock6 R1-nj B1Pl1 | <0.1% | + |
| (Z-21-/AF4031PR//Z-21-1-B-)1-1-1-1-B- | <0.1% | + |
| FF6096 | <0.1% | + |
| ID5829 | <0.1% | + |
| XO5744 | <0.1% | + |
| ID3002 | <0.1% | + |
| AF4031PR | <0.1% | + |
| AX5707 | <0.1% | + |

Example 11

PCR Experiments to Determine the Presence or Absence of GRMZM2G471240 in the Haploid Inducer Lines In order to develop a PCR test that would distinguish between RWK/Stock6 and NIL haplotypes, two primer pairs were designed: one pair should amplify the RWK/Stock6 frame-shift allele, while the other should amplify the B73/NIL allele.

For STOCK6/RWK allele (mutant, frameshift allele):

```
rwk.F1     TACGCCGTGCGCTAACATA

rwk.R1     GTACCTCGCTCCCTGTCTCC
```

SIZE: 822 bp

FOR B73/RWK-NIL

```
nil.F1     GTACGCCGTGCGCTAACA

nil.R1     TCGTACCTCCCTGTCTCCAC
```

SIZE: 821

Use: In a PCR reaction, these would be used at 500 nMol final concentration. The reaction may also contain:

1×PCR reaction buffer 200 uM of dNTPs (dATP, dCTP, dGTP, and dTTP)

<250 ng of genomic DNA deionized water

Taq enzyme (1 unit—many different types available—usually 0.2 uL or 0.5 uL depending on the units/uL magnesium chloride or magnesium sulfate (1 mM)

Reaction volume: 25 or 50 uL recommended reaction:

1. 95 degrees C. 3'
2. 95 degrees C. 30" (denature)
3. 62 degrees C. 30" (anneal)
4. 72 degrees C. 1' (extend)
5. Repeat steps 2-4, 35 times
6. 72 degrees C., 10" (final extension)
7. 4 degrees C., forever These pairs worked as expected on NIL, RWK, and Stock6 DNA, NIL gDNA only amplified the NIL primer pair. RWK and Stock6 gDNA only amplified the RWK/Stock6 primer pair, which specifically detects the frame-shift allele. The PCR products were sequenced and the sequences were identical to that from whole genome sequencing. SNPs that were identified in the whole genome sequencing were confirmed in the PCR products (data not shown). The primer pairs are “nil.F1/R1” and “rwk.F1/R1”.

Detecting the Frame-Shift Mutation in the Panel of Inducer Lines:

The “rwk.F1/R1” and “nil.F1/R1” primer pairs were used to genotype the panel of high, low, and non-inducers. The data indicates that the frame-shift allele correlates with induction capacity. 14/14 high and 7/7 low inducers amplified the RWK/Stock6 allele, but not the NIL allele, while 9/9 non-inducers amplified the NIL allele, but not the RWK/Stock6 allele (Table 2).

| GRMZM2G471240 | Induction Rate | RWK amplicon | NIL amplicon |
|---|---|---|---|
| Controls: | | | |
| Stock 6 (low) | 2.50% | + | − |
| RWK (high) | 12% | + | − |
| RWK-NIL (non) | <1% | − | + |
| Good Inducers: | | | |
| ZMS | 7% | + | − |
| Z19-PR | 7% | + | − |
| Z22 | 7% | | |
| Z21 | 7% | | |
| RWS-Z86 | 10% | + | − |
| K13 | 9% | + | − |
| (ID3002/Z22)B > 29-5 > 2-5-1-B- | 7% | + | − |
| Z-19-//AF4031PR//Z-19-)1-1-2-3-1-3-B- | 9.5% | + | − |
| ZR86 | 12% | + | − |
| ZR53 | 12% | + | − |
| ZR75 | 13% | + | − |
| (Z21/RWS)B(GS)-75-1-2-3-B- | ~8% | + | − |
| AX5707 inducer-good | ~9% | + | − |
| Poor Inducers: | | | |
| Stock6 R1-nj | 2.5% | + | − |
| (Z21/RWS//[RWS]B$)33-5- | <2% | + | − |
| (K-13-/(ZMS/SEW-PR)B > 2 > B-9//K-13-)2-4-1- | <2% | + | − |
| (K-13-/(ZMS/SEW-PR)B > 2 > B-9//K-13-)6-1-2- | <2% | + | − |
| (ZMS/SEW-PR)B > 2 > B-7-2-1-2- | <2% | + | − |
| AX5707 inducer-low | ~3% | + | − |
| Non-inducer Lines and Donors: | | | |
| Stock6 R1-nj B1P11 | <0.1% | − | + |
| (Z-21-/AF4031PR//Z-21-1-B-)1-1-1-1-B- | <0.1% | − | + |
| FF6096 | <0.1% | − | + |
| ID5829 | <0.1% | − | + |
| XO5744 | <0.1% | − | + |
| ID3002 | <0.1% | − | + |
| AF4031PR | <0.1% | − | + |
| AX5707 | <0.1% | − | + |

Example 12

A Method to Knock Out GRMZM2G471240 Expression

Any unique GRMZM2G471240 transcript sequence ranging from 200-1000 contiguous bases can be used to make an RNAi molecule targeting this gene. Sequences comprising the double stranded RNA can separate by an intron, or other DNA strand that doesn't constrain formation of the GRMZM2G471240 double-strand RNA. Any number of constitutive promoters could be selected. A short list of some constitutive promoters include ZmUbi1, ZmUbi158, ZmUbi361, SbUbiCh3, SbUbiCh4. Pollen specific: Pollen-specific genes have been described for maize (Lopez I, Anthony, R. G., Maciver, S. K., Jaing, C.-J., Khan, S., Weeds, A. G., Hussey, P. J. (1996) Pollen specific expression of maize genes encoding actin depolymerizing factor-like proteins. Proc Natl Acad Sci USA 93:7415-7420.) Such information can be used to identify other maize pollen-specific genes and produce pollen-specific expression cassettes. A general expression cassette design strategy is given in U.S. Pat. No. 812,958. Use of the NOS, AGS terminator components in the design is optional. The gene regulatory sequences are derived from the ZmABP2 gene (Lopez I, Anthony, R. G., Maciver, S. K., Jaing, C.-J., Khan, S., Weeds, A. G., Hussey, P. J. (1996) Pollen specific expression of maize genes encoding actin depolymerizing factor-like proteins. Proc Natl Acad Sci USA 93:7415-7420.). Expression constructs have been built comprising The promoter of GRMZM2G471240 as in SEQ ID NO: 58 operably linked to the hairpin construct in SEQ ID NO: 60 operably linked to the terminator of SEQ ID NO:59. Another construct was made with The promoter of GRMZM2G471240 as in SEQ ID NO: 58 operably linked to the hairpin construct in SEQ ID NO: 61 operably linked to the terminator of SEQ ID NO:59.

Example 13

Generation of Transgenic Maize Plants

Transformation of immature maize embryos is performed essentially as described in Negrotto et al., Plant Cell Reports 19:798-803 (2000). Various media constituents described therein can be substituted.

*Agrobacterium* strain LBA4404 (Invitrogen) containing the plant transformation plasmid is grown on YEP (yeast extract (5 g/L), peptone (10 g/L), NaCl (5 g/L), 15 g/l agar, pH 6.8) solid medium for 2 to 4 days at 28° C. Approximately 0.8×109 Agrobacteria are suspended in LS-inf media supplemented with 100 μM acetosyringone (As) (LSAs medium) (Negrotto et al., Plant Cell Rep 19:798-803 (2000)). Bacteria are pre-induced in this medium for 30-60 minutes.

Immature embryos from maize line, A188, or other suitable maize genotypes are excised from 8-12 day old ears into liquid LS-inf+100 μM As (LSAs). Embryos are vortexed for 5 seconds and rinsed once with fresh infection medium. Infection media is removed and *Agrobacterium* solution is then added and embryos are vortexed for 30 seconds and allowed to settle with the bacteria for 5 minutes. The embryos are then transferred scutellum side up to LSAs medium and cultured in the dark for two to three days. Subsequently, between 20 and 25 embryos per petri plate are transferred to LSDc medium supplemented with cefotaxime (250 mg/l) and silver nitrate (1.6 mg/l) (Negrotto et al., Plant Cell Rep 19:798-803 (2000)) and cultured in the dark for 28° C. for 10 days.

Immature embryos producing embryogenic callus are transferred to LSD1M0.5S medium (LSDc with 0.5 mg/l 2,4-D instead of Dicamba, 10 g/l mannose, 5 g/l sucrose and no silver nitrate). The cultures are selected on this medium for 6 weeks with a subculture step at 3 weeks. Surviving calli are transferred either to LSD1M0.5S medium to be bulked-up or to Reg1 medium (as described in Negrotto et al., Plant Cell Rep 19:798-803 (2000)). Calli transformed with an *agrobacterium* binary vector carrying the RNAi expression cassette comprising or SEQ ID NO: 61 are surviving selection indicating successful transformation. An *agrobacterium* binary vector carrying the RNAi expression cassette comprising or SEQ ID NO: 60 will be transformed into maize. Following culturing in the light (16 hour light/8 hour dark regiment), green tissues will be transferred to Reg2 medium without growth regulators (as described in Negrotto et al., Plant Cell Rep 19:798-803 (2000)) and incubated for 1-2 weeks. Plantlets will be transferred to Magenta GA-7 boxes (Magenta Corp, Chicago Ill.) containing Reg3 medium (as described in Negrotto et al. (2000)) and grown in the light. Plants that are PCR positive for PMI and negative for Spectinomycin will be transferred to soil and grown in the greenhouse.

Example 14

Haploid Induction

TO transgenic plants expressing an RNAi construct which silences GRMZM2G471240 will be tested for haploid induction capacity. The pollen from each plant is to be crossed onto an ear to induce fertilization, and the resulting progeny of the cross subjected to ploidy analysis. Ploidy analysis can be defined in this case as any experimental test where the ploidy level of an individual plant is determined. In crosses between two non-inducing lines, the resulting progeny should be almost exclusively diploid, or 2N. However, if a haploid induction line is the male parent, the resulting progeny will be a mixed population of haploids (1N), diploids (2N), aneuploids (somewhere between 1N and 2N), and chimeras (containing tissues with mixed ploidy). The determination of haploid induction capacity can be made binary by setting a cutoff value for the haploid induction rate, which is defined as the number of haploid embryos over the total number of viable embryos. The rate should be at least greater than 0.5%.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of creating a new haploid inducer maize plant with a silenced patatin-like phospholipase 2A, comprising transcribing a polynucleotide sequence that silences the patatin-like phospholipase 2A in maize, wherein said polynucleotide sequence comprises a first sequence selected from the group consisting of:

a) a polynucleotide sequence comprising the nucleic acid sequence set forth in SEQ ID NO: 32 or the complement thereof;

b) a functional fragment comprising at least 22 contiguous bases of SEQ ID NO: 32 or the complement thereof; and c) a polynucleotide sequence having at least 95% sequence identity as determined using the BLASTN alignment tool to the nucleic acid sequence set forth in SEQ ID NO: 32 or the complement thereof;

and a second sequence that is the complement of the first sequence, wherein the polynucleotide sequence expresses a double-stranded ribonucleotide sequence which silences the patatin-like phospholipase 2A when contacted with a maize plant and thus creates a new haploid inducer maize plant.

2. The method of claim 1, wherein the contacting is achieved by transforming the plant with a polynucleotide sequence which when expressed produces a double-stranded ribonucleotide sequence that silences the patatin-like phospholipase 2A.

* * * * *